(12) United States Patent
Pi et al.

(10) Patent No.: US 8,933,235 B2
(45) Date of Patent: Jan. 13, 2015

(54) PYRIDINEDIONE CARBOXAMIDE INHIBITORS OF ENDOTHELIAL LIPASE

(71) Applicant: Bristol-Myers Squibb Company, Princeton, NJ (US)

(72) Inventors: Zulan Pi, Pennington, NJ (US); John Lloyd, Yardley, PA (US); Jennifer X. Qiao, Princeton, NJ (US); Tammy C. Wang, Lawrenceville, NJ (US); George O. Tora, Langhorne, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/347,662

(22) PCT Filed: Sep. 24, 2012

(86) PCT No.: PCT/US2012/056829
§ 371 (c)(1),
(2) Date: Mar. 27, 2014

(87) PCT Pub. No.: WO2013/048930
PCT Pub. Date: Apr. 4, 2013

(65) Prior Publication Data
US 2014/0235673 A1 Aug. 21, 2014

Related U.S. Application Data

(60) Provisional application No. 61/541,122, filed on Sep. 30, 2011.

(51) Int. Cl.
| | | |
|---|---|---|
| *A61K 31/47* | (2006.01) | |
| *C07D 213/62* | (2006.01) | |
| *C07D 413/04* | (2006.01) | |
| *C07D 213/89* | (2006.01) | |
| *C07D 401/04* | (2006.01) | |
| *C07D 401/12* | (2006.01) | |
| *C07D 213/81* | (2006.01) | |
| *C07D 409/04* | (2006.01) | |

(52) U.S. Cl.
CPC .......... *C07D 213/81* (2013.01); *C07D 413/04* (2013.01); *C07D 213/89* (2013.01); *C07D 401/04* (2013.01); *C07D 401/12* (2013.01); *C07D 409/04* (2013.01)
USPC .......................................... 546/298; 514/314

(58) Field of Classification Search
None
See application file for complete search history.

(56) References Cited

U.S. PATENT DOCUMENTS

| 7,217,727 | B2 | 5/2007 | Eacho et al. |
| 7,595,403 | B2 | 9/2009 | Eacho et al. |
| 2005/0261322 | A1 | 11/2005 | Naidu et al. |
| 2006/0211755 | A1 | 9/2006 | Eacho et al. |
| 2007/0155744 | A1 | 7/2007 | Jones et al. |
| 2008/0287448 | A1 | 11/2008 | Zoller et al. |
| 2009/0054478 | A1 | 2/2009 | Zoller et al. |
| 2009/0076068 | A1 | 3/2009 | Zoller et al. |

FOREIGN PATENT DOCUMENTS

| GB | 2 345 058 | 6/2000 |
| WO | WO99/32611 A1 | 7/1999 |
| WO | WO03/042206 A1 | 5/2003 |
| WO | WO2004/093872 A1 | 11/2004 |
| WO | WO2004/094393 A1 | 11/2004 |
| WO | WO2004/094394 A1 | 11/2004 |
| WO | WO2005/074513 A2 | 8/2005 |
| WO | WO2007/042178 A1 | 4/2007 |
| WO | WO2007/110215 A1 | 10/2007 |
| WO | WO2007/110216 A1 | 10/2007 |
| WO | WO2008/122352 A1 | 10/2008 |
| WO | WO2009/123164 A1 | 10/2009 |
| WO | WO2009/133834 A1 | 11/2009 |

OTHER PUBLICATIONS

Bevilacqua, M. et al., "Selectins", J. Clinical Invest., vol. 91, pp. 379-387 (1993).
deLemos, A. et al., "Identification of Genetic Variants in Endothelial Lipase in Persons With Elevated High-Density Lipoprotein Cholesterol", Circulation, vol. 106, pp. 1321-1326 (2002).
Folkman, J. et al., "Angiogenic Factors", Science, vol. 235, pp. 442-447 (1987).
Folkman, J. et al., "Angiogenesis" *Minireview*. The J. of Biological Chemistry, vol. 267(16) pp. 10931-10934 (1992).
Gordon, D.J. et al, "High-Density Lipoprotein—The Clinical Implications of Recent studies", New England J. Of Medicine, vol. 321(19), pp. 1311-1316 (1989).
Gordon, D.J. et al., "High-Density Lipoprotein Cholesterol and Cardiovascular Disease", Circulation, vol. 79, pp. 8-15 (1989).
Hirata, K. et al., "Cloning of a Unique Lipase from Endothelial Cells Extends the Lipase Gene Family", The J. Of Biological Chemistry, vol. 274(20), pp. 14170-14175 (1999).
Janssens, S.P. et al., "Cloning and Expression of a cDNA Encoding Human Endothelium-derived Relaxing Factor/Nitric Oxide Synthase", The J. of Biological Chemistry, vol. 267(21), pp. 14519-14522 (1992).
Jaye, M. et al., "A novel endothelial-derived lipase that modulates HDL metabolism", Nature Genetics, vol. 21, pp. 424-428 (1999).
Jin, W. et al., "Lipases and HDL metabolism" Trends in Endocrinology & Metabolism, vol. 13(4), pp. 174-178 (2002).
Lamas, S. et al., "Endothelial nitric oxide synthase: Molecular cloning and characterization of a distinct constitutive enzyme isoform", PNAS, vol. 89, pp. 6348-6352 (1992).
Lüscher, T.F. et al., "Endothelium-Derived Contracting Factors", Hypertension, vol. 19, pp. 117-130 (1992).

(Continued)

Primary Examiner — Heidi Reese
(74) Attorney, Agent, or Firm — Jing G. Sun

(57) ABSTRACT

The present invention provides compounds of Formula (I) as defined in the specification and compositions comprising any of such novel compounds. These compounds are endothelial lipase inhibitors which may be used as medicaments.

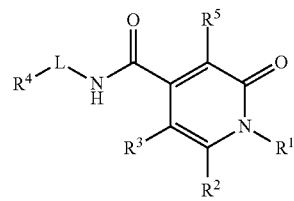

20 Claims, No Drawings

(56) References Cited

OTHER PUBLICATIONS

McCoy, M.G. et al., "Characterization of the lipolytic activity of endothelial lipase", Journal of Lipid Research, vol. 43, pp. 921-929 (2002).

Romanovski, V. et al., "Potential Agents for Removal of Actinides from Waste Solutions", Spectrum 96 International Conference on Nuclear and Hazardous Waste Management Conference Proceedings, vol. 3, pp. 2330-2334 (1996).

Ross, R., "The pathogenesis of atherosclerosis: a perspective for the 1990s" Nature, vol. 362(80), pp. 801-809 (1993).

Strauss, J.G. et al., "Endothelial cell-derived lipase mediates uptake and binding of high-density lipoprotein (HDL) particles and the selective uptake of HDL-associated cholesterol esters independent of its enzymic activity", Biochem. J., vol. 368, pp. 69-79 (2002).

Veeck, A. et al., "Hydroxypyridinone Extraction Agents for Pu(IV)", Solvent Extraction and Ion Exchange, vol. 22(6), pp. 1037-1068 (2004).

Williams, T.J. et al., "Adhesion Molecules Involved in the Microvascular Inflammatory Response", Am Rev. Respir. Disease, vol. 146, pp. S45-S50 (1992).

Wong, H. et al., "The lipase gene family", Journal of Lipid Research, vol. 43, pp. 993-999 (2002).

Yanagisawa, M. et al., "A novel potent vasoconstrictor peptide produced by vascular endothelial cells", Nature, vol. 332, pp. 411-415 (1988).

PYRIDINEDIONE CARBOXAMIDE INHIBITORS OF ENDOTHELIAL LIPASE

CROSS-REFERENCE TO RELATED APPLICATIONS

The present application is a 371 application of PCT/US2010/056829 filed Sep. 24, 2012, which claims priority benefit of U.S. provisional application Ser. No. 61/541,122, filed Sep. 30, 2011; each of which is fully incorporated by reference herein.

FIELD OF THE INVENTION

The present invention provides novel pyridinedione carboxamide compounds and analogues, which are endothelial lipase (EL) inhibitors, compositions containing them, and methods of using them, for example, for the treatment and/or prophylaxis of dyslipidemias and the sequelae thereof.

BACKGROUND OF THE INVENTION

Cardiovascular disease is a major health risk throughout the industrialized world. Atherosclerosis, the most prevalent of cardiovascular diseases, is the principal cause of heart attack, and stroke, and thereby the principal cause of death in the United States.

Atherosclerosis is a complex disease involving many cell types and molecular factors (for a detailed review, see Ross, *Nature*, 362(80):1-809 (1993)). Results from epidemiologic studies have clearly established an inverse relationship between levels of high density lipoprotein (HDL), which transports endogenous cholesterol from tissues to the liver as well as mediating selective cholesteryl ester delivery to steroidogenic tissues, and the risk for atherosclerosis (Gordon et al., *N. Engl. J. Med.*, 321:1311-1316 (1989)).

The metabolism of HDL is influenced by several members of the triacylglycerol (TG) lipase family of proteins, which hydrolyze triglycerides, phospholipids, and cholesteryl esters, generating fatty acids to facilitate intestinal absorption, energy production, or storage. Of the TG lipases, lipoprotein lipase (LPL) influences the metabolism of HDL cholesterol by hydrolyzing triglycerides in triglyceride-rich lipoproteins, resulting in the transfer of lipids and apolipoproteins to HDL and is responsible for hydrolyzing chylomicron and very low density lipoprotein (VLDL) in muscle and adipose tissues. Hepatic lipase (HL) hydrolyzes HDL triglyceride and phospholipids, generating smaller, lipid-depleted HDL particles, and plays a role in the uptake of HDL cholesterol (Jin et al., *Trends Endocrinol. Metab.*, 13:174-178 (2002); Wong et al., *J. Lipid Res.*, 43:993-999 (2002)). Endothelial lipase (also known as EDL, EL, LIPG, endothelial-derived lipase, and endothelial cell-derived lipase) is synthesized in endothelial cells, a characteristic that distinguishes it from the other members of the family.

Recombinant endothelial lipase protein has substantial phospholipase activity but has been reported to have less hydrolytic activity toward triglyceride lipids (Hirata et al., *J. Biol. Chem.*, 274:14170-14175 (1999); Jaye et al., *Nat. Genet.*, 21:424-428 (1999)). However, endothelial lipase does exhibit triglyceride lipase activity ex vivo in addition to its HDL phospholipase activity, and endothelial lipase was found to hydrolyze HDL more efficiently than other lipoproteins (McCoy et al., *J. Lipid Res.*, 43:921-929 (2002)). Overexpression of the human endothelial lipase gene in the livers of mice markedly reduces plasma concentrations of HDL cholesterol and its major protein apolipoprotein A-I (apoA-I) (Jaye et al., *Nat. Genet.*, 21:424-428 (1999)).

Various types of compounds have been reported to modulate the expression of endothelial lipase, for example, 3-oxo-1,3-dihydro-indazole-2-carboxamides (WO 2004/093872, US 2006/0211755A1), 3-oxo-3-H-benzo[d]isoxazole-2-carboxamides (WO 2004/094393, U.S. Pat. No. 7,217,727), and benzisothiazol-3-one-2-carboxamides (WO 2004/094394, U.S. Pat. No. 7,595,403) by Eli Lilly & Co.; diacylindazole derivatives (WO 2007/042178, US 2008/0287448A1) and imidazopyridin-2-one derivatives (WO 2007/110215, US 2009/0076068A1), and azolopyridin-3-one derivatives (WO 2007/110216, US 2009/0054478A1) by Sanofi-Aventis; heterocyclic derivatives (WO 2009/123164) and keto-amide derivatives (WO 2009/133834) by Shionogi & Co., Ltd. However, because endothelial lipase is a relatively new member in the lipase gene family, a full understanding of the potential of endothelial lipase inhibitors to human health, as well as the inhibitors of other lipases in general, requires more studies.

Thus, there is a clear need for new types of compounds capable of inhibiting the activity of lipases, particularly endothelial lipase, that would constitute effective treatments to the diseases or disorders associated with the activity of such lipases.

SUMMARY OF THE INVENTION

The present disclosure provides novel pyridinedione carboxamide compounds and their analogues, including stereoisomers, tautomers, pharmaceutically acceptable salts, or solvates thereof, which are useful as EL inhibitors.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of dyslipidemias and the sequelae thereof.

The compounds of the invention may be used in therapy.

The compounds of the invention may be used for the manufacture of a medicament for the treatment and/or prophylaxis of dyslipidemias and the sequelae thereof.

The compounds of the invention can be used alone, in combination with other compounds of the present invention, or in combination with one or more, preferably one to two, other agent(s).

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

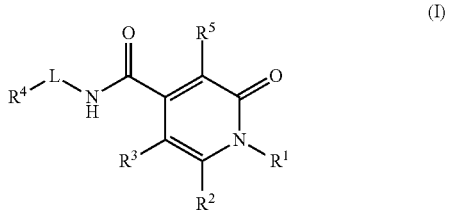

or a stereoisomer, a tautomer, a pharmaceutically acceptable salt, or a solvate thereof, wherein:

$R^1$ is independently selected from the group consisting of: H, $C_{1-6}$ alkyl substituted with 0-3 $R^a$, $C_{2-6}$ alkenyl substituted with 0-3 $R^a$, and $-(CH_2)_n-W-(CH_2)_m-R^{1a}$;

W is independently selected from the group consisting of: a bond, NH, O, S, $N(C_{1-4}$ alkyl), CO, CONH, $CON(C_{1-4}$ alkyl), NHCO, $SO_2$, $NHSO_2$, $SO_2NH$, $NHCO_2$, and $CHR^f$;

$R^{1a}$ is independently selected from the group consisting of: $C_{3-10}$ carbocycle and a 5- to 10-membered heterocycle comprising: carbon atoms and 1-4 heteroatoms selected from N, $NR^e$, O, and $S(O)_p$; and wherein said carbocycle and heterocycle are substituted with 0-3 $R^c$;

$R^2$ and $R^3$ are, independently at each occurrence, selected from the group consisting of: H, halogen, $CF_3$, $OCF_3$, $C_{1-6}$ alkyl substituted with 0-3 $R^a$, $C_{2-6}$ alkenyl substituted with 0-3 $R^a$, $-CO_2(C_{1-4}$ alkyl), $-SO_2$(phenyl), $-(CH_2)_n-(C_{3-6}$ cycloalkyl substituted with 0-3 $R^c$), $-(CH_2)_n$-(phenyl substituted with 0-3 $R^b$), $-(CH_2)_n$-(naphthyl substituted with 0-3 $R^b$), and $-(CH_2)_n$-(5- to 10 membered heterocycle comprising: carbon atoms and 1-4 heteroatoms selected from N, $NR^e$, O, and $S(O)_p$), wherein said heterocycle is substituted with 0-3 $R^c$;

$R^4$ is independently selected from the group consisting of: $C_{3-10}$ carbocycle and a 5- to 10-membered heterocycle comprising: carbon atoms and 1-4 heteroatoms selected from N, $NR^e$, O, and $S(O)_p$; wherein said carbocycle and heterocycle are substituted with 0-3 $R^d$;

$R^5$ is independently selected from the group consisting of: $OR^6$, CN, and $NR^7R^8$;

$R^6$ is independently selected from the group consisting of: H and $C_{1-6}$ alkyl substituted with 0-1 $CO_2H$;

$R^7$ is independently selected from the group consisting of: H, $C_{1-6}$ alkyl substituted with 0-1 $R^a$, $-(CH_2)_n$-(phenyl substituted with 0-3 $R^b$), and $-(CH_2)_n$-(5- to 6-membered heterocycle comprising: carbon atoms and 1-4 heteroatoms selected from N, $NR^e$, O, and $S(O)_p$); and wherein said heterocycle is substituted with 0-3 $R^c$;

$R^8$ is independently selected from the group consisting of: H and $C_{1-6}$ alkyl;

alternatively, $NR^7R^8$ is a 5- to 6-membered heterocycle comprising: carbon atoms and 1-4 heteroatoms selected from N, $NR^e$, O, and $S(O)_p$;

L is independently a hydrocarbon or hydrocarbon-heteroatom linker optionally substituted with 0-2 $R^g$; wherein said hydrocarbon linker has one to eight carbon atoms and may be straight or branched, saturated or unsaturated; and said hydrocarbon-heteroatom linker has one to seven carbon atoms and one group selected from O, $-CO-$, S, $-SO-$, $-SO_2-$, NH, and $N(C_{1-4}$ alkyl);

$R^a$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, CN, $NH_2$, $NO_2$, $NH(C_{1-4}$ alkyl), $N(C_{1-4}$ alkyl)$_2$, $CO_2H$, $CO_2(C_{1-4}$ alkyl), $NHCO(C_{1-4}$ alkyl substituted with 0-1 $NH_2$), $N(C_{1-4}$ alkyl)$CO(C_{1-4}$ alkyl), $NHCO_2(C_{1-4}$ alkyl), $CONHSO_2(C_{1-4}$ alkyl), $SO_2(C_{1-4}$ alkyl), $CONH_2$, $CONH(C_{1-4}$ alkyl), $NHSO_2(C_{1-4}$ alkyl), $N(C_{1-4}$ alkyl)$SO_2(C_{1-4}$ alkyl), and phenoxy;

$R^b$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, $OCF_2CHF_2$, $OCH_2CF_3$, CN, $NH_2$, $NO_2$, $NH(C_{1-4}$ alkyl), $N(C_{1-4}$ alkyl)$_2$, $CO_2H$, $CO_2(C_{1-4}$ alkyl), $CONH_2$, $CONH(C_{1-4}$ alkyl), $CON(C_{1-4}$ alkyl)$_2$, $NHCO_2(C_{1-4}$ alkyl), $NHSO_2(C_{1-4}$ alkyl), $N(C_{1-4}$ alkyl)$SO_2(C_{1-4}$ alkyl), $SO_2(C_{1-4}$ alkyl), $SO_2NH_2$, phenyl, benzyl, and phenoxy;

$R^c$ is, independently at each occurrence, selected from the group consisting of: =O and $R^b$;

$R^d$ is, independently at each occurrence, selected from the group consisting of: =O, halogen, OH, $C_{1-6}$ alkyl substituted with 0-1 OH, $C_{1-4}$ alkoxy, $C_{1-4}$ haloalkyl, $C_{1-4}$ haloalkoxy, $CF_3$, $OCF_3$, $OCF_2CF_2H$, $OCH_2CF_3$, CN, $NH_2$, $NO_2$, $NH(C_{1-4}$ alkyl), $N(C_{1-4}$ alkyl)$_2$, $CO_2H$, $CO_2(C_{1-4}$ alkyl), $CO(C_{1-4}$ alkyl), $NHCO(C_{1-4}$ alkyl), $-CH_2NHCO(C_{1-4}$ alkyl), $CONH_2$, $CONH(C_{1-4}$ alkyl), $CON(C_{1-4}$ alkyl)$_2$, $SO_2(C_{1-4}$ alkyl), $SO_2NH_2$, $-SO_2NH(C_{1-4}$ alkyl), $-SO_2NH(C_{3-6}$ cycloalkyl), $-NHSO_2(C_{1-4}$ alkyl), $-CH_2NHSO_2(C_{1-4}$ alkyl), and $Si(C_{1-4}$ alkyl)$_3$;

$R^e$ is, independently at each occurrence, selected from the group consisting of: H, $C_{1-4}$ alkyl, $CO(C_{1-4}$ alkyl), $CO_2(C_{1-4}$ alkyl), $CO_2$(benzyl), and $-(CH_2)_n$-(phenyl optionally substituted with 0-2 halogens);

$R^f$ is, independently at each occurrence, selected from the group consisting of: $C_{1-4}$ alkyl, $C_{2-4}$ alkenyl, $CO_2(C_{1-4}$ alkyl), $CONH_2$, $C_{3-6}$ cycloalkyl, phenyl, and benzyl;

$R^g$ is, independently at each occurrence, selected from the group consisting of: halogen, OH, $C_{1-4}$ alkyl, $C_{2-4}$ alkenyl, $C_{1-4}$ haloalkyl, $C_{1-4}$ alkyoxy, $CO_2(C_{1-4}$ alkyl), $C_{3-6}$ cycloalkyl, and phenyl;

m is, independently at each occurrence, selected from 0, 1, and 2;

n is, independently at each occurrence, selected from 0, 1, 2, 3, and 4; and p is, independently at each occurrence, selected from 0, 1, and 2;

provided that:
 (i) when $R^1$ is methyl, $R^2$ and $R^3$ are H, $R^5$ is OH, and L is $-(CH_2)_3-$, then $R^4$ is other than unsubstituted phenyl;
 (ii) when L is $CH_2$, then $R^4$ is other than halogen monosubstituted phenyl or methoxy bi-substituted phenyl; or
 (iii) when $R^1$ is methyl, $R^2$ and $R^3$ are H, $R^5$ is OH, and L is $-(CH_2)_2-$, then $R^4$ is other than methoxy mono-substituted indolyl.

In a second aspect, the present invention includes a compound of Formula (I), or a stereoisomer, a tautomer, a pharmaceutically acceptable salt, or a solvate thereof, within the scope of the first aspect, wherein:

$R^1$ is independently selected from the group consisting of: $C_{1-6}$ alkyl substituted with 0-2 $R^a$, $C_{2-6}$ alkenyl substituted with 0-2 $R^a$, and $-(CH_2)_n-W-R^{1a}$;

W is independently selected from the group consisting of: a bond, NH, $N(C_{1-4}$ alkyl), CO, CONH, $CON(C_{1-4}$ alkyl), $SO_2$, $NHCO_2$, and $CHR^f$;

$R^{1a}$ is independently selected from the group consisting of: $C_{3-6}$ cycloalkyl substituted with 0-3 $R^c$, phenyl substituted with 0-3 $R^b$, naphthyl substituted with 0-2 $R^b$, tetrahydronaphthyl substituted with 0-2 $R^b$, dihydroindenyl substituted with 0-2 $R^c$, and a 5- to 10-membered heterocycle comprising: carbon atoms and 1-4 heteroatoms selected from N, $NR^e$, O, and $S(O)_p$; and wherein said heterocycle is substituted with 0-3 $R^c$;

$R^2$ is independently selected from the group consisting of: H, halogen, $CF_3$, $OCF_3$, $C_{1-6}$ alkyl substituted with 0-2 $R^a$, $C_{2-6}$ alkenyl substituted with 0-2 $R^a$, $—CO_2(C_{1-4}$ alkyl), $—SO_2(phenyl)$, $—(CH_2)_n—(C_{3-6}$ cycloalkyl substituted with 0-3 $R^c$), $—(CH_2)_n$-(phenyl substituted with 0-3 $R^b$), $—(CH_2)_n$-(naphthyl substituted with 0-3 $R^b$), and $—(CH_2)_n$-(5- to 10 membered heterocycle comprising: carbon atoms and 1-4 heteroatoms selected from N, $NR^e$, O, and $S(O)_p$), wherein said heterocycle is substituted with 0-3 $R^c$;

$R^3$ is independently selected from the group consisting of: H, halogen, $CF_3$, $OCF_3$, $C_{1-6}$ alkyl substituted with 0-2 $R^a$, and phenyl substituted with 0-2 $R^b$;

$R^4$ is independently selected from the group consisting of: $C_{5-6}$ cycloalkyl, phenyl, naphthyl, tetrahydronaphthyl, dihydroindenyl, and a 5- to 10-membered heterocycle comprising: carbon atoms and 1-4 heteroatoms selected from N, $NR^e$, O, and $S(O)_p$; and wherein each moiety is substituted with 0-3 $R^d$;

$R^5$ is independently selected from the group consisting of: OH, $O(C_{1-4}$ alkyl substituted with 0-1 $CO_2H$), CN, and $NR^7R^8$; and L is independently a hydrocarbon or hydrocarbon-heteroatom linker optionally substituted with 0-1 $R^g$; wherein said hydrocarbon linker has one to six carbon atoms and may be straight or branched, saturated or unsaturated; and said hydrocarbon-heteroatom linker has one to five carbon atoms and one group selected from O, —CO—, S, —SO—, —$SO_2$—, NH, and $N(C_{1-4}$ alkyl);

provided that:
(i) when $R^1$ is methyl, $R^2$ and $R^3$ are H, $R^5$ is OH, and L is $—(CH_2)_3—$, then $R^4$ is other than unsubstituted phenyl;
(ii) when L is $CH_2$, then $R^4$ is other than halogen mono-substituted phenyl or methoxy bi-substituted phenyl; or
(iii) when $R^1$ is methyl, $R^2$ and $R^3$ are H, $R^5$ is OH, and L is $—(CH_2)_2—$, then $R^4$ is other than methoxy mono-substituted indolyl.

In a third aspect, the present invention includes a compound of Formula (I), or a stereoisomer, a tautomer, a pharmaceutically acceptable salt, or a solvate thereof, within the scope of the first or second aspect, wherein:

$R^1$ is independently selected from the group consisting of: $C_{1-6}$ alkyl substituted with 0-2 $R^a$, $C_{2-6}$ alkenyl substituted with 0-2 $R^a$, and $—(CH_2)_n—W—R^{1a}$;

W is independently selected from the group consisting of: a bond, CO, CONH, $CON(C_{1-4}$ alkyl), $SO_2$, and $CHR^f$;

$R^{1a}$ is independently selected from the group consisting of: $C_{3-6}$ cycloalkyl substituted with 0-3 $R^c$, phenyl substituted with 0-3 $R^b$, and a 5- to 6-membered heterocycle comprising: carbon atoms and 1-4 heteroatoms selected from N, $NR^e$, O, and $S(O)_p$; and wherein said heterocycle is substituted with 0-3 $R^c$;

$R^5$ is independently selected from the group consisting of: OH and $C_{1-6}$ alkoxy; and provided that:
(i) when $R^1$ is methyl, $R^2$ and $R^3$ are H, $R^5$ is OH, and L is $—(CH_2)_3—$, then $R^4$ is other than unsubstituted phenyl;
(ii) when L is $CH_2$, then $R^4$ is other than halogen mono-substituted phenyl or methoxy bi-substituted phenyl; or
(iii) when $R^1$ is methyl, $R^2$ and $R^3$ are H, $R^5$ is OH, and L is $—(CH_2)_2—$, then $R^4$ is other than methoxy mono-substituted indolyl.

In a fourth aspect, the present invention includes a compound of Formula (I), or a stereoisomer, a tautomer, a pharmaceutically acceptable salt, or a solvate thereof, within the scope of any of the above aspects, wherein:

$R^1$ is independently selected from the group consisting of: H, $C_{1-4}$ alkyl substituted with 0-1 $R^a$, $—CH_2CO_2(C_{1-4}$ alkyl), cyclopropyl, cyclopropylmethyl, phenyl, 4-$CF_3$-phenyl, 3-halo-4-$CO_2(C_{1-4}$ alkyl)-phenyl, 2-($C_{1-4}$ alkoxy)-5-halo-phenyl, benzyl, 2-halo-benzyl, 3-$CF_3$-benzyl, 4-$CO_2H$-benzyl, 4-$CO_2(C_{1-4}$ alkyl)-benzyl, 4-$SO_2(C_{1-4}$ alkyl)-benzyl, 2-halo-phenethyl, 4-halo-phenethyl, 2-OH-phenethyl, $—SO_2$(phenyl), and pyrid-4-yl;

$R^2$ is independently selected from the group consisting of: H, halogen, $CF_3$, $OCF_3$, $C_{1-4}$ alkyl, $C_{2-4}$ alkenyl, $—SO_2$(phenyl), phenyl substituted with 0-2 $R^b$, naphthyl substituted with 0-2 $R^b$, and a heterocycle selected from: thienyl, oxadiazolyl, pyridyl, indolyl, quinolinyl, and isoquinolinyl; wherein said heterocycle is substituted with 0-2 $R^c$;

$R^3$ is independently selected from the group consisting of: H, $C_{1-4}$ alkyl and phenyl substituted with 0-2 $R^b$;

$R^4$ is independently selected from the group consisting of: phenyl substituted with 0-3 $R^d$, naphthyl, tetrahydronaphthyl, pyrrolidinyl, morpholinyl,

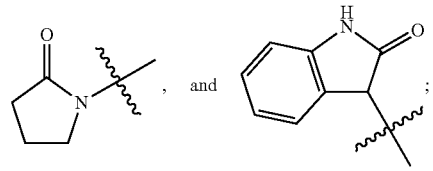 [SMILES: *N1CCCC1=O ; *C1C(=O)Nc2ccccc21]

L is independently selected from the group consisting of: $C_{1-6}$ alkylene, $C_{2-6}$ alkenylene, $—O—C_{2-5}$ alkylene-, $—S—C_{2-4}$ alkylene-, $—SO_2—C_{2-4}$ alkylene-, $—(CH_2)_{0-2}CH(C_{3-6}$ cycloalkyl)$(CH_2)_{0-2}—$, and $—(CH_2)_{0-2}CH(Ph)(CH_2)_{0-2}—$; wherein said alkylene and alkenylene may be straight or branched;

$R^a$ is, independently at each occurrence, selected from the group consisting of: halogen, OH, $C_{1-4}$ alkyl, $C_{1-4}$ alkoxy, $C_{1-4}$ haloalkyl, $CF_3$, $OCF_3$, $CO_2H$, and $CO_2(C_{1-4}$ alkyl);

$R^d$ is, independently at each occurrence, selected from the group consisting of: halogen, $C_{1-6}$ alkyl, $C_{1-4}$ alkoxy, $C_{1-4}$ haloalkyl, $CF_3$, $OCF_3$, $CO_2(C_{1-4}$ alkyl), and $NO_2$; and provided that:
(i) when $R^1$ is methyl, $R^2$ and $R^3$ are H, and L is $—(CH_2)_3—$, then $R^4$ is other than phenyl; or
(ii) when L is $CH_2$, then $R^4$ is other than phenyl halogen mono-substituted phenyl or methoxy bi-substituted phenyl.

In a fifth aspect, the present invention includes a compound of Formula (I), wherein $R^5$ is OH, further characterized by Formula (II):

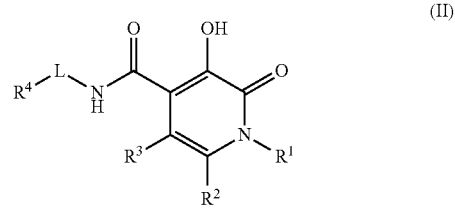

or a stereoisomer, a tautomer, a pharmaceutically acceptable salt, or a solvate thereof, within the scope of any of the above aspects wherein:

$R^1$ is independently selected from the group consisting of: H, $C_{1-4}$ alkyl substituted with 0-1 $CF_3$, —$CH_2CO_2(C_{1-4}$ alkyl), cyclopropyl, cyclopropylmethyl, phenyl, 4-$CF_3$-phenyl, 3-halo-4-$CO_2(C_{1-4}$ alkyl)-phenyl, benzyl, 2-halo-benzyl, 3-$CF_3$-benzyl, 4-$CO_2H$-benzyl, 4-$CO_2(C_{1-4}$ alkyl)-benzyl, 4-$SO_2(C_{1-4}$ alkyl)-benzyl, 2-halo-phenethyl, 4-halo-phenethyl, 2-OH-phenethyl, and pyrid-4-yl;

$R^2$ is independently selected from the group consisting of: H, halogen, $C_{1-4}$ alkyl, $C_{2-4}$ alkenyl, $CF_3$, phenyl, 3-halo-phenyl, 4-halo-phenyl, 3-$C_{1-4}$ alkyl-phenyl, 3-$CF_3$-phenyl, 4-$CF_3$-phenyl, 3-$OCF_3$-phenyl, 4-$OCF_3$-phenyl, 4-OH-phenyl, 4-CN-phenyl, 3-$NH_2$-phenyl, 3-$N(C_{1-4}$ alkyl)$_2$-phenyl, 3-$CO_2H$-phenyl, 3-$CONH_2$-phenyl, 4-$CONH_2$-phenyl, 3-$CON(C_{1-4}$ alkyl)$_2$-phenyl, 4-$CON(C_{1-4}$ alkyl)$_2$-phenyl, 3-$NHSO_2(C_{1-4}$ alkyl)-phenyl, 4-$NHSO_2(C_{1-4}$ alkyl)-phenyl, 3-$SO_2(C_{1-4}$ alkyl)-phenyl, 4-$SO_2(C_{1-4}$ alkyl)-phenyl, 3-$SO_2NH_2$-phenyl, 3-biphenyl, 4-biphenyl, 3-halo-4-halo-phenyl, 3-halo-5-halo-phenyl, 3-$C_{1-4}$ alkyl-4-halo-phenyl, 3-$CF_3$-5-halo-phenyl, 3-$CF_3$-4-halo-phenyl, 3-halo-4-$CF_3$-phenyl, 3-$CF_3$-4-OH-phenyl, 3,5-di$CF_3$-phenyl, 3-$OCF_2CHF_2$-5-halo-phenyl, 1-naphthyl, 2-naphthyl, thien-2-yl, thien-3-yl, 5-($C_{1-4}$ alkyl)-1,2,4-oxadiazol-3-yl, pyrid-4-yl, 1-$C_{1-4}$ alkyl-indol-5-yl, 3-quinolinyl, 5-quinolinyl, 6-quinolinyl, and 5-isoquinolinyl;

$R^3$ is independently selected from the group consisting of: H, $C_{1-4}$ alkyl, 3-halo-5-halo-phenyl, and 3-$CF_3$-5-halo-phenyl;

$R^4$ is independently selected from the group consisting of: phenyl, 2-($C_{1-4}$ alkyl)-phenyl, 3-($C_{1-4}$ alkyl)-phenyl, 4-($C_{1-4}$ alkyl)-phenyl, 2-($C_{1-4}$ alkoxy)-phenyl, 3-($C_{1-4}$ alkoxy)-phenyl, 4-($C_{1-4}$ alkoxy)-phenyl, 2-halo-phenyl, 3-halo-phenyl, 4-halo-phenyl, 2-$CF_3$-phenyl, 3-$CF_3$-phenyl, 4-$CF_3$-phenyl, 3-$OCF_3$-phenyl, 4-$OCF_3$-phenyl, 3-$CO_2(C_{1-4}$ alkyl)-phenyl, 4-$CO_2(C_{1-4}$ alkyl)-phenyl, 2-$NO_2$-phenyl, 3-$NO_2$-phenyl, 4-$NO_2$-phenyl, 2-halo-4-halo-phenyl, 3-halo-4-halo-phenyl, 3-halo-5-halo-phenyl, 2-halo-6-halo-phenyl, 1-naphthyl, 2-naphthyl, and

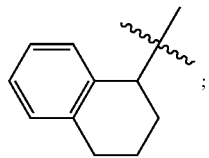 [SMILES: *C1CCCc2ccccc21]

and

L is independently selected from the group consisting of: $C_{1-6}$ alkylene, $C_{2-6}$ alkenylene, —O—$C_{2-5}$ alkylene-, —S—$C_{2-4}$ alkylene-, and —$(CH_2)_2CH(Ph)$—; wherein said alkylene and alkenylene may be straight or branched;

provided that when $R^1$ is methyl, $R^2$ is H, and L is —$(CH_2)_3$—, then $R^4$ is other than phenyl.

In a sixth aspect, the present invention includes a compound of Formula (II), or a stereoisomer, a tautomer, a pharmaceutically acceptable salt, or a solvate thereof, within the scope of any of the above aspects wherein:

$R^1$ is independently selected from the group consisting of: H, methyl, ethyl, isopropyl, isobutyl, $CH_2CF_3$, $CH_2CH_2CF_3$, —$CH_2CO_2Et$, cyclopropyl, cyclopropylmethyl, phenyl, 4-$CF_3$-phenyl, 3-F-4-$CO_2Me$-phenyl, benzyl, 2-F-benzyl, 3-$CF_3$-benzyl, 4-$CO_2H$-benzyl, 4-$CO_2Me$-benzyl, 4-$SO_2Me$-benzyl, 2-F-phenethyl, 4-F-phenethyl, 2-OH-phenethyl, and pyrid-4-yl;

$R^2$ is independently selected from the group consisting of: H, Br, ethyl, isopropyl, ethenyl, $CF_3$, phenyl, 3-F-phenyl, 4-F-phenyl, 3-Cl-phenyl, 4-Cl-phenyl, 3-Et-phenyl, 3-(i-Pr)-phenyl, 3-$CF_3$-phenyl, 4-$CF_3$-phenyl, 3-$OCF_3$-phenyl, 4-$OCF_3$-phenyl, 4-OH-phenyl, 4-CN-phenyl, 3-$NH_2$-phenyl, 3-$N(Me)_2$-phenyl, 3-$CO_2H$-phenyl, 3-$CONH_2$-phenyl, 4-$CONH_2$-phenyl, 3-$CON(Me)_2$-phenyl, 4-$CON(Me)_2$-phenyl, 3-$NHSO_2Me$-phenyl, 4-$NHSO_2Me$-phenyl, 3-$SO_2Me$-phenyl, 4-$SO_2Me$-phenyl, 3-$SO_2NH_2$-phenyl, 3-biphenyl, 4-biphenyl, 3,4-diF-phenyl, 3,5-diF-phenyl, 3-$CH_3$-4-F-phenyl, 3-$CF_3$-5-F-phenyl, 3-$CF_3$-4-Cl-phenyl, 3-Cl-4-$CF_3$-phenyl, 3-$CF_3$-4-OH-phenyl, 3,5-di$CF_3$-phenyl, 3-$OCF_2CHF_2$-5-F-phenyl, 1-naphthyl, 2-naphthyl, thien-2-yl, thien-3-yl, 5-Me-1,2,4-oxadiazol-3-yl, pyrid-4-yl, 1-Me-indol-5-yl, 3-quinolinyl, 5-quinolinyl, 6-quinolinyl, and 5-isoquinolinyl;

$R^3$ is independently selected from the group consisting of: H, methyl, 3-F-5-F-phenyl, and 3-$CF_3$-5-F-phenyl;

$R^4$ is independently selected from the group consisting of: phenyl, 2-Me-phenyl, 3-Me-phenyl, 4-Me-phenyl, 2-OMe-phenyl, 3-OMe-phenyl, 4-OMe-phenyl, 2-F-phenyl, 3-F-phenyl, 4-F-phenyl, 2-Cl-phenyl, 3-Cl-phenyl, 4-Cl-phenyl, 2-$CF_3$-phenyl, 3-$CF_3$-phenyl, 4-$CF_3$-phenyl, 3-$OCF_3$-phenyl, 4-$OCF_3$-phenyl, 3-$CO_2Me$-phenyl, 4-$CO_2Me$-phenyl, 2-$NO_2$-phenyl, 3-$NO_2$-phenyl, 4-$NO_2$-phenyl, 3,5-diF-phenyl, 2,4-diCl-phenyl, 3,4-diCl-phenyl, 2,6-diCl-phenyl, 1-naphthyl, 2-naphthyl, and

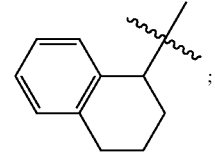 [SMILES: *C1CCCc2ccccc21]

and

L is independently selected from the group consisting of: $CH_2$, —$CH(CH_3)$—, —$(CH_2)_2$—, —$(CH_2)_3$—, —$(CH_2)_4$—, —$(CH_2)_2CH(CH_3)$—, —$(CH_2)_3CH(CH_3)$—, —$(CH_2)_2CH(Et)$-, —$(CH_2)_2$—CH(CH=$CH_2$)—, —$(CH_2)_2CH(Ph)$—, —$O(CH_2)_2$—, —$O(CH_2)_3$—, —$O(CH_2)_4$—, —$O(CH_2)_2CH(CH_3)$—, and —$S(CH_2)_3$—;

provided that when $R^1$ is methyl, $R^2$ is H, and L is —$(CH_2)_3$—, then $R^4$ is other than phenyl.

In a seventh aspect, the present invention includes a compound of Formula (II), or a stereoisomer, a tautomer, a pharmaceutically acceptable salt, or a solvate thereof, within the scope of any of the above aspects wherein:

$R^1$ is independently selected from the group consisting of: H, methyl, ethyl, isopropyl, isobutyl, $CH_2CF_3$, —$CH_2CO_2Et$, cyclopropyl, cyclopropylmethyl, phenyl, 4-$CF_3$-phenyl, 3-F-4-$CO_2Me$-phenyl, benzyl, 2-F-benzyl, 4-$CO_2H$-benzyl, 4-$CO_2Me$-benzyl, 4-$SO_2Me$-benzyl, 4-F-phenethyl, 2-OH-phenethyl, and pyrid-4-yl;

$R^2$ is independently selected from the group consisting of: H, Br, ethyl, isopropyl, ethenyl, $CF_3$, phenyl, 3-F-phenyl, 4-F-phenyl, 4-Cl-phenyl, 3-Et-phenyl, 3-(i-Pr)-phenyl, 3-$CF_3$-phenyl, 4-$CF_3$-phenyl, 3-$OCF_3$-phenyl, 4-$OCF_3$-phenyl, 4-OH-phenyl, 4-CN-phenyl, 3-$NH_2$-phenyl, 3-$N(Me)$-2-phenyl, 4-$CONH_2$-phenyl, 3-$CON(Me)$-2-phenyl, 4-$CON(Me)$-2-phenyl, 3-$NHSO_2Me$-phenyl, 4-$SO_2Me$-phenyl, 3-$SO_2NH_2$-phenyl, 3-biphenyl, 4-biphenyl, 3,4-diF-phenyl, 3,5-diF-phenyl, 3-$CH_3$-4-F-phenyl, 3-$CF_3$-5-F-phenyl, 3-CF₃-4-Cl-phenyl, 3-Cl-4-CF₃-phenyl, 3-CF₃-4-OH-phenyl, 3,5-diCF₃-phenyl, 3-OCF₂CHF₂-5-F-phenyl, 1-naphthyl, thien-2-yl, thien-3-yl, pyrid-4-yl, 1-Me-indol-5-yl, 3-quinolinyl, 5-quinolinyl, 6-quinolinyl, and 5-isoquinolinyl;

R³ is independently selected from the group consisting of: H, methyl, 3-F-5-F-phenyl, and 3-CF₃-5-F-phenyl;

R⁴ is independently selected from the group consisting of: phenyl, 2-Me-phenyl, 3-Me-phenyl, 4-Me-phenyl, 3-OMe-phenyl, 2-F-phenyl, 3-F-phenyl, 4-F-phenyl, 2-Cl-phenyl, 3-Cl-phenyl, 4-Cl-phenyl, 2-CF₃-phenyl, 3-CF₃-phenyl, 4-CF₃-phenyl, 3-OCF₃-phenyl, 3-CO₂Me-phenyl, 4-CO₂Me-phenyl, 2-NO₂-phenyl, 3-NO₂-phenyl, 3,5-diF-phenyl, 2,4-diCl-phenyl, 3,4-diCl-phenyl, 2,6-diCl-phenyl, 1-naphthyl, 2-naphthyl, and

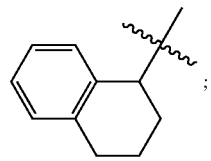 [SMILES: *C1CCCc2ccccc21]

and

L is independently selected from the group consisting of: CH₂, —CH(CH₃)—, —(CH₂)₂—, —(CH₂)₃—, —(CH₂)₄—, —(CH₂)₂CH(CH₃)—, —(CH₂)₂—CH(CH=CH₂)—, —O(CH₂)₃—, —O(CH₂)₄—, —O(CH₂)₂CH(CH₃)—, and —S(CH₂)₃—;

provided that when R¹ is methyl, R² is H, and L is —(CH₂)₃—, then R⁴ is other than phenyl.

In an eighth aspect, the present invention includes a compound of Formula (II), or a stereoisomer, a tautomer, a pharmaceutically acceptable salt, or a solvate thereof, within the scope of any of the above aspects wherein:

R¹ is independently selected from the group consisting of: methyl, ethyl, isopropyl, isobutyl, CH₂CF₃, cyclopropyl, cyclopropylmethyl, phenyl, 4-CF₃-phenyl, 3-F-4-CO₂Me-phenyl, benzyl, 2-F-benzyl, 4-CO₂Me-benzyl, 4-SO₂Me-benzyl, 4-F-phenethyl, and pyrid-4-yl;

R² is independently selected from the group consisting of: H, Br, ethyl, isopropyl, ethenyl, CF₃, phenyl, 3-F-phenyl, 4-F-phenyl, 3-Et-phenyl, 3-(i-Pr)-phenyl, 3-CF₃-phenyl, 4-CF₃-phenyl, 3-OCF₃-phenyl, 4-OCF₃-phenyl, 4-OH-phenyl, 4-CN-phenyl, 3-CON(Me)-2-phenyl, 3-biphenyl, 4-biphenyl, 3,4-diF-phenyl, 3,5-diF-phenyl, 3-CF₃-5-F-phenyl, 3-CF₃-4-Cl-phenyl, 3-Cl-4-CF₃-phenyl, 3-CF₃-4-OH-phenyl, 3,5-diCF₃-phenyl, 3-OCF₂CHF₂-5-F-phenyl, 1-naphthyl, thien-2-yl, thien-3-yl, 3-quinolinyl, and 6-quinolinyl;

R³ is independently selected from the group consisting of: H, methyl, 3-F-5-F-phenyl, and 3-CF₃-5-F-phenyl;

R⁴ is independently selected from the group consisting of: phenyl, 2-Me-phenyl, 3-Me-phenyl, 4-Me-phenyl, 3-OMe-phenyl, 2-F-phenyl, 3-F-phenyl, 4-F-phenyl, 2-Cl-phenyl, 3-Cl-phenyl, 4-Cl-phenyl, 2-CF₃-phenyl, 3-CF₃-phenyl, 4-CF₃-phenyl, 3-CO₂Me-phenyl, 4-CO₂Me-phenyl, 2-NO₂-phenyl, 3-NO₂-phenyl, 3,4-diCl-phenyl, 2,6-diCl-phenyl, 1-naphthyl, and 2-naphthyl; and L is independently selected from the group consisting of: —(CH₂)₂—, —(CH₂)₃—, —(CH₂)₄—, —(CH₂)₂CH(CH₃)—, —O(CH₂)₃—, —O(CH₂)₄—, —O(CH₂)₂CH(CH₃)—, and —S(CH₂)₃—;

provided that when R¹ is methyl, R² is H, and L is —(CH₂)₃—, then R⁴ is other than phenyl.

In a ninth aspect, the present invention includes a compound of Formula (III):

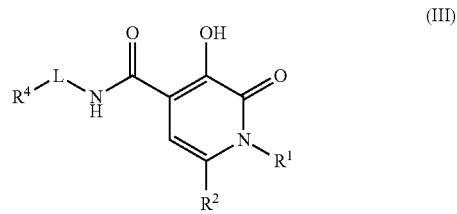

or a stereoisomer, a tautomer, a pharmaceutically acceptable salt, or a solvate thereof, within the scope of any of the above aspects.

In a tenth aspect, the present invention provides a compound selected from the exemplified examples or a stereoisomer, a tautomer, a pharmaceutically acceptable salt, or a solvate thereof.

In another aspect, the present invention provides a compound selected from any subset list of the exemplified examples or any one of the exemplified examples or a stereoisomer, a tautomer, a pharmaceutically acceptable salt, or a solvate thereof, within the scope of the tenth aspect.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising additional therapeutic agent(s).

In another embodiment, the present invention provides a method for the treatment and/or prophylaxis of dyslipidemias and the sequelae thereof comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of endothelial lipase that can be prevented, modulated, or treated according to the present invention include, but are not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

In one embodiment, the present invention provides a method for the treatment and/or prophylaxis of atherosclerosis, coronary heart disease, cerebrovascular disorders and dyslipidemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of dyslipidemias and the sequelae thereof.

In another embodiment, the present invention also provides the use of a compound of the present invention for the manufacture of a medicament for the treatment and/or prophylaxis of dyslipidemias and the sequelae thereof.

In another embodiment, the present invention provides a method for the treatment and/or prophylaxis of dyslipidemias and the sequelae thereof, comprising: administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of dyslipidemias and the sequelae thereof.

The compounds of the present invention may be employed in combination with additional therapeutic agent(s) selected from one or more, preferably one to three, of the following therapeutic agents: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acytransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

In another embodiment, additional therapeutic agent(s) used in combined pharmaceutical compositions or combined methods or combined uses, are selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyll" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle," "carbocyclyl," or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2] bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, J. Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl," "$C_{6-10}$ aryl," or "aromatic residue" may be unsubstituted or substituted with 1 to 5 groups, preferably 1 to 3 groups, selected from —OH, —OCH$_3$, —Cl, —F, —Br, —I, —CN, —NO$_2$, —NH$_2$, —N(CH$_3$)H, —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

The term "benzyl," as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

As a person of ordinary skill in the art would be able to understand, a ketone (—CH—C—O) group in a molecule may tautomerize to its enol form (—C=C—OH), as shown in the following equation:

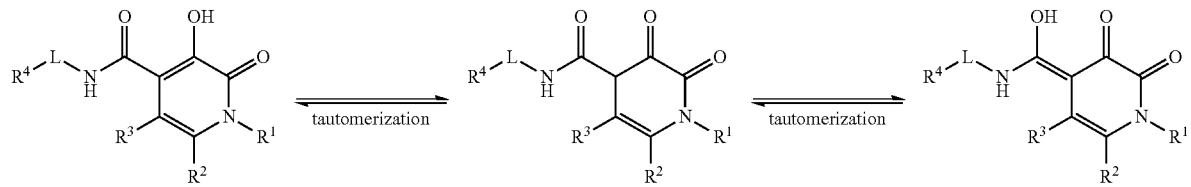

Likewise, an imine (—CH—C=NHR) group in a molecule may tautomerize to its enamine form (—C=C—NHR), as shown in the following equation:

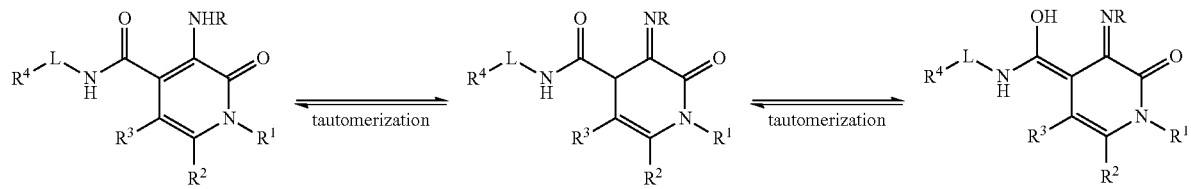

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of Formula (I), Formula (II), Formula (III), or Formula (IV) may have prodrug forms. Any compound that will be converted in vivo to provide the bioactive agent (i.e., a compound of Formula (I), Formula (II), Formula (III), or Formula (IV)) is a prodrug within the scope and spirit of the invention. Various forms of prodrugs are well known in the art. For examples of such prodrug derivatives, see:

a) Design of Prodrugs, Bundgaard, H., ed., Elsevier (1985), and *Methods in Enzymology*, 112:309-396, Widder, K. et al., eds., Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield Formula (I), Formula (II), Formula (III), or Formula (IV) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I), Formula (II), Formula (III), or Formula (IV) include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyloxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "nL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mw" for microwave, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc tert-butyloxycarbonyl
AcOH or HOAc acetic acid
$AlCl_3$ aluminum chloride
$BBr_3$ boron tribromide
$BCl_3$ boron trichloride
BOP reagent benzotriazol-1-yloxytris(dimethylamino)phosphonium hexafluorophosphate
Cbz carbobenzyloxy
$CH_2Cl_2$ dichloromethane
$CH_3CN$ or ACN acetonitrile
$CDCl_3$ deutero-chloroform
$CDCl_3$ chloroform
mCPBA or m-CPBA meta-chloroperbenzoic acid
$Cs_2CO_3$ cesium carbonate
$Cu(OAc)_2$ copper (II) acetate
DCE 1,2 dichloroethane
DCM dichloromethane
DEA diethylamine DIC or DIPCDI diisopropylcarbodiimide
DIEA, DIPEA or diisopropylethylamine Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
EDC N-(3-dimthylaminopropyl)-N'-ethylcarbodiimide
EDTA ethylenediaminetetraacetic acid
$Et_3N$ or TEA triethylamine
EtOAc ethyl acetate
$Et_2O$ diethyl ether
EtOH ethanol
HCl hydrochloric acid
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group
LiOH lithium hydroxide
MeOH methanol
$MgSO_4$ magnesium sulfate
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
$NH_3$ ammonia
$NH_4Cl$ ammonium chloride
$NH_4OH$ ammonium hydroxide
NIS N-iodosuccinimide
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
PS-Pd(Ph$_3$)$_4$ tetrakis(triphenylphosphine)palladium (0) on polystyrene support
i-PrOH or IPA isopropanol
PS polystyrene
PyBOP (benzotriazol-1-yloxy)tripyrrolidinophosphonium hexafluorophosphate
$SiO_2$ silica oxide
$SnCl_2$ tin(II) chloride
TBAF tetra-n-butylammonium fluoride
TBAI tetra-n-butylammonium iodide
TEA triethylamine
TFA trifluoroacetic acid
THF tetrahydrofuran
$TMSCHN_2$ trimethylsilyldiazomethane Synthesis The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., *Comprehensive Organic Transformations*, VCH, New York (1989). Preferred methods include, but are not limited to, those described below. All references cited herein are hereby incorporated in their entirety herein by reference.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups In Organic Synthesis*, Wiley and Sons (1991)).

Compounds of the present invention may be prepared by procedures illustrated in the accompanying schemes.

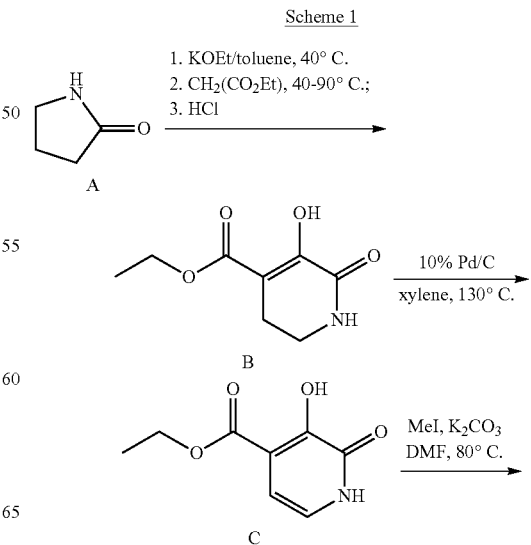

Scheme 1

-continued

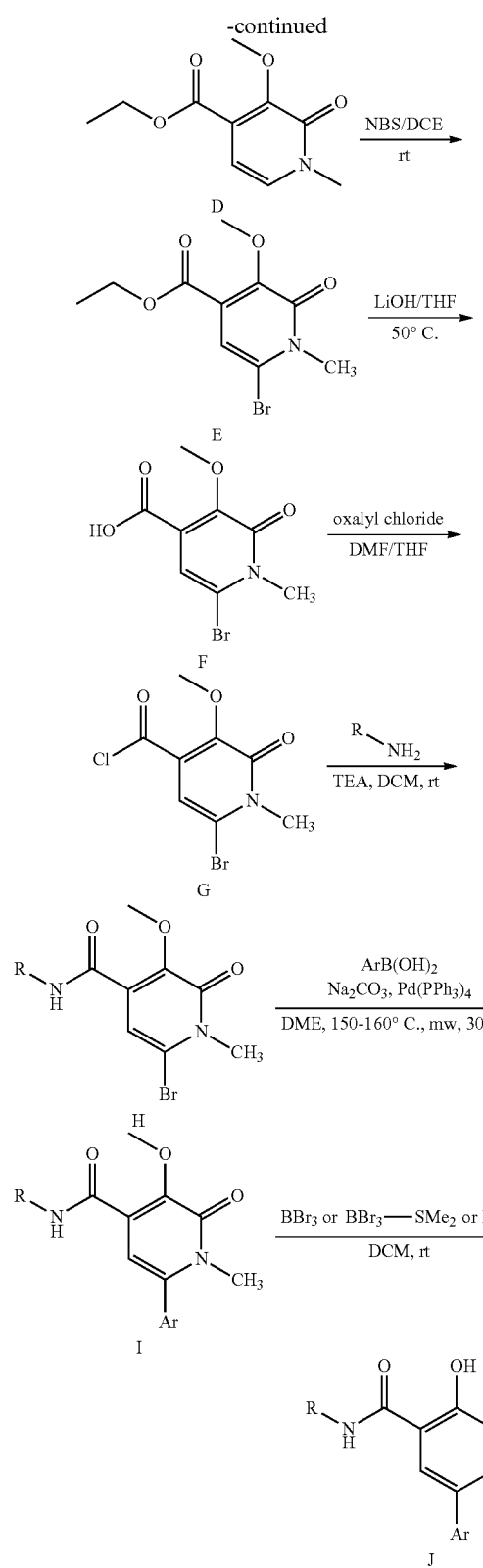

as 10% Pd/C in an inert solvent such as xylene. The hydroxyl-pyridinedione (C) can be converted to the corresponding dimethylpyridinedione derivative (D) by reacting with a methylation reagent such as methyl iodide in the presence of a base such as potassium carbonate. The pyridinedione derivative (D) can be treated with a brominating agent such as NBS in a solvent such as THF to provide the C6 bromide (E). The resulting ester (E) can be hydrolyzed using an aqueous hydroxide base such as lithium hydroxide or sodium hydroxide with a co-solvent such as THF to give the pyridinedione carboxylic acid (F). The carboxylic acid (F) can be converted to the acid chloride (G) by the treatment with oxalyl chloride in the presence of a catalytic amount of DMF in a solvent such as THF. The acid chloride (G) can be converted to the amide (H) by the treatment with an amine in the presence of a base such as TEA in a solvent such as DCM. The resulting pyridinedione bromide (H) can be converted to the corresponding aryl pyridinedione (I) by reacting with a boronic acid in the presence of tetrakis(triphenylphosphine)palladium and sodium carbonate in an organic solvent such as DME. The methoxy group on the amide (I) could be cleaved using boron tribromide-methyl sulfide complex, boron tribromide solution in dichloromethane or boron trichloride to provide the pyridinedione (J).

Scheme 2

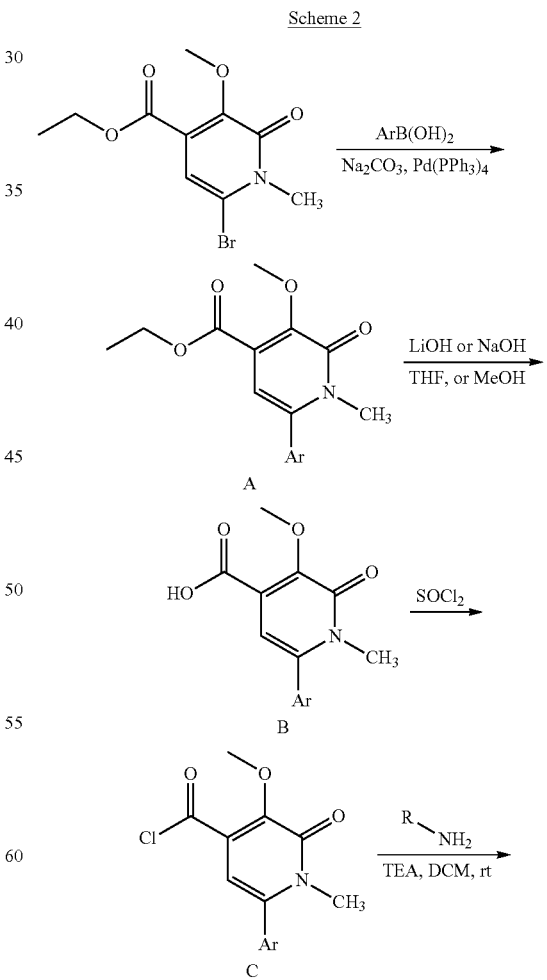

Pyrrolidinone (A) was treated with a base such as potassium ethoxide and subsequent reaction with diethoxy oxalate followed by decarboxylation of the resulting product gave the hydroxyl-tetrahydropyridinedione (B). The hydroxyl-tetrahydrapyridinedione (B) was transformed to the hydroxyl-pyridinedione (C) by the treatment with a reducing agent such The pyridinedione bromide (Compound E, Scheme 1) can be converted to the corresponding C6 aryl pyridinedione (A) by the treatment with a boronic acid in the presence of a palladium catalyst such as trakis(triphenylphosphine)palladium and a base such as sodium carbonate in an organic solvent such as DME. The ester (A) can be hydrolyzed to the corresponding carboxylic acid (B) using methods known in the art of organic synthesis such as treatment with aqueous sodium hydroxide or lithium hydroxide. The carboxylic acid (B) can be converted to the acid chloride (C) by the treatment with thionyl chloride. Treatment of the resulting acid chloride (C) with an amine in the presence of a base such as TEA provided the corresponding amide (D). The methoxy group on amide (D) could be cleaved using boron tribromide-methyl sulfide complex, boron tribromide solution in dichloromethane or boron trichloride to provide the pyridinedione (E).

The pyridinedione ester (Compound D, Scheme 1) can be treated with NIS in DMF to provide the C6 iodide (A). The resulting iodide (A) was converted to trifluoromethyl pyridinedione (B) by the treatment with methyl 2,2-difluoro-2-(fluorosulfonyl)acetate in the presence of copper (I) iodide in a solvent such as DMF. The ester (B) can be hydrolyzed using an aqueous hydroxide base such as lithium hydroxide or sodium hydroxide with a co-solvent such as THF or methanol to provide the acid (C). The acid (C) can be coupled to an amine using standard peptide coupling conditions such as PyBOP/DIPEA or EDC/HOBT/DIPEA in a solvent such as dichloromethane or THF to produce the amide (D). The methoxy group on amide (D) could be cleaved using boron tribromide-methyl sulfide complex, boron tribromide solution in dichloromethane or boron trichloride to provide the pyridinedione (E).

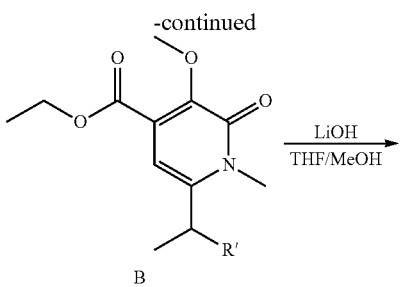

B

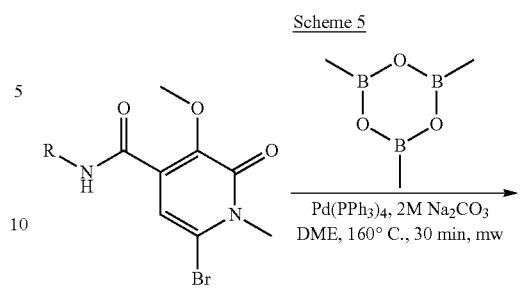

Scheme 5

The conversion from C6 bromide (Compound H, Scheme 1) to C6 methyl pyridinedione (A) can be achieved by coupling with trimethoxyboroxine in the presence of tetrakis(triphenylphosphine)palladium and sodium carbonate in an organic solvent such as DME. The methoxy group on amide (A) could be cleaved using boron tribromide-methyl sulfide complex, boron tribromide solution in dichloromethane or boron trichloride to provide the pyridinedione (B).

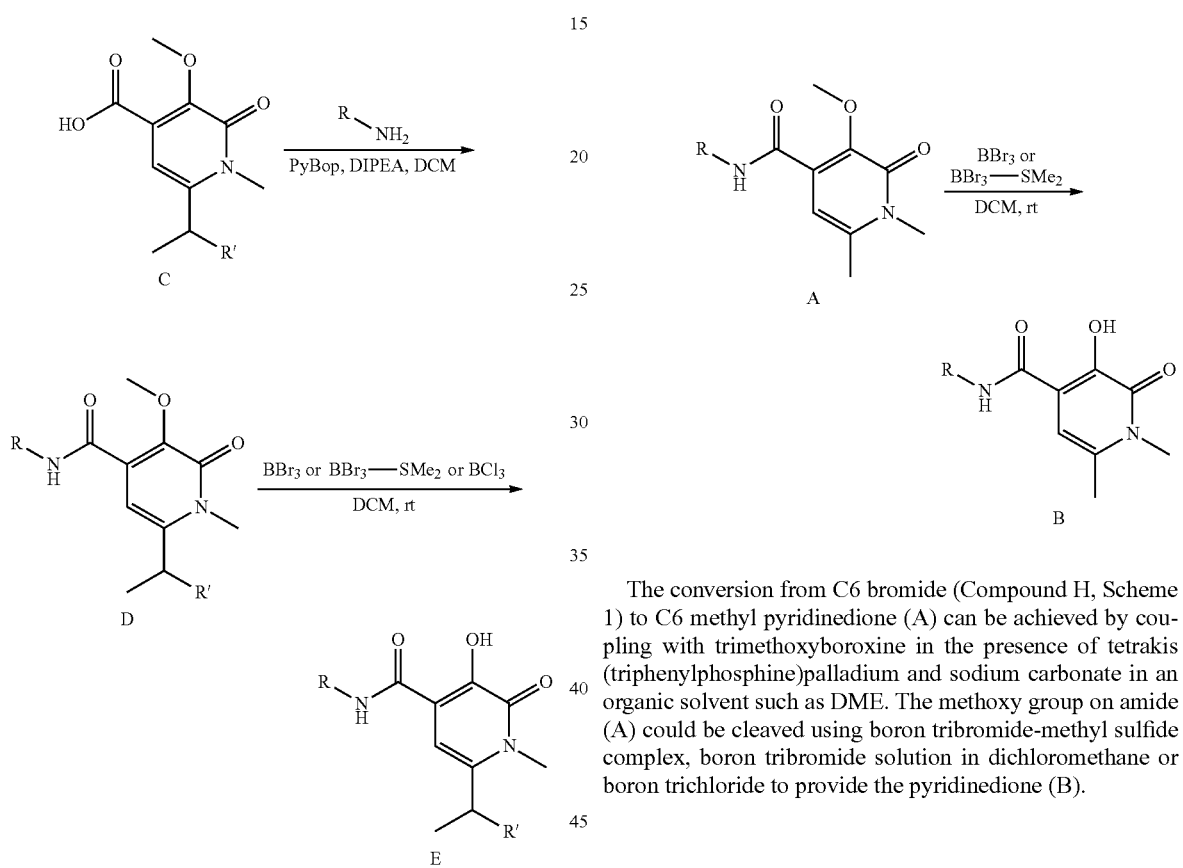

The pyridinedione C6 bromide (Compound E, Scheme 1) can be converted to the corresponding vinyl pyridinedione derivative (A) by reacting with a vinyl tributyltin in the presence of dichlorobis(triphenylphosphine)palladium (II) in an inert solvent such as toluene. The resulting vinyl pyridinedione (A) can be reduced to the alkyl pyridinedione (B) by catalytic hydrogenation with palladium on carbon as the catalyst and MeOH as the solvent. The ester (B) can be hydrolyzed to the corresponding carboxylic acid (C) using methods known in the art of organic synthesis such as treatment with aqueous sodium hydroxide or lithium hydroxide. The acid (C) can be coupled to an amine using standard peptide coupling conditions such as PyBOP/DIPEA or EDC/HOBT/DIPEA in a solvent such as dichloromethane or THF to produce the amide (D). The methoxy group on amide (D) could be cleaved using boron tribromide-methyl sulfide complex, boron tribromide solution in dichloromethane or boron trichloride to provide the pyridinedione (E).

Scheme 6

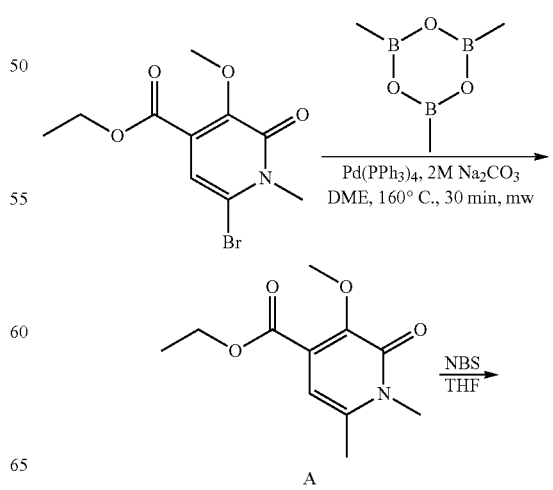

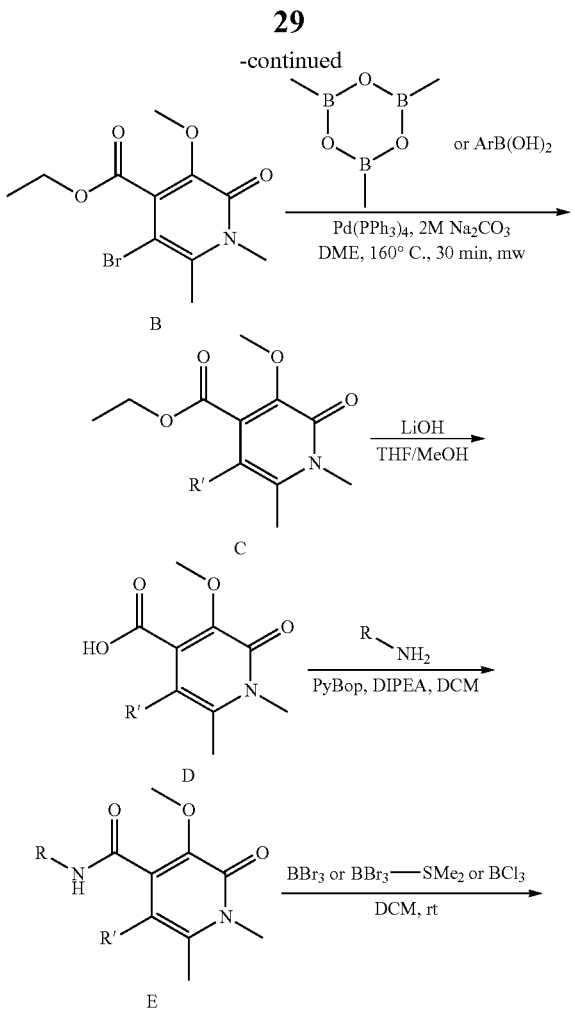

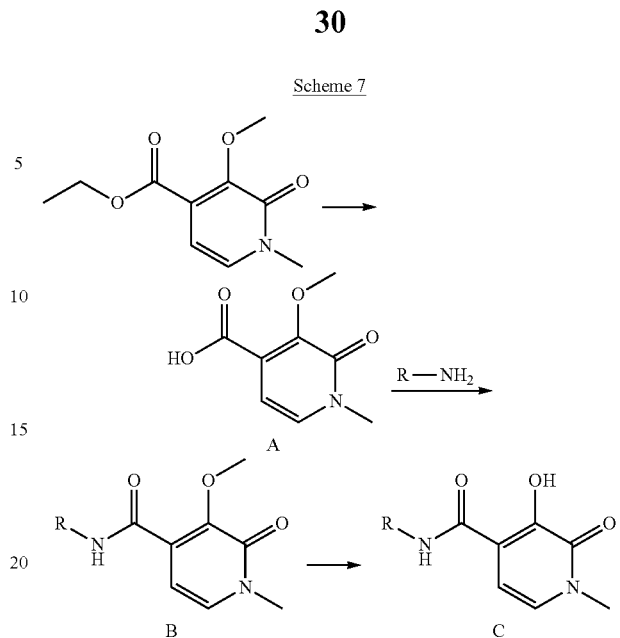

Scheme 7

The pyridinedione ester (Compound D, Scheme 1) could be hydrolyzed using an aqueous hydroxide base such as lithium hydroxide or sodium hydroxide with a co-solvent such as THF or methanol to provide the acid (A). The acid (A) can be coupled to an amine using standard peptide coupling conditions such as PyBOP/DIPEA or EDC/HOBT/DIPEA in a solvent such as dichloromethane or THF to produce the amide (B). The methoxy group on amide (B) could be cleaved using boron tribromide-methyl sulfide complex, boron tribromide solution in dichloromethane or boron trichloride to provide the pyridinedione (C).

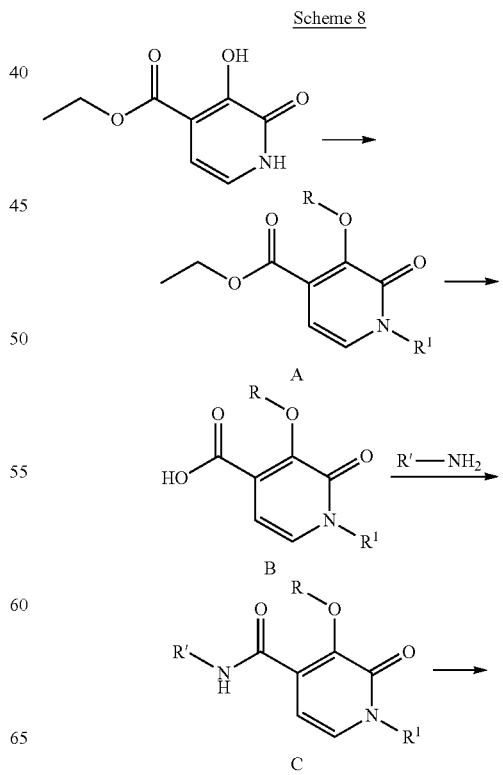

Scheme 8

The conversion of C6 bromide (Compound E, Scheme 1) to C6 methyl pyridinedione (A) can be achieved by cross coupling with trimethoxyboroxine in the presence of tetrakis(triphenylphosphine)palladium and sodium carbonate in DME. The resulting methyl pyridinedione (A) can be converted to bromide (B) by treatment with NBS in an organic solvent such as THF. The bromide (B) can react with trimethoxyboroxine or aryl boronic acids in the presence of tetrakis(triphenylphosphine)palladium and sodium carbonate in DME to afford dimethylpyridinedione ester (C). The resulting ester (C) can be hydrolyzed to the corresponding carboxylic acid (D) using methods known in the art of organic synthesis such as treatment with aqueous sodium hydroxide or lithium hydroxide. The acid (D) can be coupled to an amine using standard peptide coupling conditions such as PyBOP/DIPEA or EDC/HOBT/DIPEA in a solvent such as dichloromethane or THF to produce the amide (E). The methoxy group on amide (E) could be cleaved using boron tribromide-methyl sulfide complex, boron tribromide solution in dichloromethane or boron trichloride to provide the pyridinedione (F).

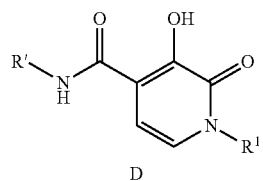

D

The pyridinedione (Compound C, Scheme 1) can be bis-alkylated with an alkyl halide such as ethyl iodide or methyl iodide or benzyl bromide using a base such as potassium carbonate or cesium carbonate in an inert solvent like THF or DMF to provide ester (A). The ester (A) can be hydrolyzed using an aqueous hydroxide base such as lithium hydroxide or sodium hydroxide with a co-solvent such as THF or methanol to provide the acid (B). The acid (B) can be coupled to an amine using standard peptide coupling conditions such as PyBOP/DIPEA or EDC/HOBT/DIPEA in a solvent such as dichloromethane or THF to produce the amide (C). The alkoxy group on amide (C) could be cleaved using boron tribromide-methyl sulfide complex, boron tribromide solution in dichloromethane or boron trichloride to provide the pyridinedione (D).

Scheme 9

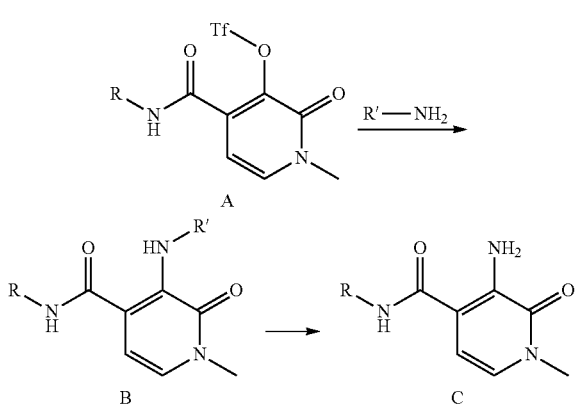

Pyridinedione (Compound D where R=Me, Scheme 9) can be converted to the corresponding triflate (A) with trifluorosulfonic anhydride in and an organic base such as pyridine or triethylamine in a solvent such as dichloromethane or THF. The triflate (A) can displaced with an amine in an inert solvent like dioxane or THF with heating to yield the C3 aminopyridinedione (B). If the amine used in this reaction contained a cleavable group such as 4-methoxybenzylamine, the 4-methoxybenzyl group may be removed using a strong acid such as trifluoroacetic acid to provide the primary aminopyridinedione (C).

Scheme 10

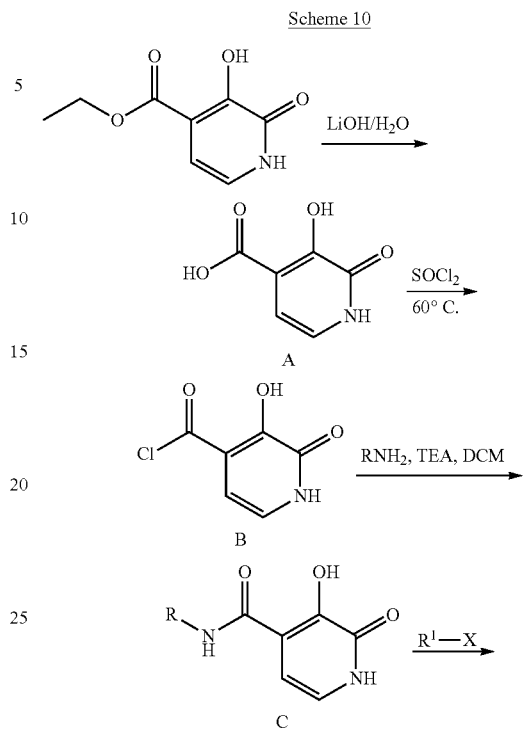

The pyridinedione ester (Compound C, Scheme 1) can be hydrolyzed using an aqueous hydroxide base such as lithium hydroxide or sodium hydroxide with a co-solvent such as water to give the pyridinedione carboxylic acid (A). The carboxylic acid (A) can be converted to the acid chloride (B) by the treatment with thionyl chloride. The acid chloride (B) can be converted to the amide (C) by the treatment with an amine in the presence of a base such as TEA in a solvent such as DCM. The resulting amide (C) can be mono alkylated with 1 equivalent of alkyl halide using a base such as potassium carbonate or cesium carbonate in an inert solvent like THF or DMF to provide compound (D).

Scheme 11

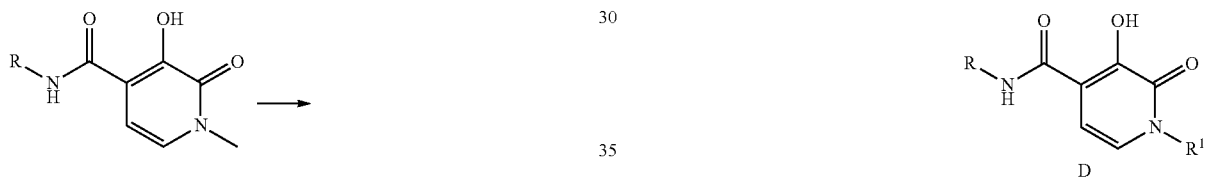

-continued

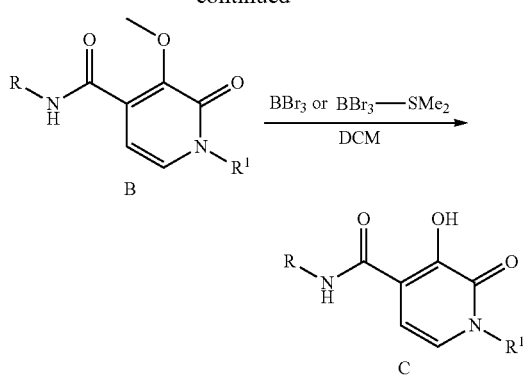

The pyridinedione amide (Compound C, Scheme 10) can mono alkylated with an alkylating agent such as TMS-diazomethane in an solvent such as DCM to give the methoxy pyridinedione (A). The methoxy pyridinedione (A) be coupled with and organoboronic acid using copper (I) acetate in an inert solvent like THF or dichloromethane to provide compound (B). The methoxy group on compound (B) could be cleaved using boron trichloride-methyl sulfide complex, boron tribromide solution in dichloromethane or boron trichloride to provide the pyridinedione (C).

Scheme 12

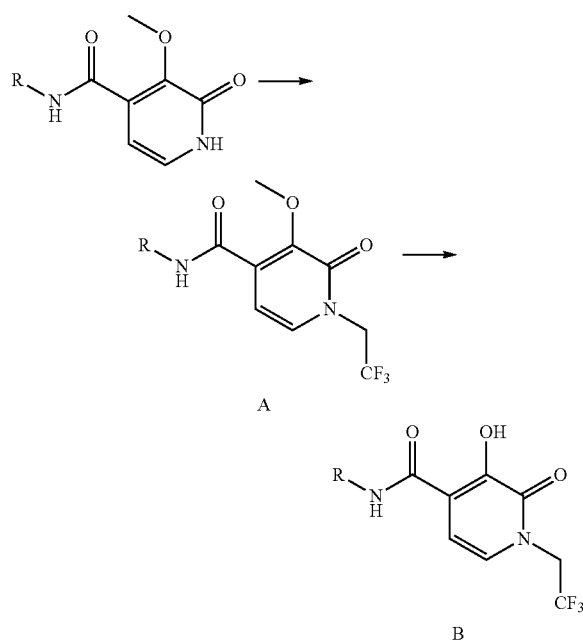

Pyridinedione (Compound A, Scheme 11) can be treated with 2,2,2-Trifluoroethyl trichloromethanesulfonate using a base such as cesium carbonate or potassium carbonate in an inert solvent such as dichloromethane or THF to provide the N1 trifluoroethyl compound (A). The methoxy group on the N1 trifluoroethyl compound (A) can be cleaved using boron trichloride-methyl sulfide complex, boron tribromide solution in dichloromethane or boron trichloride to provide the pyridinedione (B).

General Methods

The following methods were used in the exemplified Examples, except where noted otherwise.

Analytical HPLC and LC/MS Methods Employed in Characterization of Examples

Reverse phase analytical HPLC/MS was performed on Shimadzu LC10AS systems coupled with Waters ZMD Mass Spectrometers (Methods A-C, E and F) or Waters Aquity system coupled with a Waters Micromass ZQ Mass Spectrometer (Method D). Chiral analytical LC was performed on a Berger Analytical SFC instrument (Method G).

Method A: Linear gradient of 0 to 100% B over 4 min, with 1 min hold at 100% B;
UV visualization at 220 nm
Column: Phenomenex Luna C18 4.6×50 mm
Flow rate: 4 mL/min
Solvent A: 0.1% trifluoroacetic acid, 90% water, 10% acetonitrile
Solvent B: 0.1% trifluoroacetic acid, 90% acetonitrile, 10% water.

Method B: Linear gradient of 0 to 100% B over 4 min, with 1 min hold at 100% B;
UV visualization at 220 nm
Column: Phenomenex Luna C18 4.6×50 mm
Flow rate: 4 mL/min
Solvent A: 10 mM ammonium acetate, 90% water, 10% acetonitrile
Solvent B: 10 mM ammonium acetate, 90% acetonitrile, 10% water.

Method C: Linear gradient of 0 to 100% B over 4 min, with 1 min hold at 100% B;
UV visualization at 220 nm
Column: Phenomenex Luna C18 4.6×50 mm
Flow rate: 4 mL/min
Solvent A: 0.1% trifluoroacetic acid, 90% water, 10% methanol
Solvent B: 0.1% trifluoroacetic acid, 90% methanol, 10% water.

Method D: Linear gradient of 0 to 100% B over 2 min, with 1 min hold at 100% B;
UV visualization at 220 nm
Column: Phenomenex Luna C18 2.0×30 mm
Flow rate: 1 mL/min
Solvent A: 0.1% trifluoroacetic acid, 90% water, 10% methanol
Solvent B: 0.1% trifluoroacetic acid, 90% methanol, 10% water.

Method E: Linear gradient of 2 to 98% B over 1 min, with 0.5 min hold time at 98% B;
UV visualization at 220 nm
Column: Waters BEH C18 2.1×50 mm
Flow rate: 0.8 mL/min
Solvent A: 0.05% TFA, 100% water
Solvent B: 0.05% TFA, 100% CAN Method F: Linear gradient of 0 to 100% B over 4 min, with 1 min hold at 100% B;
UV visualization at 220 nm
Column. Mac-Mod Halo C18, 4.6×50 mm
Flow rate: 4 mL/min
Solvent A: 10 mM ammonium acetate, 95% water, 5% ACN
Solvent B: 10 mM ammonium acetate, 95% ACN, 5% water Preparative HPLC Methods Employed in the Purification of Products Method I: Linear gradient of 0 to 100% B over 10 min, with 5 min hold time at 100% B; Shimadzu LC-8A binary pumps; Waters ZQ mass spectrometer using Waters Masslynx 4.0 SP4 MS software;

UV visualization at 220 nm;
Column: Waters SunFire 19×100 mm 5 µm C18;
Flow rate: 20 mL/min;
Peak collection triggered by mass spectrometry;
Solvent A: 0.1% TFA, 10% ACN, 90% water;
Solvent B: 0.1% TFA, 90% ACN, 10% water.
Method J: Linear gradient of 20 to 100% B over 10 min, with 5 min hod time at 100% B; Shimadzu LC-8A binary pumps; Shimadzu SPD-20A UV detector;
UV visualization at 220 nm;
Column: Phenomenex Luna AXIA 21.1×100 mm 5 µm C18;
Flow rate: 20 mL/min;
Peak collection triggered by UV absorbance;
Solvent A: 0.1% TFA, 10% MeOH, 90% water;
Solvent B: 0.1% TFA, 90% MeOH, 10% water.
Method K: Linear gradient of 20 to 100% B over 10 min, with 2 min hold time at 100% B; Shimadzu LC-8A binary pumps; Shimadzu SPD-10A UV detector;
UV visualization at 220 nm;
Column: Phenomenex Luna AXIA 21.1×100 mm 5 µm C18;
Flow rate: 20 mL/min;
Peak collection triggered by UV absorbance;
Solvent A: 0.1% TFA, 10% ACN, 90% water;
Solvent B: 0.1% TFA, 90% ACN, 10% water.
Method L: Linear gradient of 20 to 100% B over 10 min, with 2 min hold time at 100% B; Shimadzu LC-8A binary pumps; Shimadzu SPD-10A UV detector;
UV visualization at 220 nm;
Column: YMC Sunfire, 5 µm, C18 column, 30×100 mm;
Flow rate: 40 mL/min;
Peak collection triggered by UV absorbance;
Solvent A: 0.1% TFA, 10% MeOH, 90% water;
Solvent B: 0.1% TFA, 90% MeOH, 10% water.
Method M: Linear gradient of 20 to 55% B over 20 min;
UV visualization at 220 nm;
Column: Axia Luna 5 µm C18 30×100 mm;
Flow rate: 40 mL/min;
Solvent A: 0.1% TFA, 10% ACN, 90% water;
Solvent B: 0.1% TFA, 90% ACN, 10% water.
Method N: Linear gradient of 20 to 100% B over 20 min, with 2 min hold time at 100% B;
UV visualization at 220 nm;
Column: Axia Luna 5 µm C18 30×100 mm;
Flow rate: 40 mL/min;
Solvent A: 0.1% TFA, 10% ACN, 90% water;
Solvent B: 0.1% TFA, 90% ACN, 10% water.

NMR Employed in Characterization of Examples $^1$H NMR spectra were obtained with Bruker or JEOL fourier transform spectrometers operating at frequencies as follows: $^1$H NMR: 400 MHz (Bruker or JEOL) or 500 MHz (JEOL). $^{13}$C NMR: 100 MHz (Bruker or JEOL). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

Biology

The endothelium occupies a pivotal position at the interface between the circulating humoral and cellular elements of the blood, and the solid tissues which constitute the various organs. In this unique position, endothelial cells regulate a large number of critical processes, including leukocyte adherence and transit through the blood vessel wall, local control of blood vessel tone, modulation of the immune response, the balance between thrombosis and thrombolysis, and new blood vessel development. Thus, endothelial cell dysfunction has been postulated as a central feature of vascular diseases such as hypertension and atherosclerosis. (WO 1999/032611 and references cited therein, e.g., Folkman et al., *Science*, 235:442-447 (1987); Yanagisawa et al., *Nature*, 332:411-415 (1988); Folkman et al., *J. Biol. Chem.*, 267:10931-10934 (1992); Janssens et al., *J. Biol. Chem.*, 267:14519-14522 (1992); Lamas et al., *Proc. Natl. Acad. Sci. U.S.A.*, 89:6348-6352 (1992); Luscher et al., *Hypertension*, 19:117-130 (1992); Williams et al., *Am. Rev. Respir. Dis.*, 146:S45-S50 (1992); and Bevilacqua et al., *J. Clin. Invest.*, 91:379-387 (1993)).

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S., where cardiovascular disease accounts for 44% of all deaths, with 53% of these associated with atherosclerotic coronary heart disease.

Risk for development of atherosclerosis has been shown to be strongly correlated with certain plasma lipid levels. While elevated low density lipoprotein-cholesterol (LDL-C) may be the most recognized form of dyslipidemia, it is by no means the only significant lipid associated contributor to CHD. Low high density lipoprotein-cholesterol (HDL-C) is also a known risk factor for CHD (Gordon, D. J. et al., *Circulation*, 79:8-15 (1989)).

High LDL-C and triglyceride levels are positively correlated, while high levels of HDL-C are negatively correlated with the risk for developing cardiovascular diseases. Thus, dyslipidemia is not a unitary risk profile for CHD but may be comprised of one or more, preferably one to three, lipid aberrations.

At least 50% of the variation in HDL cholesterol levels is genetically determined. The phenotype of elevated HDL cholesterol is often dominantly inherited, but homozygous deficiency of HL or of the cholesteryl ester transfer protein (CETP), which result in elevated HDL cholesterol, are recessive conditions. Recently, several genetic variations in the human endothelial lipase gene have been identified, six of which potentially produce functional variants of the protein, and the frequencies of these variants were found to be associated with elevated levels of HDL cholesterol in human subjects (deLemos et al., *Circulation*, 106:1321-1326 (2002)).

Notably, the endothelial lipase-mediated binding and uptake of HDL particles and the selective uptake of HDL-derived cholesterol esters have been reported to be independent of its enzymatic lipolytic activity (Strauss et al., *Biochem. J.*, 368:69-79 (2002)).

Because of the beneficial effects widely associated with elevated HDL levels, an agent which inhibits EL activity in humans, by virtue of its HDL increasing ability, are expected to be useful for the treatment, prevention, the arrestment and/or regression of atherosclerosis, coronary heart disease, cerebrovascular disorders etc., especially those (but not restricted thereto) which are characterized by one or more of the following factors: (a) high plasma triglyceride concentrations, high postprandial plasma triglyceride concentrations; (b) low HDL cholesterol concentration; (c) low apoA lipoprotein concentrations; (d) high LDL cholesterol concentrations; (e) small dense LDL cholesterol particles; and (f) high apoB lipoprotein concentrations.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-atherosclerosis agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an anti-atherosclerosis agent, e.g., an endothelial lipase inhibitor. Exemplary subjects include human beings of any age with risk factors for atherosclerosis and its associated coronary artery disease. Common risk factors include, but are not limited to, age, sex, weight, and family history.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit endothelial lipase and/or to prevent or treat the disorders listed herein. When applied to a combination, the term refers to combined amounts of the active ingredients that result in the preventive or therapeutic effect, whether administered in combination, serially, or simultaneously.

Biological Activity

Endothelial lipase activity was measured using a fluorescent substrate, A10070, (Invitrogen, CA) doped into an artificial vesicle containing DMPG (Avanti Polar Lipids) as the excipient. Vesicles were prepared by combining 285 uL of 1 mM DMPG in a 1:1 mixture of MeOH and $CHCl_3$ with 15 uL of 1 mM A10070 in a 1:1 mixture of MeOH and $CHCl_3$. The mixture was dried under nitrogen and resuspended in 150 uL of 50 mM HEPES pH 8.0 buffer containing 100 mM NaCl and 0.2 mM EDTA. The sample was allowed to sit at rt for 15 min and then was sonicated 3×4 mins on ice with a Branson Sonicator using duty cycle 1. This preparation provides vesicles with a mole fraction of 0.05 for the FRET substrate.

The enzymatic assay was measured using white, opaque 96-well half area plates. Each well contained 60 uL of assay buffer (50 mM HEPES pH 8.0, 50 mM NaCl and 1 mM $CaCl_2$) and 2 ul of a DMSO solution containing compound of interest. Conditioned media obtained from HT-1080 cells, which were transformed by RAGE technology (Athersys) to overexpress endogenous EL, was added and the reaction was allowed to incubate for 20 min at 37° C. with gentle agitation. The reaction was started by the addition of 20 uL of a 1:4 dilution of vesicles. The final total reaction volume was 100 uL. The reaction rates were measured on a Gemini plate reader with an excitation wavelength of 488 nm and a emission of 530 nm. Readings were taken every 20 seconds for 10 min with agitation between each reading. The slope of the linear portion of the readout was used to calculate the rate of the reaction.

Examples 1-208 were tested in the EL assay described above and found having EL inhibitory activity. The EL $IC_{50}$ values measured for the following examples are listed in Table 1.

TABLE 1

| Ex. No. | HLE_EL_CRC $IC_{50}$ (nM) |
| --- | --- |
| 7 | <10.00 |
| 8 | <10.00 |
| 19 | <10.00 |
| 45 | 198.50 |
| 48 | <10.00 |
| 51 | 178.30 |
| 56 | 215.60 |
| 60 | 198.10 |
| 64 | <10.00 |
| 71 | <10.00 |
| 77 | <10.00 |
| 81 | <10.0 |
| 88 | <10.00 |
| 89 | <10.00 |
| 113 | 5815.00 |
| 114 | 6861.00 |
| 115 | 1787.00 |
| 118 | 2700.00 |
| 119 | 1618.00 |
| 120 | 167.40 |
| 126 | 2464.00 |
| 127 | 8665.00 |
| 128 | 6624.00 |
| 129 | 3556.00 |
| 136 | 2199.00 |
| 137 | 1661.00 |
| 142 | 215.80 |
| 186 | 171.5 |
| 188 | 200 |
| 189 | 210.30 |
| 194 | 210.3 |
| 198 | 181.90 |

Accordingly, the compounds of the present invention can be administered to mammals, preferably humans, for the treatment of a variety of conditions and disorders, including, but not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

VI. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., HMG-CoA reductase inhibitors or other pharmaceutically active material.

The compounds of the present invention may be employed in combination with other EL inhibitors or one or more, preferably one to three, other suitable therapeutic agents useful in the treatment of the aforementioned disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

The compounds of the present invention may be employed in combination with additional therapeutic agent(s) selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acytransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

The compounds of the present invention may be employed in combination with additional therapeutic agent(s) selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα inhibitors; α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, $β_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the endothelial lipase. Such compounds may be provided in a commercial kit, for example, for use in pharmaceutical research involving endothelial lipase or HDL activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving endothelial lipase.

The present invention also encompasses an article of manufacture. As used herein, article of manufacture is intended to include, but not be limited to, kits and packages.

The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment and/or prophylaxis of dyslipidemias and the sequelae thereof. In another embodiment, the package insert states that the pharmaceutical composition can be used in combination (as defined previously) with a second therapeutic agent for the treatment and/or prophylaxis of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention should become apparent in the course of the above descriptions of exemplary embodiments that are given for illustration of the invention and are not intended to be limiting thereof.

EXAMPLES

The following Examples have been prepared, isolated and characterized using the methods disclosed herein. The following examples demonstrate a partial scope of the invention and are not meant to be limiting of the scope of the invention.

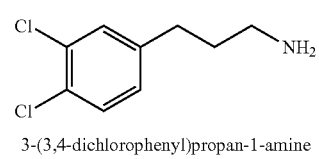

3-(3,4-dichlorophenyl)propan-1-amine

Intermediate 1.

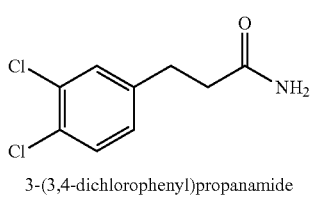

3-(3,4-dichlorophenyl)propanamide

Intermediate 1A.

To a cold (0° C.) solution of 3-(3,4-dichlorophenyl)propanoic acid (5.000 g, 22.82 mmol) in $CH_2Cl_2$ (100 mL) was added oxalyl chloride (13 mL, 25 mmol) dropwise, followed by 8 drops of DMF. The mixture was stirred at 0° C. for 20 min, then allowed to warm to rt and stirred for and additional 2.5 h. The reaction mixture was concentrated to dryness. The residue was dissolved in $Et_2O$. The ethereal solution was slowly added to 150 mL of 28-30% solution of aqueous ammonium hydroxide cooled to 0° C. The reaction mixture was stirred at rt for 16 h. The layers were separated and the aqueous layer was extracted with ethyl acetate. The combined organic extracts were dried over sodium sulfate and concentrated in vacuo to give 4.6 g (93%) of Intermediate 1A. HPLC/MS (Method D) RT=0.82 min, [M+1]+218.1.

Intermediate 1

To a suspension of 1.0 M lithium aluminum hydride in THF (14 mL, 14 mmol) stirring under argon in a 3-necked round bottomed flask was added a solution of Intermediate 1A (1.00 g, 4.59 mmol) dissolved in anhydrous THF (30 mL). The suspension was heated to 60° C. for 1.5 h. The reaction mixture was cooled to 0° C. and quenched by slow addition of 1N NaOH (15 mL), followed by addition of 25% aqueous solution of Na/K tartrate (15 mL). The mixture was stirred for 10 min then ethyl acetate (100 mL) was added. After stirring an additional 1 h, the organic and aqueous phases were separated. The aqueous layer was washed with 100 mL of EtOAc. The combined organic layers were dried over anhydrous $Na_2SO_4$, filtered and evaporated in vacuo to give 869 mg (92%) of Intermediate 1. HPLC/MS (Method D) RT=0.71, [M+1]$^+$204.1; $^1$H NMR (400 MHz, chloroform-d) δ ppm 1.26-1.52 (m, 2 H) 1.68-1.78 (m, 2 H) 2.61 (t, J=7.53 Hz, 2 H) 2.71 (t, J=7.03 Hz, 2 H) 7.01 (dd, J=8.16, 1.88 Hz, 1 H) 7.26 (d, J=1.76 Hz, 1 H) 7.32 (d, J=8.28 Hz, 1 H).

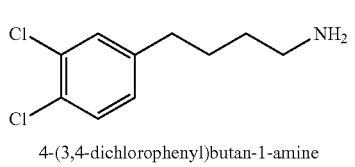

4-(3,4-dichlorophenyl)butan-1-amine

Intermediate 2.

Intermediate 2A.

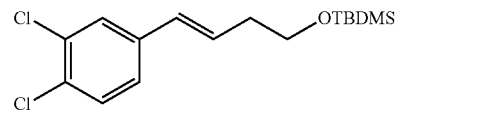

(E)-tert-butyl(4-(3,4-dichlorophenyl)but-3-enyloxy)dimethylsilane

4-Bromo-1,2-dichlorobenzene (0.9 mL, 7.0 mmol), (E)-tert-butyldimethyl(4-(4,4,5,5-tetramethyl-1,3,2-dioxaborolan-2-yl)but-3-enyloxy)silane (3 mL, 8.3 mmol), KF (1.2 g, 21 mmol), Pd(OAc)$_2$ (0.16 g, 0.70 mmol), and 2-(di-tert-butylphosphino)biphenyl (0.41 g, 1.4 mmol) were combined in a 20 mL microwave tube and the tube was sealed, evacuated and backfilled with argon. Degassed THF (20 mL) and H$_2$O (0.25 mL, 14 mmol) were added under argon and the mixture was heated to 150° C. for 60 min using microwave irradiation. The reaction mixture was cooled to rt and stirred for 3 days. The reaction mixture was diluted with ethyl acetate (200 mL). The organic layer was washed with water (200 mL) and brine (100 mL), dried over Na$_2$SO$_4$ and concentrated to give a black oil that was stored overnight at −20 C. The crude product was dissolved in hexanes/DCM and purified by silica gel chromatography (100% hexanes for 10 min, 0-3% ethyl acetate in hexanes over 20 min) to obtain 2.0 g (68.6% yield) of Intermediate 2A. HPLC/MS (Method C) RT=4.80 min, [M–C$_6$H$_{16}$OSi]+199.1.

Intermediate 2B.

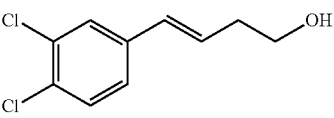

(E)-4-(3,4-dichlorophenyl)but-3-en-1-ol

To solution of Intermediate 2A (2.2 g, 5.2 mmol) in THF (50 mL) cooled to 0° C. was added TBAF (6.3 mL, 6.3 mmol) via dropwise addition. The reaction mixture was stirred at 0° C. for 1 h and diluted with ethyl acetate (200 mL). The organic layer was washed with water (2×100 mL), dried over Na$_2$SO$_4$ and dried in vacuo. The product was purified by silica gel chromatography (80 g silica gel; linear gradient 0-25% ethyl aceatate for 30 min) to obtain 917 mg (97% yield) of Intermediate 2B. HPLC/MS (Method D) RT=1.00 min, [M–H$_2$O+1]$^+$199.1.

Intermediate 2C.

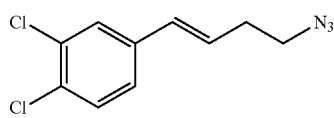

(E)-4-(4-azidobut-1-enyl)-1,2-dichlorobenzene

To a solution of Intermediate 2B (1.3 g, 4.4 mmol) in DMF (7 mL) was added NaN$_3$ (0.86 g, 13 mmol). The reaction mixture was stirred at rt for 16 h. The reaction mixture was diluted with EtOAc (100 mL). The organic layer was washed with 10% aqueous LiCl solution (3×200 mL), dried over Na$_2$SO$_4$ and dried in vacuo. The product was purified by silica gel chromatography to provide Intermediate 2C (570 mg, 87% yield). HPLC/MS (Method C) RT=4.02 min [M+Na]$^+$ 263.2.

Intermediate 2

To a solution of Intermediate 2C (570 mg, 2.3 mmol) ethyl acetate (40 mL) was added platinum(IV) oxide (53 mg, 0.23 mmol). The contents were purged with hydrogen and stirred under 1 atm hydrogen for 1.5 h. The reaction was sparged with Ar, then filtered and dried in vacuo to provide 444 mg (69% yield) of Intermediate 2 as a crude product that was used without further purification. HPLC/MS (Method D) RT=0.77 min, [M+1]+218.1. $^1$H NMR (400 MHz, chloroform-d) δ 1.44-1.51 (m, 2 H) 1.57-1.75 (m, 4 H) 2.57 (t, J=7.65 Hz, 2 H) 2.71 (t, J=7.03 Hz, 2 H) 6.99 (dd, J=8.28, 2.01 Hz, 1 H) 7.24-7.26 (m, 1 H) 7.32 (d, J=8.28 Hz, 1 H).

Intermediate 3.

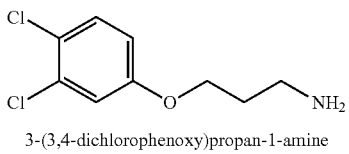

3-(3,4-dichlorophenoxy)propan-1-amine

Intermediate 3A.

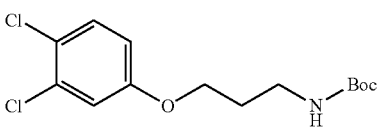

tert-butyl 3-(3,4-dichlorophenoxy)propylcarbamate

To a solution of tert-butyl 3-bromopropylcarbamate (0.5 g, 2.1 mmol) and 3,4-dichlorophenol (0.38, 2.3 mmol) in DMF (10.5 mL) was added Cs$_2$CO$_3$ (1.02 g, 3.10 mmol). The reaction mixture was stirred at rt for 72 h. The reaction mixture was diluted with water and extracted with EtOAc (3×). The combined organic extracts were washed with saturated aqueous NaCl solution, dried over Na$_2$SO$_4$, filtered and evaporated to dryness. The crude product was purified by silica gel chromatography to provide Intermediate 3A (543 mg, 56% yield). HPLC/MS (Method B) RT=3.85 min, [M+1]$^+$320.2.

Intermediate 3

To a solution of Intermediate 3A (540 mg, 1.7 mmol) in CH$_2$Cl$_2$ (9 mL) was added TFA (1 mL). The reaction mixture was stirred at rt for 1 h and washed with 1 N aqueous NaOH. The aqueous layers were combined and washed with CH$_2$Cl$_2$. The combined organic layers were washed with water and saturated aqueous NaCl, dried over Na$_2$SO$_4$, filtered and evaporate to dryness in vacuo to obtain Intermediate 3 (255 mg, 65% yield). HPLC/MS (Method C) RT=2.30 min, [M+1]$^+$220.1; $^1$H NMR (500 MHz, CHCl$_3$-d$_1$) δ 1.26 (s, 2 H) 1.87-1.96 (m, 2 H) 2.90 (t, J=6.60 Hz, 2 H) 4.02 (t, J=6.05 Hz, 2 H) 6.75 (dd, J=8.80, 2.75 Hz, 1 H) 7.00 (d, J=2.75 Hz, 1 H) 7.31 (d, J=8.80 Hz, 1 H).

Intermediate 4.

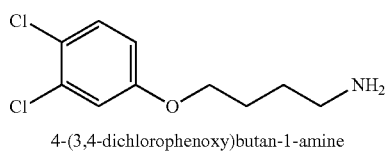

4-(3,4-dichlorophenoxy)butan-1-amine

-continued

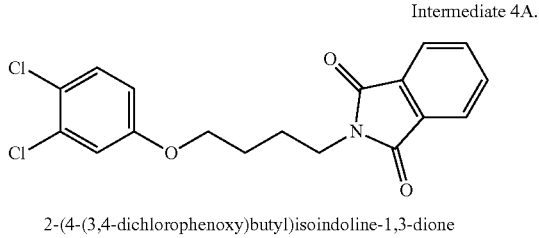

Intermediate 4A.

2-(4-(3,4-dichlorophenoxy)butyl)isoindoline-1,3-dione

To a solution of 2-(4-bromobutyl)isoindoline-1,3-dione (0.60 g, 2.1 mmol) and 3,4-dichlorophenol (0.38 g, 2.3 mmol) in DMF (11 mL) was added cesium carbonate (1.0 g, 3.2 mmol). The reaction was stirred at rt over for 72 h. The reaction mixture was diluted with water and extracted with EtOAc. The combined organic extracts were washed with saturated aqueous NaCl:water (1:1), dried over $Na_2SO_4$, filtered and evaporated to dryness. The product was purified by silica gel chromatography to provide Intermediate 4A (541 mg, 69% yield).

Intermediate 4

To a solution of Intermediate 4A (400 mg, 1.1 mmol) in EtOH (5 mL) was added hydrazine hydrate (0.32 mL, 6.6 mmol). The reaction mixture was stirred at 60° C. for 16 h. The reaction mixture was cooled to rt. EtOAc was added and the mixture was stirred for 5 min. The solids were removed by filtering the mixture. The filtrate was evaporated to dryness in vacuo yielding a solid/oil mixture. The semisolid was washed with $Et_2O$. The combined $Et_2O$ washings were evaporated in vacuo to give Intermediate 4 (226 mg, 84% yield). HPLC/MS (Method C) RT=2.50 min, $[M+1]^+$234.1; $^1$H NMR (500 MHz, DMSO-$d_6$) δ 1.39-1.48 (m, 2 H) 1.66-1.75 (m, 2 H) 2.55 (t, J=6.87 Hz, 2 H) 3.97 (t, J=6.32 Hz, 2 H) 6.93 (dd, J=9.07, 2.47 Hz, 1 H) 7.20 (d, J=2.20 Hz, 1 H) 7.48 (d, J=8.80 Hz, 1 H).

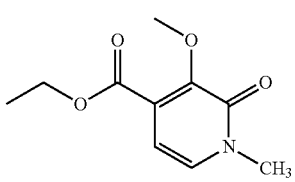

Intermediate 5.

ethyl 3-methoxy-1-methyl-2-oxo-1,2-dihydropyridine-4-carboxylate

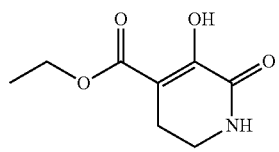

Intermediate 5A.

ethyl 5-hydroxy-6-oxo-1,2,3,6-tetrahydropyridine-4-carboxylate

To a vigorously stirred suspension of pentane-washed (3×400 mL) potassium hydride (123 g of pre-washed KH in mineral oil; 1.07 mol) in 1.2 L of toluene in an oven-dried three neck, round-bottom reaction flask was added dropwise 300 mL (5.1 mol) of absolute EtOH over 15 min. The resulting warm homogeneous solution was allowed to cool to 40° C. To this stirred mixture was added a solution of 79 mL (5.04 mol) pyrrolidinone and 144 mL (1.06 mol) of diethyl oxalate in 250 mL of toluene with a slow steady-stream addition. Toluene (300 mL) and ethanol (200 mL) were added to dilute the thick yellow suspension that had formed. The reaction was stirred at 90° C. for 18 hours followed by cooling to 40° C. before quenching with 6 N HCl (400 mL). The layers were separated. The aqueous layer was extracted with DCM (2×500 mL). The combined organic layers were dried over $MgSO_4$ and concentrated. The crude solid was purified by recrystallization (EtOAc) and the purified material was recovered by vacuum filtration. The solid was dried in a vacuum oven at 50° C. overnight to afford Intermediate 5A (130 g, 68%) as a yellow crystalline solid. mp. 142-148° C.

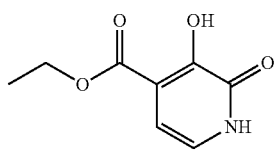

Intermediate 5B.

ethyl 3-hydroxy-2-oxo-1,2-dihydropyridine-4-carboxylate

To a solution of Intermediate 5A (20 g) in xylene (400 mL) was added 10% Pd/C (4 g). The mixture was heated at 130° C. for 24 h. The reaction was filtered through a pad of Celite®. Methanol was used for filtration and washing. The filtrate was concentrated and the residue was purified by silica gel chromatography (0-100% EtOAc/hexane) to give Intermediate 5B (15 g, 80% yield).

Intermediate 5

To a solution of Intermediate 5B (2.0 g, 10.92 mmol) in DMF (15 mL) was added potassium carbonate (4.53 g, 32.8 mmol) and iodomethane (2.72 mL, 43.7 mmol). The reaction was heated at 80° C. for 3 days. The reaction mixture was diluted with DCM, washed with water, dried over $MgSO_4$, filtered and concentrated. The residue was dissolved in a small amount of DCM and charged to a 80 g silica gel cartridge which was eluted with a 25 min gradient from 0-100% EtOAc/hexane to give Intermediate 5 (1.47 g, 6.96 mmol, 63.7% yield) as an off-white solid. HPLC/MS (Method D) RT=1.2 min, $[M+1]^+$212.1; $^1$H NMR (400 MHz, CHLOROFORM-d) δ ppm 7.07 (1 H, d, J=7.28 Hz), 6.33 (1 H, d, J=7.03 Hz), 4.36 (2 H, q, J=7.03 Hz), 4.01 (3 H, s), 3.57 (3 H, s), 1.38 (3 H, t, J=7.15 Hz).

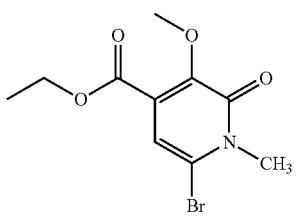

Intermediate 6.

ethyl 6-bromo-3-methoxy-1-methyl-2-oxo-1,2-dihydropyridine-4-carboxylate

To a solution of Intermediate 5 (109 mg, 0.516 mmol) in DCE (2.0 mL) was added NBS (110 mg, 0.619 mmol). The reaction was stirred at rt overnight. The reaction was concentrated. The residue was diluted with EtOAc, washed with water and brine, dried over anhydrous sodium sulfate, filtered and evaporated. The residue was dissolved in a small amount of DCM and charged to a 12 g silica gel cartridge which was eluted with a 25 min gradient from 0-100% EtOAc/hexane to give Intermediate 6 (138 mg, 0.476 mmol, 69.2% yield) as a white solid. HPLC/MS (Method D) RT=1.4 min, [M+1]$^+$ 291.9; $^1$H NMR (400 MHz, CHLOROFORM-d) δ ppm 7.29 (1 H, s), 4.42 (2 H, q, J=7.28 Hz), 3.99 (3 H, s), 3.55 (3 H, s), 1.39 (3 H, t, J=7.15 Hz).

Intermediate 7.

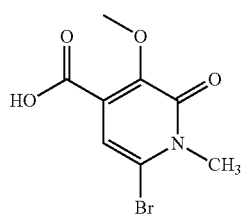

6-bromo-3-methoxy-1-methyl-2-oxo-1,2-dihydropyridine-4-carboxylic acid

To a solution of lithium hydroxide (8 mg, 0.334 mmol) in water (0.2 mL) was added a solution of Intermediate 6 (40 mg, 0.138 mmol) in THF (2 mL). The reaction was heated at 50° C. overnight. The reaction was acidified with concentrated HCl (30 μL) and concentrated. The residue was extracted with DCM. The organic washings were combined, dried over MgSO$_4$, filtered and concentrated to give Intermediate 7 (25 mg, 0.095 mmol, 69.2% yield) as a yellow solid. HPLC/MS (Method D) RT=0.2 min, [M+1]$^+$261.9.

Intermediate 8.

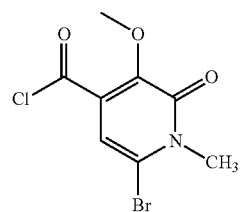

6-bromo-3-methoxy-1-methyl-2-oxo-1,2-dihydropyridine-4-carbonyl chloride

To a solution of Intermediate 7 (25 mg, 0.095 mmol) in THF (6 mL) was added oxalyl chloride (0.072 mL, 0.14 mmol) and one drop of DMF. The reaction was stirred at rt for 1 h. The reaction was concentrated to give Intermediate 8 (29 mg, 0.10 mmol, 110% yield).

Intermediate 9.

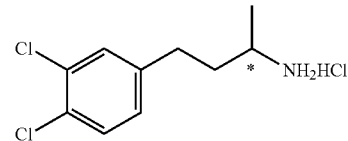

4-(3,4-dichlorophenyl)butan-2-amine hydrochloride (chiral)

Intermediate 9A.

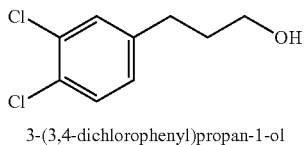

3-(3,4-dichlorophenyl)propan-1-ol

To a solution of 3-(3,4-dichlorophenyl)propanoic acid (3.000 g, 13.69 mmol) in THF (30 mL) was added dropwise to a solution of BH$_3$.THF (41.1 mL, 1M, 41.1 mmol). The reaction mixture was heated to reflux for 18 h. The reaction mixture was quenched by addition of 2 N HCl (48 mL). After being stirred for 1 h, the THF was evaporated. The resulting aqueous solution was adjusted to pH 8 by the addition of 1N NaOH. The aqueous layer was extracted with EtOAc three times. The combined organic layers were washed with brine, dried over Na$_2$SO$_4$, filtered and evaporated to dryness to yield Intermediate 9A (2.89 g, 14.1 mmol, 103% yield) as a colorless oil. HPLC/MS (Method E) RT=1.13 min, [M+1]$^+$ No ionization.

Intermediate 9B.

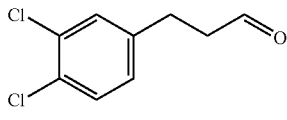

3-(3,4-dichlorophenyl)propanal

Intermediate 9A (4.9 g, 24 mmol) in DCM (50 mL) was added slowly to a suspension of Dess-Martin periodinane (15.5 g, 36.6 mmol) in DCM (50 mL). The mixture was stirred at rt for 1 h, then quenched with saturated NaHCO$_3$ (50 mL) followed by the addition of 20% sodium thiosulfate (50 mL). The reaction mixture was stirred till both organic layer and aqueous layer became clear. The organic layer was separated, and the aqueous layer was extracted by DCM once more. The combined organic layers were dried over MgSO$_4$, filtered and concentrated. The residue was dry loaded onto silica and purified by silica gel chromatography (EtOAc/Hexanes 0-10% over 20 min, column 120 g, flow rate 85 mL/min) to give Intermediate 9B (3.9 g, 19 mmol, 79% yield) as a pale yellow oil.

Intermediate 9C.

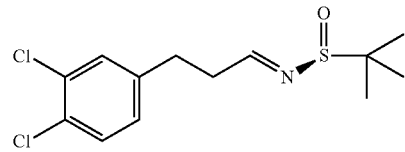

(S,E)-N-(3-(3,4-dichlorophenyl)propylidene)-2-methylpropane-2-sulfinamide

To a solution of Intermediate 9B (1.00 g, 4.92 mmol) in CH$_2$Cl$_2$ (5 mL) was added (S)-2-methylpropane-2-sulfinamide (0.716 g, 5.91 mmol) followed by the addition of pyridine 4-methylbenzenesulfonate (0.062 g, 0.25 mmol) and MgSO4 (2.96 g, 24.6 mmol). The reaction mixture was stirred at rt for 18 h, then filtered through a Celite® pad. The solvents were removed from the filtrate under reduced pressure and the residue was purified by silica gel chromatography (EtOAc/

Hexanes 0-30% over 15 min, column 80 g, flow rate 85 mL/min) to give Intermediate 9C (1.2 g, 3.9 mmol, 80% yield) as a white solid. HPLC/MS (Method E) RT=1.13 min, [M+1]+306.0.

Intermediate 9D.

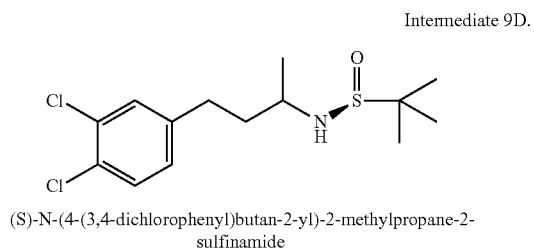 [SMILES: CC(CCc1ccc(Cl)c(Cl)c1)N[S@@](=O)C(C)(C)C]

(S)-N-(4-(3,4-dichlorophenyl)butan-2-yl)-2-methylpropane-2-sulfinamide

Methylmagnesium bromide in toluene/THF (14 mL, 1.4 M, 20 mmol) was added slowly to a solution of Intermediate 9C (4.000 g, 13.06 mmol) in DCM (50 mL) and the reaction mixture heated to reflux for 2.5 h. The reaction mixture was allowed to cool to rt and diluted with DCM. The solution was washed with saturated NH$_4$Cl, the organic layers separated and dried over MgSO$_4$, filtered and concentrated. The residue was purified by silica gel chromatography (EtOAc/Hexanes 0-50% over 30 min, column 330 g, flow rate 100 mL/min) to give Intermediate 9D (2.80 g, 8.69 mmol, 66.5% yield) as a white solid. HPLC/MS (Method E) RT=1.12 min, [M+1]+ 322.1; Chiral HPLC (Method L) retention time=4.55 min, ee=100%.

Intermediate 9

To a solution of Intermediate 9D (2.66 g, 8.27 mmol) in Et$_2$O (12 mL) was added HCl in Et$_2$O (12 mL, 2M, 25 mmol) and the reaction mixture was stirred at rt for 1 h. The white precipitate was filtered and rinsed with Et$_2$O to afford Intermediate 9 (1.81 g, 100% crude) as a white solid. HPLC/MS (Method E) RT=0.74 min, [M+1]$^+$219.9.

Intermediate 10.

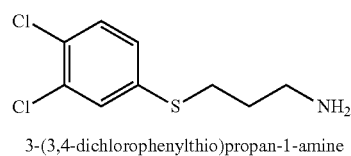

3-(3,4-dichlorophenylthio)propan-1-amine

Intermediate 10A.

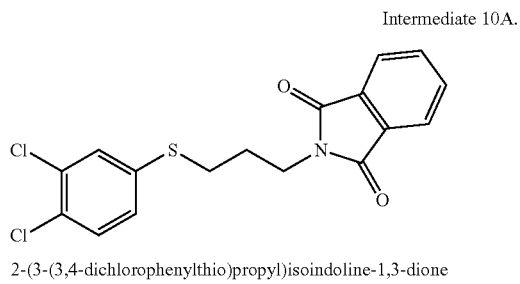

2-(3-(3,4-dichlorophenylthio)propyl)isoindoline-1,3-dione 3,4-dichlorobenzenethiol (500 mg, 2.79 mmol) and 2-(3-bromopropyl)isoindoline-1,3-dione (823 mg, 3.07 mmol) were stirred in DMF (2 mL) at rt. Cs$_2$CO$_3$ (1640 mg, 5.03 mmol) was added. The resulting mixture was stirred at rt overnight. H$_2$O was added and the reaction mixture extracted with EtOAc (2×). The combined organic layers were dried over MgSO$_4$, filtered and concentrated to give the crude product. After triturating with Et$_2$O the white precipitate was dried to give the Intermediate 10A (760 mg, 2.075 mmol, 74.3% yield). HPLC/MS (Method D) RT=4.00 min, [M+1]$^+$=365.8.

Intermediate 10

To a heterogeneous solution of Intermediate 10A (100 mg, 0.273 mmol), in EtOH (1 mL) was added hydrazine (0.052 mL, 1.6 mmol). The reaction mixture was stirred at 60° C. for 3 h and diluted with EtOAc, filtered and the filter cake washed with MeOH. The solvent was dried over Na$_2$SO$_4$ and evaporated under reduced pressure to give Intermediate 10 (63 mg, 0.27 mmol, 98% yield). HPLC/MS (Method D) RT=1.68 min, [M+1]$^+$237.1. $^1$H NMR (500 MHz, CHCl$_3$-d$_1$) δ 1.64 (s, 2 H) 1.71-1.73 (m, 2 H) 2.79-2.81 (t, J=6.60 Hz, 2 H) 2.98-3.00 (t, J=6.05 Hz, 2 H) 7.42 (s, 2.75 Hz, 1 H) 7.29-7.40 (d, J=2.75 Hz, 2 H).

Intermediate 11.

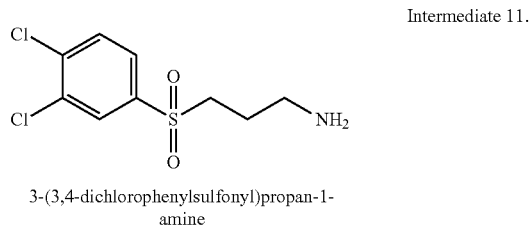

3-(3,4-dichlorophenylsulfonyl)propan-1-amine

Intermediate 11A.

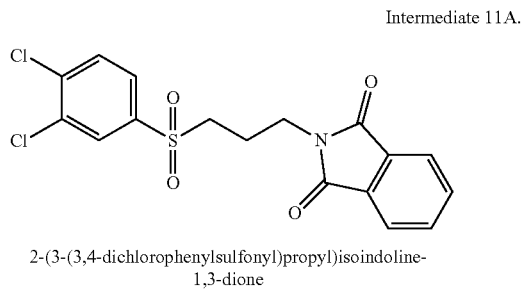

2-(3-(3,4-dichlorophenylsulfonyl)propyl)isoindoline-1,3-dione

To a solution of Intermediate 10A (100 mg, 0.273 mmol) in 2-propanol (2 mL) was added oxone (185 mg, 0.300 mmol) and water (1 ml). The reaction mixture was stirred at rt for 6 h. The reaction mixture was partitioned between H$_2$O and EtOAc. The EtOAc layer was separated and dried over Na$_2$SO$_4$, filtered and the filtrate was evaporated under reduced pressure to give Intermediate 11A. HPLC/MS (Method D) RT=1.97 min, [M+1]$^+$398.

Intermediate 11

To a heterogeneous solution of Intermediate 11A (100 mg, 0.273 mmol) in EtOH (1 mL) was added hydrazine (0.052 mL, 1.6 mmol). The reaction mixture was stirred at 60° C. for 3 h and diluted with EtOAc, filtered and washed the filter cake with MeOH. The solvent was dried over Na$_2$SO$_4$ and evaporated under reduced pressure to give Intermediate 11 (63 mg, 0.267 mmol, 98% yield). HPLC/MS (Method C) RT=1.67 min, [M+1]$^+$237.1

Intermediate 12.

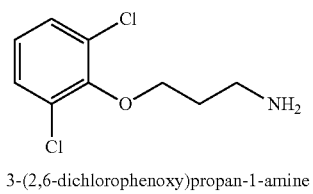

3-(2,6-dichlorophenoxy)propan-1-amine

Intermediate 12A.

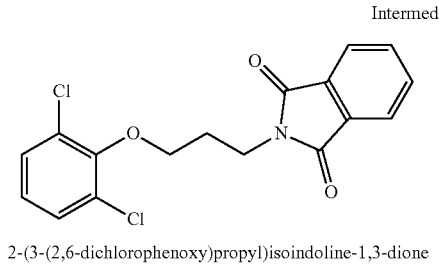

2-(3-(2,6-dichlorophenoxy)propyl)isoindoline-1,3-dione

A solution of 2,6-dichlorophenol (500 mg, 3.07 mmol), tetrabutylammonium iodide (227 mg, 0.613 mmol) and 2-(3-bromopropyl)isoindoline-1,3-dione (905 mg, 3.37 mmol) in THF (5 mL) was stirred at rt. $Cs_2CO_3$ (1800 mg, 5.52 mmol) was added. The resulting mixture was stirred at 50° C. for 16 h then allowed to cool. $H_2O$ was added and the reaction mixture was extracted with EtOAc (2×). The combined organic layers were dried over $MgSO_4$, filtered and concentrated to give crude Intermediate 12A (1000 mg, 2.9 mmol, 94% yield). The crude residue was triturated with ether, and the resulting white powder was dried under vacuum to give Intermediate 12A (1010 mg, 2.88 mmol, 94% yield). HPLC/MS (Method D) RT=2.17 min, [M+1]$^+$351.

Intermediate 12

To a heterogeneous solution of Intermediate 12A (1010 mg, 2.88 mmol) in EtOH (1 mL) was added hydrazine (0.549 mL, 17.3 mmol). The reaction mixture was stirred at 60° C. for 3 h and diluted with ether, filtered and washed the filter cake with ether. The solvent was evaporated under reduced pressure to give Intermediate 12 (630 mg, 2.8 mmol, 98% yield). HPLC/MS (Method D) RT=1.37 min, [M+1]$^+$222; $^1$H NMR (400 MHz, CHLOROFORM-d) δ ppm 7.29 (1 H, s), 4.42 (2 H, q, J=7.28 Hz), 3.99 (3 H, s), 3.55 (3 H, s), 1.39 (3 H, t, J=7.15 Hz).

The following intermediates were synthesized using the methodology described in Intermediate 12.

Intermediate 13

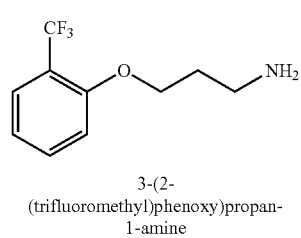

3-(2-(trifluoromethyl)phenoxy)propan-1-amine

Intermediate 14

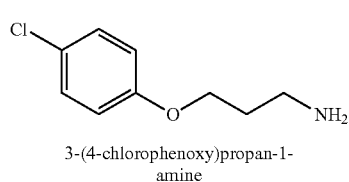

3-(4-chlorophenoxy)propan-1-amine

Intermediate 15

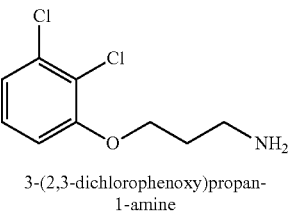

3-(2,3-dichlorophenoxy)propan-1-amine

Intermediate 16.

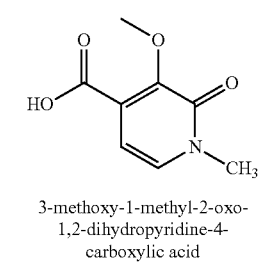

3-methoxy-1-methyl-2-oxo-1,2-dihydropyridine-4-carboxylic acid

To a solution of Intermediate 5 (2.2 g, 10 mmol) in THF (3 mL) was added LiOH (10.8 mg, 0.451 mmol) and the reaction mixture was stirred at rt for 16 h. The reaction mixture was acidified to pH=1 using HCl (12.50 mL, 12.50 mmol) concentrated and then evaporated to dryness to provide Intermediate 16 (1.9 g, 10.37 mmol, 100% yield) as a gray solid. HPLC/MS (Method D) RT=0.42 min, [M+1]$^+$184. $^1$H NMR (400 MHz, DMSO-d$_6$) δ ppm 7.28 (1 H, d, J=7.1 Hz), 5.97 (1 H, d, J=6.6 Hz), 3.62 (3 H, s), 3.31 (3 H, s).

The following intermediates were synthesized using the methodology described in Intermediate 16.

Intermediate 17

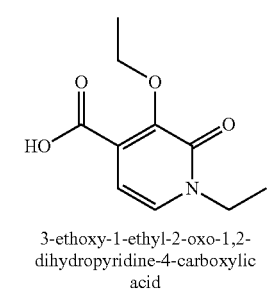

3-ethoxy-1-ethyl-2-oxo-1,2-dihydropyridine-4-carboxylic acid

Intermediate 18

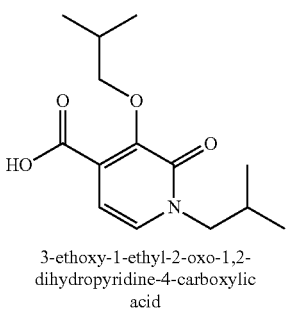

3-ethoxy-1-ethyl-2-oxo-1,2-dihydropyridine-4-carboxylic acid

Intermediate 19

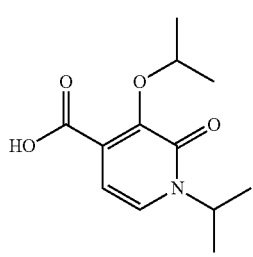

3-isopropoxy-1-isopropyl-2-
oxo-1,2-dihydropyridine-4-
carboxylic acid

Intermediate 20

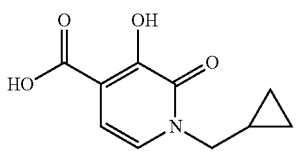

1-(cyclopropylmethyl)-3-
hydroxy-2-oxo-1,2-
dihydropyridine-4-carboxylic
acid

Intermediate 21

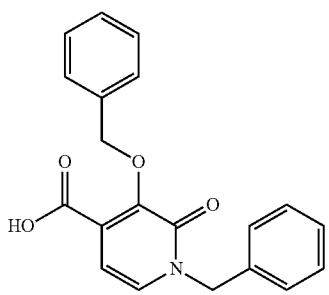

1-benzyl-3-(benzyloxy)-2-oxo-
1,2-dihydropyridine-4-
carboxylic acid

Intermediate 22.

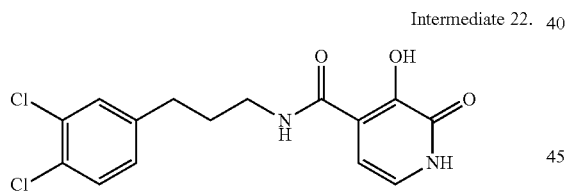

N-(3-(3,4-dichlorophenyl)propyl)-3-hydroxy-2-oxo-1,2-
dihydropyridine-4-carboxamide Intermediate 22A.

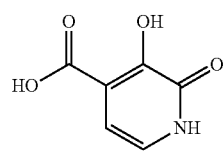

3-hydroxy-2-oxo-1,2-
dihydropyridine-4-
carboxylic acid

To a heterogeneous solution of ethyl 3-hydroxy-2-oxo-1, 2-dihydropyridine-4-carboxylate (Intermediate 5B) (200 mg, 1.09 mmol) in THF (3 mL) was added LiOH (26.1 mg, 1.09 mmol) and H₂O (1 mL). The reaction mixture was stirred for 16 h. The reaction mixture was adjusted to pH 2 and filtered. The filter cake was evaporated to dryness to give Intermediate 22A (160 mg, 1.0 mmol, 94% yield). HPLC/MS (Method D) RT=0.45 min, [M+1]⁺155.9.

Intermediate 22B.

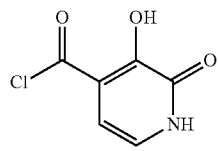

3-hydroxy-2-oxo-1,2-dihydropyridine-4-carbonyl chloride

To a solution of Intermediate 22A (400 mg, 2.58 mmol) was added thionyl chloride (0.376 mL, 5.16 mmol). The reaction mixture was stirred at 60° C. for 3 h. The reaction mixture was allowed to cool to rt, then concentrated under reduced pressure to give Intermediate 22B (430 mg, 2.5 mmol, 96% yield). HPLC/MS (Method D) RT=0.72 min, [M+1]⁺174.

Intermediate 22

To a solution of Intermediate 22B (1.041 g, 6.000 mmol) in DCM (10 mL) was added 3-(3,4-dichlorophenyl)propan-1-amine (Intermediate 1) (1.23 g, 6.00 mmol), followed by Et₃N (2.091 mL, 15.00 mmol). The reaction was heterogeneous and stirred for 1 h. The reaction mixture became homogeneous. The reaction mixture was partitioned between H₂O and DCM. The DCM portion was dried over Na₂SO₄, and then filtered. The filtrate was evaporated under reduced pressure and dried in vacuo to give Intermediate 22 (1.97 g, 5.77 mmol, 96.0% yield). HPLC/MS (Method D) RT=1.99 min, [M+1]⁺340.9. ¹H NMR (400 MHz, METHANOL-d₃) δ ppm 7.38-7.41 (2 H, m), 7.16 (1 H, dd, J=8.1, 2.0 Hz), 6.91 (1 H, d, J=7.0 Hz), 6.61 (1 H, d, J=7.0 Hz), 3.42 (2 H, t, J=6.8 Hz), 2.69 (2 H, t, J=7.7 Hz), 1.93 (2 H, t, J=7.5 Hz).

Intermediate 23.

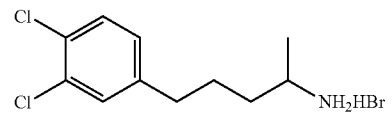

5-(3,4-dichlorophenyl)pentan-2-amine hydrobromide (Isomer A)

Intermediate 23A.

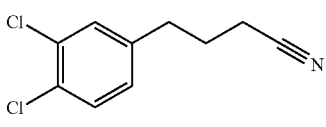

4-(3,4-dichlorophenyl)butanenitrile

Intermediate 9A (2.0 g, 9.75 mmol) was dissolved in pyridine (20 mL) and treated with methane sulfonyl chloride (0.836 mL, 10.73 mmol) drop wise while maintaining temperature below 20° C. The mixture was stirred at rt for 3 h, the mixture was added to concentrated hydrochloric acid (10 mL) in crushed ice. The layers were separated, and the aqueous layer was extracted with ethyl acetate. The combined organic layers were washed with saturated sodium bicarbonate, brine, dried over sodium sulfate and concentrated. The resulting light yellow sulfonate ester was immediately dissolved in dimethylformamide (20 mL) and water (4 mL) and cooled to 0° C. Solid potassium cyanide (0.953 g, 14.63 mmol) was added, and the mixture was stirred at rt for 72 h. The mixture was then diluted with water and extracted with ethyl acetate.

The organic layers were pooled together and washed with H₂O (2×), brine (2×), dried over sodium sulfate filtered and concentrated. The residue was purified by silica gel chromatography (0-80% ethyl acetate/hexane) to afford Intermediate 23A (1.06 g, 51%) as a white solid.

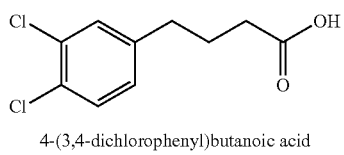

Intermediate 23B 4-(3,4-dichlorophenyl)butanoic acid

Intermediate 23A (900 mg, 4.20 mmol) was dissolved in ethanol (10 mL) and treated with aqueous sodium hydroxide (50% in water, 10 mL). The reaction mixture was heated at reflux for 3 h. After cooling to rt, the mixture was concentrated in vacuo. The residue was dissolved in ethyl acetate and washed with water (2×). The aqueous layer was pooled together and acidified to pH ~2.0 with concentrated hydrochloric acid. The resulting mixture was extracted with ethyl acetate (2×). The organic layers were pooled together and washed with brine (2×), dried over sodium sulfate, filtered and concentrated to afford Intermediate 23B (1.0 g, 102% yield) as a white solid. LC/MS (HPLC Method D): RT=1.97 min, (M+H)⁺=233.

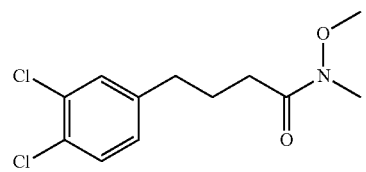

Intermediate 23C.

4-(3,4-dichlorophenyl)-N-methoxy-N-methylbutanamide

Intermediate 23B (1.0 g, 4.29 mmol), N,O-dimethylhydroxyamine hydrochloride (0.502 g, 5.15 mmol), 1-(3-dimethylaminoproppyl)-3-ethylcarbodiimide hydrochloride (1.069 g, 5.58 mmol), 1-hydroxybenzotriazole (0.66 g, 4.29 mmol) and triethylamine (1.2 mL, 8.58 mmol) were combined in dichloromethane (20 mL) at rt. The resulting mixture was stirred at rt for 3 h. The reaction mixture was diluted with dichloromethane, washed with brine, dried over magnesium sulfate, filtered and concentrated. The residue was purified by ISCO chromatography (40 g silica gel cartridge, using 0-100% ethyl acetate/hexanes) to give Intermediate 23C (1.0 g, 84%) as a clear oil. LC/MS (HPLC Method D) RT=2.06 min, (M+H)⁺=276.0.

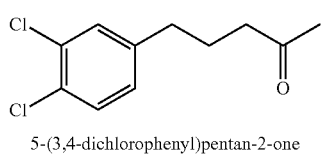

Intermediate 23D.

5-(3,4-dichlorophenyl)pentan-2-one

To a solution of Intermediate 23C (1.0 g, 3.62 mmol) in THF (10 mL) at 0° C. was added dropwise methyl magnesium bromide (1.4 M in toluene/THF, 7.76 mL, 10.86 mmol). After 2 h, the cooling bath was removed, and the reaction was stirred at rt for 1 h. The reaction mixture was cooled to 0° C. and quenched with careful addition of ammonium chloride and then diluted with diethyl ether. The layers were separated, and the aqueous layer was extracted with ether (2×). The combined organic layers were washed with brine (2×), dried over sodium sulfate, filtered and concentrated. The residue was purified by purified by ISCO chromatography (40 g cartridge using hexanes/ethyl acetate 0-50%) to afford Intermediate 23D (0.62 g, 74%).

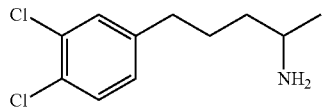

Intermediate 23E.

5-(3,4-dichlorophenyl)pentan-2-amine (racemic)

Ammonium formate (1.364 g, 21.63 mmol) was added to a solution of Intermediate 23D (0.5 g, 2.16 mmol) in methanol (10 mL). The reaction mixture was stirred at rt for 20 min, and then treated with sodium cyanoborohydride (0.82 g, 12.98 mmol) in portions followed by addition of a few drops of acetic acid. The reaction mixture was stirred at rt for 2 h and concentrated. The residue was dissolved in methylene chloride and washed with saturated sodium bicarbonate (2×), brine (2×), dried over sodium sulfate, filtered and concentrated to afford Intermediate 23E (racemic) (0.5 g, 100%) which was taken directly to next step without purification. LC/MS (HPLC Method D) RT=1.66 min, (M+H)⁺=232.0.

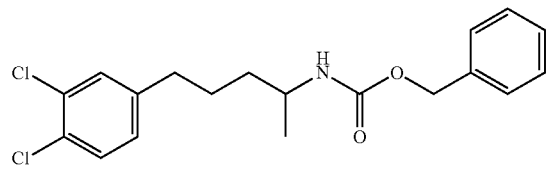

Intermediate 23F. benzyl 5-(3,4-dichlorophenyl)pentan-2-ylcarbamate (Isomer A) and Intermediate 23G. benzyl 5-(3,4-dichlorophenyl)pentan-2-ylcarbamate (Isomer B)

Intermediate 23E (0.5 g, 2.154 mmol) and sodium carbonate (0.502 g, 4.74 mmol) were combined in THF (10 mL) and treated with benzyl chloroformate (0.31 mL, 2.15 mmol) dropwise over 15 min. The reaction was stirred at rt overnight. The mixture was concentrated in vacuo and the residue was diluted with dichloromethane, washed with saturated sodium bicarbonate (2×) and brine (2×), dried over sodium sulfate filtered and concentrated. The product was purified on ISCO chromatography (40 g silica gel cartridge using hexanes/ethyl acetate 0-50%) to give (440 mg, 56%) as a clear oil. The enantiomers were separated on chiral prep HPLC (chiral AD 10 micron 4.6×250 mm, 15 min 5% solvent A isocratic. A=EtOH/MeOH (50/50). B=heptane) to afford Intermediate 23F (Isomer A) (220 mg, 0.601 mmol, 28%) and Intermediate 23G (Isomer B) 225 mg, 0.61 mmol, 28%). For Intermediate 23F (Isomer A): ¹H NMR (400 MHz, CHLOROFORM-d) δ ppm 7.23-7.31 (6 H, m), 7.17 (1 H, br. s.), 6.91 (1 H, d, J=7.5 Hz), 5.02 (2 H, s), 4.42 (1 H, br. s.), 3.62-3.75 (1 H, m), 2.42-2.57 (2 H, m), 1.51-1.62 (2 H, m), 1.32-1.41 (2 H, m), 1.07 (3 H, d). Chiral HPLC (chiral AD 10 micron 4.6×250 mm, 15 min 5% isocratic. A=EtOH/MeOH (50/50).

B=Heptane) RT=10.04 min, 100% ee. For Intermediate 23G (Isomer B): $^1$H NMR (400 MHz, CHLOROFORM-d) δ ppm 7.23-7.31 (6 H, m), 7.17 (1 H, s), 6.91 (1 H, d, J=7.5 Hz), 5.02 (2 H, s), 4.42 (1 H, br. s.), 3.62-3.76 (1 H, m), 2.40-2.57 (2 H, m), 1.50-1.61 (2 H, m), 1.31-1.41 (2 H, m), 1.06 (3 H, d). Chiral HPLC (chiral AD 10 micron 4.6×250 mm, 15 min 5% isocratic. A=EtOH/MeOH (50/50). B=Heptane) RT=13.49 min, 100% ee.

Intermediate 23

Intermediate 23F (Isomer A) (220 mg, 0.6 mmol) was combined with hydrobromic acid (33% in acetic acid, 0.5 ml, 3.04 mmol), and the resulting mixture was stirred at rt for 1.5 h. The reaction mixture was triturated with ether (20 mL) to afford a white precipitate which was filtered and washed with cold ether (2×). The white powder was dried for several hours in vacuo to afford Intermediate 23 (Isomer A, 120 mg, 64%). LC/MS (HPLC method D) retention time=1.68 min, (M+H)$^+$= 232.1.

Intermediate 24.

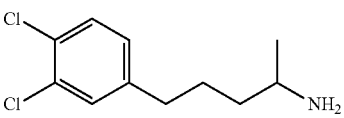

5-(3,4-Dichlorophenyl)pentan-2-amine hydrobromide (Isomer B)

Intermediate 23G (Isomer B) (225 mg, 0.61 mmol) was combined with hydrobromic acid (33% in acetic acid, 0.5 mL, 3.04 mmol), and the resulting mixture was stirred at rt for 1.5 h. The reaction was quenched with water and concentrated. The crude hydrobromic acid salt was loaded onto an SCX cartridge in methanol. The cartridge was flushed with several volumes of methanol which was discarded. The product was eluted with 2 M ammonia in methanol and concentrated to give Intermediate 24 (Isomer B, 150 mg, 78%) as a white powder. LC/MS (HPLC Method D) RT=1.68 min, (M+H)$^+$= 232.1.

Example 1

N-(3-(3,4-dichlorophenyl)propyl)-3-hydroxy-1-methyl-2-oxo-6-(3-(trifluoromethyl)phenyl)-1,2-dihydropyridine-4-carboxamide

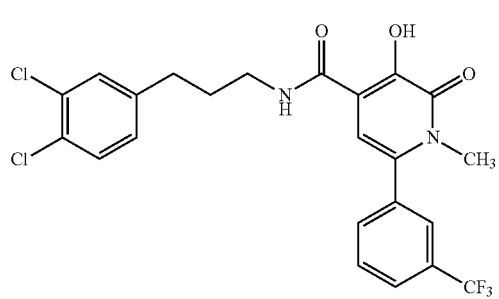 [SMILES: Cn1c(-c2cccc(C(F)(F)F)c2)cc(C(=O)NCCCc2ccc(Cl)c(Cl)c2)c(O)c1=O]

Example 1A 6-bromo-N-(3-(3,4-dichlorophenyl)propyl)-3-hydroxy-1-methyl-2-oxo-1,2-dihydropyridine-4-carboxamide

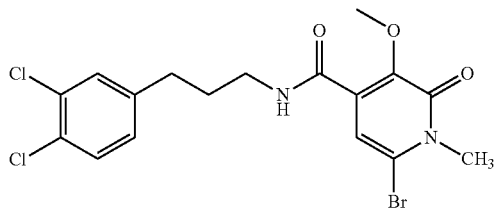 [SMILES: COc1c(C(=O)NCCCc2ccc(Cl)c(Cl)c2)cc(Br)n(C)c1=O]

To solution of Intermediate 1 (24.87 mg, 0.1030 mmol) in DCM (1 mL) was added TEA (0.043 mL, 0.31 mmol) followed by the addition of a solution of Intermediate 8 in DCM (1 mL). The reaction was stirred at rt overnight. The reaction was diluted with EtOAc, the solution washed with brine, dried over MgSO$_4$, filtered and concentrated to give the crude product. The crude product was dissolved in a small amount of DCM and charged to a 12 g silica gel cartridge which was eluted with a 25 min gradient from 0-100% EtOAc/hexane to give Example 1A (36 mg, 0.080 mmol, 78% yield) as a white solid.

Example 1B

N-(3-(3,4-dichlorophenyl)propyl)-3-methoxy-1-methyl-2-oxo-6-(3-(trifluoromethyl)phenyl)-1,2-dihydropyridine-4-carboxamide

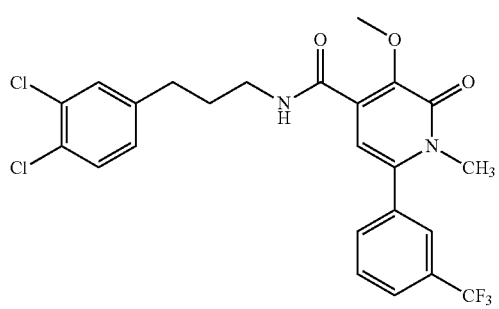 [SMILES: COc1c(C(=O)NCCCc2ccc(Cl)c(Cl)c2)cc(-c2cccc(C(F)(F)F)c2)n(C)c1=O]

To a solution of Example 1A (25 mg, 0.056 mmol) in DME (1.0 mL) (warmed slightly to give a clear solution) was added 3-(trifluoromethyl)phenylboronic acid (21.20 mg, 0.112 mmol), sodium carbonate (0.084 mL, 0.17 mmol), and Tetrakis(triphenylphosphine)palladium (0)-resin bound (0.11 mmol/g) (24 mg, 2.8 μmol) in a microwave vial. The reaction was degassed and heated at 110° C. for 6 h. The reaction was diluted with DCM, filtered and concentrated. The residue was dissolved in a small amount of DCM and charged to a 12 g silica gel cartridge which was eluted with a 25 min gradient from 0-100% EtOAc/hexane to give Example 1B (33 mg, 0.040 mmol, 71% yield) as a yellow solid. HPLC/MS (Method D) RT=2.1 min, [M+1]$^+$513.0.

Example 1

To a solution of Example 1B (11 mg, 0.025 mmol) in DCM (1.0 mL) was added boron tribromide-methyl sulfide complex (0.016 mL, 0.074 mmol) at rt. The reaction was stirred at rt overnight. The reaction was quenched with MeOH and concentrated. The residue was dissolved in MeOH and purified by reverse phase preparative HPLC (Method H) to give Example 1 (7 mg, 0.02 mmol, 70% yield) as a white solid. HPLC/MS (Method D) RT=0.2 min, [M+1]$^+$261.9. $^1$H NMR (400 MHz, CHLOROFORM-d) δ ppm 7.36-7.44 (3 H, m), 7.29-7.36 (3 H, m), 7.13-7.17 (1 H, m), 6.91 (1 H, dd, J=8.28, 2.01 Hz), 6.78 (1 H, s), 5.78 (1 H, br. s.), 3.64 (3 H, s), 3.24 (2 H, q, J=6.78 Hz), 2.36-2.43 (2 H, m), 1.53-1.70 (2 H, m, J=7.50, 7.50, 7.34, 7.03 Hz).

Examples 2-47 were synthesized from Example 1A and corresponding boronic acids following a similar procedure described for Example 1. The HPLC-MS data (retention time, mass and conditions) of Example 2-47 are listed in Table 2.

TABLE 2

| Ex. # | Structure | Name | RT (min) | [M + 1]$^+$ | LC/MS Methods |
|---|---|---|---|---|---|
| 2 | 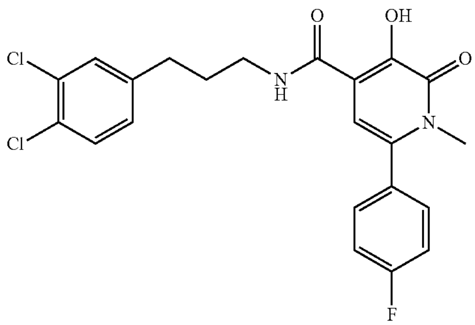 [SMILES: Cn1c(-c2ccc(F)cc2)cc(C(=O)NCCCc2ccc(Cl)c(Cl)c2)c(O)c1=O] | N-(3-(3,4-dichlorophenyl)propyl)-6-(4-fluorophenyl)-3-hydroxy-1-methyl-2-oxo-1,2-dihydropyridine-4-carboxamide | 2.0 | 448.9 | D |
| 3 | 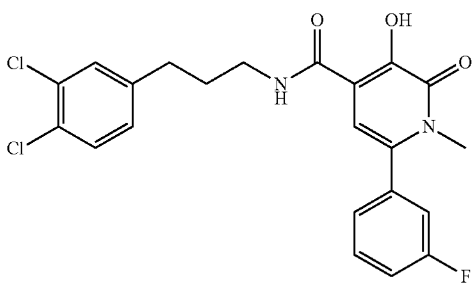 [SMILES: Cn1c(-c2cccc(F)c2)cc(C(=O)NCCCc2ccc(Cl)c(Cl)c2)c(O)c1=O] | N-(3-(3,4-dichlorophenyl)propyl)-6-(3-fluorophenyl)-3-hydroxy-1-methyl-2-oxo-1,2-dihydropyridine-4-carboxamide | 2.0 | 449.0 | D |
| 4 | 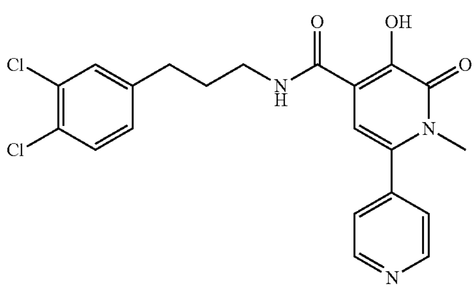 [SMILES: Cn1c(-c2ccncc2)cc(C(=O)NCCCc2ccc(Cl)c(Cl)c2)c(O)c1=O] | N-(3-(3,4-dichlorophenyl)propyl)-3-hydroxy-1-methyl-2-oxo-6-(pyridin-4-yl)-1,2-dihydropyridine-4-carboxamide | 1.54 | 431.9 | D |
| 5 | 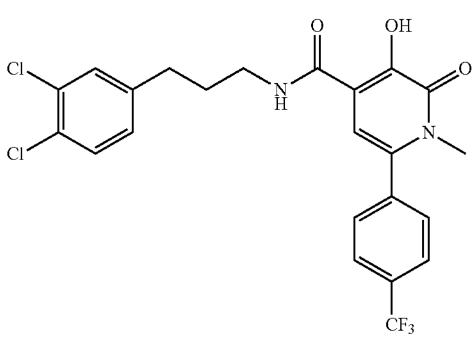 | N-(3-(3,4-dichlorophenyl)propyl)-3-hydroxy-1-methyl-2-oxo-6-(4-(trifluoromethyl)phenyl)-1,2-dihydropyridine-4-carboxamide | 2.1 | 498.9 | D |

TABLE 2-continued

| Ex. # | Structure | Name | RT (min) | [M + 1]+ | LC/MS Methods |
|---|---|---|---|---|---|
| 6 | 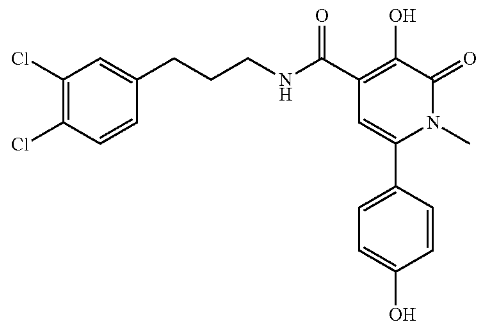 | N-(3-(3,4-dichlorophenyl) propyl)-3-hydroxy-6-(4-hydroxyphenyl)-1-methyl-2-oxo-1,2-dihydropyridine-4-carboxamide | 1.8 | 446.9 | D |
| 7 | 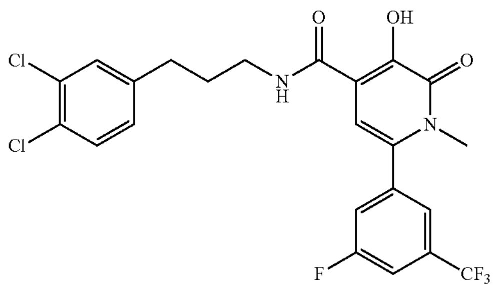 [SMILES: Cn1c(-c2cc(F)cc(C(F)(F)F)c2)cc(C(=O)NCCCc2ccc(Cl)c(Cl)c2)c(O)c1=O] | N-(3-(3,4-dichlorophenyl) propyl)-6-(3-fluoro-5-(trifluoromethyl)phenyl)-3-hydroxy-1-methyl-2-oxo-1,2-dihydropyridine-4-carboxamide | 2.2 | 517.0 | D |
| 8 | 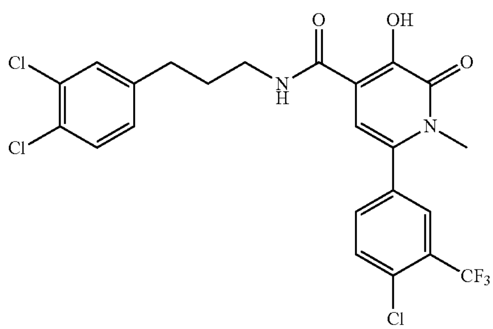 [SMILES: Cn1c(-c2ccc(Cl)c(C(F)(F)F)c2)cc(C(=O)NCCCc2ccc(Cl)c(Cl)c2)c(O)c1=O] | 6-(4-chloro-3-(trifluoromethyl) phenyl)-N-(3-(3,4-dichlorophenyl)propyl)-3-hydroxy-1-methyl-2-oxo-1,2-dihydropyridine-4-carboxamide | 2.2 | 5.33.0 | D |
| 9 | 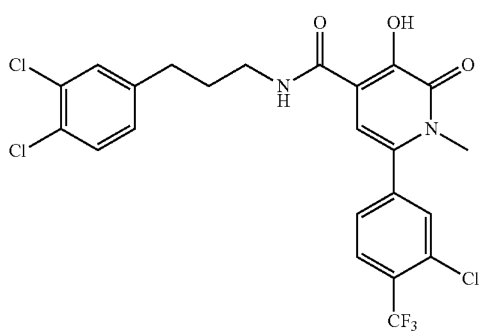 [SMILES: Cn1c(-c2ccc(C(F)(F)F)c(Cl)c2)cc(C(=O)NCCCc2ccc(Cl)c(Cl)c2)c(O)c1=O] | 6-(3-chloro-4-(trifluoromethyl) phenyl)-N-(3-(3,4-dichlorophenyl)propyl)-3-hydroxy-1-methyl-2-oxo-1,2-dihydropyridine-4-carboxamide | 2.2 | 533.0 | D |
| 10 | 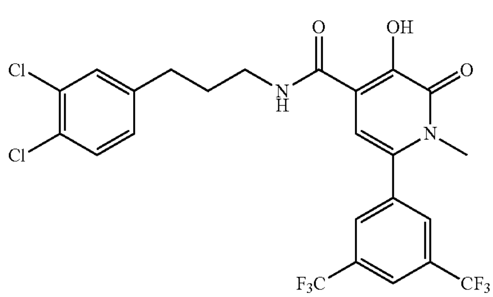 | 6-(3,5-bis(trifluoromethyl) phenyl)-N-(3-(3,4-dichlorophenyl)propyl)-3-hydroxy-1-methyl-2-oxo-1,2-dihydropyridine-4-carboxamide | 2.2 | 513.0 | D |

TABLE 2-continued

| Ex. # | Structure | Name | RT (min) | [M + 1]+ | LC/MS Methods |
|---|---|---|---|---|---|
| 11 | 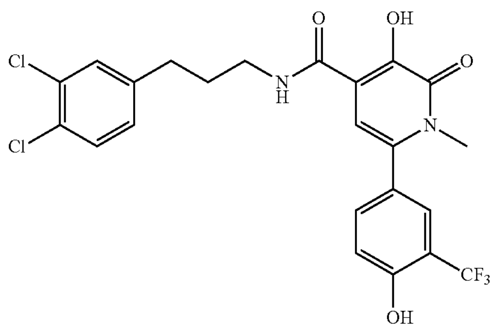 [SMILES: Cn1c(-c2ccc(O)c(C(F)(F)F)c2)cc(C(=O)NCCCc2ccc(Cl)c(Cl)c2)c(O)c1=O] | N-(3-(3,4-dichlorophenyl) propyl)-3-hydroxy-6-(4-hydroxy-3-(trifluoromethyl) phenyl)-1-methyl-2-oxo-1,2-dihydropyridine-4-carboxamide | 2.0 | 515.0 | D |
| 12 | 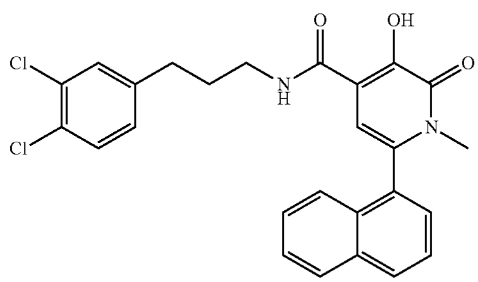 [SMILES: Cn1c(-c2cccc3ccccc23)cc(C(=O)NCCCc2ccc(Cl)c(Cl)c2)c(O)c1=O] | N-(3-(3,4-dichlorophenyl) propyl)-3-hydroxy-1-methyl-6-(naphthalen-1-yl)-2-oxo-1,2-dihydropyridine-4-carboxamide | 2.62 | 480.87 | F |
| 13 | 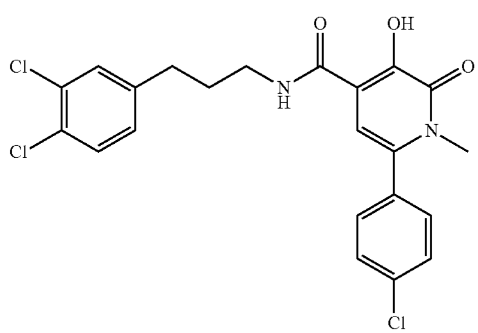 [SMILES: Cn1c(-c2ccc(Cl)cc2)cc(C(=O)NCCCc2ccc(Cl)c(Cl)c2)c(O)c1=O] | N-(3-(3,4-dichlorophenyl) propyl)-6-(4-chlorophenyl)-3-hydroxy-1-methyl-2-oxo-1,2-dihydropyridine-4-carboxamide | 2.52 | 464.83 | F |
| 14 | 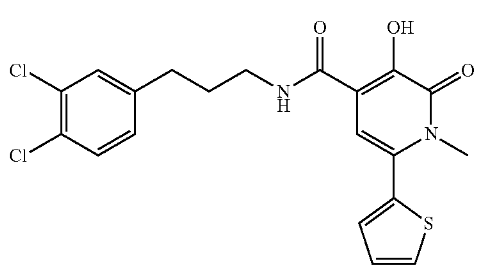 [SMILES: Cn1c(-c2cccs2)cc(C(=O)NCCCc2ccc(Cl)c(Cl)c2)c(O)c1=O] | N-(3-(3,4-dichlorophenyl) propyl)-3-hydroxy-1-methyl-2-oxo-6-(thiophen-2-yl)-1,2-dihydropyridine-4-carboxamide | 2.31 | 436.86 | F |
| 15 | 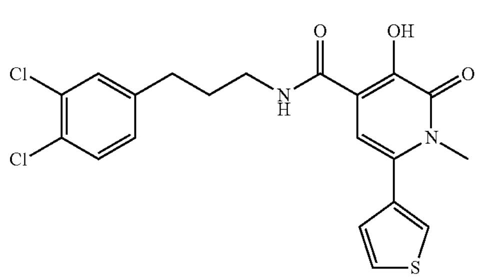 [SMILES: Cn1c(-c2ccsc2)cc(C(=O)NCCCc2ccc(Cl)c(Cl)c2)c(O)c1=O] | N-(3-(3,4-dichlorophenyl) propyl)-3-hydroxy-1-methyl-2-oxo-6-(thiophen-3-yl)-1,2-dihydropyridine-4-carboxamide | 2.32 | 436.86 | F |

TABLE 2-continued

| Ex. # | Structure | Name | RT (min) | [M + 1]+ | LC/MS Methods |
|---|---|---|---|---|---|
| 16 | 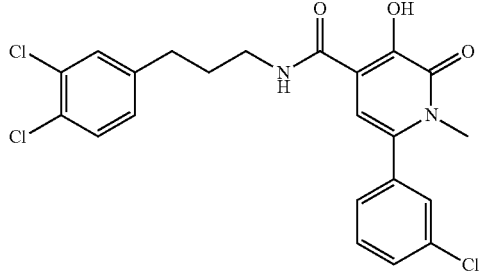 [SMILES: Cn1c(-c2cccc(Cl)c2)cc(C(=O)NCCCc2ccc(Cl)c(Cl)c2)c(O)c1=O] | 6-(3-chlorophenyl)-N-(3-(3,4-dichlorophenyl)propyl)-3-hydroxy-1-methyl-2-oxo-1,2-dihydropyridine-4-carboxamide | 2.53 | 464.83 | F |
| 17 | 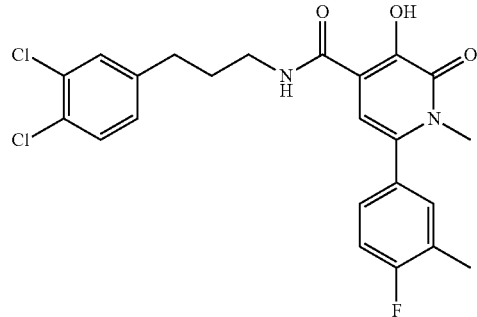 | N-(3-(3,4-dichlorophenyl)propyl)-6-(4-fluoro-3-methylphenyl)-3-hydroxy-1-methyl-2-oxo-1,2-dihydropyridine-4-carboxamide | 2.50 | 462.9 | F |
| 18 | 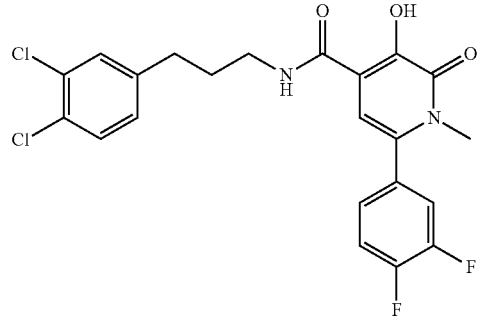 [SMILES: Cn1c(-c2ccc(F)c(F)c2)cc(C(=O)NCCCc2ccc(Cl)c(Cl)c2)c(O)c1=O] | N-(3-(3,4-dichlorophenyl)propyl)-6-(3,4-difluorophenyl)-3-hydroxy-1-methyl-2-oxo-1,2-dihydropyridine-4-carboxamide | 2.43 | 466.84 | F |
| 19 | 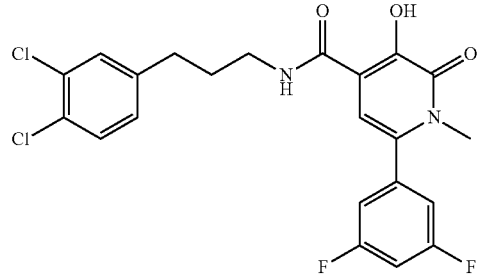 [SMILES: Cn1c(-c2cc(F)cc(F)c2)cc(C(=O)NCCCc2ccc(Cl)c(Cl)c2)c(O)c1=O] | N-(3-(3,4-dichlorophenyl)propyl)-6-(3,5-difluorophenyl)-3-hydroxy-1-methyl-2-oxo-1,2-dihydropyridine-4-carboxamide | 2.47 | 466.84 | F |
| 20 | 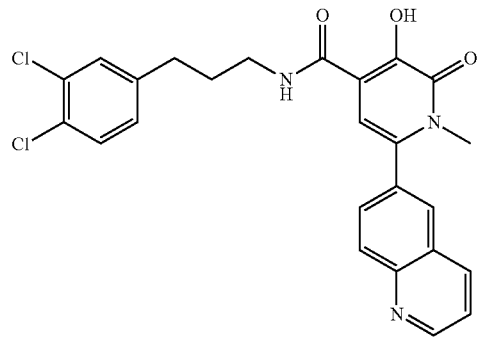 [SMILES: Cn1c(-c2ccc3ncccc3c2)cc(C(=O)NCCCc2ccc(Cl)c(Cl)c2)c(O)c1=O] | N-(3-(3,4-dichlorophenyl)propyl)-3-hydroxy-1-methyl-2-oxo-6-(quinolin-6-yl)-1,2-dihydropyridine-4-carboxamide | 2.00 | 481.86 | F |

TABLE 2-continued

| Ex. # | Structure | Name | RT (min) | [M + 1]+ | LC/MS Methods |
|---|---|---|---|---|---|
| 21 | 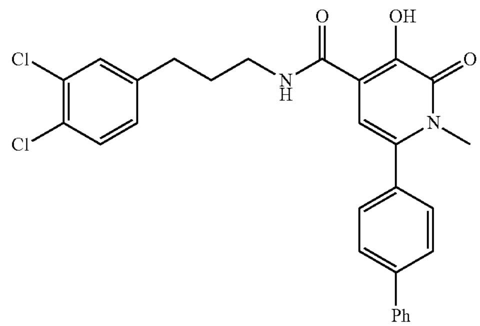 | 6-(biphenyl-3-yl)-N-(3-(3,4-dichlorophenyl)propyl)-3-hydroxy-1-methyl-2-oxo-1,2-dihydropyridine-4-carboxamide | 2.75 | 506.9 | F |
| 22 | 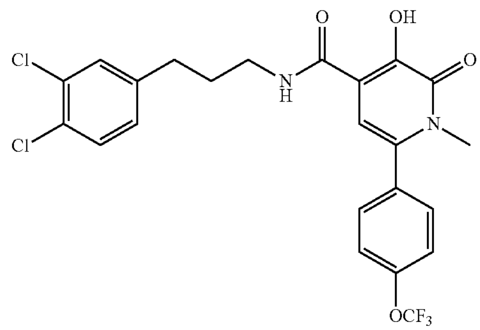 [SMILES: Cn1c(-c2ccc(OC(F)(F)F)cc2)cc(C(=O)NCCCc2ccc(Cl)c(Cl)c2)c(O)c1=O] | N-(3-(3,4-dichlorophenyl)propyl)-3-hydroxy-1-methyl-2-oxo-6-(4-(trifluoromethoxy)phenyl)-1,2-dihydropyridine-4-carboxamide | | | F |
| 23 | 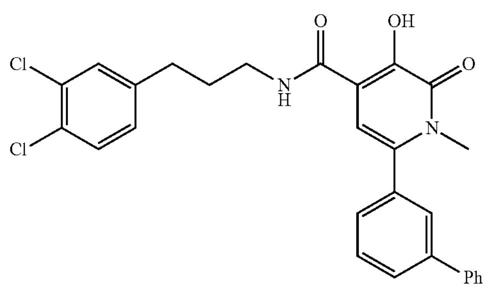 [SMILES: Cn1c(-c2cccc(-c3ccccc3)c2)cc(C(=O)NCCCc2ccc(Cl)c(Cl)c2)c(O)c1=O] | 6-(biphenyl-3-yl)-N-(3-(3,4-dichlorophenyl)propyl)-3-hydroxy-1-methyl-2-oxo-1,2-dihydropyridine-4-carboxamide | 2.79 | 506.92 | F |
| 24 | 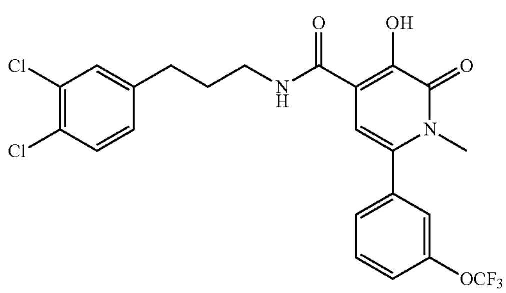 [SMILES: Cn1c(-c2cccc(OC(F)(F)F)c2)cc(C(=O)NCCCc2ccc(Cl)c(Cl)c2)c(O)c1=O] | N-(3-(3,4-dichlorophenyl)propyl)-3-hydroxy-1-methyl-2-oxo-6-(3-(trifluoromethoxy)phenyl)-1,2-dihydropyridine-4-carboxamide | 2.69 | 514.84 | F |
| 25 | 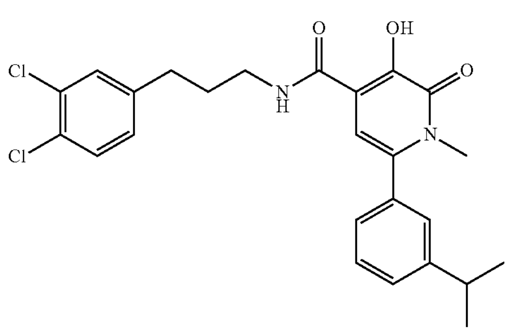 [SMILES: CC(C)c1cccc(-c2cc(C(=O)NCCCc3ccc(Cl)c(Cl)c3)c(O)c(=O)n2C)c1] | N-(3-(3,4-dichlorophenyl)propyl)-3-hydroxy-6-(3-isopropylphenyl)-1-methyl-2-oxo-1,2-dihydropyridine-4-carboxamide | 2.78 | 472.93 | F |

TABLE 2-continued

| Ex. # | Structure | Name | RT (min) | [M + 1]+ | LC/MS Methods |
|---|---|---|---|---|---|
| 26 | 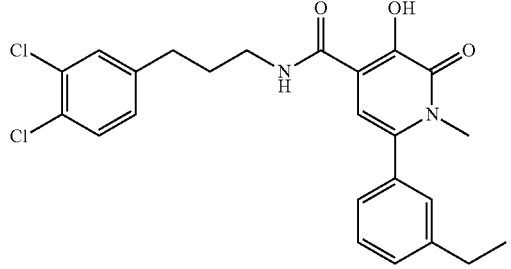 [SMILES: CCc1cccc(-c2cc(C(=O)NCCCc3ccc(Cl)c(Cl)c3)c(O)c(=O)n2C)c1] | N-(3-(3,4-dichlorophenyl) propyl)-6-(3-ethylphenyl)-3-hydroxy-1-methyl-2-oxo-1,2-dihydropyridine-4-carboxamide | 2.65 | 458.9 | F |
| 27 | 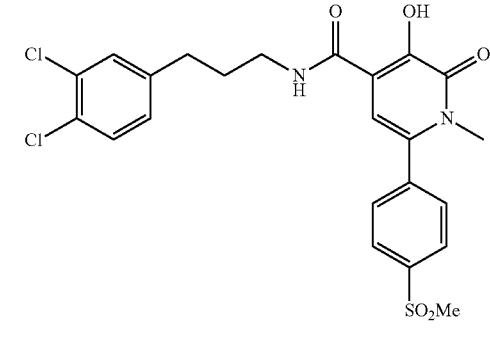 [SMILES: Cn1c(-c2ccc(S(C)(=O)=O)cc2)cc(C(=O)NCCCc2ccc(Cl)c(Cl)c2)c(O)c1=O] | N-(3-(3,4-dichlorophenyl) propyl)-3-hydroxy-1-methyl-6-(4-(methylsulfonyl) phenyl)-2-oxo-1,2-dihydropyridine-4-carboxamide | 1.98 | 508.83 | F |
| 28 | 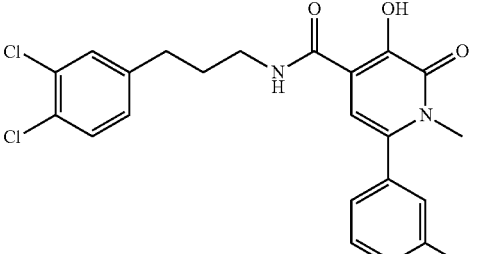 | N-(3-(3,4-dichlorophenyl) propyl)-3-hydroxy-1-methyl-6-(3-(methylsulfonyl) phenyl)-2-oxo-1,2-dihydropyridine-4-carboxamide | 2.04 | 508.83 | F |
| 29 | 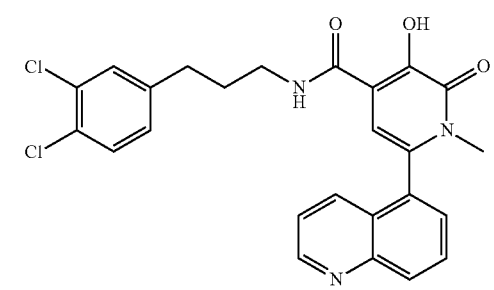 [SMILES: Cn1c(-c2cccc3ncccc23)cc(C(=O)NCCCc2ccc(Cl)c(Cl)c2)c(O)c1=O] | N-(3-(3,4-dichlorophenyl) propyl)-3-hydroxy-1-methyl-2-oxo-6-(quinolin-5-yl)-1,2-dihydropyridine-4-carboxamide | 2.02 | 481.88 | F |
| 30 | 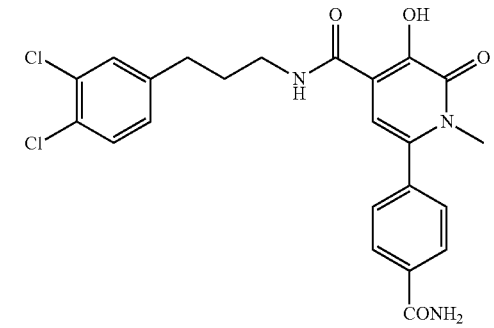 [SMILES: Cn1c(-c2ccc(C(N)=O)cc2)cc(C(=O)NCCCc2ccc(Cl)c(Cl)c2)c(O)c1=O] | 6-(4-carbamoylphenyl)-N-(3-(3,4-dichlorophenyl) propyl)-3-hydroxy-1-methyl-2-oxo-1,2-dihydropyridine-4-carboxamide | 1.68 | 473.87 | F |

TABLE 2-continued

| Ex. # | Structure | Name | RT (min) | [M + 1]+ | LC/MS Methods |
|---|---|---|---|---|---|
| 31 | 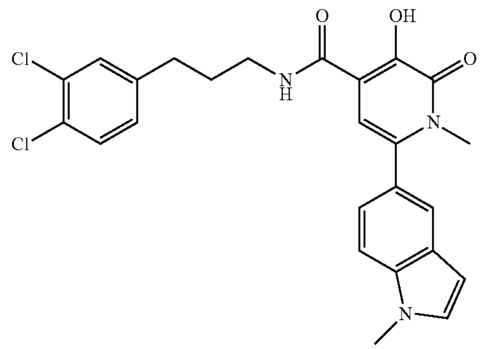 [SMILES: Cn1c(-c2ccc3c(ccn3C)c2)cc(C(=O)NCCCc2ccc(Cl)c(Cl)c2)c(O)c1=O] | N-(3-(3,4-dichlorophenyl)propyl)-3-hydroxy-1-methyl-6-(1-methyl-1H-indol-5-yl)-2-oxo-1,2-dihydropyridine-4-carboxamide | 2.41 | 483.9 | F |
| 32 | 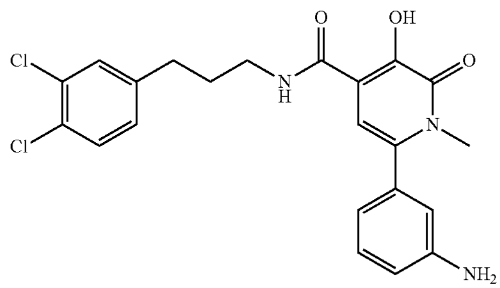 [SMILES: Cn1c(-c2cccc(N)c2)cc(C(=O)NCCCc2ccc(Cl)c(Cl)c2)c(O)c1=O] | 6-(3-aminophenyl)-N-(3-(3,4-dichlorophenyl)propyl)-3-hydroxy-1-methyl-2-oxo-1,2-dihydropyridine-4-carboxamide | 2.03 | 445.89 | F |
| 33 | 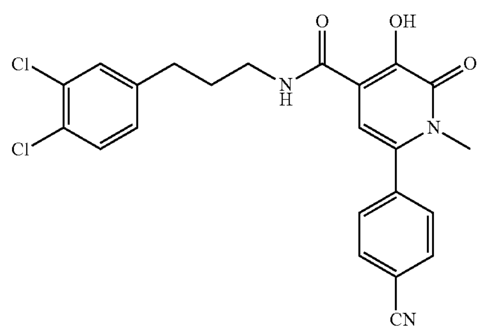 [SMILES: Cn1c(-c2ccc(C#N)cc2)cc(C(=O)NCCCc2ccc(Cl)c(Cl)c2)c(O)c1=O] | 6-(4-cyanophenyl)-N-(3-(3,4-dichlorophenyl)propyl)-3-hydroxy-1-methyl-2-oxo-1,2-dihydropyridine-4-carboxamide | 2.19 | 455.88 | F |
| 34 | 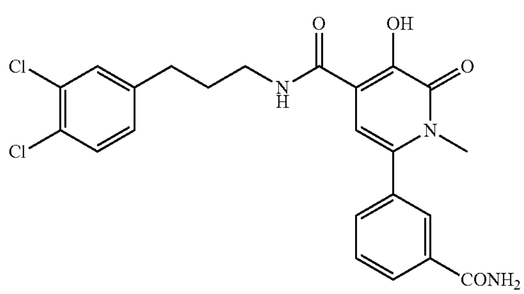 [SMILES: Cn1c(-c2cccc(C(N)=O)c2)cc(C(=O)NCCCc2ccc(Cl)c(Cl)c2)c(O)c1=O] | 6-(3-carbamoylphenyl)-N-(3-(3,4-dichlorophenyl)propyl)-3-hydroxy-1-methyl-2-oxo-1,2-dihydropyridine-4-carboxamide | 1.79 | 473.89 | F |
| 35 | 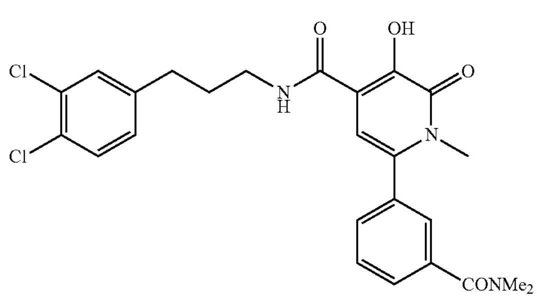 | N-(3-(3,4-dichlorophenyl)propyl)-6-(3-(dimethylcarbamoyl)phenyl)-3-hydroxy-1-methyl-2-oxo-1,2-dihydropyridine-4-carboxamide | 2.00 | 501.89 | F |

TABLE 2-continued

| Ex. # | Structure | Name | RT (min) | [M + 1]+ | LC/MS Methods |
|---|---|---|---|---|---|
| 36 | 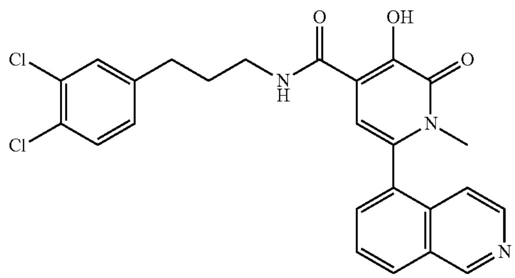 [SMILES: Cn1c(-c2cccc3cnccc23)cc(C(=O)NCCCc2ccc(Cl)c(Cl)c2)c(O)c1=O] | N-(3-(3,4-dichlorophenyl)propyl)-3-hydroxy-6-(isoquinolin-5-yl)-1-methyl-2-oxo-1,2-dihydropyridine-4-carboxamide | 2.03 | 481.87 | F |
| 37 | 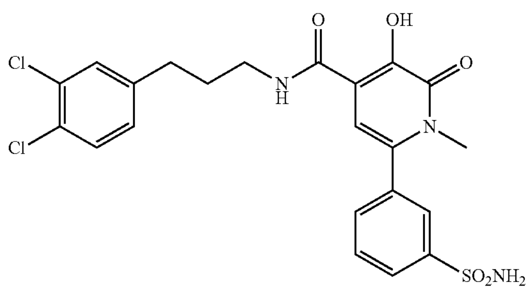 [SMILES: Cn1c(-c2cccc(S(N)(=O)=O)c2)cc(C(=O)NCCCc2ccc(Cl)c(Cl)c2)c(O)c1=O] | N-(3-(3,4-dichlorophenyl)propyl)-3-hydroxy-1-methyl-2-oxo-6-(3-sulfamoylphenyl)-1,2-dihydropyridine-4-carboxamide | 1.92 | 509.82 | F |
| 38 | 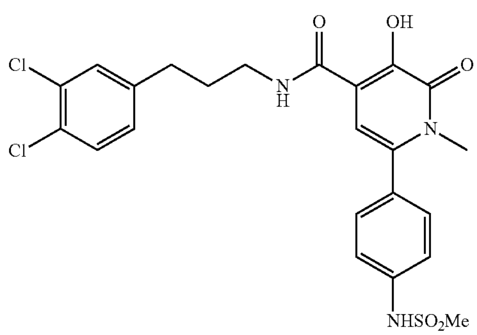 | N-(3-(3,4-dichlorophenyl)propyl)-3-hydroxy-1-methyl-6-(4-(methylsulfonamido)phenyl)-2-oxo-1,2-dihydropyridine-4-carboxamide | 1.92 | 523.96 | F |
| 39 | 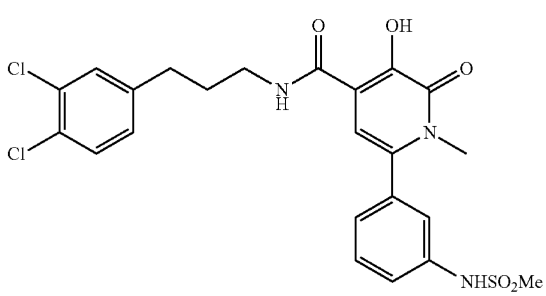 | N-(3-(3,4-dichlorophenyl)propyl)-3-hydroxy-1-methyl-6-(3-(methylsulfonamido)phenyl)-2-oxo-1,2-dihydropyridine-4-carboxamide | 2.06 | 523.99 | F |
| 40 | 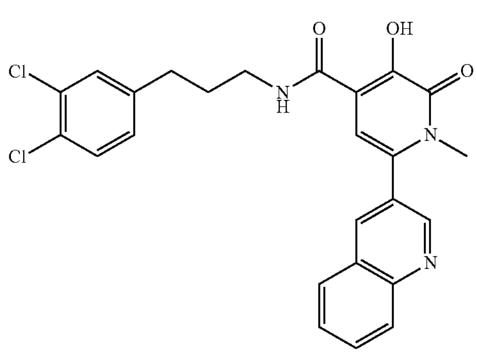 [SMILES: Cn1c(-c2cnc3ccccc3c2)cc(C(=O)NCCCc2ccc(Cl)c(Cl)c2)c(O)c1=O] | N-(3-(3,4-dichlorophenyl)propyl)-3-hydroxy-1-methyl-2-oxo-6-(quinolin-3-yl)-1,2-dihydropyridine-4-carboxamide | 2.20 | 482.04 | F |

TABLE 2-continued

| Ex. # | Structure | Name | RT (min) | [M + 1]+ | LC/MS Methods |
|---|---|---|---|---|---|
| 41 | 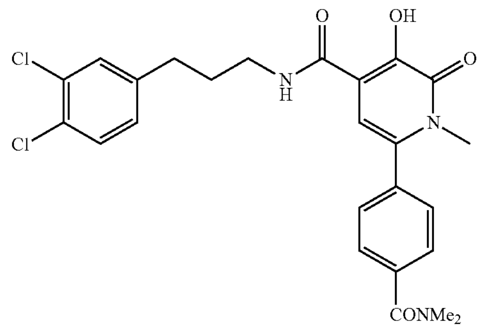 | N-(3-(3,4-dichlorophenyl) propyl)-6-(4-(dimethylcarbamoyl) phenyl)-3-hydroxy-1-methyl-2-oxo-1,2-dihydropyridine-4-carboxamide | 1.93 | 501.99 | F |
| 42 | 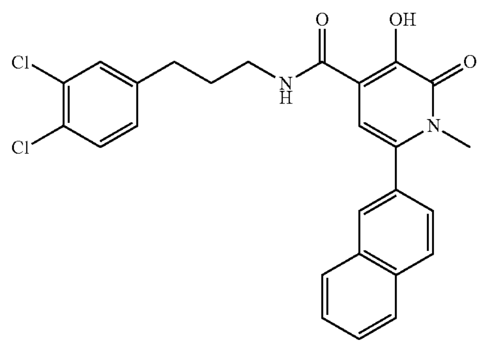 | N-(3-(3,4-dichlorophenyl) propyl)-3-hydroxy-1-methyl-6-(naphthalen-2-yl)-2-oxo-1,2-dihydropyridine-4-carboxamide | 2.63 | 481.04 | F |
| 43 | 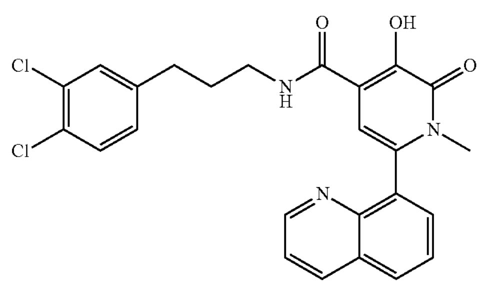 [SMILES: Cn1c(-c2cccc3cccnc23)cc(C(=O)NCCCc2ccc(Cl)c(Cl)c2)c(O)c1=O] | N-(3-(3,4-dichlorophenyl) propyl)-3-hydroxy-1-methyl-2-oxo-6-(quinolin-8-yl)-1,2-dihydropyridine-4-carboxamide | 2.25 | 482.03 | F |
| 44 | 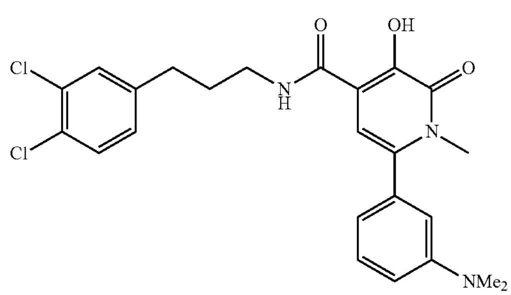 [SMILES: Cn1c(-c2cccc(C(=O)O)c2)cc(C(=O)NCCCc2ccc(Cl)c(Cl)c2)c(O)c1=O] | N-(3-(3,4-dichlorophenyl) propyl)-6-(3-(dimethylamino)phenyl)-3-hydroxy-1-methyl-2-oxo-1,2-dihydropyridine-4-carboxamide | 2.52 | 474.07 | F |
| 45 | 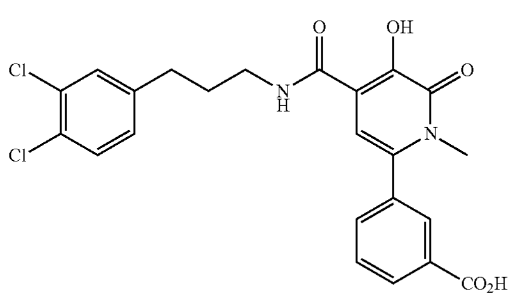 | 3-(4-(3-(3,4-dichlorophenyl) propylcarbamoyl)-5-hydroxy-1-methyl-6-oxo-1,6-dihydropyridin-2-yl)benzoic acid | 1.83 | 475.1 | D |

TABLE 2-continued

| Ex. # | Structure | Name | RT (min) | [M + 1]+ | LC/MS Methods |
|---|---|---|---|---|---|
| 46 | 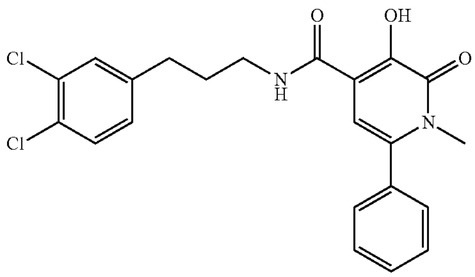 [SMILES: Cn1c(-c2ccccc2)cc(C(=O)NCCCc2ccc(Cl)c(Cl)c2)c(O)c1=O] | N-(3-(3,4-dichlorophenyl)propyl)-3-hydroxy-1-methyl-2-oxo-6-phenyl-1,2-dihydropyridine-4-carboxamide | 2.0 | 431.0 | D |
| 47 | 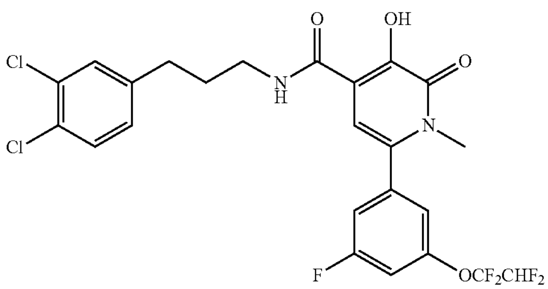 | N-(3-(3,4-dichlorophenyl)propyl)-6-(3-fluoro-5-(1,1,2,2-tetrafluoroethoxy)phenyl)-3-hydroxy-1-methyl-2-oxo-1,2-dihydropyridine-4-carboxamide | 2.2 | 565.2 | D |

Example 48

N-(3-(2-chlorophenoxy)propyl)-6-(3-fluoro-5-(trifluoromethyl)phenyl)-3-hydroxy-1-methyl-2-oxo-1,2-dihydropyridine-4-carboxamide

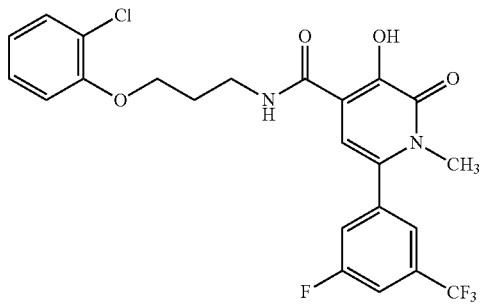 [SMILES: Cn1c(-c2cc(F)cc(C(F)(F)F)c2)cc(C(=O)NCCCOc2ccccc2Cl)c(O)c1=O]

A mixture of Intermediate 6 (319 mg, 1.10 mmol), 3-fluoro-5-(trifluoromethyl)phenylboronic acid (343 mg, 1.65 mmol), sodium carbonate (2 M) (1.649 mL, 3.300 mmol) in DME (9 mL) was placed in a microwave vial and degassed with argon. Pd(Ph$_3$)$_4$ (63.5 mg, 0.0550 mmol) was added to the mixture and the resulting reaction mixture degassed with argon. The sealed tube was heated at 160° C., in the microwave for 30 min. The reaction was filtered and the filtrate was concentrated with Celite® and charged to a 40 g silica gel cartridge which was eluted with a 30 min gradient from 0-100% EtOAc/hexane to give Example 48A (240 mg, 0.643 mmol, 58.5% yield) as a yellow solid. HPLC/MS (Method D) RT=2.0 min, [M+1]$^+$374.1.

Example 48A ethyl 6-(3-fluoro-5-(trifluoromethyl)phenyl)-3-methoxy-1-methyl-2-oxo-1,2-dihydropyridine-4-carboxylate

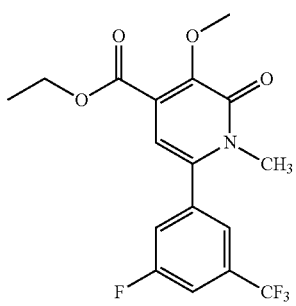 [SMILES: CCOC(=O)c1cc(-c2cc(F)cc(C(F)(F)F)c2)n(C)c(=O)c1OC]

Example 48B 6-(3-fluoro-5-(trifluoromethyl)phenyl)-3-methoxy-1-methyl-2-oxo-1,2-dihydropyridine-4-carboxylic acid

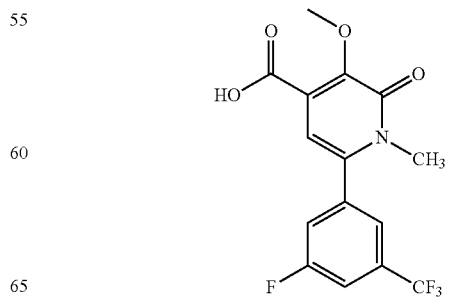

To a solution of Example 48A (102 mg, 0.273 mmol) in THF (3 mL) in MeOH (1 mL) was added lithium hydroxide (19.63 mg, 0.8200 mmol) and water (0.5 mL). The reaction was heated at 65° C. overnight. The reaction was acidified with HCl (0.091 mL, 1.1 mmol) and concentrated to give Example 48B (127 mg, 0.272 mmol, 100% yield) as a grey solid. HPLC/MS (Method D) RT=1.68 min, [M+1]$^+$346.0.

Example 48C

N-(3-(2-chlorophenoxy)propyl)-6-(3-fluoro-5-(trifluoromethyl)phenyl)-3-methoxy-1-methyl-2-oxo-1,2-dihydropyridine-4-carboxamide

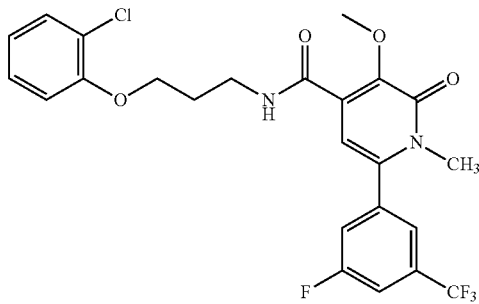 [SMILES: COc1c(C(=O)NCCCOc2ccccc2Cl)cc(-c2cc(F)cc(C(F)(F)F)c2)n(C)c1=O]

To a solution of Example 48B (32 mg, 0.069 mmol) in DCM (1.5 mL) and DMF (150 µL) was added 3-(2-chlorophenoxy)propan-1-aminium chloride (15.23 mg, 0.069 mmol), DIPEA (50 µL, 0.286 mmol) and benzotriazol-1-yloxytripyrrolidino-phosphonium hexafluorophosphate (PyBOP) (35.7 mg, 0.069 mmol). The mixture was stirred for 48 h at rt. The reaction was concentrated and the residue was purified by silica gel chromatography (4 g column, eluted with 0-100% EtOAc/hexane over 25 min. gradient) to give Example 48C (39 mg, 0.065 mmol, 94% yield) as a yellow solid which was used directly in the next reaction.

Example 48

To a solution of Example 48C (39.3 mg, 0.0770 mmol) in DCM (1.5 mL) and was added boron tribromide (1.0 M in DCM, 0.230 mL, 0.230 mmol) at rt. The reaction was stirred at rt for 3 h. The reaction was quenched with MeOH (0.5 mL) and water (5 drops) and stirred at rt for 10 min. The reaction mixture was concentrated and the residue was dissolved in MeOH and purified by reverse phase preparative HPLC (column: Phenomenex Luna, 5µ, C18, 30×250 mm, 20 min gradient from 30-100% B. A=H$_2$O/ACN/TFA 90/10/0.1. B=ACN/H$_2$O/TFA 90/10/0.1) to give Example 48 (5 mg, 10 mmol, 13% yield) as a white solid. HPLC/MS (Method D) RT=2.2 min, [M+1]$^+$533.0. $^1$H NMR (400 MHz, CHLOROFORM-d) δ ppm 7.39 (1 H, s), 7.32 (1 H, dd, J=7.91, 1.63 Hz), 7.27 (1 H, br. s.), 7.23-7.26 (1 H, m), 7.21 (1 H, dd, J=7.91, 1.38 Hz), 7.05 (1 H, t, J=5.14 Hz), 6.87-6.95 (2 H, m), 6.86 (1 H, s), 4.05-4.13 (2 H, m), 3.68 (3 H, s), 3.57-3.65 (2 H, m), 2.00-2.04 (2 H, m).

Examples 49-81 were synthesized from Example 48B and the corresponding amines following a similar procedure described for Example 48. The HPLC-MS data (retention time, mass and conditions) for examples 49-81 are listed in Table 3.

TABLE 3

| Ex. # | Structure | Name | RT (min) | [M + 1]$^+$ | LC/MS Methods |
|---|---|---|---|---|---|
| 49 | 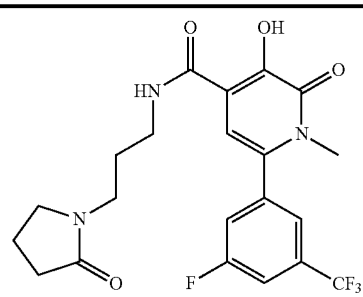 | 6-(3-fluoro-5-(trifluoromethyl)phenyl)-3-hydroxy-1-methyl-2-oxo-N-(3-(2-oxopyrrolidin-1-yl)propyl)-1,2-dihydropyridine-4-carboxamide | 1.6 | 456.04 | F |
| 50 | 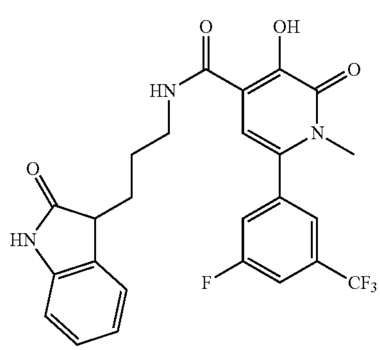 [SMILES: Cn1c(-c2cc(F)cc(C(F)(F)F)c2)cc(C(=O)NCCCC2C(=O)Nc3ccccc32)c(O)c1=O] | 6-(3-fluoro-5-(trifluoromethyl)phenyl)-3-hydroxy-1-methyl-2-oxo-N-(2-(2-oxoindolin-3-yl)ethyl)-1,2-dihydropyridine-4-carboxamide | 1.9 | 490.02 | F |

TABLE 3-continued

| Ex. # | Structure | Name | RT (min) | [M + 1]+ | LC/MS Methods |
|---|---|---|---|---|---|
| 51 | 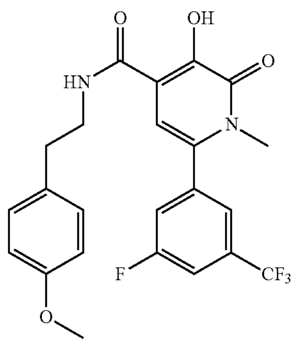 [SMILES: COc1ccc(CCNC(=O)c2cc(-c3cc(F)cc(C(F)(F)F)c3)n(C)c(=O)c2O)cc1] | 6-(3-fluoro-5-(trifluoromethyl)phenyl)-3-hydroxy-N-(4-methoxyphenethyl)-1-methyl-2-oxo-1,2-dihydropyridine-4-carboxamide | 2.3 | 465.01 | F |
| 52 | 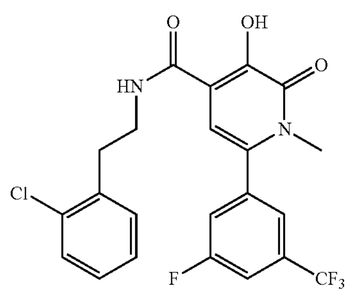 [SMILES: Cn1c(-c2cc(F)cc(C(F)(F)F)c2)cc(C(=O)NCCc2ccccc2Cl)c(O)c1=O] | N-(2-chlorophenethyl)-6-(3-fluoro-5-(trifluoromethyl)phenyl)-3-hydroxy-1-methyl-2-oxo-1,2-dihydropyridine-4-carboxamide | 2.5 | 468.98 | F |
| 53 | 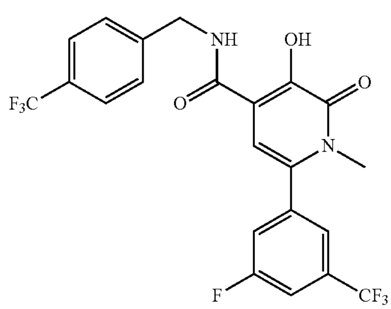 [SMILES: Cn1c(-c2cc(F)cc(C(F)(F)F)c2)cc(C(=O)NCc2ccc(C(F)(F)F)cc2)c(O)c1=O] | 6-(3-fluoro-5-(trifluoromethyl)phenyl)-3-hydroxy-1-methyl-2-oxo-N-(4-(trifluoromethyl)benzyl)-1,2-dihydropyridine-4-carboxamide | 2.5 | 489 | F |
| 54 | 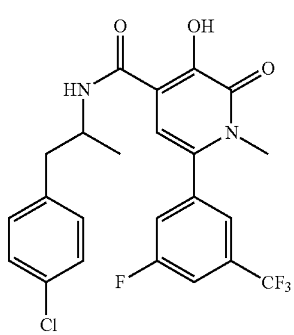 [SMILES: CC(Cc1ccc(Cl)cc1)NC(=O)c1cc(-c2cc(F)cc(C(F)(F)F)c2)n(C)c(=O)c1O] | N-(1-(4-chlorophenyl)propan-2-yl)-6-(3-fluoro-5-(trifluoromethyl)phenyl)-3-hydroxy-1-methyl-2-oxo-1,2-dihydropyridine-4-carboxamide | 2.7 | 482.97 | F |

TABLE 3-continued

| Ex. # | Structure | Name | RT (min) | [M + 1]+ | LC/MS Methods |
|---|---|---|---|---|---|
| 55 | 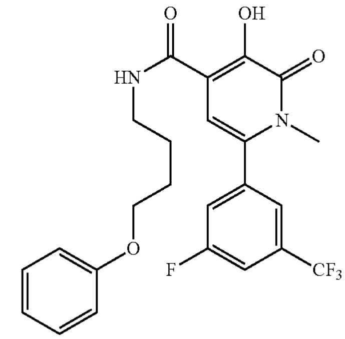 [SMILES: Cn1c(-c2cc(F)cc(C(F)(F)F)c2)cc(C(=O)NCCCCOc2ccccc2)c(O)c1=O] | 6-(3-fluoro-5-(trifluoromethyl)phenyl)-3-hydroxy-1-methyl-2-oxo-N-(4-phenoxybutyl)-1,2-dihydropyridine-4-carboxamide | 2.5 | 479.04 | F |
| 56 | 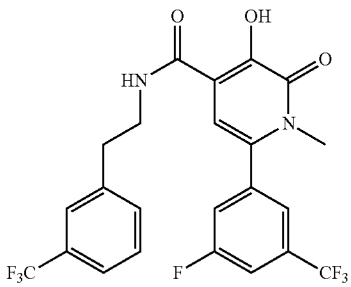 [SMILES: Cn1c(-c2cc(F)cc(C(F)(F)F)c2)cc(C(=O)NCCc2cccc(C(F)(F)F)c2)c(O)c1=O] | 6-(3-fluoro-5-(trifluoromethyl)phenyl)-3-hydroxy-1-methyl-2-oxo-N-(3-(trifluoromethyl)phenethyl)-1,2-dihydropyridine-4-carboxamide | 2.6 | 502.98 | F |
| 57 | 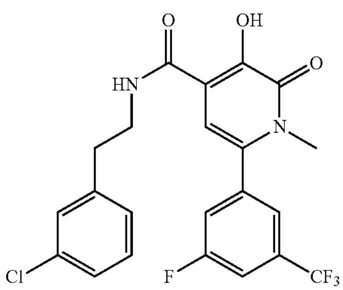 [SMILES: Cn1c(-c2cc(F)cc(C(F)(F)F)c2)cc(C(=O)NCCc2cccc(Cl)c2)c(O)c1=O] | N-(3-chlorophenethyl)-6-(3-fluoro-5-(trifluoromethyl)phenyl)-3-hydroxy-1-methyl-2-oxo-1,2-dihydropyridine-4-carboxamide | 2.5 | 468.96 | F |
| 58 | 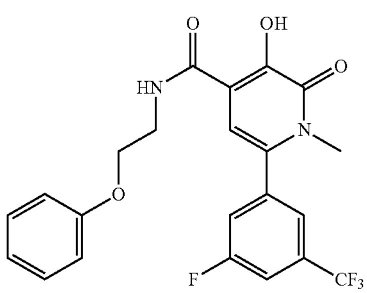 [SMILES: Cn1c(-c2cc(F)cc(C(F)(F)F)c2)cc(C(=O)NCCOc2ccccc2)c(O)c1=O] | 6-(3-fluoro-5-(trifluoromethyl)phenyl)-3-hydroxy-1-methyl-2-oxo-N-(2-phenoxyethyl)-1,2-dihydropyridine-4-carboxamide | 2.3 | 451.03 | F |
| 59 | 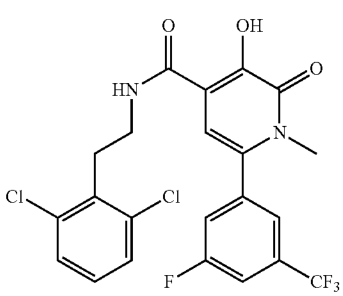 [SMILES: Cn1c(-c2cc(F)cc(C(F)(F)F)c2)cc(C(=O)NCCc2c(Cl)cccc2Cl)c(O)c1=O] | N-(2,6-dichlorophenethyl)-6-(3-fluoro-5-(trifluoromethyl)phenyl)-3-hydroxy-1-methyl-2-oxo-1,2-dihydropyridine-4-carboxamide | 2.6 | 502.93 | F |

TABLE 3-continued

| Ex. # | Structure | Name | RT (min) | [M + 1]+ | LC/MS Methods |
|---|---|---|---|---|---|
| 60 | 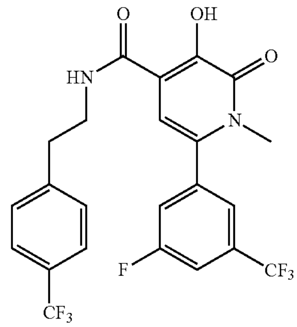 [SMILES: Cn1c(-c2cc(F)cc(C(F)(F)F)c2)cc(C(=O)NCCc2ccc(C(F)(F)F)cc2)c(O)c1=O] | 6-(3-fluoro-5-(trifluoromethyl)phenyl)-3-hydroxy-1-methyl-2-oxo-N-(4-(trifluoromethyl)phenethyl)-1,2-dihydropyridine-4-carboxamide | 2.6 | 502.97 | F |
| 61 | 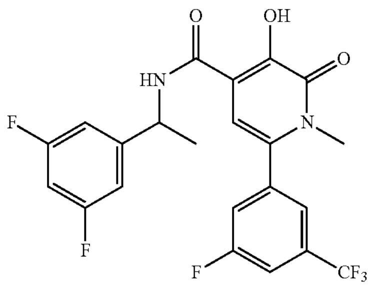 [SMILES: CC(NC(=O)c1cc(-c2cc(F)cc(C(F)(F)F)c2)n(C)c(=O)c1O)c1cc(F)cc(F)c1] | N-(1-(3,5-difluorophenyl)ethyl)-6-(3-fluoro-5-(trifluoromethyl)phenyl)-3-hydroxy-1-methyl-2-oxo-1,2-dihydropyridine-4-carboxamide | 2.4 | 470.97 | F |
| 62 | 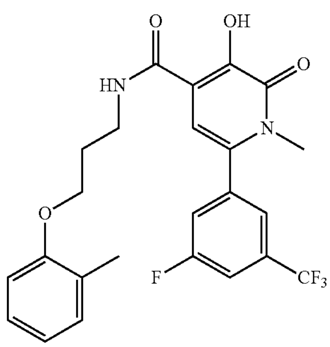 [SMILES: Cc1ccccc1OCCCNC(=O)c1cc(-c2cc(F)cc(C(F)(F)F)c2)n(C)c(=O)c1O] | 6-(3-fluoro-5-(trifluoromethyl)phenyl)-3-hydroxy-1-methyl-2-oxo-N-(3-(o-tolyloxy)propyl)-1,2-dihydropyridine-4-carboxamide | 2.6 | 479.04 | F |
| 63 | 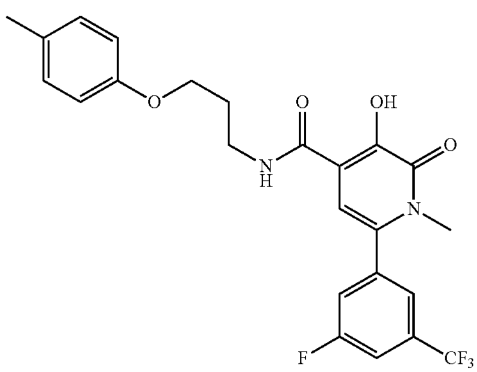 [SMILES: Cc1ccc(OCCCNC(=O)c2cc(-c3cc(F)cc(C(F)(F)F)c3)n(C)c(=O)c2O)cc1] | 6-(3-fluoro-5-(trifluoromethyl)phenyl)-3-hydroxy-1-methyl-2-oxo-N-(3-(p-tolyloxy)propyl)-1,2-dihydropyridine-4-carboxamide | 2.6 | 479.02 | F |

TABLE 3-continued

| Ex. # | Structure | Name | RT (min) | [M + 1]⁺ | LC/MS Methods |
|---|---|---|---|---|---|
| 64 | 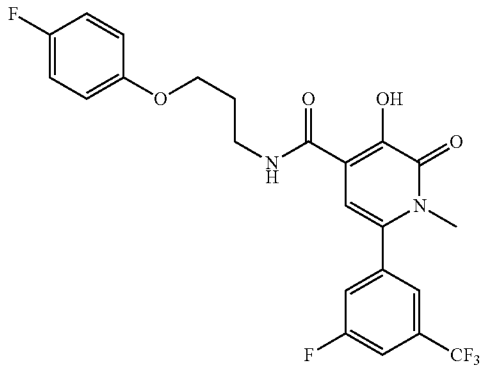 [SMILES: Cn1c(-c2cc(F)cc(C(F)(F)F)c2)cc(C(=O)NCCCOc2ccc(F)cc2)c(O)c1=O] | 6-(3-fluoro-5-(trifluoromethyl)phenyl)-N-(3-(4-fluorophenoxy)propyl)-3-hydroxy-1-methyl-2-oxo-1,2-dihydropyridine-4-carboxamide | 2.4 | 483.02 | F |
| 65 | 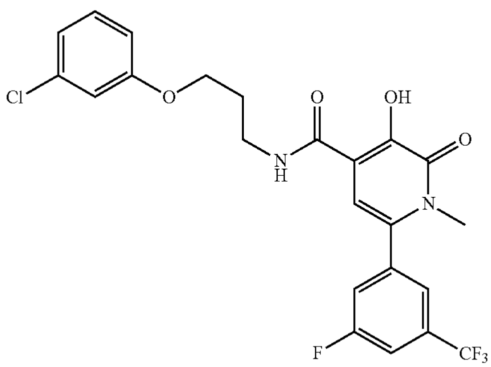 [SMILES: Cn1c(-c2cc(F)cc(C(F)(F)F)c2)cc(C(=O)NCCCOc2cccc(Cl)c2)c(O)c1=O] | N-(3-(3-chlorophenoxy)propyl)-6-(3-fluoro-5-(trifluoromethyl)phenyl)-3-hydroxy-1-methyl-2-oxo-1,2-dihydropyridine-4-carboxamide | 2.6 | 498.96 | F |
| 66 | 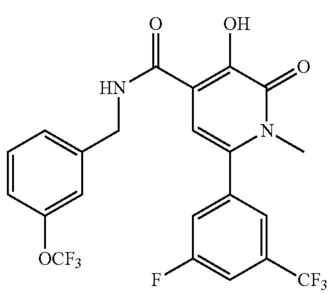 [SMILES: Cn1c(-c2cc(F)cc(C(F)(F)F)c2)cc(C(=O)NCc2cccc(OC(F)(F)F)c2)c(O)c1=O] | 6-(3-fluoro-5-(trifluoromethyl)phenyl)-3-hydroxy-1-methyl-2-oxo-N-(3-(trifluoromethoxy)benzyl)-1,2-dihydropyridine-4-carboxamide | 2.6 | 504.98 | F |
| 67 | 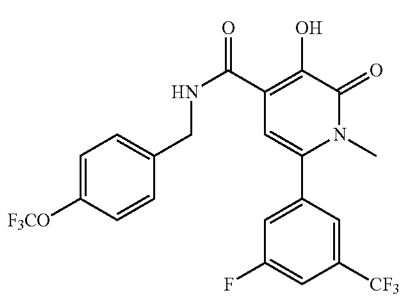 [SMILES: Cn1c(-c2cc(F)cc(C(F)(F)F)c2)cc(C(=O)NCc2ccc(OC(F)(F)F)cc2)c(O)c1=O] | 6-(3-fluoro-5-(trifluoromethyl)phenyl)-3-hydroxy-1-methyl-2-oxo-N-(4-(trifluoromethoxy)benzyl)-1,2-dihydropyridine-4-carboxamide | 2.6 | 504.98 | F |

TABLE 3-continued

| Ex. # | Structure | Name | RT (min) | [M + 1]⁺ | LC/MS Methods |
|---|---|---|---|---|---|
| 68 | 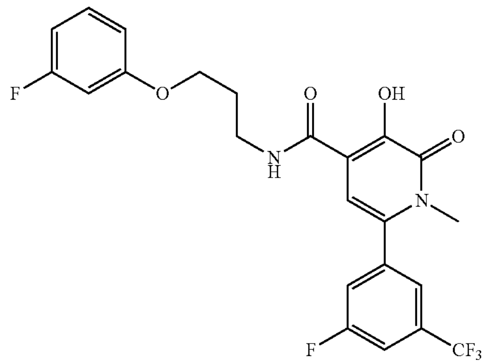 [SMILES: Cn1c(-c2cc(F)cc(C(F)(F)F)c2)cc(C(=O)NCCCOc2cccc(F)c2)c(O)c1=O] | 6-(3-fluoro-5-(trifluoromethyl)phenyl)-N-(3-(3-fluorophenoxy)propyl)-3-hydroxy-1-methyl-2-oxo-1,2-dihydropyridine-4-carboxamide | 2.5 | 483.02 | F |
| 69 | 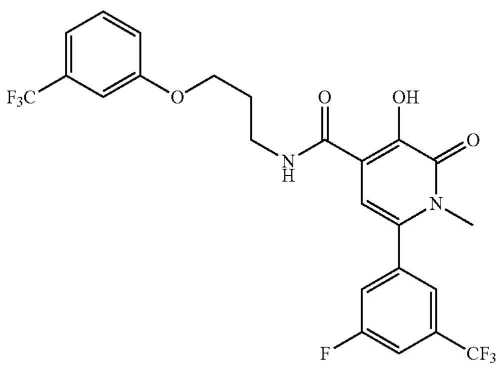 [SMILES: Cn1c(-c2cc(F)cc(C(F)(F)F)c2)cc(C(=O)NCCCOc2cccc(C(F)(F)F)c2)c(O)c1=O] | 6-(3-fluoro-5-(trifluoromethyl)phenyl)-3-hydroxy-1-methyl-2-oxo-N-(3-(3-(trifluoromethyl)phenoxy)propyl)-1,2-dihydropyridine-4-carboxamide | 2.7 | 532.99 | F |
| 70 | 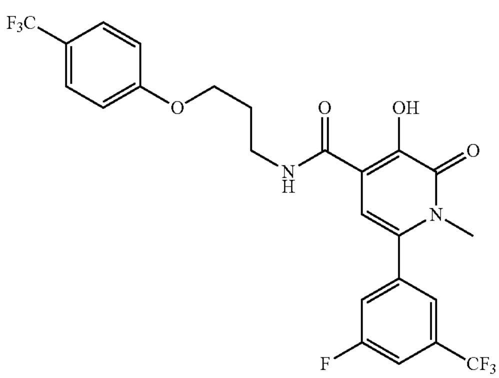 [SMILES: Cn1c(-c2cc(F)cc(C(F)(F)F)c2)cc(C(=O)NCCCOc2ccc(C(F)(F)F)cc2)c(O)c1=O] | 6-(3-fluoro-5-(trifluoromethyl)phenyl)-3-hydroxy-1-methyl-2-oxo-N-(3-(4-(trifluoromethyl)phenoxy)propyl)-1,2-dihydropyridine-4-carboxamide | 2.7 | 532.99 | F |
| 71 | 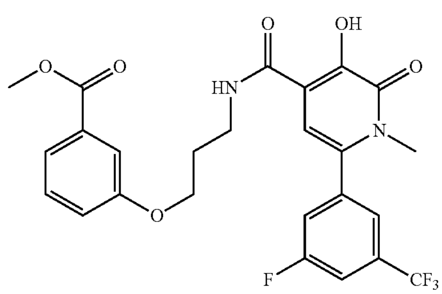 [SMILES: COC(=O)c1cccc(OCCCNC(=O)c2cc(-c3cc(F)cc(C(F)(F)F)c3)n(C)c(=O)c2O)c1] | methyl 3-(3-(6-(3-fluoro-5-(trifluoromethyl)phenyl)-3-hydroxy-1-methyl-2-oxo-1,2-dihydropyridine-4-carboxamido)propoxy)benzoate | 2.4 | 523.03 | F |

TABLE 3-continued

| Ex. # | Structure | Name | RT (min) | [M + 1]+ | LC/MS Methods |
|---|---|---|---|---|---|
| 72 | 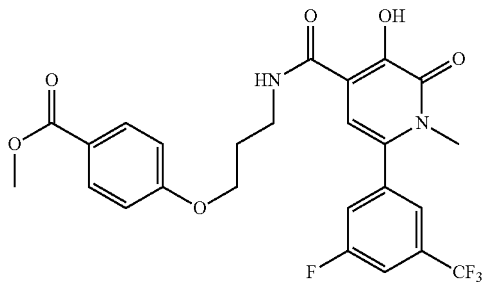 [SMILES: COC(=O)c1ccc(OCCCNC(=O)c2cc(-c3cc(F)cc(C(F)(F)F)c3)n(C)c(=O)c2O)cc1] | methyl 4-(3-(6-(3-fluoro-5-(trifluoromethyl)phenyl)-3-hydroxy-1-methyl-2-oxo-1,2-dihydropyridine-4-carboxamido)propoxy)benzoate | 2.3 | 523.02 | F |
| 73 | 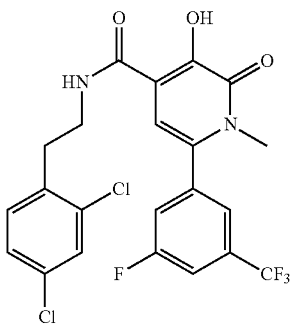 [SMILES: Cn1c(-c2cc(F)cc(C(F)(F)F)c2)cc(C(=O)NCCc2ccc(Cl)cc2Cl)c(O)c1=O] | N-(2,4-dichlorophenethyl)-6-(3-fluoro-5-(trifluoromethyl)phenyl)-3-hydroxy-1-methyl-2-oxo-1,2-dihydropyridine-4-carboxamide | 2.7 | 502.93 | F |
| 74 | 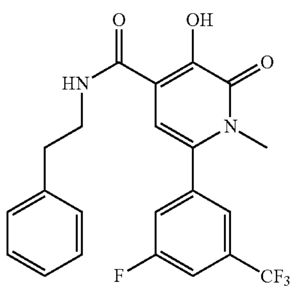 [SMILES: Cn1c(-c2cc(F)cc(C(F)(F)F)c2)cc(C(=O)NCCc2ccccc2)c(O)c1=O] | 6-(3-fluoro-5-(trifluoromethyl)phenyl)-3-hydroxy-1-methyl-2-oxo-N-phenethyl-1,2-dihydropyridine-4-carboxamide | 2.3 | 435.23 | F |
| 75 | 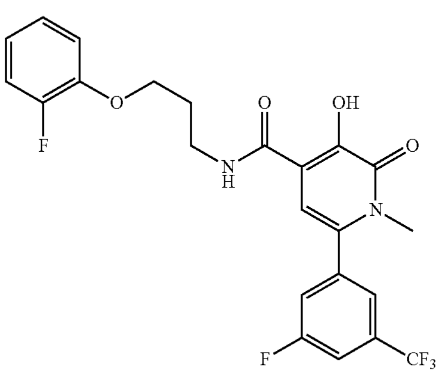 [SMILES: Cn1c(-c2cc(F)cc(C(F)(F)F)c2)cc(C(=O)NCCCOc2ccccc2F)c(O)c1=O] | 6-(3-fluoro-5-(trifluoromethyl)phenyl)-N-(3-(2-fluorophenoxy)propyl)-3-hydroxy-1-methyl-2-oxo-1,2-dihydropyridine-4-carboxamide | 2.4 | 483.18 | F |
| 76 | 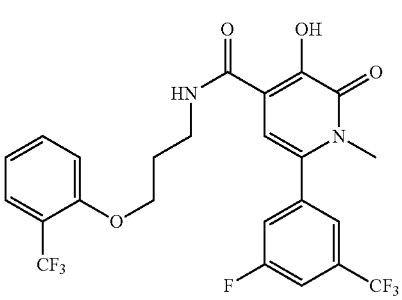 [SMILES: Cn1c(-c2cc(F)cc(C(F)(F)F)c2)cc(C(=O)NCCCOc2ccccc2C(F)(F)F)c(O)c1=O] | 6-(3-fluoro-5-(trifluoromethyl)phenyl)-3-hydroxy-1-methyl-2-oxo-N-(3-(2-(trifluoromethyl)phenoxy)propyl)-1,2-dihydropyridine-4-carboxamide | 2.1 | 533.1 | D |

TABLE 3-continued

| Ex. # | Structure | Name | RT (min) | [M + 1]+ | LC/MS Methods |
|---|---|---|---|---|---|
| 77 | 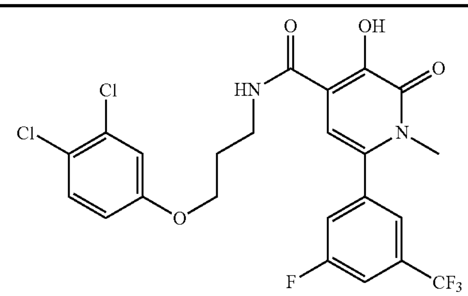 | N-(3-(3,4-dichlorophenoxy)propyl)-6-(3-fluoro-5-(trifluoromethyl)phenyl)-3-hydroxy-1-methyl-2-oxo-1,2-dihydropyridine-4-carboxamide | 2.2 | 533.1 | D |
| 78 | Isomer A | N-(4-(3,4-dichlorophenyl)butan-2-yl)-3-hydroxy-1-methyl-2-oxo-6-(3-(trifluoromethyl)phenyl)-1,2-dihydropyridine-4-carboxamide (Isomer A) | 2.2 | 513.0 | D |
| 79 | Isomer B | N-(4-(3,4-dichlorophenyl)butan-2-yl)-3-hydroxy-1-methyl-2-oxo-6-(3-(trifluoromethyl)phenyl)-1,2-dihydropyridine-4-carboxamide (Isomer B) | 2.2 | 513.0 | D |
| 80 | 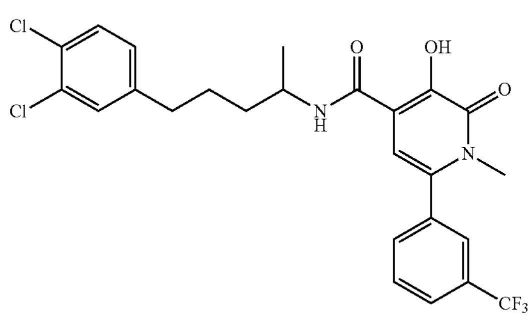 [SMILES: CC(CCCc1ccc(Cl)c(Cl)c1)NC(=O)c1cc(-c2cccc(C(F)(F)F)c2)n(C)c(=O)c1O] | N-(5-(3,4-dichlorophenyl)pentan-2-yl)-3-hydroxy-1-methyl-2-oxo-6-(3-(trifluoromethyl)phenyl)-1,2-dihydropyridine-4-carboxamide (Isomer A) | 2.3 | 527.1 | D |

TABLE 3-continued

| Ex. # | Structure | Name | RT (min) | [M + 1]+ | LC/MS Methods |
|---|---|---|---|---|---|
| 81 | 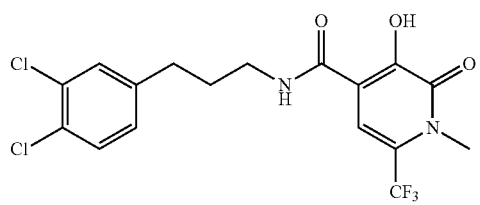 | 6-(3-fluoro-5-(trifluoromethyl)phenyl)-3-hydroxy-1-methyl-N-(3-(2-nitrophenoxy)propyl)-2-oxo-1,2-dihydropyridine-4-carboxamide | 2.26 | 210.19 | F |

Example 82

N-(3-(3,4-dichlorophenyl)propyl)-3-hydroxy-1-methyl-2-oxo-6-(trifluoromethyl)-1,2-dihydropyridine-4-carboxamide

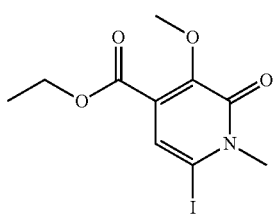 [SMILES: CCOC(=O)c1cc(I)n(C)c(=O)c1OC]

Example 82A ethyl 6-iodo-3-methoxy-1-methyl-2-oxo-1,2-dihydropyridine-4-carboxylate

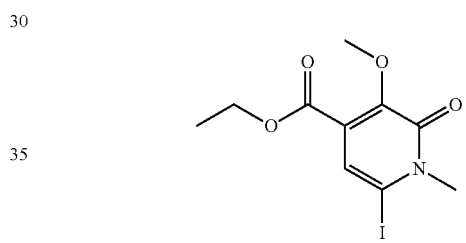

To a solution of Intermediate 5 (101 mg, 0.478 mmol) in DMF (0.5 mL) was added NIS (108 mg, 0.478 mmol) at rt. The reaction was stirred at rt for 3 days. An additional equivalent of NIS (67 mg, 0.30 mmol) was added and the reaction mixture heated at 60° C. overnight. The reaction was allowed to cool, diluted with DCM (40 mL) and the organic portion washed with water and brine, dried over magnesium sulfate, filtered and concentrated. The residue was dissolved in a small amount of DCM and charged to a 12 g silica gel cartridge which was eluted with a 25 min gradient from 0-100% EtOAc/hexane to give Example 82A (81 mg, 50.2% yield) as a yellow solid.

Example 82B ethyl 6-iodo-3-methoxy-1-methyl-2-oxo-1,2-dihydropyridine-4-carboxylate To a solution of Example 82A (31 mg, 0.092 mmol) in DMF (3 mL) at rt under argon was added copper (I) iodide (35.0 mg, 0.184 mmol) and methyl 2,2-difluoro-2-(fluorosulfonyl)acetate (35.3 mg, 0.184 mmol). The reaction mixture was heated at 95° C. overnight. The reaction was allowed to cool to rt. DCM (30 mL) was added to the reaction mixture and the organic portion was washed with water (3×10 mL), brine (10 mL). The organic phase was dried over MgSO$_4$, filtered and concentrated to give the crude product. The crude product was dissolved in a small amount of DCM and charged to a 12 g silica gel cartridge which was eluted with a 25 min gradient from 0-100% EtOAc/hexane to give Example 82B (18 mg, 0.064 mmol, 70% yield) as a colorless oil.

Example 82C 3-methoxy-1-methyl-2-oxo-6-(trifluoromethyl)-1,2-dihydropyridine-4-carboxylic acid

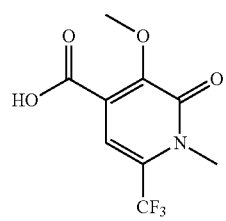

To a solution of Example 82B (18 mg, 0.064 mmol) in THF (1.5 mL) and MeOH (0.5 mL) was added lithium hydroxide (14 mg, 0.59 mmol) and water (0.25 mL). The reaction was heated at 65° C. overnight. Additional lithium hydroxide was added (10. mg, 0.42 mmol) and heating resumed at 65° C. for 5 h. The reaction mixture was concentrated to give Example 82C (16 mg, 0.064 mmol, 99% yield) as an off-white solid which was used without purification.

Example 82D

N-(3-(3,4-dichlorophenyl)propyl)-3-methoxy-1-methyl-2-oxo-6-(trifluoromethyl)-1,2-dihydropyridine-4-carboxamide

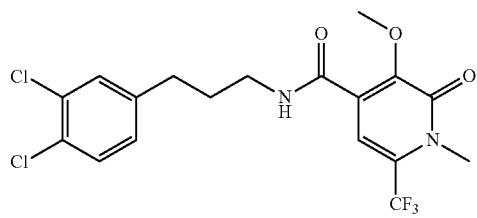 [SMILES: COc1c(C(=O)NCCCc2ccc(Cl)c(Cl)c2)cc(C(F)(F)F)n(C)c1=O]

To a solution of Example 82C (16 mg, 0.064 mmol) in DCM (1.5 mL) was added the HCl salt of Intermediate 1 (15.40 mg, 0.06400 mmol), DIPEA (0.034 mL, 0.19 mmol) and PyBOP (33.3 mg, 0.0640 mmol). The reaction was stirred at rt overnight. The reaction was concentrated and the residue was purified by reverse phase preparative HPLC (Axia Luna, 5μ, C18 column, 30×100 mm, 10 min gradient from 20-100% B. A=$H_2O$/ACN/TFA 90/10/0.1. B=ACN/$H_2O$/TFA 90/10/0.1) to give Example 82D (7.5 mg, 0.017 mmol, 27% yield) as a colorless solid.

Example 82

To a solution of example 82D (7 mg, 0.02 mmol) in DCM (1.5 mL) and was added boron tribromide, 1.0 M in DCM (0.032 mL, 0.032 mmol) at rt. The reaction was stirred at rt for 3 h. The reaction was quenched with MeOH (0.5 mL) and water (5 drops) and stirred at rt 10 min. The reaction mixture was concentrated and the residue was dissolved in MeOH and purified by reverse phase preparative HPLC (column: Phenomenex Luna, 5μ, C18, 30×250 mm, 20 min gradient from 30-100% B. A=$H_2O$/ACN/TFA 90/10/0.1. B=ACN/$H_2O$/TFA 90/10/0.1) to give Example 82 (3.4 mg, 49.7% yield) as a white solid. 1H NMR (400 MHz, CHLOROFORM-d) δ ppm 7.32-7.38 (2 H, m), 7.28 (1 H, d, J=2.01 Hz), 7.03 (1 H, dd, J=8.28, 2.01 Hz), 6.11 (1 H, br. s.), 3.67 (3 H, s), 3.48 (2 H, q, J=6.78 Hz), 2.61-2.75 (2 H, m), 1.84-1.98 (2 H, m).

Examples 83-101 were synthesized from Example 82C and the corresponding amines according to the methodology described for Example 82. The HPLC-MS data (retention time, mass and conditions) for Examples 83-101 are listed in Table 4.

TABLE 4

| Ex. # | Structure | Name | RT (min) | [M + 1]$^+$ | LC/MS Methods |
|---|---|---|---|---|---|
| 83 | 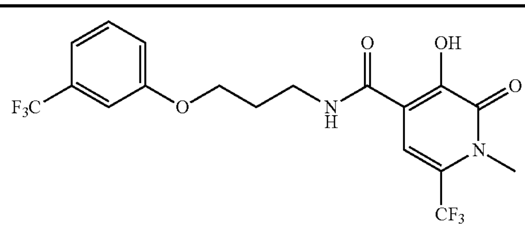 | 3-hydroxy-1-methyl-2-oxo-6-(trifluoromethyl)-N-(3-(3-(trifluoromethyl)phenoxy)propyl)-1,2-dihydropyridine-4-carboxamide | 1.9 | 439.1 | D |
| 84 | 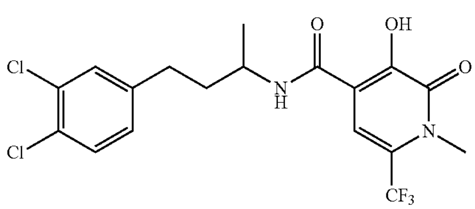 [SMILES: CC(CCc1ccc(Cl)c(Cl)c1)NC(=O)c1cc(C(F)(F)F)n(C)c(=O)c1O] | N-(4-(3,4-dichlorophenyl)butan-2-yl)-3-hydroxy-1-methyl-2-oxo-6-(trifluoromethyl)-1,2-dihydropyridine-4-carboxamide | 2.0 | 437.1 | D |
| 85 | 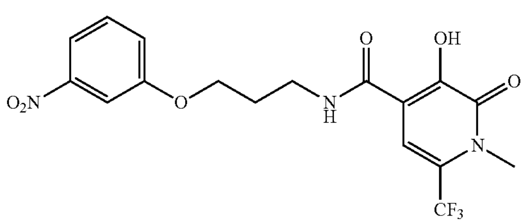 [SMILES: Cn1c(C(F)(F)F)cc(C(=O)NCCCOc2cccc([N+](=O)[O-])c2)c(O)c1=O] | 3-hydroxy-1-methyl-N-(3-(3-nitrophenoxy)propyl)-2-oxo-6-(trifluoromethyl)-1,2-dihydropyridine-4-carboxamide | 1.8 | 415.95 | F |

TABLE 4-continued

| Ex. # | Structure | Name | RT (min) | [M + 1]+ | LC/MS Methods |
|---|---|---|---|---|---|
| 86 | 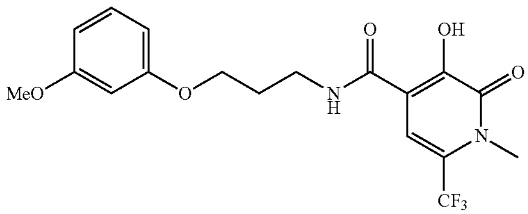 [SMILES: COc1cccc(OCCCNC(=O)c2cc(C(F)(F)F)n(C)c(=O)c2O)c1] | 3-hydroxy-N-(3-(3-methoxyphenoxy)propyl)-1-methyl-2-oxo-6-(trifluoromethyl)-1,2-dihydropyridine-4-carboxamide | 1.8 | 400.98 | F |
| 87 | 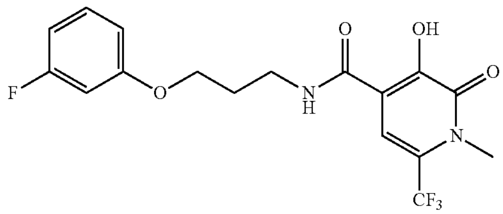 [SMILES: Cn1c(C(F)(F)F)cc(C(=O)NCCCOc2cccc(F)c2)c(O)c1=O] | N-(3-(3-fluorophenoxy)propyl)-3-hydroxy-1-methyl-2-oxo-6-(trifluoromethyl)-1,2-dihydropyridine-4-carboxamide | 1.9 | 388.98 | F |
| 88 | 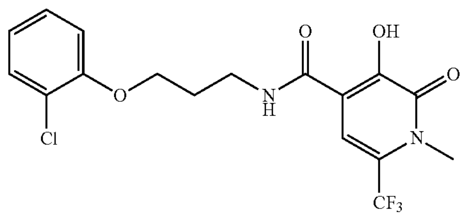 [SMILES: Cn1c(C(F)(F)F)cc(C(=O)NCCCOc2ccccc2Cl)c(O)c1=O] | N-(3-(2-chlorophenoxy)propyl)-3-hydroxy-1-methyl-2-oxo-6-(trifluoromethyl)-1,2-dihydropyridine-4-carboxamide | 2.0 | 404.96 | F |
| 89 | 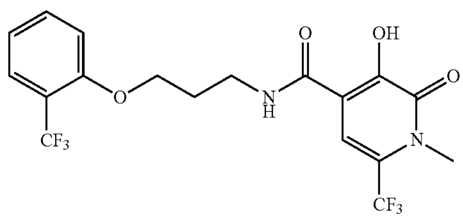 [SMILES: Cn1c(C(F)(F)F)cc(C(=O)NCCCOc2ccccc2C(F)(F)F)c(O)c1=O] | 3-hydroxy-1-methyl-2-oxo-6-(trifluoromethyl)-N-(3-(2-(trifluoromethyl)phenoxy)propyl)-1,2-dihydropyridine-4-carboxamide | 2.1 | 438.95 | F |
| 90 | 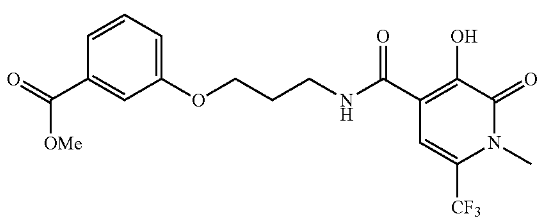 [SMILES: COC(=O)c1cccc(OCCCNC(=O)c2cc(C(F)(F)F)n(C)c(=O)c2O)c1] | methyl 3-(3-(3-hydroxy-1-methyl-2-oxo-6-(trifluoromethyl)-1,2-dihydropyridine-4-carboxamido)propoxy)benzoate | 1.8 | 428.95 | F |
| 91 | 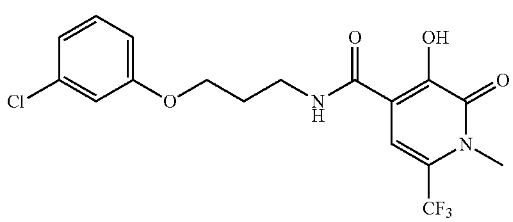 [SMILES: Cn1c(C(F)(F)F)cc(C(=O)NCCCOc2cccc(Cl)c2)c(O)c1=O] | N-(3-(3-chlorophenoxy)propyl)-3-hydroxy-1-methyl-2-oxo-6-(trifluoromethyl)-1,2-dihydropyridine-4-carboxamide | 2.1 | 404.96 | F |
| 92 | 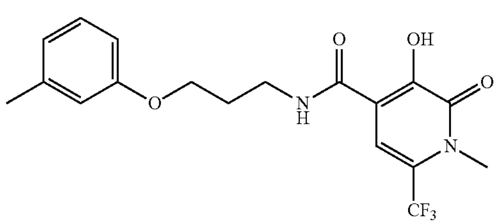 | 3-hydroxy-1-methyl-2-oxo-N-(3-(m-tolyloxy)propyl)-6-(trifluoromethyl)-1,2-dihydropyridine-4-carboxamide | 2.0 | 385 | F |

TABLE 4-continued

| Ex. # | Structure | Name | RT (min) | [M + 1]+ | LC/MS Methods |
|---|---|---|---|---|---|
| 93 | 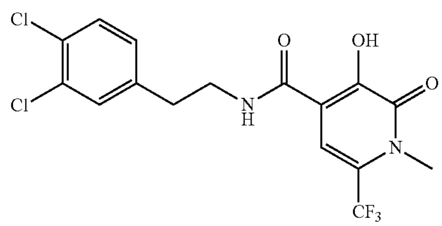 [SMILES: Cn1c(C(F)(F)F)cc(C(=O)NCCc2ccc(Cl)c(Cl)c2)c(O)c1=O] | N-(3,4-dichlorophenethyl)-3-hydroxy-1-methyl-2-oxo-6-(trifluoromethyl)-1,2-dihydropyridine-4-carboxamide | 2.1 | 408.92 | F |
| 94 | 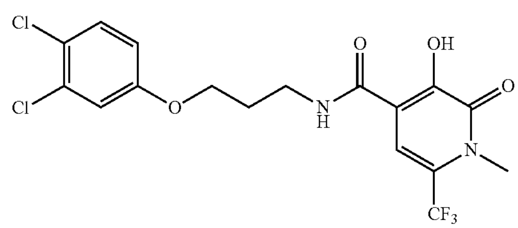 [SMILES: Cn1c(C(F)(F)F)cc(C(=O)NCCCOc2ccc(Cl)c(Cl)c2)c(O)c1=O] | N-(3-(3,4-dichlorophenoxy)propyl)-3-hydroxy-1-methyl-2-oxo-6-(trifluoromethyl)-1,2-dihydropyridine-4-carboxamide | 2.3 | 438.87 | F |
| 95 | 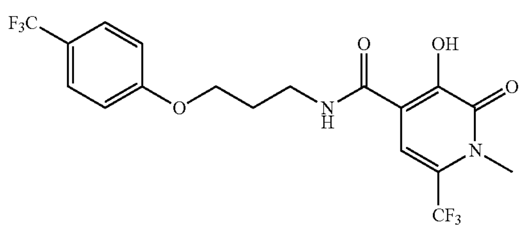 [SMILES: Cn1c(C(F)(F)F)cc(C(=O)NCCCOc2ccc(C(F)(F)F)cc2)c(O)c1=O] | 3-hydroxy-1-methyl-2-oxo-6-(trifluoromethyl)-N-(3-(4-(trifluoromethyl)phenoxy)propyl)-1,2-dihydropyridine-4-carboxamide | 2.2 | 439.04 | F |
| 96 | 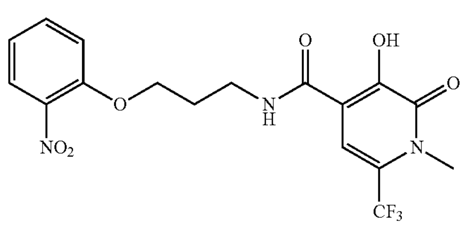 [SMILES: Cn1c(C(F)(F)F)cc(C(=O)NCCCOc2ccccc2[N+](=O)[O-])c(O)c1=O] | 3-hydroxy-1-methyl-N-(3-(2-nitrophenoxy)propyl)-2-oxo-6-(trifluoromethyl)-1,2-dihydropyridine-4-carboxamide | 2.0 | 415.96 | F |
| 97 | 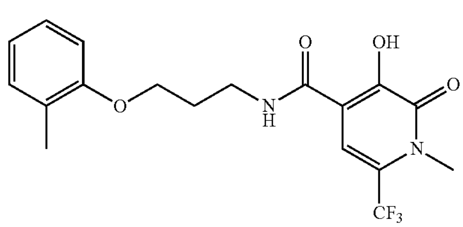 [SMILES: Cc1ccccc1OCCCNC(=O)c1cc(C(F)(F)F)n(C)c(=O)c1O] | 3-hydroxy-1-methyl-2-oxo-N-(3-(o-tolyloxy)propyl)-6-(trifluoromethyl)-1,2-dihydropyridine-4-carboxamide | 2.3 | 385.02 | F |
| 98 | 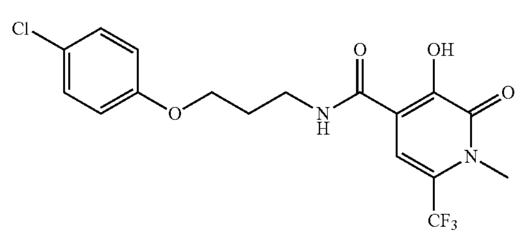 [SMILES: Cn1c(C(F)(F)F)cc(C(=O)NCCCOc2ccc(Cl)cc2)c(O)c1=O] | N-(3-(4-chlorophenoxy)propyl)-3-hydroxy-1-methyl-2-oxo-6-(trifluoromethyl)-1,2-dihydropyridine-4-carboxamide | 2.3 | 404.94 | F |

TABLE 4-continued

| Ex. # | Structure | Name | RT (min) | [M + 1]+ | LC/MS Methods |
|---|---|---|---|---|---|
| 99 | 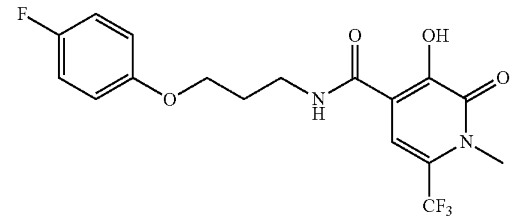 [SMILES: Cn1c(C(F)(F)F)cc(C(=O)NCCCOc2ccc(F)cc2)c(O)c1=O] | N-(3-(4-fluorophenoxy)propyl)-3-hydroxy-1-methyl-2-oxo-6-(trifluoromethyl)-1,2-dihydropyridine-4-carboxamide | 2.1 | 388.98 | F |
| 100 | 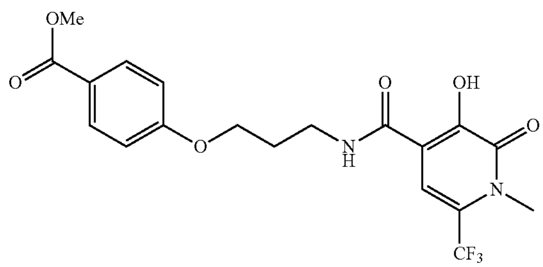 [SMILES: COC(=O)c1ccc(OCCCNC(=O)c2cc(C(F)(F)F)n(C)c(=O)c2O)cc1] | methyl 4-(3-(3-hydroxy-1-methyl-2-oxo-6-(trifluoromethyl)-1,2-dihydropyridine-4-carboxamido)propoxy)benzoate | 1.8 | 428.99 | F |
| 101 | 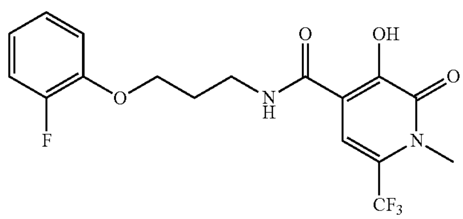 | N-(3-(2-fluorophenoxy)propyl)-3-hydroxy-1-methyl-2-oxo-6-(trifluoromethyl)-1,2-dihydropyridine-4-carboxamide | 1.8 | 388.98 | F |

Example 102

N-(3-(3,4-dichlorophenyl)propyl)-6-ethyl-3-hydroxy-1-methyl-2-oxo-1,2-dihydropyridine-4-carboxamide

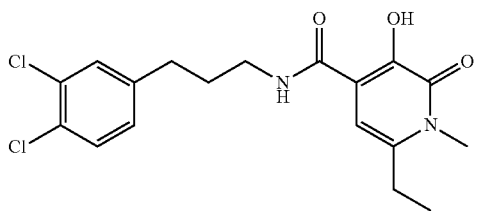 [SMILES: CCc1cc(C(=O)NCCCc2ccc(Cl)c(Cl)c2)c(O)c(=O)n1C]

Example 102A ethyl 3-methoxy-1-methyl-2-oxo-6-vinyl-1,2-dihydropyridine-4-carboxylate

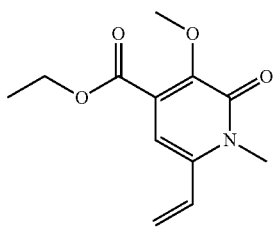 [SMILES: C=Cc1cc(C(=O)OCC)c(OC)c(=O)n1C]

To a solution of Intermediate 6 (258 mg, 0.889 mmol) in toluene (4 mL) and was added tributyl(vinyl)stannane (0.390 mL, 1.33 mmol) and bis(triphenylphosphine)palladium(ii) chloride (Pd(PPh$_3$)$_2$Cl$_2$) (62.4 mg, 0.0890 mmol) in a microwave vial. The reaction was heated at 80° C. overnight. The reaction was filtered and the filtrate was concentrated. The residue was dissolved in a small amount of DCM and charged to a 24 g silica gel cartridge which was eluted with a 30 min gradient from 0-100% EtOAc/hexane to give Example 102A (206 mg, 0.868 mmol, 98.0% yield) as a yellow solid. LCMS RT=1.4 min, (M+H)$^+$=238.1 (Phenomenex Luna C18, 4.6× 30 mm, 2 min gradient with 10-90% MeOH/water/0.1% TFA).

Example 102B ethyl 6-ethyl-3-methoxy-1-methyl-2-oxo-1,2-dihydropyridine-4-carboxylate

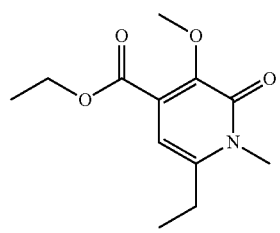 [SMILES: CCOC(=O)c1cc(CC)n(C)c(=O)c1OC]

To a solution of Example 102A (100 mg, 0.421 mmol) in MeOH (3 mL) was added Pd/C (10%) (14 mg, 0.013 mmol). The reaction was stirred under H$_2$ atmosphere at rt for 2 h. The reaction was filtered and concentrated to give Example 102B (99 mg, 0.414 mmol, 98% yield).

Example 102C 6-ethyl-3-methoxy-1-methyl-2-oxo-1,2-dihydropyridine-4-carboxylic acid

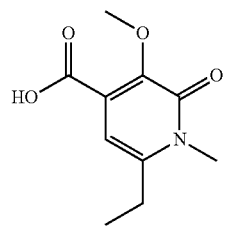

A solution of Example 102B (103 mg, 0.430 mmol) in THF (6 mL) and MeOH (2 mL) was added lithium hydroxide (30.9 mg, 1.29 mmol) and water (0.5 mL). The reaction was heated at 55° C. overnight. The reaction was acidified with HCl (0.143 mL, 1.70 mmol) and concentrated to give Example 102C (198 mg, 0.422 mmol, 98.0% yield) as a gray solid. LCMS RT=0.7 min, (M+H)$^+$=212.1 (Phenomenex Luna C18, 4.6×30 mm, 2 min gradient with 10-90% MeOH/water/0.1% TFA).

Example 102D

N-(3-(3,4-dichlorophenyl)propyl)-6-ethyl-3-methoxy-1-methyl-2-oxo-1,2-dihydropyridine-4-carboxamide

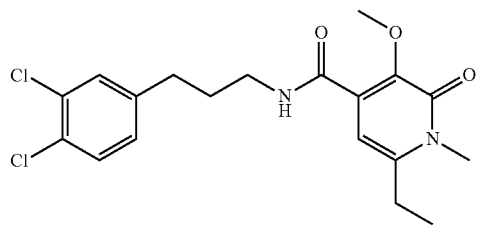 [SMILES: CCc1cc(C(=O)NCCCc2ccc(Cl)c(Cl)c2)c(OC)c(=O)n1C]

To a solution of Example 102C (43 mg, 0.143 mmol) in DCM (1.5 mL) was added 3-(3,4-dichlorophenyl)propan-1-amine hydrochloride (intermediate 1) (28 mg, 0.12 mmol), DIPEA (0.050 mL, 0.29 mmol) and PyBOP (74.2 mg, 0.143 mmol) at rt. DMF (0.4 mL) was added to the reaction mixture and the resulting solution stirred at rt overnight. Celite® was added to the reaction mixture and the solvents were removed under reduced pressure and the residue purified by ISCO flash chromatography (12 g column, eluted with 0-10% MeOH/DCM over 30 min gradient) to give Example 102D (30 mg, 0.076 mmol, 53% yield) as a yellow solid. LCMS RT=1.99 min, (M+H)$^+$=397.1 (column: Phenomenex Luna C18, 4.6×30 mm, 2 min gradient with 10-90% MeOH/water/0.1% TFA).

Example 102

To a solution of Example 102D (30 mg, 0.076 mmol) in CHCl$_3$ (1.5 mL) was added boron tribromide, 1.0 M in DCM (0.11 mL, 0.11 mmol) at rt. The reaction was stirred at rt overnight. The reaction was quenched with MeOH (0.5 mL) and water (5 drops) and stirred at rt 10 min. The reaction mixture was concentrated and the residue was dissolved in MeOH and purified by reverse phase preparative HPLC (YMC Sunfire, 5μ, C18 column, 30×100 mm, 10 min gradient from 20-100% B. A=H$_2$O/MeOH/TFA 90/10/0.1. B=MeOH/H$_2$O/TFA 90/10/0.1) to give Example 102 (6.9 mg, 0.017 mmol, 23% yield) as a yellow solid. LCMS 2.0 min, m/z=383.0 (M+H)$^+$ (Phenomenex Luna C18, 4.6×30 mm, 2 min gradient with 10-90% MeOH/water/0.1% TFA). 1H NMR (400 MHz, CHLOROFORM-d) δ ppm 7.35 (1 H, d, J=8.03 Hz), 7.29 (1 H, d, J=2.01 Hz), 7.04 (1 H, dd, J=8.03, 2.01 Hz), 6.64 (1 H, s), 6.43 (1 H, br. s.), 3.60 (3 H, s), 3.43-3.50 (2 H, m), 2.67-2.73 (2 H, m), 2.64 (2 H, q, J=7.53 Hz), 1.93 (2 H, ddd, J=14.93, 7.40, 7.28 Hz), 1.13 (3 H, t, J=7.40 Hz).

Example 103

N-(3-(3,4-dichlorophenyl)propyl)-3-hydroxy-6-isopropyl-1-methyl-2-oxo-1,2-dihydropyridine-4-carboxamide

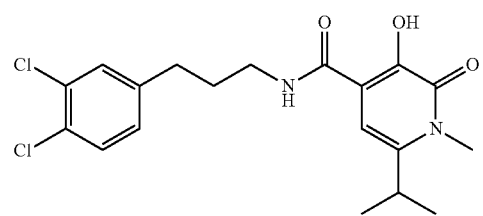 [SMILES: CC(C)c1cc(C(=O)NCCCc2ccc(Cl)c(Cl)c2)c(O)c(=O)n1C]

Example 103A ethyl 3-methoxy-1-methyl-2-oxo-6-(prop-1-en-2-yl)-1,2-dihydropyridine-4-carboxylate

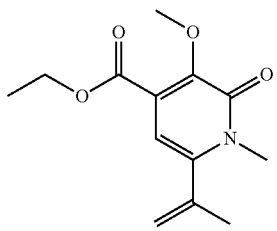 [SMILES: C=C(C)c1cc(C(=O)OCC)c(OC)c(=O)n1C]

To a solution of Intermediate 6 (305 mg, 1.05 mmol) in toluene (5 mL) and was added tributyl(prop-1-en-2-yl)stannane (522 mg, 1.58 mmol) and bis(triphenylphosphine)palladium(II) chloride (Pd(Ph$_3$)$_2$Cl$_2$) (73.8 mg, 0.105 mmol) in a microwave vial. The reaction mixture was flushed with argon and heated at 95° C. overnight. The reaction was filtered and new catalyst bis(triphenylphosphine)palladium(II) chloride (Pd(Ph$_3$)$_2$Cl$_2$) (65 mg, 0.093 mmol) and tributyl(prop-1-en-2-yl)stannane (300 μL, 1.051 mmol) was added. The reaction was heated at 100° C. for 5 h. The reaction was concentrated and the residue was diluted with DCM/MeOH and filtered. The filtrate was concentrated and the residue was dissolved in a small amount of DCM and charged to a 12 g silica gel cartridge which was eluted with a 25 min gradient from 0-100% EtOAc/hexane to give Example 103A (129 mg, 0.513 mmol, 48.8% yield) as a yellow oil. LCMS RT=1.56 min, (M+H)+=252.1 (Phenomenex Luna C18, 4.6×30 mm, 2 min gradient with 10-90% MeOH/water/0.1% TFA).

Example 103B ethyl 6-isopropyl-3-methoxy-1-methyl-2-oxo-1,2-dihydropyridine-4-carboxylate

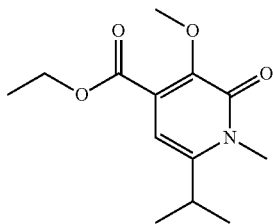 [SMILES: CCOC(=O)c1cc(C(C)C)n(C)c(=O)c1OC]

To a solution of Example 103A (129 mg, 0.513 mmol) in MeOH (3 mL) was added Pd(OH)$_2$ (20%, 18 mg). The reaction was stirred under H$_2$ atmosphere at rt for 4 days. The reaction was filtered and the filtrate was concentrated to give Example 103B (115 mg, 0.454 mmol, 88.0% yield) as a viscous oil. LCMS RT=1.57 min, (M+H)+=254.1 (Phenomenex Luna C18, 4.6×30 mm, 2 min gradient with 10-90% MeOH/water/0.1% TFA).

Example 103C 6-isopropyl-3-methoxy-1-methyl-2-oxo-1,2-dihydropyridine-4-carboxylic acid

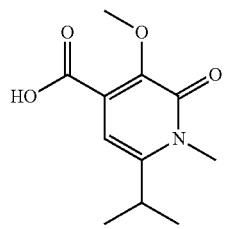 [SMILES: COc1c(C(=O)O)cc(C(C)C)n(C)c1=O]

A solution of Example 103B (115 mg, 0.454 mmol) in THF (6 mL) and MeOH (2 mL) was added lithium hydroxide (43.5 mg, 1.82 mmol) and water (1 mL). The reaction was heated at 65° C. overnight. Additional LiOH (11 mg, 0.46 mmol) was and heated resumed at 65° C. overnight. The reaction was acidified with HCl (0.227 mL, 2.72 mmol) and concentrated to give Example 103C (247 mg, 1.10 mmol, 242% yield) as a gray solid. LCMS RT=1.1 min, (M+H)+=226.1 (Phenomenex Luna C18, 4.6×30 mm, 2 min gradient with 10-90% MeOH/water/0.1% TFA).

Example 103D

N-(3-(3,4-dichlorophenyl)propyl)-6-isopropyl-3-methoxy-1-methyl-2-oxo-1,2-dihydropyridine-4-carboxamide

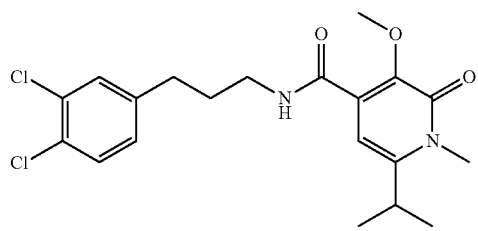 [SMILES: COc1c(C(=O)NCCCc2ccc(Cl)c(Cl)c2)cc(C(C)C)n(C)c1=O]

To a solution of Example 103C (53 mg, 0.24 mmol) in DCM (1.5 mL) was added 3-(3,4-dichlorophenyl)propan-1-aminium chloride (28 mg, 0.12 mmol), DIPEA (0.082 mL, 0.47 mmol) and PyBOP (122 mg, 0.235 mmol) at rt. DMF (0.4 mL) was added to the reaction mixture. The reaction was stirred at rt for 3 days. Celite® was added to the reaction and the solvents removed under reduced pressure. The residue was purified silica gel chromatography (12 g column, eluted with 0-10% MeOH/DCM over 30 min gradient) to give Example 103D (48 mg, 0.12 mmol, 50% yield) as a yellow oil.

Example 103

To a solution of Example 103D (48 mg, 0.058 mmol) in CHCl$_3$ (1.5 mL) and was added boron tribromide (1.0 M in DCM, 0.088 mL, 0.088 mmol) at rt. The reaction was stirred at rt overnight. The reaction was quenched with MeOH (0.5 mL) and water (5 drops) and stirred at rt 10 min. The reaction was concentrated. The residue was dissolved in MeOH and purified by reverse phase preparative HPLC (column: Phenomenex Luna, 5µ, C18, 30×250 mm, 20 min gradient from 30-100% B. A=H$_2$O/ACN/TFA 90/10/0.1. B=ACN/H$_2$O/TFA 90/10/0.1) to give Example 103 (8.6 mg, 0.021 mmol, 36% yield) as a yellow solid. LCMS RT=2.0 min, (M+H)+=397.1 (Phenomenex Luna C18, 4.6×30 mm, 2 min gradient with 10-90% MeOH/water/0.1% TFA). 1H NMR (400 MHz, CHLOROFORM-d) δ ppm 7.33-7.37 (1 H, m), 7.29 (1 H, d, J=2.01 Hz), 7.04 (1 H, dd, J=8.03, 2.01 Hz), 6.67 (1 H, s), 6.21-6.29 (1 H, m), 3.61 (3 H, s), 3.43-3.51 (2 H, m), 3.25 (1 H, ddd, J=13.43, 6.90, 6.78 Hz), 2.67-2.76 (2 H, m), 1.93 (2 H, ddd, J=15.06, 7.40, 7.15 Hz), 1.18 (3 H, s), 1.16 (3 H, s).

Example 104

N-(3-(3,4-dichlorophenyl)propyl)-3-hydroxy-1-methyl-2-oxo-6-vinyl-1,2-dihydropyridine-4-carboxamide

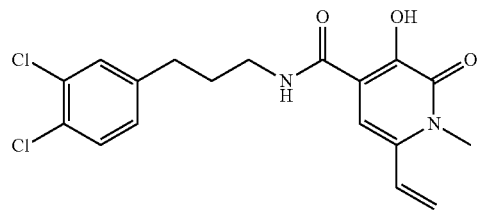 [SMILES: C=Cc1cc(C(=O)NCCCc2ccc(Cl)c(Cl)c2)c(O)c(=O)n1C]

Example 104A

N-(3-(3,4-dichlorophenyl)propyl)-3-methoxy-1-methyl-2-oxo-6-vinyl-1,2-dihydropyridine-4-carboxamide

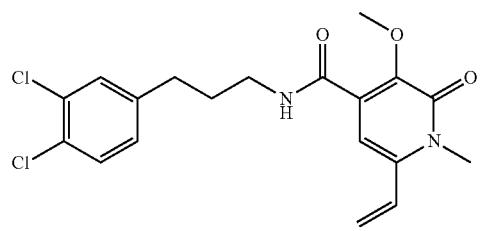 [SMILES: C=Cc1cc(C(=O)NCCCc2ccc(Cl)c(Cl)c2)c(OC)c(=O)n1C]

To a solution of Example 1A (50 mg, 0.112 mmol) in toluene (1.5 mL) and was added tributyl(vinyl)stannane (100 μL, 0.342 mmol) and Pd(Ph₃)₂Cl₂ (7.83 mg, 0.011 mmol) in a microwave vial. The reaction mixture was flushed with argon and heated at 80° C. overnight. The reaction mixture was concentrated, and the residue was diluted with DCM and filtered. The filtrate was concentrated, and the residue was dissolved in a small amount of DCM and charged to a 12 g silica gel cartridge which was eluted with a 25 minute gradient from 0-100% EtOAc/hexane to give N-(3-(3,4-dichlorophenyl)propyl)-3-methoxy-1-methyl-2-oxo-6-vinyl-1,2-dihydropyridine-4-carboxamide (36 mg, 0.091 mmol, 82% yield). LCMS RT=1.8 min, (M+H)⁺=395.0 (Phenomenex Luna C18, 4.6×30 mm, 2 min gradient with 10-90% MeOH/water/0.1% TFA).

Example 104

To a solution of Example 104A (37 mg, 0.094 mmol) in DCM (1.5 mL) was added BBr₃ (1.0 M in DCM, 0.281 mL, 0.281 mmol) at rt. The reaction was stirred at rt overnight. The reaction was quenched with the addition of MeOH (0.5 mL) and water (5 drops) and stirred at rt for 10 min. The reaction mixture was concentrated, and the residue was dissolved in MeOH, filtered and purified by reverse phase preparative HPLC(YMC Sunfire, 5μ, C18 column, 30×100 mm, 10 min gradient from 30-90% B. A=H₂O/MeOH/TFA 90/10/0.1. B=MeOH/H₂O/TFA 90/10/0.1) to give Example 104 (12 mg, 0.028 mmol, 30.3% yield) as a light yellow solid. LCMS RT=1.9 min, (M+H)⁺=381.0 (Phenomenex Luna C18, 4.6×30 mm, 2 min gradient with 10-90% MeOH/water/0.1% TFA). ¹H NMR (400 MHz, CHLOROFORM-d) δ ppm 7.42 (1 H, br. s.), 7.35 (1 H, d, J=8.28 Hz), 7.29 (1 H, d, J=2.01 Hz), 7.04 (1 H, dd, J=8.28, 2.01 Hz), 6.93 (1 H, s), 4.63 (1 H, dd), 3.56-3.66 (3 H, m), 3.37-3.52 (3 H, m), 2.63-2.74 (2 H, m), 1.86-2.00 (2 H, m), 1.43 (2 H, d, J=6.27 Hz).

Example 105

N-(3-(3,4-dichlorophenyl)propyl)-3-hydroxy-1,6-dimethyl-2-oxo-1,2-dihydropyridine-4-carboxamide

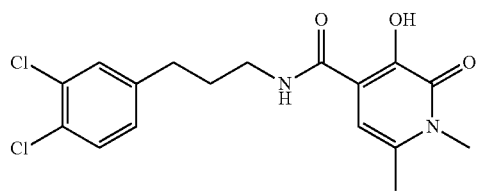 [SMILES: Cc1cc(C(=O)NCCCc2ccc(Cl)c(Cl)c2)c(O)c(=O)n1C]

Example 105A

N-(3-(3,4-dichlorophenyl)propyl)-3-methoxy-1,6-dimethyl-2-oxo-1,2-dihydropyridine-4-carboxamide

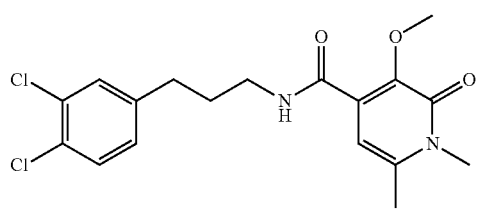 [SMILES: COc1c(C(=O)NCCCc2ccc(Cl)c(Cl)c2)cc(C)n(C)c1=O]

A mixture of Example 1A (31 mg, 0.069 mmol), 2,4,6-trimethyl-1,3,5,2,4,6-trioxatriborinane (0.019 mL, 0.14 mmol), sodium carbonate (2 M) (0.104 mL, 0.208 mmol) in DME (1 mL) was placed in a microwave vial and degassed. Pd(Ph₃P)₄ (7.99 mg, 6.92 μmol) was added to the mixture and then degassed. The sealed tube was heated at 110° C. for 2 h. The reaction was diluted with a mixture of DCM/EtOAc and filtered. The filtrate was concentrated to give Example 105A (37 mg, assumed 100%) which was used directly in the next reaction. LC-MS RT=1.91 min, (M+H)⁺=83.0 (Phenomenex Luna C18, 4.6×30 mm, 2 min gradient with 10-90% MeOH/water/0.1% TFA).

Example 105

To a solution of Example 105A (0.069 mmol) in DCM (1.5 mL) and was added BBr₃ (1.0 M in DCM, 0.290 mL, 0.290 mmol) at rt. The reaction was stirred at rt overnight. The reaction was quenched with MeOH (0.5 mL) and water (5 drops), stirred at rt for 10 min and concentrated. The residue was dissolved in MeOH, filtered and purified by reverse phase preparative HPLC(YMC Sunfire, 5p, C18 column, 30×100 mm, 10 min gradient from 30-90% B. A=H₂O/MeOH/TFA 90/10/0.1. B=MeOH/H₂O/TFA 90/10/0.1) to give Example 105 (4.3 mg, 11 μmol, 16% yield) as a light yellow solid. LC-MS RT=1.91 min, (M+H)⁺=368.9 (Phenomenex Luna C18, 4.6×30 mm, 2 min gradient with 10-90% MeOH/water/0.1% TFA). 1H NMR (400 MHz, CHLOROFORM-d) δ ppm 7.35 (1 H, d, J=8.28 Hz), 7.30 (1 H, d, J=2.01 Hz), 7.04 (1 H, dd, J=8.16, 2.13 Hz), 6.66 (1 H, d, J=1.00 Hz), 6.62 (1 H, br. s.), 3.59 (3 H, s), 3.40-3.52 (2 H, m), 2.62-2.77 (2 H, m), 2.21 (3 H, d, J=1.00 Hz), 1.93 (2 H, ddd, J=14.87, 7.34, 7.15 Hz).

Example 106

N-(3-(3,4-dichlorophenyl)propyl)-3-hydroxy-1,5,6-trimethyl-2-oxo-1,2-dihydropyridine-4-carboxamide

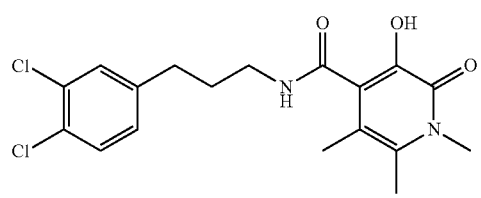 [SMILES: Cc1c(C(=O)NCCCc2ccc(Cl)c(Cl)c2)c(O)c(=O)n(C)c1C]

Example 106A ethyl 3-methoxy-1,6-dimethyl-2-oxo-1,2-dihydropyridine-4-carboxylate

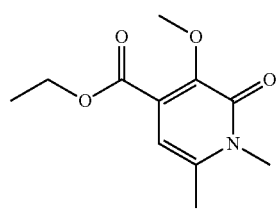 [SMILES: CCOC(=O)c1cc(C)n(C)c(=O)c1OC]

A mixture of Intermediate 6 (200 mg, 0.689 mmol), 2,4,6-trimethyl-1,3,5,2,4,6-trioxatriborinane (0.288 mL, 2.07 mmol), sodium carbonate (2 M) (1.034 mL, 2.068 mmol) in DME (4 mL) was placed in a microwave vial and degassed. Pd(Ph$_3$)$_4$ (39.8 mg, 0.034 mmol) was added to the mixture and then degassed further. The sealed tube was heated at 160° C. in a microwave reactor for 30 min. The reaction was diluted with a mixture of DCM/EtOAc and filtered. The filtrate was concentrated to give the crude product. The crude product was dissolved in a small amount of DCM and charged to a 12 g silica gel cartridge which was eluted with a 25 min gradient from 0-100% EtOAc/hexane to give Example 106A (94.6 mg, 0.420 mmol, 60.9% yield).

Example 106B ethyl 5-bromo-3-methoxy-1,6-dimethyl-2-oxo-1,2-dihydropyridine-4-carboxylate

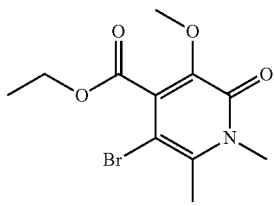 [SMILES: CCOC(=O)c1c(Br)c(C)n(C)c(=O)c1OC]

To a solution of Example 106A (156 mg, 0.706 mmol) in DCM (3 mL) was added NBS (126 mg, 0.706 mmol). The mixture was stirred at rt overnight. The reaction mixture was diluted with DCM, the organic portion washed with water and brine, dried over MgSO$_4$, filtered and concentrated to give the crude product. The crude product was dissolved in a small amount of DCM and charged to a 24 g silica gel cartridge which was eluted with a 25 min gradient from 0-100% EtOAc/hexane to give Example 106B (121 mg, 0.398 mmol, 56.4% yield) as a yellow viscous oil.

Example 106C ethyl 3-methoxy-1,5,6-trimethyl-2-oxo-1,2-dihydropyridine-4-carboxylate

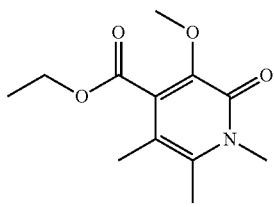 [SMILES: CCOC(=O)c1c(C)c(C)n(C)c(=O)c1OC]

To a solution of Example 106B (130 mg, 0.427 mmol) in DME (3 mL) in a 20 mL microwave vial was added 2,4,6-trimethyl-1,3,5,2,4,6-trioxatriborinane (0.178 mL, 1.28 mmol) and sodium carbonate (2 M) (0.641 mL, 1.28 mmol). The mixture was degassed and PS-Pd(Ph$_3$)$_4$ (0.11 mmol/g loading, 190 mg, 0.021 mmol, 0.050 eq) was added and then degassed. The sealed tube was heated at 180° C., microwave for 30 min. The reaction was diluted with DCM, dried over MgSO$_4$, filtered and concentrated to give Example 106C (105 mg, 0.395 mmol, 92.0% yield) as a yellow oil. LCMS RT=1.40 min, (M+H)$^+$=240.1 (Phenomenex Luna C18, 4.6×30 mm, 2 min gradient with 10-90% MeOH/water/0.1% TFA).

Example 106D 3-methoxy-1,5,6-trimethyl-2-oxo-1,2-dihydropyridine-4-carboxylic acid

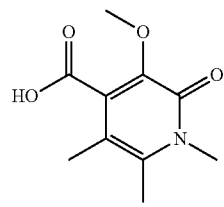

To a solution of Example 106C (103 mg, 0.430 mmol) in THF (6 mL) and MeOH (2. mL) was added lithium hydroxide (30.9 mg, 1.29 mmol) and water (0.5 mL). The reaction was heated at 55° C. overnight. The reaction was acidified with HCl (0.143 mL, 1.72 mmol) and concentrated to give Example 106D (136 mg, 0.425 mmol, 99.0% yield) as a gray solid. LCMS RT=0.6 min, (M+H)$^+$=212.1 (Phenomenex Luna C18, 4.6×30 mm, 2 min gradient with 10-90% MeOH/water/0.1% TFA).

Example 106E

N-(3-(3,4-dichlorophenyl)propyl)-3-methoxy-1,5,6-trimethyl-2-oxo-1,2-dihydropyridine-4-carboxamide

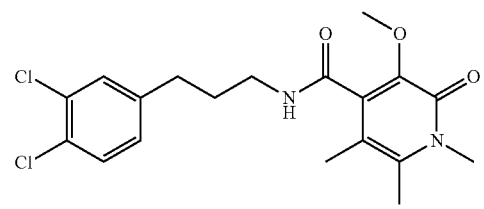 [SMILES: COc1c(C(=O)NCCCc2ccc(Cl)c(Cl)c2)c(C)c(C)n(C)c1=O]

To a solution of Example 106D (30 mg, 0.12 mmol) in DCM (1.5 mL) was added 3-(3,4-dichlorophenyl)propan-1-aminium (24.76 mg, 0.1210 mmol), DIPEA (0.042 mL, 0.24 mmol) and benzotriazol-1-yloxytripyrrolidino-phosphonium hexafluorophosphate (PyBOP) (62.8 mg, 0.121 mmol) at rt. DMF (0.2 mL) was added to the solution and. the resulting solution stirred at rt for 3 h during which time a white precipitate formed. The reaction was concentrated. The residue was dissolved in DCM, loaded on a 12 g column, eluted with 0-10% MeOH/DCM over 20 min gradient to give Example 106D (39 mg, 0.098 mmol, 81% yield) as a yellow solid. LCMS RT=1.96 min, (M+H)$^+$=397.0 (Phenomenex Luna C18, 4.6×30 mm, 2 min gradient with 10-90% MeOH/water/0.1% TFA).

Example 106

To a solution of Example 106E (39 mg, 0.098 mmol) in DCM (1.5 mL) and was added boron tribromide, 1.0 M in DCM (0.29 mL, 0.29 mmol) at rt. The reaction was stirred at rt overnight. The reaction was quenched with MeOH (0.5 mL) and water (5 drops) and stirred at rt 10 min. The reaction was concentrated. The residue was dissolved in MeOH and purified by reverse phase preparative HPLC (YMC Sunfire, 5μ, C18 column, 30×100 mm, 10 min gradient from 20-100% B. A=H₂O/MeOH/TFA 90/10/0.1. B=MeOH/H₂O/TFA 90/10/0.1) to give Example 106 (11 mg, 0.027 mmol, 28% yield) as a yellow solid. LCMS RT=1.9 min, (M+H)⁺=383.0 (Phenomenex Luna C18, 4.6×30 mm, 2 min gradient with 10-90% MeOH/water/0.1% TFA). 1H NMR (400 MHz, CHLOROFORM-d/MeOD) δ ppm 7.27-7.35 (2 H, m), 7.06 (1 H, dd, J=8.03, 2.01 Hz), 3.59 (3 H, s), 3.35-3.43 (2 H, m), 3.31 (7 H, d, J=1.51 Hz), 2.63-2.72 (2 H, m), 2.28 (3 H, s), 2.05 (3 H, s), 1.83-1.93 (2 H, m).

Example 107

N-(4-(3,4-dichlorophenyl)butan-2-yl)-3-hydroxy-1,5,6-trimethyl-2-oxo-1,2-dihydropyridine-4-carboxamide

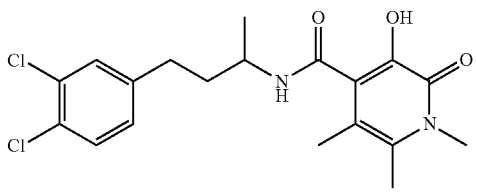 [SMILES: Cc1c(C(=O)NC(C)CCc2ccc(Cl)c(Cl)c2)c(O)c(=O)n(C)c1C]

Example 107 (yellow solid) was synthesized from Example 106D and Intermediate 9 following the methodology described for Example 103. LCMS RT=2.0 min, (M+H)⁺= 397.0 (M+H)⁺ (Phenomenex Luna C18, 4.6×30 mm, 2 min gradient with 10-90% MeOH/water/0.1% TFA). ¹NMR (400 MHz, CHLOROFORM-d) δ ppm 7.32-7.37 (1 H, m), 7.28-7.32 (1 H, m), 7.06 (1 H, dd, J=8.03, 2.01 Hz), 5.99 (1 H, d, J=8.78 Hz), 4.16-4.33 (1 H, m), 3.67 (3 H, s), 2.62-2.83 (2 H, m), 2.28-2.35 (3 H, m), 2.15 (3 H, s), 1.77-1.93 (2 H, m).

Example 108

N-(3-(3,4-dichlorophenyl)propyl)-5-(3,5-difluorophenyl)-3-hydroxy-1,6-dimethyl-2-oxo-1,2-dihydropyridine-4-carboxamide

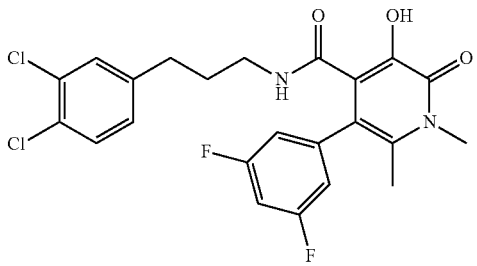 [SMILES: Cc1c(-c2cc(F)cc(F)c2)c(C(=O)NCCCc2ccc(Cl)c(Cl)c2)c(O)c(=O)n1C]

Example 108A ethyl 5-(3,5-difluorophenyl)-3-methoxy-1,6-dimethyl-2-oxo-1,2-dihydropyridine-4-carboxylate

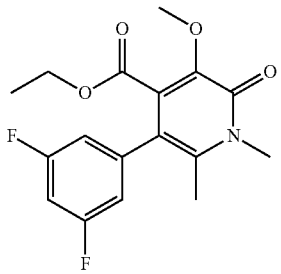 [SMILES: CCOC(=O)c1c(-c2cc(F)cc(F)c2)c(C)n(C)c(=O)c1OC]

To a solution of Example 106B (35 mg, 0.12 mmol) in DME (2 mL) in a 2.5 mL microwave vial was added 3,5-difluorophenylboronic acid (36.3 mg, 0.230 mmol) and sodium carbonate (2 M) (0.173 mL, 0.345 mmol). The mixture was degassed and PS-Pd(Ph₃)₄ (0.11 mmol/g loading, 61 mg) was added and then degassed. The sealed tube was heated in a microwave reactor at 180° C. for 30 min. The reaction was diluted with DCM, dried over MgSO₄, filtered. The filtrate was concentrated to give the crude product. The crude product was dissolved in a small amount of DCM and charged to a 4 g silica gel cartridge which was eluted with a 25 min gradient from 0-100% EtOAc/hexane to give Example 108A (28 mg, 0.083 mmol, 72% yield) as a colorless solid.

Example 108B 5-(3,5-difluorophenyl)-3-methoxy-1,6-dimethyl-2-oxo-1,2-dihydropyridine-4-carboxylic acid A solution of Example 108A (28 mg, 0.083 mmol) in THF (1.5 mL) and MeOH (0.5 mL) in a microwave vial was added lithium hydroxide (5.96 mg, 0.249 mmol) and water (0.25 mL). The reaction was heated at 70° C. overnight. The reaction was acidified with HCl (0.028 mL, 0.33 mmol) and concentrated to give Example 108B (71 mg, 0.083 mmol, 100% yield) as a white solid. LCMS RT=1.59 min, (M+H)⁺= 310.1 (Phenomenex Luna C18, 4.6×30 mm, 2 min gradient with 10-90% MeOH/water/0.1% TFA).

Example 108C

N-(3-(3,4-dichlorophenyl)propyl)-5-(3,5-difluorophenyl)-3-methoxy-1,6-dimethyl-2-oxo-1,2-dihydropyridine-4-carboxamide

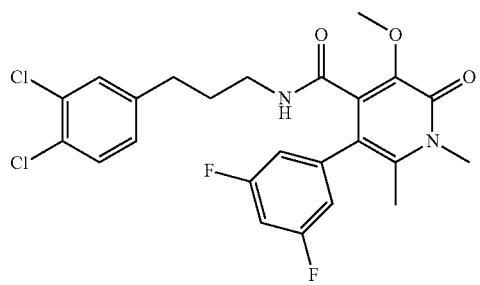 [SMILES: COc1c(C(=O)NCCCc2ccc(Cl)c(Cl)c2)c(-c2cc(F)cc(F)c2)c(C)n(C)c1=O]

To a solution of Example 108B (71 mg, 0.083 mmol) in DCM (1.5 mL) and DMF (0.3 mL) was added 3-(3,4-dichlorophenyl)propan-1-aminium chloride (Intermediate 1) (19.88 mg, 0.08300 mmol), DIPEA (50 μL, 0.29 mmol) and PyBOP (43.0 mg, 0.083 mmol) at rt. The reaction was stirred at rt for 3 days. The reaction was diluted with MeOH, filtered and purified by reverse phase preparative HPLC (YMC Sunfire, 5μ, C18 column, 30×100 mm, 10 min gradient from 20-100% B. A=$H_2O$/MeOH/TFA 90/10/0.1. B=MeOH/$H_2O$/TFA 90/10/0.1) to give Example 108C (23 mg, 0.046 mmol, 56% yield) as a colorless solid. LCMS RT=2.1 min, $(M+H)^+$= 495.1 (Phenomenex Luna C18, 4.6×30 mm, 2 min gradient with 10-90% MeOH/water/0.1% TFA).

Example 108

To a solution of Example 108C (23 mg, 0.046 mmol) in $CHCl_3$ (1.5 mL) and was added boron tribromide, 1.0 M in DCM (0.139 mL, 0.139 mmol) at rt. The reaction was stirred at rt overnight. The reaction was quenched with MeOH (0.5 mL) and water (5 drops) and stirred at rt 10 min. The reaction was concentrated. The residue was dissolved in MeOH and purified by reverse phase preparative HPLC (column: Phenomenex Luna, 5μ, C18, 30×250 mm, 20 min gradient from 30-100% B. A=$H_2O$/ACN/TFA 90/10/0.1. B=ACN/$H_2O$/TFA 90/10/0.1) to give Example 108 (12.7 mg, 0.0260 mmol, 56.3% yield) as a white solid. 1H NMR (400 MHz, CHLOROFORM-d) δ ppm 7.35 (1 H, d, J=8.03 Hz), 7.30 (1 H, d, J=2.01 Hz), 7.26 (1 H, s), 7.05 (1 H, dd, J=8.28, 2.01 Hz), 6.95 (1 H, tt, J=8.78, 2.26 Hz), 6.72-6.82 (1 H, m), 6.25 (1 H, br. s.), 3.49 (2 H, q, J=6.78 Hz), 3.29 (3 H, s), 2.71 (2 H, t, J=7.78 Hz), 1.90-2.03 (2 H, m), 1.89 (3 H, s).

Examples 109

N-(3-(3,4-dichlorophenyl)propyl)-5-(3-fluoro-5-(trifluoromethyl)phenyl)-3-hydroxy-1,6-dimethyl-2-oxo-1,2-dihydropyridine-4-carboxamide

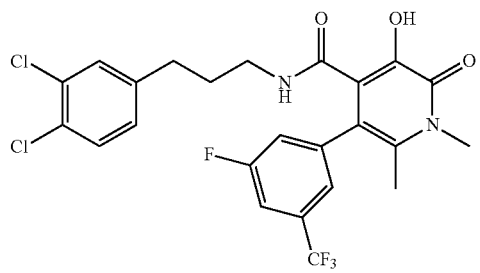 [SMILES: Cc1c(-c2cc(F)cc(C(F)(F)F)c2)c(C(=O)NCCCc2ccc(Cl)c(Cl)c2)c(O)c(=O)n1C]

Examples 109 was synthesized by appropriate application of the method described for Example 108. LCMS (Method D) RT=2.2 min, $(M+H)^+$=531.1.

Example 110

N-(4-(3,4-dichlorophenyl)butan-2-yl)-3-hydroxy-1-methyl-2-oxo-1,2-dihydropyridine-4-carboxamide (Isomer A)

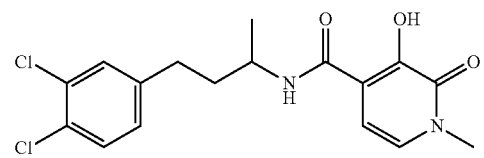 [SMILES: CC(CCc1ccc(Cl)c(Cl)c1)NC(=O)c1ccn(C)c(=O)c1O]

Example 110A

N-(4-(3,4-dichlorophenyl)butan-2-yl)-3-methoxy-1-methyl-2-oxo-1,2-dihydropyridine-4-carboxamide

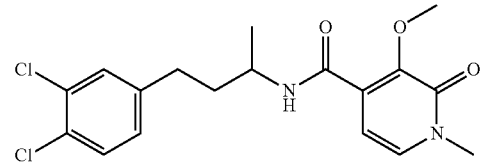 [SMILES: COc1c(C(=O)NC(C)CCc2ccc(Cl)c(Cl)c2)ccn(C)c1=O]

To a solution of Intermediate 9 (75 mg, 0.26 mmol) and Intermediate 16 (47.2 mg, 0.258 mmol) in DCM (0.5 mL) was added sequentially EDCI (59.3 mg, 0.309 mmol), HOBT (47.4 mg, 0.309 mmol) and N-methylmorpholine (0.113 mL, 1.03 mmol) and the reaction mixture was stirred for 18 h at rt. The reaction mixture was diluted with DCM and the organic portion washed with brine, dried over $MgSO_4$, filtered and concentrated. The residue was dissolved in MeOH and purified by reverse phase preparative HPLC (Method L) to give Example 110A (70.7 mg, 0.181 mmol, 81.0% yield). HPLC/MS (Method E) RT=0.97 min, $[M+1]^+$383.2.

Example 110

To a solution of Example 110A (57.6 mg, 0.150 mmol) in $CH_2Cl_2$ (1 mL) was added boron tribromide-methyl sulfide complex (0.406 mL, 0.406 mmol) and the reaction mixture was stirred at rt for 1 h. The reaction mixture was quenched with MeOH and was stirred at rt for 10 min then concentrated, dissolved in DCM, the organic portion washed with brine, dried over $MgSO_4$, filtered and concentrated. The residue was purified by reverse phase preparative HPLC (Method M) to give Example 110 (36.9 mg, 0.0990 mmol, 65.9% yield) as a white solid. HPLC/MS (Method E) RT=0.96 min, [M+1]+ 369.2; 1H NMR (400 MHz, CHLOROFORM-d) δ ppm 1.16-1.35 (3 H, m), 1.75-1.94 (2 H, m), 2.56-2.73 (2 H, m), 3.64 (3 H, s), 4.10-4.34 (1 H, m), 6.83-6.91 (2 H, m), 7.02 (1 H, dd, J=8.2, 2.1 Hz), 7.28 (1 H, d, J=2.0 Hz), 7.29-7.36 (1 H, m), 7.52 (1 H, d, J=8.0 Hz).

By appropriate application of the method described for Example 110, Examples 111-149 were synthesized. The amine components used in Examples 114-126 may be synthesized using the methodology described for Intermediate 9. The HPLC-MS data (retention time, mass and conditions) for Examples 111-149 are listed in Table 5.

TABLE 5

| Ex. # | Structure | Name | RT (min) | [M + 1]+ | LC/MS Methods |
|---|---|---|---|---|---|
| 111 | Isomer B | N-(4-(3,4-dichlorophenyl)butan-2-yl)-3-hydroxy-1-methyl-2-oxo-1,2-dihydropyridine-4-carboxamide | 0.96 | 369.2 | E |
| 112 | 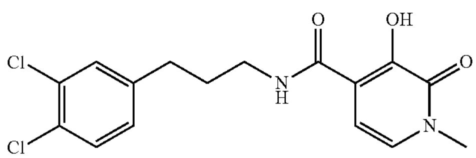 [SMILES: Cn1ccc(C(=O)NCCCc2ccc(Cl)c(Cl)c2)c(O)c1=O] | N-(3-(3,4-dichlorophenyl)propyl)-3-hydroxy-1-methyl-2-oxo-1,2-dihydropyridine-4-carboxamide | 0.94 | 355.3 | E |
| 113 | 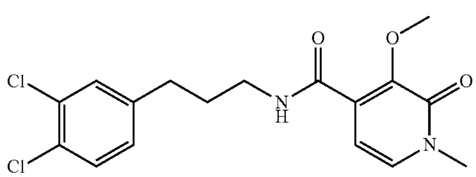 [SMILES: COc1c(C(=O)NCCCc2ccc(Cl)c(Cl)c2)ccn(C)c1=O] | N-(3-(3,4-dichlorophenyl)propyl)-3-methoxy-1-methyl-2-oxo-1,2-dihydropyridine-4-carboxamide | 0.94 | 369.2 | E |
| 114 | Isomer A | N-(1-(3,4-dichlorophenyl)-4-methylpentan-3-yl)-3-hydroxy-1-methyl-2-oxo-1,2-dihydropyridine-4-carboxamide | 1.11 | 397.1 | E |
| 115 | Isomer B | N-(1-(3,4-dichlorophenyl)-4-methylpentan-3-yl)-3-hydroxy-1-methyl-2-oxo-1,2-dihydropyridine-4-carboxamide | 1.11 | 397.1 | E |

TABLE 5-continued

| Ex. # | Structure | Name | RT (min) | [M + 1]+ | LC/MS Methods |
|---|---|---|---|---|---|
| 116 | Isomer A | N-(1-(3,4-dichlorophenyl)pentan-3-yl)-3-hydroxy-1-methyl-2-oxo-1,2-dihydropyridine-4-carboxamide | 1.01 | 383.1 | E |
| 117 | Isomer B | N-(1-(3,4-dichlorophenyl)pentan-3-yl)-3-hydroxy-1-methyl-2-oxo-1,2-dihydropyridine-4-carboxamide | 1.01 | 383.1 | E |
| 118 | Isomer A | N-(1-cyclopropyl-3-(3,4-dichlorophenyl)propyl)-3-hydroxy-1-methyl-2-oxo-1,2-dihydropyridine-4-carboxamide | 1.02 | 395.1 | E |
| 119 | Isomer B | N-(1-cyclopropyl-3-(3,4-dichlorophenyl)propyl)-3-hydroxy-1-methyl-2-oxo-1,2-dihydropyridine-4-carboxamide | 1.03 | 395.1 | E |
| 120 | Isomer A | N-(3-(3,4-dichlorophenyl)-1-phenylpropyl)-3-hydroxy-1-methyl-2-oxo-1,2-dihydropyridine-4-carboxamide | 1.06 | 431.1 | E |
| 121 | Isomer B | N-(3-(3,4-dichlorophenyl)-1-phenylpropyl)-3-hydroxy-1-methyl-2-oxo-1,2-dihydropyridine-4-carboxamide | 1.06 | 431.1 | E |

TABLE 5-continued

| Ex. # | Structure | Name | RT (min) | [M + 1]+ | LC/MS Methods |
|---|---|---|---|---|---|
| 122 | Isomer A | N-(5-(3,4-dichlorophenyl)pent-1-en-3-yl)-3-hydroxy-1-methyl-2-oxo-1,2-dihydropyridine-4-carboxamide | 0.99 | 381.1 | E |
| 123 | Isomer B | N-(5-(3,4-dichlorophenyl)pent-1-en-3-yl)-3-hydroxy-1-methyl-2-oxo-1,2-dihydropyridine-4-carboxamide | 0.99 | 381.1 | E |
| 124 | Isomer A | N-(5-(3,4-dichlorophenyl)pentan-2-yl)-3-hydroxy-1-methyl-2-oxo-1,2-dihydropyridine-4-carboxamide | 2.11 | 383.0 | D |
| 125 | Isomer B | N-(5-(3,4-dichlorophenyl)pentan-2-yl)-3-hydroxy-1-methyl-2-oxo-1,2-dihydropyridine-4-carboxamide | 2.12 | 383.0 | D |
| 126 | 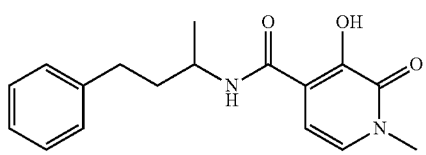 [SMILES: CC(CCc1ccccc1)NC(=O)c1ccn(C)c(=O)c1O] | 3-hydroxy-1-methyl-2-oxo-N-(4-phenylbutan-2-yl)-1,2-dihydropyridine-4-carboxamide | 1.6 | 301.17 | I |
| 127 | 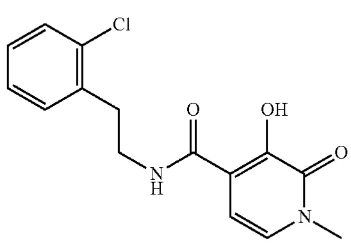 [SMILES: Cn1ccc(C(=O)NCCc2ccccc2Cl)c(O)c1=O] | N-(2-chlorophenethyl)-3-hydroxy-1-methyl-2-oxo-1,2-dihydropyridine-4-carboxamide | 1.49 | 307.07 | I |
| 128 | 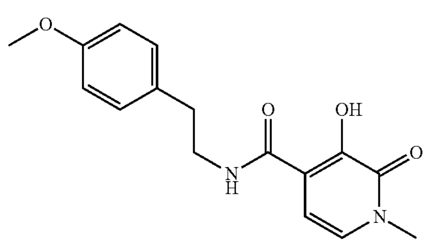 | 3-hydroxy-N-(4-methoxyphenethyl)-1-methyl-2-oxo-1,2-dihydropyridine-4-carboxamide | 1.29 | 303.13 | I |

TABLE 5-continued

| Ex. # | Structure | Name | RT (min) | [M + 1]+ | LC/MS Methods |
|---|---|---|---|---|---|
| 129 | 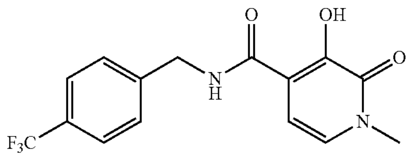 [SMILES: Cn1ccc(C(=O)NCc2ccc(C(F)(F)F)cc2)c(O)c1=O] | 3-hydroxy-1-methyl-2-oxo-N-(4-(trifluoromethyl)benzyl)-1,2-dihydropyridine-4-carboxamide | 1.52 | 327.08 | I |
| 130 | 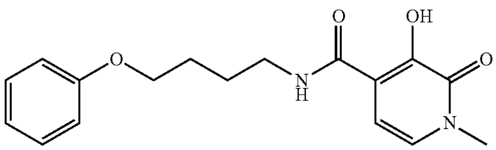 [SMILES: Cn1ccc(C(=O)NCCCCOc2ccccc2)c(O)c1=O] | 3-hydroxy-1-methyl-2-oxo-N-(4-phenoxybutyl)-1,2-dihydropyridine-4-carboxamide | 1.53 | 317.15 | I |
| 131 | 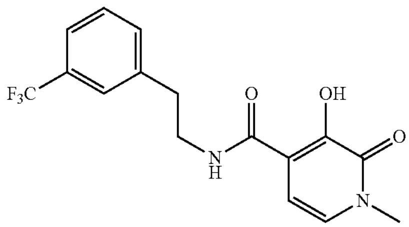 [SMILES: Cn1ccc(C(=O)NCCc2cccc(C(F)(F)F)c2)c(O)c1=O] | 3-hydroxy-1-methyl-2-oxo-N-(3-(trifluoromethyl)phenethyl)-1,2-dihydropyridine-4-carboxamide | 1.65 | 341.13 | I |
| 132 | 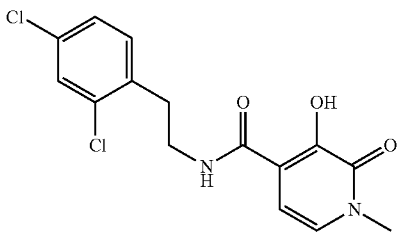 [SMILES: Cn1ccc(C(=O)NCCc2ccc(Cl)cc2Cl)c(O)c1=O] | N-(2,4-dichlorophenethyl)-3-hydroxy-1-methyl-2-oxo-1,2-dihydropyridine-4-carboxamide | 1.74 | 341 | I |
| 133 | 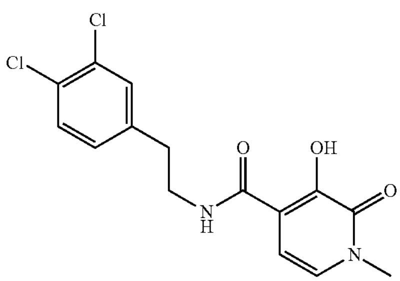 [SMILES: Cn1ccc(C(=O)NCCc2ccc(Cl)c(Cl)c2)c(O)c1=O] | N-(3,4-dichlorophenethyl)-3-hydroxy-1-methyl-2-oxo-1,2-dihydropyridine-4-carboxamide | 1.7 | 341.02 | I |
| 134 | 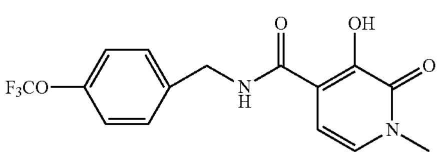 [SMILES: Cn1ccc(C(=O)NCc2ccc(OC(F)(F)F)cc2)c(O)c1=O] | 3-hydroxy-1-methyl-2-oxo-N-(4-(trifluoromethoxy)benzyl)-1,2-dihydropyridine-4-carboxamide | 1.63 | 343.05 | I |
| 135 | 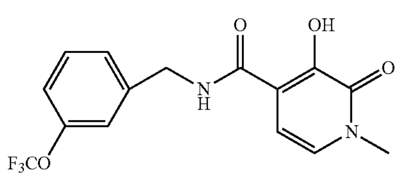 [SMILES: Cn1ccc(C(=O)NCc2cccc(OC(F)(F)F)c2)c(O)c1=O] | 3-hydroxy-1-methyl-2-oxo-N-(3-(trifluoromethoxy)benzyl)-1,2-dihydropyridine-4-carboxamide | 1.63 | 343.1 | I |
| 136 | 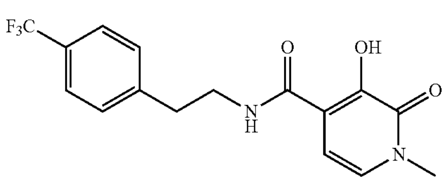 [SMILES: Cn1ccc(C(=O)NCCc2ccc(C(F)(F)F)cc2)c(O)c1=O] | 3-hydroxy-1-methyl-2-oxo-N-(4-(trifluoromethyl)phenethyl)-1,2-dihydropyridine-4-carboxamide | 1.67 | 341.11 | I |

TABLE 5-continued

| Ex. # | Structure | Name | RT (min) | [M + 1]+ | LC/MS Methods |
|---|---|---|---|---|---|
| 137 | 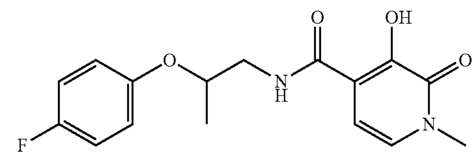 [SMILES: CC(CNC(=O)c1ccn(C)c(=O)c1O)Oc1ccc(F)cc1] | N-(2-(4-fluorophenoxy)propyl)-3-hydroxy-1-methyl-2-oxo-1,2-dihydropyridine-4-carboxamide | 1.43 | 321.09 | I |
| 138 | 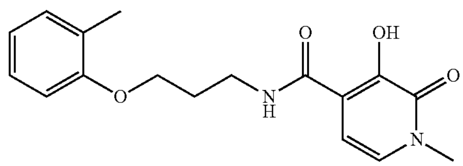 [SMILES: Cc1ccccc1OCCCNC(=O)c1ccn(C)c(=O)c1O] | 3-hydroxy-1-methyl-2-oxo-N-(3-(o-tolyloxy)propyl)-1,2-dihydropyridine-4-carboxamide | 1.62 | 317.09 | I |
| 139 | 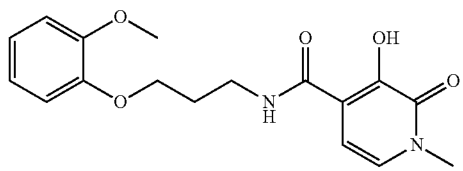 [SMILES: COc1ccccc1OCCCNC(=O)c1ccn(C)c(=O)c1O] | 3-hydroxy-N-(3-(2-methoxyphenoxy)propyl)-1-methyl-2-oxo-1,2-dihydropyridine-4-carboxamide | 1.32 | 333.11 | I |
| 140 | 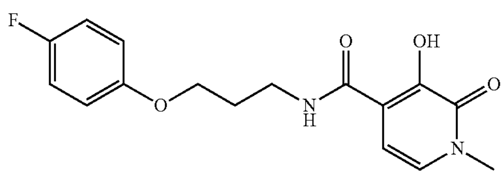 [SMILES: Cn1ccc(C(=O)NCCCOc2ccc(F)cc2)c(O)c1=O] | N-(3-(4-fluorophenoxy)propyl)-3-hydroxy-1-methyl-2-oxo-1,2-dihydropyridine-4-carboxamide | 1.45 | 321.05 | I |
| 141 | 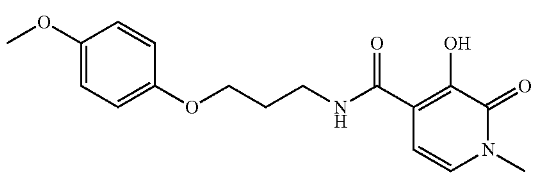 | 3-hydroxy-N-(3-(4-methoxyphenoxy)propyl)-1-methyl-2-oxo-1,2-dihydropyridine-4-carboxamide | 1.36 | 333.12 | I |
| 142 | 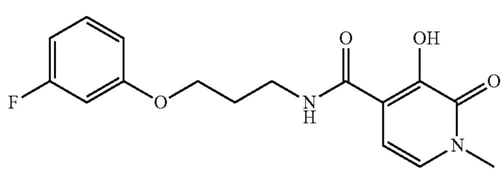 [SMILES: Cn1ccc(C(=O)NCCCOc2cccc(F)c2)c(O)c1=O] | N-(3-(3-fluorophenoxy)propyl)-3-hydroxy-1-methyl-2-oxo-1,2-dihydropyridine-4-carboxamide | 1.49 | 321.07 | I |
| 143 | 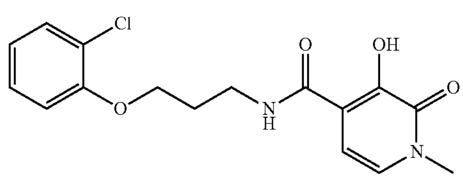 [SMILES: Cn1ccc(C(=O)NCCCOc2ccccc2Cl)c(O)c1=O] | N-(3-(2-chlorophenoxy)propyl)-3-hydroxy-1-methyl-2-oxo-1,2-dihydropyridine-4-carboxamide | 1.59 | 337.05 | I |
| 144 | 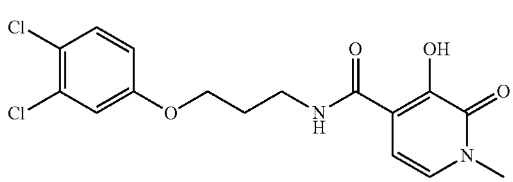 [SMILES: Cn1ccc(C(=O)NCCCOc2ccc(Cl)c(Cl)c2)c(O)c1=O] | N-(3-(3,4-dichlorophenoxy)propyl)-3-hydroxy-1-methyl-2-oxo-1,2-dihydropyridine-4-carboxamide | 1.85 | 370.97 | I |

TABLE 5-continued

| Ex. # | Structure | Name | RT (min) | [M + 1]+ | LC/MS Methods |
|---|---|---|---|---|---|
| 145 | 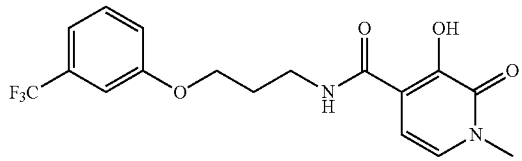 [SMILES: Cn1ccc(C(=O)NCCCOc2cccc(C(F)(F)F)c2)c(O)c1=O] | 3-hydroxy-1-methyl-2-oxo-N-(3-(3-(trifluoromethyl)phenoxy)propyl)-1,2-dihydropyridine-4-carboxamide | 1.8 | 371.1 | I |
| 146 | 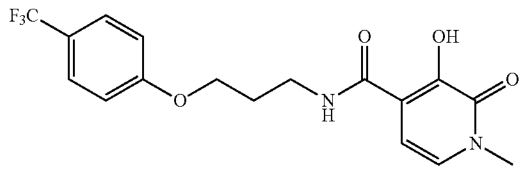 [SMILES: Cn1ccc(C(=O)NCCCOc2ccc(C(F)(F)F)cc2)c(O)c1=O] | 3-hydroxy-1-methyl-2-oxo-N-(3-(4-(trifluoromethyl)phenoxy)propyl)-1,2-dihydropyridine-4-carboxamide | 1.8 | 371.08 | I |
| 147 | 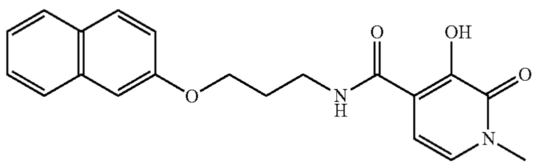 [SMILES: Cn1ccc(C(=O)NCCCOc2ccc3ccccc3c2)c(O)c1=O] | 3-hydroxy-1-methyl-N-(3-(naphthalen-2-yloxy)propyl)-2-oxo-1,2-dihydropyridine-4-carboxamide | 1.83 | 353.13 | I |
| 148 | 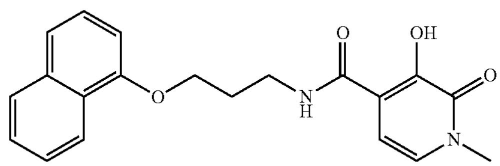 [SMILES: Cn1ccc(C(=O)NCCCOc2cccc3ccccc23)c(O)c1=O] | 3-hydroxy-1-methyl-N-(3-(naphthalen-1-yloxy)propyl)-2-oxo-1,2-dihydropyridine-4-carboxamide | 1.82 | 353.12 | I |
| 149 | 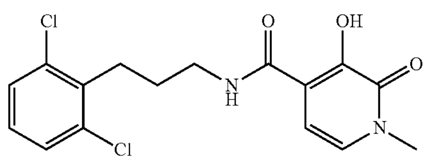 [SMILES: Cn1ccc(C(=O)NCCCc2c(Cl)cccc2Cl)c(O)c1=O] | N-(3-(2,6-dichlorophenyl)propyl)-3-hydroxy-1-methyl-2-oxo-1,2-dihydropyridine-4-carboxamide | 1.79 | 355.0 | D |

Example 150

N-(3-(3,4-dichlorophenyl)propyl)-1-ethyl-3-hydroxy-2-oxo-1,2-dihydropyridine-4-carboxamide

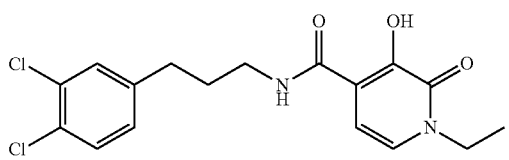 [SMILES: CCn1ccc(C(=O)NCCCc2ccc(Cl)c(Cl)c2)c(O)c1=O]

Example 150A

N-(3-(3,4-dichlorophenyl)propyl)-3-ethoxy-1-ethyl-2-oxo-1,2-dihydropyridine-4-carboxamide

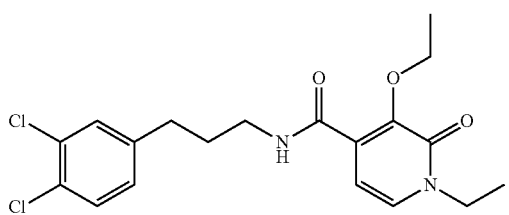 [SMILES: CCOc1c(C(=O)NCCCc2ccc(Cl)c(Cl)c2)ccn(CC)c1=O]

To a solution of Intermediate 17 (0.027 g, 0.13 mmol) in DMF (0.5 mL) was added HOBT (0.023 g, 0.15 mmol), EDCI (0.037 g, 0.19 mmol) and N-methylmorpholine (0.042 mL, 0.38 mmol). The reaction mixture was stirred at rt for 16 h. The reaction mixture was diluted with DCM and the organic portion washed with 1N HCl. Brine and dried over $MgSO_4$. and filtered. The filtrate solvent was evaporated under reduced pressure and purified using a 10 min gradient on a 12 g silica gel cartridge from 0 to 20% MeOH in DCM to yield Example 150A (37 mg, 0.093 mmol, 723% yield). HPLC/MS (method D) RT=2.03 min, [M+1]+398.0.

Example 150

To a solution of Example 150A (30 mg, 0.076 mmol) in DCM (1 mL) was added boron trichloride-methyl sulfide complex (40.6 mg, 0.227 mmol). The reaction mixture was stirred for 16 h. The reaction mixture was quenched with ice and MeOH. The reaction mixture was purified by reverse phase preparative HPLC using a 10 minute gradient of 20 to 100% B (Column: Phenomenex AXIA Luna 100×20 mm 5 µm; Solvent A: 10% MeOH-90% $H_2O$-0.1% TFA; Solvent B: 90% MeOH-10% $H_2O$-0.1% TFA) to provide Example 150 (20 mg, 0.053 mmol, 70% yield). HPLC/MS (Method D) RT=2.00 min, [M+1]+369.0. 1H NMR (400 MHz, MeOD) δ ppm 7.37-7.41 (2 H, m), 7.14 (2 H, dd, J=15.9, 7.8 Hz), 6.62 (1 H, d, J=7.3 Hz), 4.00-4.08 (2 H, m), 3.43 (2 H, t, J=6.6 Hz), 2.70 (2 H, t, J=7.3 Hz), 1.94 (2 H, quin, J=7.0 Hz), 1.34 (3 H, t, J=7.1 Hz).

Example 151

1-cyclopropyl-N-(3-(3,4-dichlorophenyl)propyl)-3-hydroxy-2-oxo-1,2-dihydropyridine-4-carboxamide

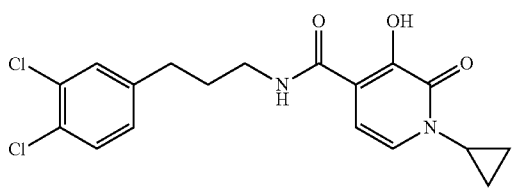 [SMILES: O=C(NCCCc1ccc(Cl)c(Cl)c1)c1ccn(C2CC2)c(=O)c1O]

Example 151A 1-cyclopropyl-N-(3-(3,4-dichlorophenyl)propyl)-3-methoxy-2-oxo-1,2-dihydropyridine-4 carboxamide

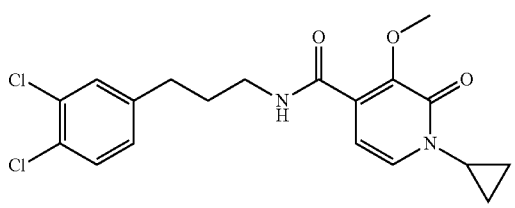 [SMILES: COc1c(C(=O)NCCCc2ccc(Cl)c(Cl)c2)ccn(C2CC2)c1=O]

To a solution of Example 184A (15 mg, 0.042 mmol,), cyclopropylboronic acid (3.63 mg, 0.0420 mmol) in DCM (2 mL) was added Cu(OAc)$_2$ (7.64 mg, 0.0420 mmol), 2,2'-bipyridine (6.60 mg, 0.0420 mmol) and Na$_2$CO$_3$ (8.95 mg, 0.0840 mmol). The reaction mixture was stirred at 70° C. for 24 h. The reaction mixture was quenched with brine and the organic solvent was evaporated under reduced pressure. The crude product was passed through a silica gel plug, dried in vacuo to give Example 151A (10 mg, 0.025 mmol, 60% yield). HPLC/MS (Method D) RT=3.63 min, [M+1]$^+$395.3.

Example 151

To a solution of Intermediate 151A (30 mg, 0.076 mmol) in DCM (1 mL) was added boron trichloride-methyl sulfide complex (40.6 mg, 0.227 mmol). The reaction mixture was stirred for 16 h. The reaction mixture was quenched with ice and MeOH. The crude reaction mixture was purified on prep HPLC using a 10 minute gradient of 20 to 100% B. (Column: Phenomenex AXIA Luna 100×20 mm 5 μm; Solvent A: 10% MeOH-90% H$_2$O-0.1% TFA; Solvent B: 90% MeOH-10% H$_2$O-0.1% TFA) to provide Example 151 (20 mg, 0.053 mmol, 70% yield). HPLC/MS (Method D) RT=2.00 min, [M+1]$^+$369.0. 1H NMR (400 MHz, MeOD) δ ppm 7.37-7.41 (2 H, m), 7.14 (2 H, dd, J=15.9, 7.8 Hz), 6.62 (1 H, d, J=7.3 Hz), 4.00-4.08 (2 H, m), 3.43 (2 H, t, J=6.6 Hz), 2.70 (2 H, t, J=7.3 Hz), 1.94 (2 H, quin, J=7.0 Hz), 1.34 (3 H, t, J=7.1 Hz).

Examples 152-169

Examples 152-169 were synthesized following the procedure described for Example 150 using acid Intermediates 17, 18, 19, 20, 21 and amine Intermediates 1, 10, 11, 12, 13, 14, 15. The analytical data (retention time, mass and conditions of LC-MS) of Example 152-169 are listed Table 6.

TABLE 6

| Ex. # | Structure | Name | RT (min) | LC/MS [M + 1]$^+$ | Methods |
|---|---|---|---|---|---|
| 152 | 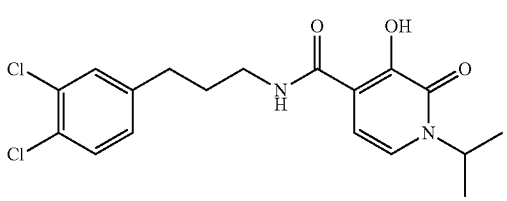 [SMILES: CC(C)n1ccc(C(=O)NCCCc2ccc(Cl)c(Cl)c2)c(O)c1=O] | N-(3-(3,4-dichlorophenyl)propyl)-3-hydroxy-1-isopropyl-2-oxo-1,2-dihydropyridine-4-carboxamide | 2.0 | 448.9 | D |
| 153 | 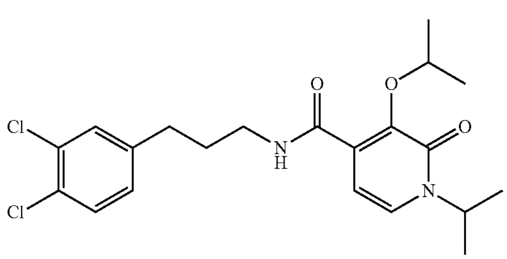 [SMILES: CC(C)Oc1c(C(=O)NCCCc2ccc(Cl)c(Cl)c2)ccn(C(C)C)c1=O] | N-(3-(3,4-dichlorophenyl)propyl)-3-isopropoxy-1-isopropyl-2-oxo-1,2-dihydropyridine-4-carboxamide | 2.0 | 449.0 | D |
| 154 | 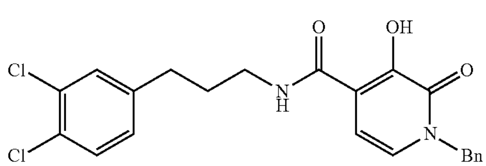 [SMILES: O=C(NCCCc1ccc(Cl)c(Cl)c1)c1ccn(Cc2ccccc2)c(=O)c1O] | 1-benzyl-N-(3-(3,4-dichlorophenyl)propyl)-3-hydroxy-2-oxo-1,2-dihydropyridine-4-carboxamide | 2.1 | 432 | D |

TABLE 6-continued

| Ex. # | Structure | Name | RT (min) | [M + 1]+ | LC/MS Methods |
|---|---|---|---|---|---|
| 155 | 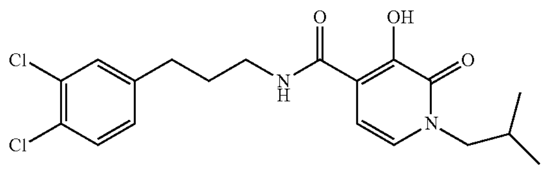 [SMILES: CC(C)Cn1ccc(C(=O)NCCCc2ccc(Cl)c(Cl)c2)c(O)c1=O] | N-(3-(3,4-dichlorophenyl)propyl)-3-hydroxy-1-isobutyl-2-oxo-1,2-dihydropyridine-4-carboxamide | 2.2 | 398 | D |
| 156 | 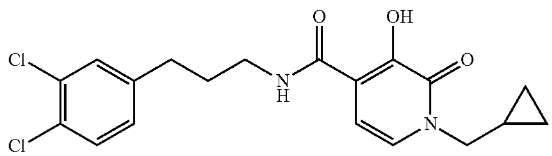 [SMILES: O=C(NCCCc1ccc(Cl)c(Cl)c1)c1ccn(CC2CC2)c(=O)c1O] | 1-(cyclopropylmethyl)-N-(3-(3,4-dichlorophenyl)propyl)-3-hydroxy-2-oxo-1,2-dihydropyridine-4-carboxamide | 2.08 | 395 | D |
| 157 | 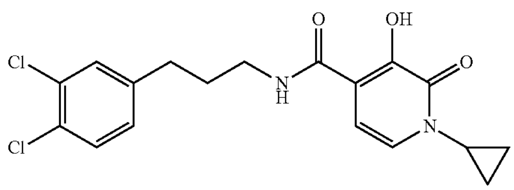 [SMILES: O=C(NCCCc1ccc(Cl)c(Cl)c1)c1ccn(C2CC2)c(=O)c1O] | 1-cyclopropyl-N-(3-(3,4-dichlorophenyl)propyl)-3-hydroxy-2-oxo-1,2-dihydropyridine-4-carboxamide | 2.74 | 381 | A |
| 158 | 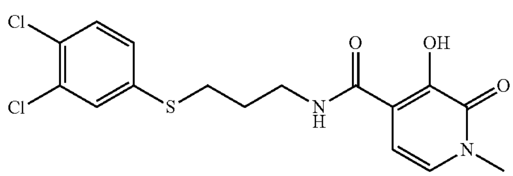 | N-(3-(3,4-dichlorophenylthio)propyl)-3-hydroxy-1-methyl-2-oxo-1,2-dihydropyridine-4-carboxamide | 3.85 | 389 | C |
| 159 | 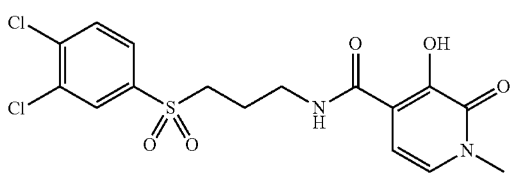 [SMILES: Cn1ccc(C(=O)NCCCS(=O)(=O)c2ccc(Cl)c(Cl)c2)c(O)c1=O] | N-(3-(3,4-dichlorophenylsulfonyl)propyl)-3-hydroxy-1-methyl-2-oxo-1,2-dihydropyridine-4-carboxamide | 1.65 | 420 | D |
| 160 | 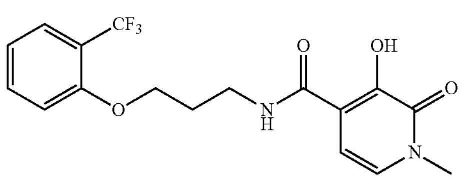 | 3-hydroxy-1-methyl-2-oxo-N-(3-(2-(trifluoromethyl)phenoxy)propyl)-1,2-dihydropyridine-4-carboxamide | 3.29 | 371 | C |
| 161 | 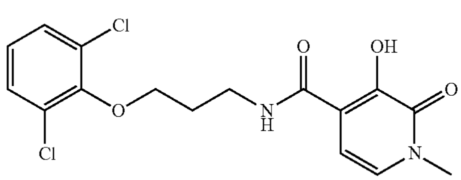 [SMILES: Cn1ccc(C(=O)NCCCOc2c(Cl)cccc2Cl)c(O)c1=O] | N-(3-(2,6-dichlorophenoxy)propyl)-3-hydroxy-1-methyl-2-oxo-1,2-dihydropyridine-4-carboxamide | 2.00 | 371 | D |
| 162 | 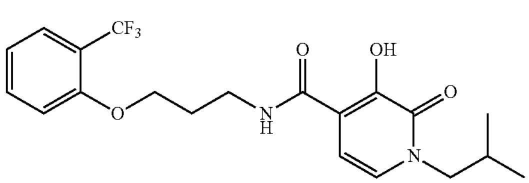 [SMILES: CC(C)Cn1ccc(C(=O)NCCCOc2ccccc2C(F)(F)F)c(O)c1=O] | 3-hydroxy-1-isobutyl-2-oxo-N-(3-(2-(trifluoromethyl)phenoxy)propyl)-1,2-dihydropyridine-4-carboxamide | 3.75 | 413 | D |

TABLE 6-continued

| Ex. # | Structure | Name | RT (min) | [M + 1]+ | LC/MS Methods |
|---|---|---|---|---|---|
| 163 | 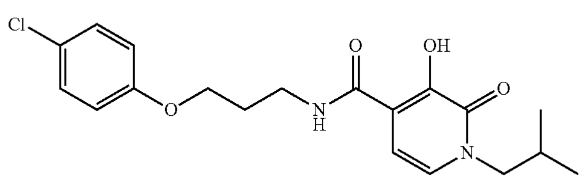 [SMILES: CC(C)Cn1ccc(C(=O)NCCCOc2ccc(Cl)cc2)c(O)c1=O] | N-(3-(4-chlorophenoxy)propyl)-3-hydroxy-1-isobutyl-2-oxo-1,2-dihydropyridine-4-carboxamide | 2.09 | 379 | D |
| 164 | 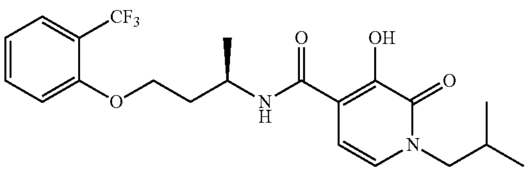 [SMILES: CC(C)Cn1ccc(C(=O)N[C@H](C)CCOc2ccccc2C(F)(F)F)c(O)c1=O] | (R)-3-hydroxy-1-isobutyl-2-oxo-N-(4-(2-(trifluoromethyl)phenoxy)butan-2-yl)-1,2-dihydropyridine-4-carboxamide | 2.07 | 427 | D |
| 165 | 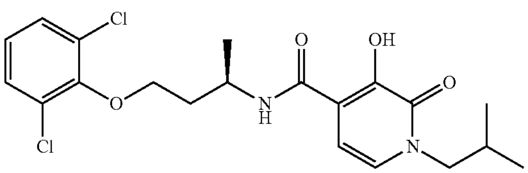 [SMILES: CC(C)Cn1ccc(C(=O)N[C@H](C)CCOc2c(Cl)cccc2Cl)c(O)c1=O] | (R)-N-(4-(2,6-dichlorophenoxy)butan-2-yl)-3-hydroxy-1-isobutyl-2-oxo-1,2-dihydropyridine-4-carboxamide | 2.15 | 427 | D |
| 166 | 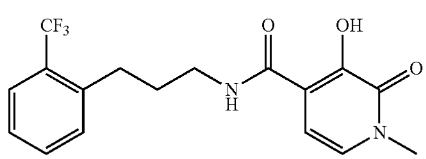 [SMILES: Cn1ccc(C(=O)NCCCc2ccccc2C(F)(F)F)c(O)c1=O] | 3-hydroxy-1-methyl-2-oxo-N-(3-(2-(trifluoromethyl)phenyl)propyl)-1,2-dihydropyridine-4-carboxamide | 1.86 | 355 | D |
| 167 | 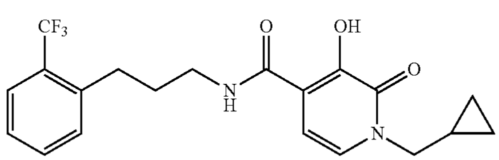 [SMILES: O=C(NCCCc1ccccc1C(F)(F)F)c1ccn(CC2CC2)c(=O)c1O] | 1-(cyclopropylmethyl)-3-hydroxy-2-oxo-N-(3-(2-(trifluoromethyl)phenyl)propyl)-1,2-dihydropyridine-4-carboxamide | 1.99 | 395 | D |
| 168 | 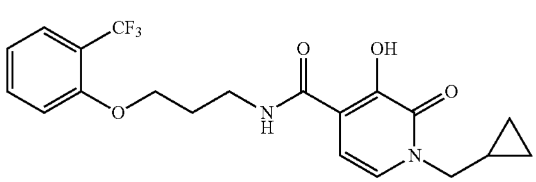 [SMILES: O=C(NCCCOc1ccccc1C(F)(F)F)c1ccn(CC2CC2)c(=O)c1O] | 1-(cyclopropylmethyl)-3-hydroxy-2-oxo-N-(3-(2-(trifluoromethyl)phenoxy)propyl)-1,2-dihydropyridine-4-carboxamide | 2.04 | 411 | D |
| 169 | 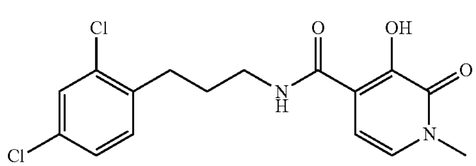 [SMILES: Cn1ccc(C(=O)NCCCc2ccc(Cl)cc2Cl)c(O)c1=O] | N-(3-(2,4-dichlorophenyl)propyl)-3-hydroxy-1-methyl-2-oxo-1,2-dihydropyridine-4-carboxamide | 2.05 | 256 | D |

Example 170

N-(3-(3,4-dichlorophenyl)propyl)-1-(2-fluorophenethyl)-3-hydroxy-2-oxo-1,2-dihydropyridine-4-carboxamide

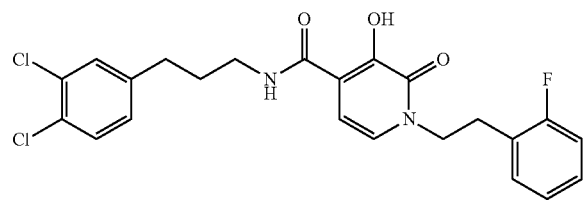 [SMILES: O=C(NCCCc1ccc(Cl)c(Cl)c1)c1ccn(CCc2ccccc2F)c(=O)c1O]

To a solution of Intermediate 22 (20 mg, 0.059 mmol) in DMF (3 mL) was added $Cs_2CO_3$ (22.92 mg, 0.07000 mmol), followed by 1-(2-bromoethyl)-2-fluorobenzene (11.90 mg, 0.05900 mmol). The reaction mixture was stirred at 50° C. overnight. The reaction mixture was filtered and partitioned between brine and EtOAc. The organic layer was washed further with brine, $H_2O$, brine and dried over $Na_2SO_4$ and decanted. The organic layer was evaporated under reduced pressure to give the crude product which was purified on prep HPLC using a 10 minute gradient from 0 to 100% B (Column: Phenomenex AXIA Luna 100×20 mm 5 μm; Solvent A: 10% MeOH-90% $H_2O$-0.1% TFA; Solvent B: 90% MeOH-10% $H_2O$-0.1% TFA) to yield Example 170 (4 mg, 0.0087 mmol, 14.8% yield). HPLC/MS (Method A) RT=4.13 min, $[M+1]^+$ 463.1. 1H NMR (400 MHz, CHLOROFORM-d) δ ppm 7.33-7.37 (1 H, m), 7.30 (1 H, s), 7.23 (1 H, d, J=4.4 Hz), 7.01-7.09 (4 H, m), 6.74 (1 H, d, J=7.0 Hz), 6.61 (1 H, d, J=7.5 Hz), 4.23 (2 H, t, J=7.0 Hz), 3.48 (2 H, t, J=6.6 Hz), 3.14 (2 H, t, J=6.8 Hz), 2.68 (2 H, t, J=7.5 Hz), 1.90-1.97 (2 H, m).

Examples 171-179 were synthesized from Intermediate 22 following the procedure described for Example 170. The analytical data (retention time, mass and conditions of LC-MS) of example 171-179 are listed in Table 7.

TABLE 7

| Ex. # | Structure | Name | RT (min) | $[M + 1]^+$ | LC/MS Methods |
|---|---|---|---|---|---|
| 171 | 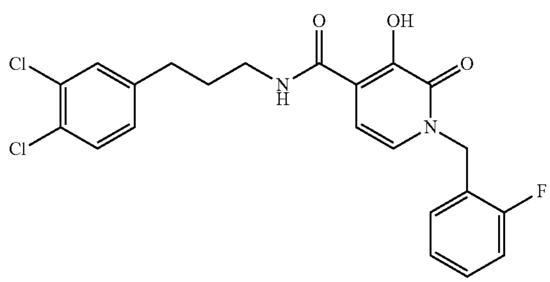 [SMILES: O=C(NCCCc1ccc(Cl)c(Cl)c1)c1ccn(Cc2ccccc2F)c(=O)c1O] | N-(3-(3,4-dichlorophenyl)propyl)-1-(2-fluorobenzyl)-3-hydroxy-2-oxo-1,2-dihydropyridine-4-carboxamide | 2.21 | 450 | D |
| 172 | 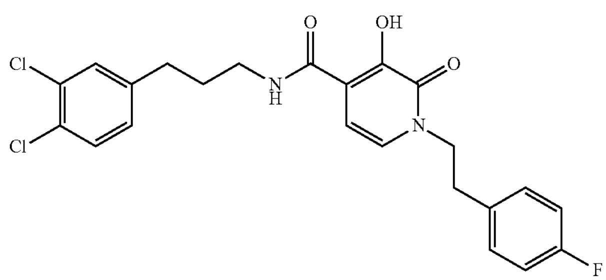 [SMILES: O=C(NCCCc1ccc(Cl)c(Cl)c1)c1ccn(CCc2ccc(F)cc2)c(=O)c1O] | N-(3-(3,4-dichlorophenyl)propyl)-1-(4-fluorophenethyl)-3-hydroxy-2-oxo-1,2-dihydropyridine-4-carboxamide | 4.18 | 465 | C |
| 173 | 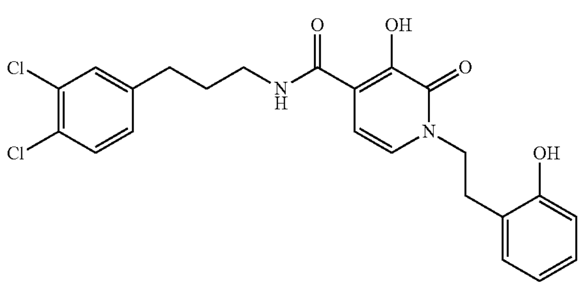 [SMILES: O=C(NCCCc1ccc(Cl)c(Cl)c1)c1ccn(CCc2ccccc2O)c(=O)c1O] | N-(3-(3,4-dichlorophenyl)propyl)-3-hydroxy-1-(2-hydroxyphenethyl)-2-oxo-1,2-dihydropyridine-4-carboxamide | 3.96 | 461 | C |

TABLE 7-continued

| Ex. # | Structure | Name | RT (min) | [M + 1]+ | LC/MS Methods |
|---|---|---|---|---|---|
| 174 | 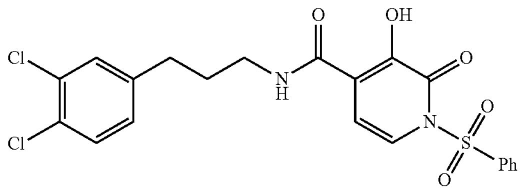 [SMILES: O=C(NCCCc1ccc(Cl)c(Cl)c1)c1ccn(S(=O)(=O)c2ccccc2)c(=O)c1O] | N-(3-(3,4-dichlorophenyl)propyl)-3-hydroxy-2-oxo-1-(phenylsulfonyl)-1,2-dihydropyridine-4-carboxamide | 2.0 | 481 | D |
| 175 | 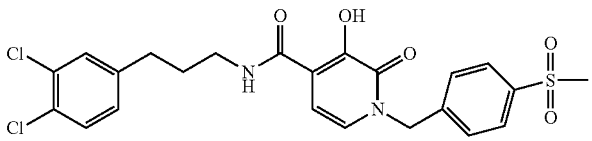 [SMILES: CS(=O)(=O)c1ccc(Cn2ccc(C(=O)NCCCc3ccc(Cl)c(Cl)c3)c(O)c2=O)cc1] | N-(3-(3,4-dichlorophenyl)propyl)-3-hydroxy-1-(4-(methylsulfonyl)benzyl)-2-oxo-1,2-dihydropyridine-4-carboxamide | 3.53 | 509 | C |
| 176 | 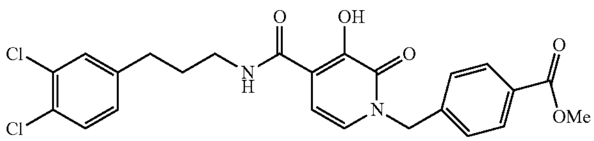 [SMILES: COC(=O)c1ccc(Cn2ccc(C(=O)NCCCc3ccc(Cl)c(Cl)c3)c(O)c2=O)cc1] | methyl 4-((4-(3-(3,4-dichlorophenyl)propylcarbamoyl)-3-hydroxy-2-oxopyridin-1(2H)-yl)methyl)benzoate | 2.08 | 490 | D |
| 177 | 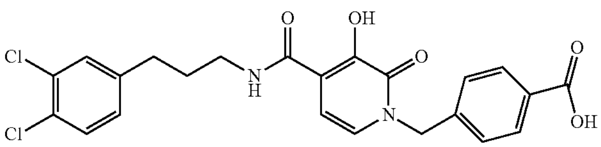 [SMILES: O=C(O)c1ccc(Cn2ccc(C(=O)NCCCc3ccc(Cl)c(Cl)c3)c(O)c2=O)cc1] | 4-((4-(3-(3,4-dichlorophenyl)propylcarbamoyl)-3-hydroxy-2-oxopyridin-1(2H)-yl)methyl)benzoic acid | 2.15 | 475 | C |
| 178 | 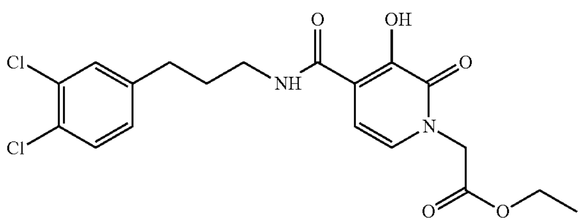 [SMILES: CCOC(=O)Cn1ccc(C(=O)NCCCc2ccc(Cl)c(Cl)c2)c(O)c1=O] | ethyl 2-(4-(3-(3,4-dichlorophenyl)propylcarbamoyl)-3-hydroxy-2-oxopyridin-1(2H)-yl)acetate | 1.98 | 427 | D |
| 179 | 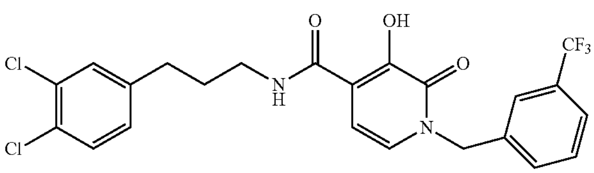 [SMILES: O=C(NCCCc1ccc(Cl)c(Cl)c1)c1ccn(Cc2cccc(C(F)(F)F)c2)c(=O)c1O] | N-(3-(3,4-dichlorophenyl)propyl)-3-hydroxy-2-oxo-1-(3-(trifluoromethyl)benzyl)-1,2-dihydropyridine-4-carboxamide | 4.16 | 499 | C |

Example 180

N-(3-(3,4-dichlorophenyl)propyl)-3-hydroxy-2-oxo-1-phenyl-1,2-dihydropyridine-4-carboxamide

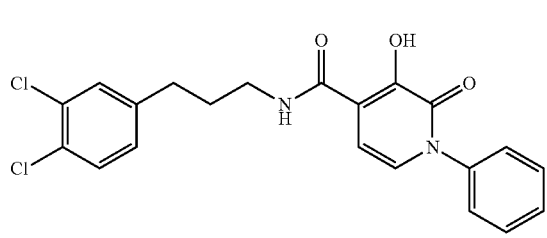 [SMILES: O=C(NCCCc1ccc(Cl)c(Cl)c1)c1ccn(-c2ccccc2)c(=O)c1O]

Example 180A

N-(3-(3,4-dichlorophenyl)propyl)-3-methoxy-2-oxo-1-phenyl-1,2-dihydropyridine-4-carboxamide

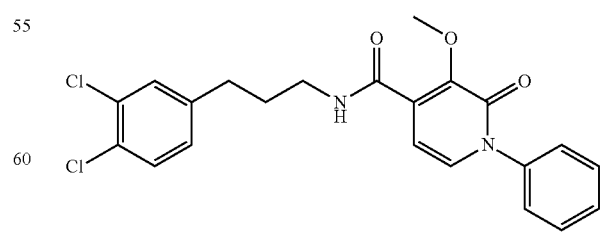

To a solution of Example 184A (30 mg, 0.084 mmol) phenylboronic acid (10.30 mg, 0.08400 mmol) in a DCM (2 mL) and THF (0.4 mL) was added Cu(OAc)$_2$ (3.06 mg, 0.0170 mmol) and pyridine (0.014 mL, 0.17 mmol). The reaction mixture was stirred at 40° C. for 16 h. The reaction mixture was quenched with 1N HCl and extracted with DCM. The DCM portion was evaporated under reduced pressure to give Example 180A (35 mg, 0.081 mmol, 96% yield). HPLC/MS (Method D) RT=2.05 min, [M+1]$^+$=431.1.

Example 180

To a solution of Example 180A (40 mg, 0.093 mmol) in DCM (1 mL) was added boron trichloride-methyl sulfide complex (100 mg, 0.556 mmol). The reaction mixture was stirred at 60° C. for 16 h. The reaction mixture was quenched with H$_2$O and MeOH, and the solvent was evaporated under reduced pressure to give the crude product. The crude product was purified on reverse phase preparative HPLC using a 10 minute gradient from 0 to 100% B (Column: Phenomenex AXIA Luna 100×20 mm 5 μm; Solvent A: 10% ACN-90% H$_2$O-0.1% TFA; Solvent B: 90% ACN-10% H$_2$O-0.1% TFA to give Example 180 (10 mg, 0.024 mmol, 25% yield). HPLC/MS (Method D) RT=2.09 min, [M+1]$^+$417. 1H NMR (400 MHz, CHLOROFORM-d) δ ppm 7.88 (1 H, br. s.), 7.48-7.56 (3 H, m), 7.41 (2 H, d, J=7.1 Hz), 7.36 (1 H, d, J=8.1 Hz), 7.31 (1 H, d, J=1.8 Hz), 6.97-7.08 (3 H, m), 3.53 (2 H, q, J=6.7 Hz), 2.70 (2 H, t, J=7.7 Hz), 1.95-2.04 (2 H, m).

Examples 181-183 were synthesized from Example 184A following the procedure described for Example 180. The analytical data (retention time, mass and conditions of LC-MS) of Example 181-183 are listed in Table 8.

TABLE 8

| Ex. # | Structure | Name | RT (min) | [M + 1]$^+$ | LC/MS Methods |
|---|---|---|---|---|---|
| 181 | 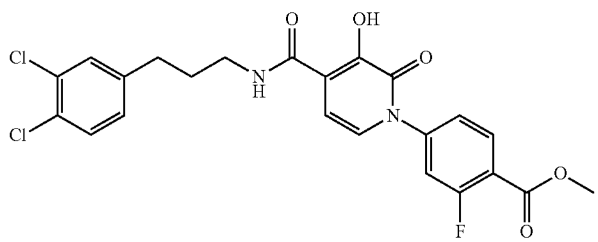 [SMILES: COC(=O)c1ccc(-n2ccc(C(=O)NCCCc3ccc(Cl)c(Cl)c3)c(O)c2=O)cc1F] | methyl 4-(4-(3-(3,4-dichlorophenyl)propylcarbamoyl)-3-hydroxy-2-oxopyridin-1(2H)-yl)-2-fluorobenzoate | 2.11 | 493 | D |
| 182 | 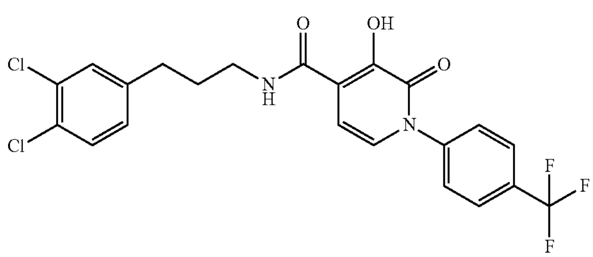 [SMILES: O=C(NCCCc1ccc(Cl)c(Cl)c1)c1ccn(-c2ccc(C(F)(F)F)cc2)c(=O)c1O] | N-(3-(3,4-dichlorophenyl)propyl)-3-hydroxy-2-oxo-1-(4-(trifluoromethyl)phenyl)-1,2-dihydropyridine-4-carboxamide | 2.21 | 485 | D |
| 183 | 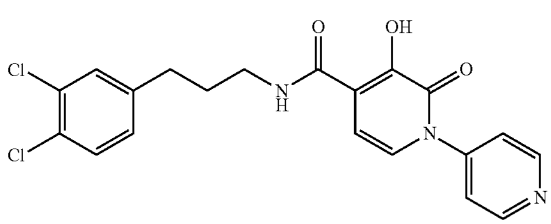 [SMILES: O=C(NCCCc1ccc(Cl)c(Cl)c1)c1ccn(-c2ccncc2)c(=O)c1O] | N-(3-(3,4-dichlorophenyl)propyl)-3-hydroxy-2-oxo-1-(pyridin-4-yl)-1,2-dihydropyridine-4-carboxamide | 2.21 | 418 | D |

Example 184

N-(3-(3,4-dichlorophenyl)propyl)-3-hydroxy-2-oxo-1-(2,2,2-trifluoroethyl)-1,2-dihydropyridine-4-carboxamide

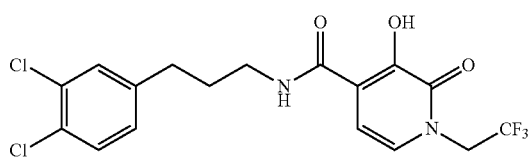 [SMILES: O=C(NCCCc1ccc(Cl)c(Cl)c1)c1ccn(CC(F)(F)F)c(=O)c1O]

Example 184A

N-(3-(3,4-dichlorophenyl)propyl)-3-methoxy-2-oxo-1,2-dihydropyridine-4-carboxamide

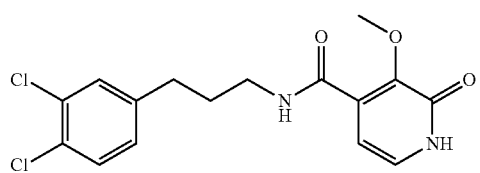 [SMILES: COc1c(C(=O)NCCCc2ccc(Cl)c(Cl)c2)cc[nH]c1=O]

To a solution of Intermediate 22 (20 mg, 0.059 mmol) in DCM (2 mL) was added (diazomethyl)trimethylsilane (0.029 mL, 0.059 mmol). The reaction mixture was stirred at rt for 16 h. The reaction mixture was evaporated under reduced pressure and the residue was loaded onto a 4 g silica gel column. Elution with 0 to 100% EtOAc in hexane for 15 min, then 0 to 20% MeOH in DCM for 10 min, yielded Example 184A (5 mg, 0.01 mmol, 20% yield). HPLC/MS (Method A) RT=3.38 min, $[M+1]^+$ 355.

Example 184B

N-(3-(3,4-dichlorophenyl)propyl)-3-methoxy-2-oxo-1-(2,2,2-trifluoroethyl)-1,2-dihydropyridine-4-carboxamide

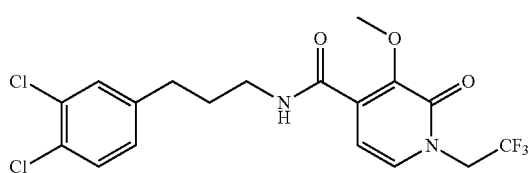 [SMILES: COc1c(C(=O)NCCCc2ccc(Cl)c(Cl)c2)ccn(CC(F)(F)F)c1=O]

To a solution of Example 184A (20 mg, 0.056 mmol) in DCM (1 mL) was added $Cs_2CO_3$ (36.7 mg, 0.113 mmol). The reaction mixture was stirred for 10 min at 60° C., then 2,2,2-Trifluoroethyl trichloromethanesulfonate (15.85 mg, 0.05600 mmol) was added. The reaction mixture was stirred at rt for 16 h, then it was partitioned between $H_2O$ and DCM. The DCM portion was separated, and the DCM evaporated under reduced pressure to give the crude product which was passed through a short silica gel column to give Example 184B (20 mg, 0.046 mmol, 81% yield). HPLC/MS (Bethod A) RT=2.07 min, $[M+1]^+$ 439.1.

Example 184

To a solution of Example 184B (0.023 g, 0.052 mmol) in DCM (0.5 mL) and DCE (0.5 mL) was added boron trichloride-methyl sulfide complex (0.056 g, 0.31 mmol). The reaction mixture was stirred at rt for 2 h. The reaction mixture was cooled and quenched with ice and MeOH. The crude material was purified by reverse phase preparative HPLC using a 10 minute gradient from 15 to 100% B (Column: Phenomenex AXIA Luna 100×20 mm 5 μm (10 min gradient); Solvent A: 10% ACN-90% $H_2O$-0.1% TFA; Solvent B: 90% ACN-10% $H_2O$-0.1% TFA to give Example 184 (12 mg, 0.028 mmol, 54.7% yield). HPLC/MS (Method D) RT=2.06 min, $[M+1]^+$= 423.1. 1H NMR (400 MHz, CHLOROFORM-d) δ ppm 7.63 (1 H, br. s.), 7.35 (1 H, d, J=8.3 Hz), 7.30 (1 H, d, J=1.5 Hz), 7.04 (1 H, dd, J=8.1, 1.8 Hz), 6.91 (2 H, s), 4.65 (2 H, q, J=8.3 Hz), 3.50 (2 H, q, J=6.8 Hz), 2.68 (2 H, t, J=7.7 Hz), 1.88-2.01 (2 H, m).

Example 185

N-(3-(3,4-dichlorophenyl)propyl)-3-hydroxy-1-methyl-6-(5-methyl-1,2,4-oxadiazol-3-yl)-2-oxo-1,2-dihydropyridine-4-carboxamide

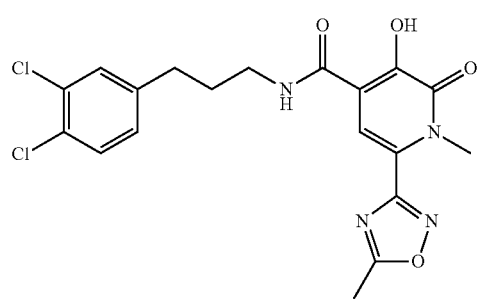 [SMILES: Cc1nc(-c2cc(C(=O)NCCCc3ccc(Cl)c(Cl)c3)c(O)c(=O)n2C)no1]

Example 185A ethyl 6-cyano-3-methoxy-1-methyl-2-oxo-1,2-dihydropyridine-4-carboxylate

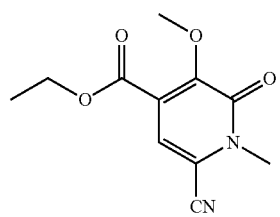 [SMILES: CCOC(=O)c1cc(C#N)n(C)c(=O)c1OC]

Ethyl 6-bromo-3-methoxy-1-methyl-2-oxo-1,2-dihydropyridine-4-carboxylate (872 mg, 3.01 mmol) (Intermediate 6) was dissolved in DMF (20 mL). Zinc cyanide (706 mg, 6.01 mmol) and zinc dust (59.0 mg, 0.902 mmol) were added and the mixture was degassed in vacuo. Bis(tri-t-butylphosphine)palladium (0) (154 mg, 0.301 mmol) was added and the mixture was stirred at 100° C. for 20 h. The reaction mixture was loaded onto Celite®, the solvent was removed then purified by flash chromatography (120 g silica gel cartridge; 0-100% ethyl acetate/hexane over 24 min, 85 mL/min.) provide Example 185A (572.52 mg, 2.424 mmol, 81% yield) as a white solid. LCMS (Phenomenex Luna C18 2.0×30 mm column, 10-90% methanol, water with 0.1% TFA gradient over 2 min., 1 mL/min.) RT=1.24 min, [M+1]⁺237.

Example 185B 6-cyano-3-methoxy-1-methyl-2-oxo-1,2-dihydropyridine-4-carboxylic acid

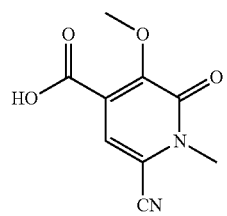

Example 185B (274.5 mg, 1.162 mmol) was dissolved in THF (4 mL). Lithium hydroxide (1.278 mL, 1.278 mmol) (1.0 M, aq.) was added and the mixture was stirred at rt for 3 h. Additional lithium hydroxide (0.465 mL, 0.465 mmol) was added and the mixture was stirred at rt for 22 h. Additional lithium hydroxide (0.232 mL, 0.232 mmol) was added and the mixture was stirred at rt for 3 h. The reaction was neutralized with hydrochloric acid (1.0 M aq., 2.092 mL, 2.092 mmol) and the solvent removed in vacuo to provide Example 185B as a yellow solid. LCMS (Phenomenex Luna C18 2.0× 30 mm column, 10-90% methanol, water with 0.1% TFA gradient over 2 min., 1 mL/min.) RT=0.24 min, [M+1]⁺209.

Example 185C 6-cyano-N-(3-(3,4-dichlorophenyl)propyl)-3-methoxy-1-methyl-2-oxo-1,2-dihydropyridine-4-carboxamide

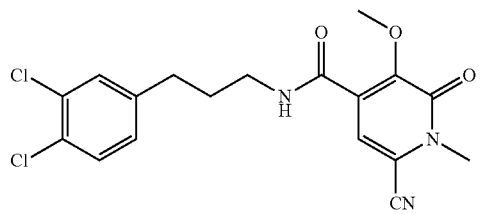 [SMILES: COc1c(C(=O)NCCCc2ccc(Cl)c(Cl)c2)cc(C#N)n(C)c1=O]

Example 185B (0.242 g, 1.162 mmol) was dissolved in dichloromethane (20 mL). 3-(3,4-Dichlorophenyl)propan-1-amine-HCl (Intermediate 1, 0.280 g, 1.162 mmol) was added. DMF (5 mL) was added. Triethylamine (0.486 mL, 3.49 mmol) was added. PyBOP (0.726 g, 1.394 mmol) was added and the mixture was stirred for 24 h. Additional DMF (5 mL) and PyBOP (0.302 g, 0.581 mmol) were added and the mixture was stirred for 3 h. Additional PyBOP (0.121 g, 0.232 mmol) was added and the mixture was stirred for 20 h. The reaction mixture was loaded onto Celite®, the solvent was removed and purified by flash chromatography (80 g silica gel cartridge; 50-100% ethyl acetate/hexane over 18 min, 60 mL/min.) to provide Example 185C (0.3 g, 0.761 mmol, 65.5% yield) as a yellow solid. LCMS (Phenomenex Luna C18 2.0×30 mm column, 10-90% methanol, water with 0.1% TFA gradient over 2 min., 1 mL/min.) RT=1.86 min, [M+1]⁺ 394.

Example 185D (Z)-N-(3-(3,4-dichlorophenyl)propyl)-6-(N'-hydroxycarbamimidoyl)-3-methoxy-1-methyl-2-oxo-1,2-dihydropyridine-4-carboxamide

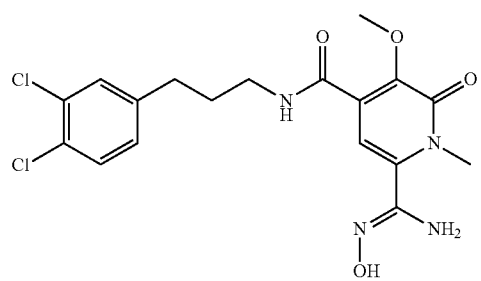 [SMILES: COc1c(C(=O)NCCCc2ccc(Cl)c(Cl)c2)cc(/C(N)=N/O)n(C)c1=O]

Example 185C (91.56 mg, 0.232 mmol) was dissolved in ethanol (3 mL). Hydroxylamine (0.071 mL, 1.161 mmol) (50% aq) was added and the mixture was stirred at rt for 15 h. The solvent was removed in vacuo to provide Example 185D (82.37 mg, 0.193 mmol, 83% yield) as a yellow solid. LCMS (Phenomenex Luna C18 2.0×30 mm column, 10-90% methanol, water with 0.1% TFA gradient over 2 min., 1 mL/min.) RT=1.64 min, [M+1]⁺427.

Example 185E (Z)-6-(N'-acetoxycarbamimidoyl)-N-(3-(3,4-dichlorophenyl)propyl)-3-methoxy-1-methyl-2-oxo-1,2-dihydropyridine-4-carboxamide

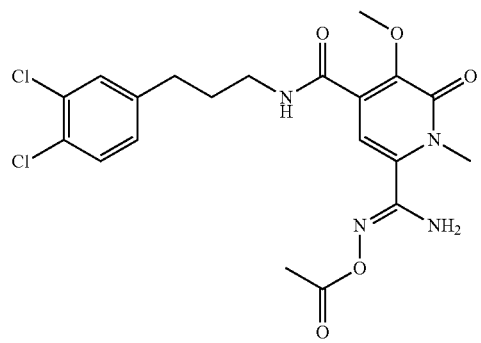 [SMILES: COc1c(C(=O)NCCCc2ccc(Cl)c(Cl)c2)cc(/C(N)=N/OC(C)=O)n(C)c1=O]

Example 185D (83 mg, 0.194 mmol) was dissolved in pyridine (3 mL). Acetyl chloride (0.041 mL, 0.583 mmol) was added and the mixture was stirred at rt for 3 h. The solvent was removed in vacuo to provide Example 185E as a yellow oil. LCMS (Phenomenex Luna C18 2.0×30 mm column, 10-90% methanol, water with 0.1% TFA gradient over 2 min., 1 mL/min.) RT=1.88 min, [M+1]+469.

Example 185F

N-(3-(3,4-dichlorophenyl)propyl)-3-methoxy-1-methyl-6-(5-methyl-1,2,4-oxadiazol-3-yl)-2-oxo-1,2-dihydropyridine-4-carboxamide

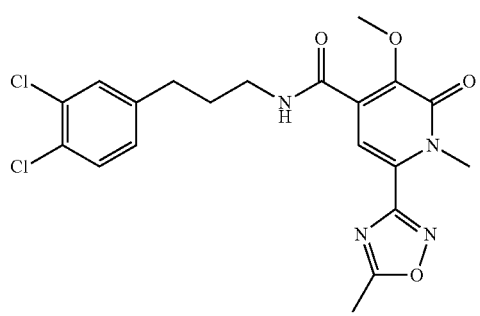 [SMILES: COc1c(C(=O)NCCCc2ccc(Cl)c(Cl)c2)cc(-c2noc(C)n2)n(C)c1=O]

Example 185E (91 mg, 0.194 mmol) was dissolved in acetonitrile (10 mL). TBAF (0.776 mL, 0.776 mmol) (1.0 M in THF) was added and the mixture was stirred at rt for 7 h. Additional TBAF (0.388 mL, 0.388 mmol) (1.0 M in THF) was added and the reaction was stirred at rt for 60 h. The reaction mixture was loaded onto Celite®, the solvent was removed and purified by flash chromatography (12 g silica gel cartridge; 0-100% ethyl acetate/hexane over 11 min, 30 mL/min then 100% ethylacetate for 14 min, 30 mL/min.) to provide Example 185F (29 mg, 0.064 mmol, 33.1% yield) as a yellow oil. LCMS (Phenomenex Luna C18 2.0×30 mm column, 10-90% methanol, water with 0.1% TFA gradient over 2 min., 1 mL/min.) RT=1.89 min, [M+1]+451.

Example 185

Example 185E (29.46 mg, 0.065 mmol) was dissolved in dichloromethane (2 mL). Boron tribromide (0.196 mL, 0.196 mmol) (1.0 M in dichloromethane) was added and the mixture was stirred at rt for 15 h. The reaction was quenched with methanol, water (5-10 drops) was added and the mixture was stirred at rt. A white precipitate formed that was collected by filtration and dried in vacuo to provide Example 185 (15 mg, 0.033 mmol, 49.9% yield) as a white solid. LCMS (Phenomenex Luna C18 2.0×30 mm column, 10-90% methanol, water with 0.1% TFA gradient over 2 min., 1 mL/min.) RT=1.85 min, [M+1]+437.; $^1$H NMR (400 MHz, CD$_3$OD) δ ppm 7.84 (1 H, s), 7.30-7.63 (2 H, m), 7.19 (1 H, dd, J=8.2, 2.2 Hz), 3.65 (3 H, s), 3.37 (2 H, t, J=6.6 Hz), 2.63-2.88 (2 H, m), 1.74-2.11 (2 H, m).

Example 186

(3-(3,4-dichlorophenyl)propyl)-3-(4-methoxybenzylamino)-1-methyl-2-oxo-1,2-dihydropyridine-4-carboxamide

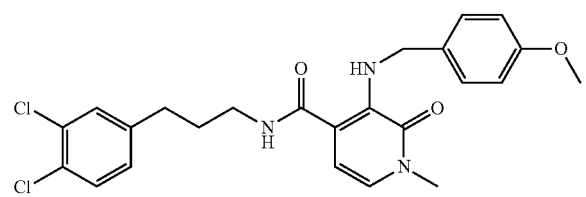 [SMILES: COc1ccc(CNc2c(C(=O)NCCCc3ccc(Cl)c(Cl)c3)ccn(C)c2=O)cc1]

Example 186A 4-(3-(3,4-dichlorophenyl)propylcarbamoyl)-1-methyl-2-oxo-1,2-dihydropyridin-3-yl trifluoromethanesulfonate

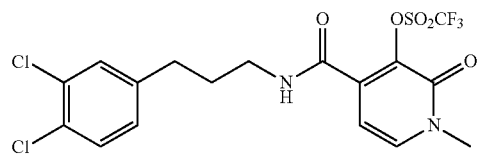

A mixture of Example 105 (40 mg, 0.11 mmol), trifluoromethanesulfonic anhydride (64 mg, 0.23 mmol), DMAP (14 mg, 0.11 mmol) and pyridine (0.027 mL, 0.34 mmol) in DCM (0.5 mL) was stirred at rt for 2 h. The reaction mixture was diluted with DCM, washed with H$_2$O, dried over MgSO$_4$, filtered and concentrated. The residue was purified by Prep-HPLC(YMC Sunfire 5 μm (C18) 30×100 mm, 20-100% MeOH (90% in H$_2$O, 0.1% TFA) using gradient over 12 min with flow rate 40 mL/min and UV detection at 220 nm) to give Example 186A (36 mg, 0.070 mmol, 63 yield). HPLC/MS (BEH C18; 2.1×50 mm, 10-90% ACN/water with 0.05% TFA, gradient over 1 min, 0.8 mL/min) RT=1.04 min, [M+H]+ 487.1.

Example 186

The reaction mixture of Example 186A (36 mg, 0.074 mmol) and (4-methoxyphenyl)methanamine (0.048 mL, 0.37 mmol) in dioxane (0.5 mL) was subject to microwave irradiation at 120° C. for 2 h. The reaction mixture was concentrated and purified by Prep-HPLC(YMC Sunfire 5 μm (C18) 30×100 mm, 20-100% MeOH (90% in H$_2$O, 0.1% TFA) using a gradient over 10 min with flow rate 40 mL/min and UV detection at 220 nm) to give Example 186 (16.50 mg, 0.031 mmol, 42.4% yield) as an orange oil. HPLC/MS (Method E) RT=1.02 min, [M+H]+ 474.2; 1H NMR (400 MHz, CHLOROFORM-d) d ppm 7.33 (1 H, d, J=8.3 Hz), 7.24 (1 H, s), 7.18 (2 H, d, J=8.3 Hz), 7.14 (1 H, br. s.), 6.98 (1 H, d, J=8.0 Hz), 6.80-6.91 (3 H, m), 6.43 (1 H, d, J=7.3 Hz), 4.23 (2 H, s), 3.74-3.82 (3 H, m), 3.59 (3 H, s), 3.36 (2 H, q, J=6.5 Hz), 2.60 (2 H, t, J=7.7 Hz), 1.81 (2 H, t, J=7.4 Hz)

Examples 187-191 were synthesized from Example 105 and Example 82 following the procedure described for Example 186. The analytical data (retention time, mass and conditions of LC-MS) of example 187-191 are listed in Table 9.

TABLE 8

| Ex. # | Structure | Name | RT (min) | [M + 1]+ | LC/MS Methods |
|---|---|---|---|---|---|
| 187 | 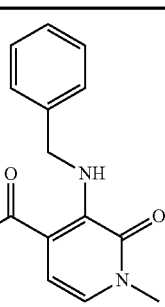 | 3-(benzylamino)-N-(3-(3,4-dichlorophenyl)propyl)-1-methyl-2-oxo-1,2-dihydropyridine-4-carboxamide | 1.05 | 444.1 | E |
| 188 | 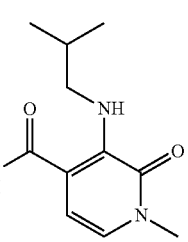 | N-(3-(3,4-dichlorophenyl)propyl)-3-(isobutylamino)-1-methyl-2-oxo-1,2-dihydropyridine-4-carboxamide | 1.1 | 410.2 | E |
| 189 | 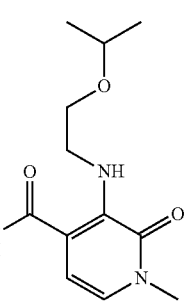 | N-(3-(3,4-dichlorophenyl)propyl)-3-(2-isopropoxyethylamino)-1-methyl-2-oxo-1,2-dihydropyridine-4-carboxamide | 1.0 | 440.2 | E |
| 190 | 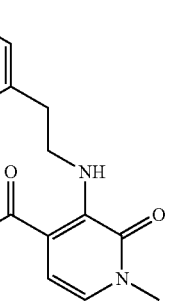 | N-(3-(3,4-dichlorophenyl)propyl)-3-(3-fluorophenethylamino)-1-methyl-2-oxo-1,2-dihydropyridine-4-carboxamide | 1.1 | 476.2 | E |
| 191 | 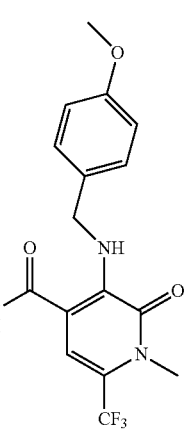 | N-(3-(3,4-dichlorophenyl)propyl)-3-(4-methoxybenzylamino)-1-methyl-2-oxo-6-(trifluoromethyl)-1,2-dihydropyridine-4-carboxamide | 2.1 | 542.1 | D |

Example 192

3-amino-N-(3-(3,4-dichlorophenyl)propyl)-1-methyl-2-oxo-1,2-dihydropyridine-4-carboxamide

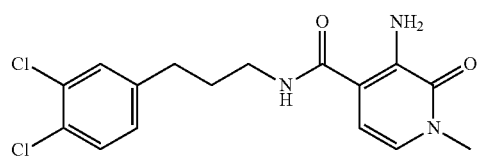 [SMILES: Cn1ccc(C(=O)NCCCc2ccc(Cl)c(Cl)c2)c(N)c1=O]

The reaction mixture of Example 186 (12 mg, 0.025 mmol) in TFA (0.5 mL) was stirred at rt for 1 h. The mixture was concentrated, and the residue was purified by Prep-HPLC (Axia Luna 5 μm C18 30×100 mm, 20-100% ACN/H$_2$O with 0.1% TFA, gradient over 14 min with flow rate 40 mL/min and UV detection at 220 nm) to give Example 192 (3.25 mg, 8.72 μmol, 34.5% yield) as a yellow solid. HPLC/MS (Method E) RT=0.95 min, [M+H]$^+$ 354.1; $^1$H NMR (400 MHz, CHLOROFORM-d) d ppm 1.93 (quin, J=7.28 Hz, 2 H) 2.67 (t, J=7.53 Hz, 2 H) 3.44 (q, J=6.44 Hz, 2 H) 3.56 (s, 3 H) 5.95 (d, J=7.28 Hz, 1 H) 6.54 (d, J=7.28 Hz, 1 H) 7.04 (d, J=8.03 Hz, 1 H) 7.30 (s, 1 H) 7.35 (d, J=8.28 Hz, 1 H).

Examples 193

3-amino-N-(3-(3,4-dichlorophenyl)propyl)-6-(3-fluoro-5-(trifluoromethyl)phenyl)-1-methyl-2-oxo-1,2-dihydropyridine-4-carboxamide Examples 193 was synthesized from Example 8 following the procedure described for Example 192. LC/MS (Method E) RT=1.1 min, [M+H]$^+$ 516.1.

Examples 194-207 were synthesized using appropriate application of the method described for Example 110. Synthesis of Example 208 is described in Intermediate 22. The HPLC-MS data (retention time, mass and conditions) for Examples 194-208 are listed in Table 10.

TABLE 8

| Ex. # | Structure | Name | RT (min) | [M + 1]$^+$ | LC/MS Methods |
|---|---|---|---|---|---|
| 194 | 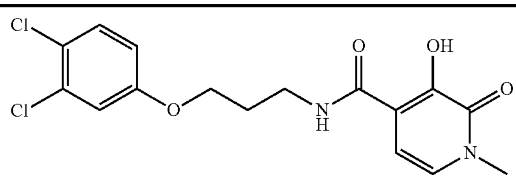 | N-(3-(3,4-dichlorophenoxy)propyl)-3-hydroxy-1-methyl-2-oxo-1,2-dihydropyridine-4-carboxamide | 1.8 | 371.0 | I |
| 195 | 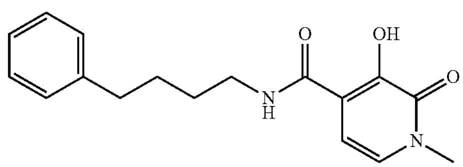 [SMILES: Cn1ccc(C(=O)NCCCCc2ccccc2)c(O)c1=O] | 3-hydroxy-1-methyl-2-oxo-N-(4-phenylbutyl)-1,2-dihydropyridine-4-carboxamide | 1.7 | 301.3 | I |
| 196 | 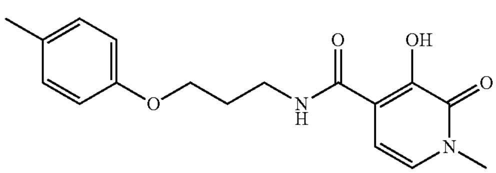 | 3-hydroxy-1-methyl-2-oxo-N-(3-(p-tolyloxy)propyl)-1,2-dihydropyridine-4-carboxamide | 1.7 | 317.3 | I |
| 197 | 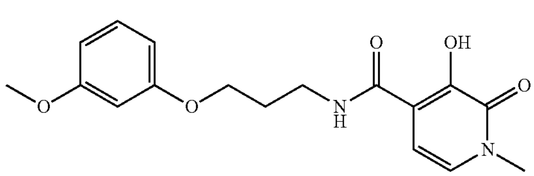 | 3-hydroxy-N-(3-(3-methoxyphenoxy)propyl)-1-methyl-2-oxo-1,2-dihydropyridine-4-carboxamide | 1.5 | 333.2 | I |
| 198 | 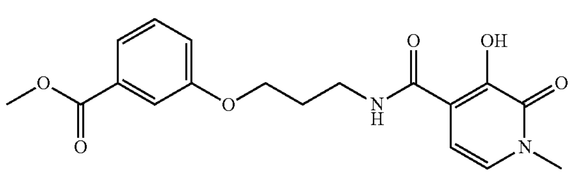 | methyl 3-(3-(3-hydroxy-1-methyl-2-oxo-1,2-dihydropyridine-4-carboxamido)propoxy)benzoate | 1.5 | 361.2 | I |

TABLE 8-continued

| Ex. # | Structure | Name | RT (min) | [M + 1]+ | LC/MS Methods |
|---|---|---|---|---|---|
| 199 | 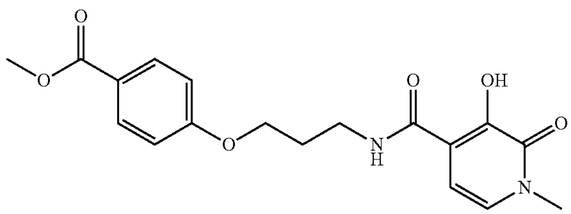 | methyl 4-(3-(3-hydroxy-1-methyl-2-oxo-1,2-dihydropyridine-4-carboxamido)propoxy)benzoate | 1.5 | 361.2 | I |
| 200 | 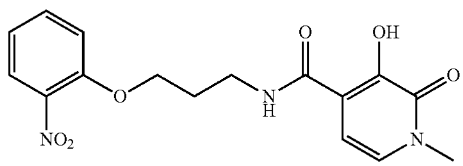 [SMILES: Cn1ccc(C(=O)NCCCOc2ccccc2[N+](=O)[O-])c(O)c1=O] | 3-hydroxy-1-methyl-N-(3-(2-nitrophenoxy)propyl)-2-oxo-1,2-dihydropyridine-4-carboxamide | 1.4 | 348.2 | I |
| 201 | 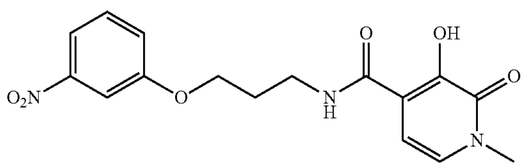 | 3-hydroxy-1-methyl-N-(3-(3-nitrophenoxy)propyl)-2-oxo-1,2-dihydropyridine-4-carboxamide | 1.5 | 348.1 | I |
| 202 | 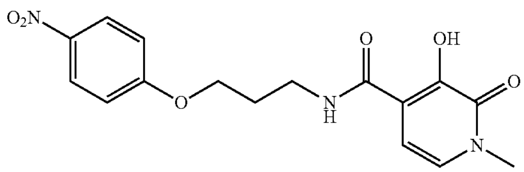 | 3-hydroxy-1-methyl-N-(3-(4-nitrophenoxy)propyl)-2-oxo-1,2-dihydropyridine-4-carboxamide | 1.4 | 348.1 | I |
| 203 | 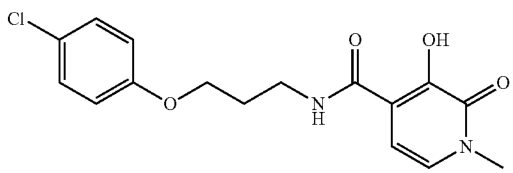 [SMILES: Cn1ccc(C(=O)NCCCOc2ccc(Cl)cc2)c(O)c1=O] | N-(3-(4-chlorophenoxy)propyl)-3-hydroxy-1-methyl-2-oxo-1,2-dihydropyridine-4-carboxamide | 1.7 | 337.1 | I |
| 204 | 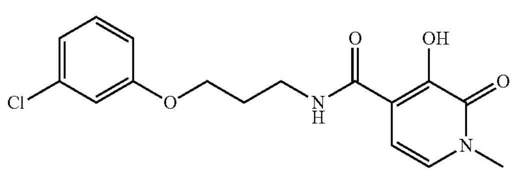 [SMILES: Cn1ccc(C(=O)NCCCOc2cccc(Cl)c2)c(O)c1=O] | N-(3-(3-chlorophenoxy)propyl)-3-hydroxy-1-methyl-2-oxo-1,2-dihydropyridine-4-carboxamide | 1.7 | 337.1 | I |
| 205 | 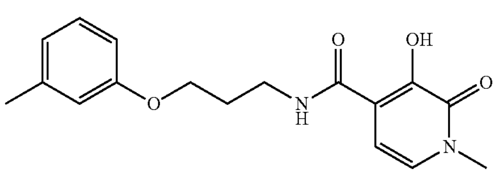 | 3-hydroxy-1-methyl-2-oxo-N-(3-(m-tolyloxy)propyl)-1,2-dihydropyridine-4-carboxamide | 1.6 | 317.2 | I |
| 206 | 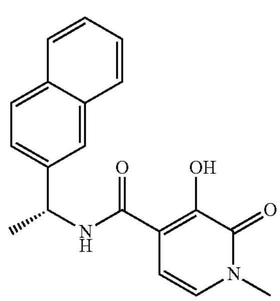 [SMILES: C[C@@H](NC(=O)c1ccn(C)c(=O)c1O)c1ccc2ccccc2c1] | (R)-3-hydroxy-1-methyl-N-(1-(naphthalen-2-yl)ethyl)-2-oxo-1,2-dihydropyridine-4-carboxamide | 1.7 | 323.2 | I |

TABLE 8-continued

| Ex. # | Structure | Name | RT (min) | [M + 1]+ | LC/MS Methods |
|---|---|---|---|---|---|
| 207 | ![structure 207] | N-(4-(3,4-dichlorophenyl)butyl)-3-hydroxy-1-methyl-2-oxo-1,2-dihydropyridine-4-carboxamide | 1.0 | 369.1 | E |
| 208 | ![structure 208] | N-(3-(3,4-dichlorophenyl)propyl)-3-hydroxy-2-oxo-1,2-dihydropyridine-4-carboxamide | 2.0 | 340.9 | D |

What is claimed is:

1. A compound of Formula (I):

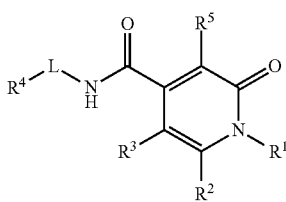

(I)

or a stereoisomer, a tautomer, or a pharmaceutically acceptable salt thereof, wherein:

$R^1$ is independently selected from the group consisting of: H, $C_{1-6}$ alkyl substituted with 0-3 $R^a$, $C_{2-6}$ alkenyl substituted with 0-3 $R^a$, and —$(CH_2)_n$—W—$(CH_2)_m$—$R^{1a}$;

W is independently selected from the group consisting of: a bond, NH, O, S, N($C_{1-4}$ alkyl), CO, CONH, CON($C_{1-4}$ alkyl), NHCO, $SO_2$, $NHSO_2$, $SO_2NH$, $NHCO_2$, and $CHR^f$;

$R^{1a}$ is independently selected from the group consisting of: $C_{3-10}$ carbocycle and a 5- to 10-membered heterocycle comprising: carbon atoms and 1-4 heteroatoms selected from N, $NR^e$, O, and $S(O)_p$; and wherein said carbocycle and heterocycle are substituted with 0-3 $R^c$;

$R^2$ and $R^3$ are, independently at each occurrence, selected from the group consisting of: H, halogen, $CF_3$, $OCF_3$, $C_{1-6}$ alkyl substituted with 0-3 $R^a$, $C_{2-6}$ alkenyl substituted with 0-3 $R^a$, —$CO_2(C_{1-4}$ alkyl), —$SO_2$(phenyl), —$(CH_2)_n$—$(C_{3-6}$ cycloalkyl substituted with 0-3 $R^c$), —$(CH_2)_n$—(phenyl substituted with 0-3 $R^b$), —$(CH_2)_n$-(naphthyl substituted with 0-3 $R^b$), and —$(CH_2)_n$-(5- to 10 membered heterocycle comprising: carbon atoms and 1-4 heteroatoms selected from N, $NR^e$, O, and $S(O)_p$), wherein said heterocycle is substituted with 0-3 $R^c$;

$R^4$ is independently selected from the group consisting of: $C_{3-10}$ carbocycle and a 5- to 10-membered heterocycle comprising: carbon atoms and 1-4 heteroatoms selected from N, $NR^e$, O, and $S(O)_p$; wherein said carbocycle and heterocycle are substituted with 0-3 $R^d$;

$R^5$ is independently selected from the group consisting of: $OR^6$, CN, and $NR^7R^8$;

$R^6$ is independently selected from the group consisting of: H and $C_{1-6}$ alkyl substituted with 0-1 $CO_2H$;

$R^7$ is independently selected from the group consisting of: H, $C_{1-6}$ alkyl substituted with 0-1 $R^a$, —$(CH_2)_n$-(phenyl substituted with 0-3 $R^b$), and —$(CH_2)_n$-(5- to 6-membered heterocycle comprising: carbon atoms and 1-4 heteroatoms selected from N, $NR^e$, O, and $S(O)_p$); and wherein said heterocycle is substituted with 0-3 $R^c$;

$R^8$ is independently selected from the group consisting of: H and $C_{1-6}$ alkyl;

alternatively, $NR^7R^8$ is a 5- to 6-membered heterocycle comprising: carbon atoms and 1-4 heteroatoms selected from N, $NR^e$, O, and $S(O)_p$;

L is independently a hydrocarbon or hydrocarbon-heteroatom linker optionally substituted with 0-2 $R^g$; wherein said hydrocarbon linker has one to eight carbon atoms and may be straight or branched, saturated or unsaturated; and said hydrocarbon-heteroatom linker has one to seven carbon atoms and one group selected from O, —CO—, S, —SO—, —$SO_2$—, NH, and N($C_{1-4}$ alkyl);

$R^a$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, CN, $NH_2$, $NO_2$, $NH(C_{1-4}$ alkyl), $N(C_{1-4}$ alkyl)$_2$, $CO_2H$, $CO_2(C_{1-4}$ alkyl), $NHCO(C_{1-4}$ alkyl substituted with 0-1 $NH_2$), $N(C_{1-4}$ alkyl)CO($C_{1-4}$ alkyl), $NHCO_2(C_{1-4}$ alkyl), $CONHSO_2(C_{1-4}$ alkyl), $SO_2(C_{1-4}$ alkyl), $CONH_2$, $CONH(C_{1-4}$ alkyl), $NHSO_2(C_{1-4}$ alkyl), $N(C_{1-4}$ alkyl)$SO_2(C_{1-4}$ alkyl), and phenoxy;

$R^b$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, $OCF_2CHF_2$, $OCH_2CF_3$, CN, $NH_2$, $NO_2$, $NH(C_{1-4}$ alkyl), $N(C_{1-4}$ alkyl)$_2$, $CO_2H$, $CO_2(C_{1-4}$ alkyl), $CONH_2$, CONH ($C_{1-4}$ alkyl), $CON(C_{1-4}$ alkyl)$_2$, $NHCO_2(C_{1-4}$ alkyl), $NHSO_2(C_{1-4}$ alkyl), $N(C_{1-4}$ alkyl)$SO_2(C_{1-4}$ alkyl), $SO_2$ ($C_{1-4}$ alkyl), $SO_2NH_2$, phenyl, benzyl, and phenoxy;

$R^c$ is, independently at each occurrence, selected from the group consisting of: =O and $R^b$;

$R^d$ is, independently at each occurrence, selected from the group consisting of: =O, halogen, OH, $C_{1-6}$ alkyl substituted with 0-1 OH, $C_{1-4}$ alkoxy, $C_{1-4}$ haloalkyl, $C_{1-4}$ haloalkoxy, $CF_3$, $OCF_3$, $OCF_2CF_2H$, $OCH_2CF_3$, CN, $NH_2$, $NO_2$, $NH(C_{1-4}$ alkyl), $N(C_{1-4}$ alkyl)$_2$, $CO_2H$, $CO_2$ ($C_{1-4}$ alkyl), $CO(C_{1-4}$ alkyl), $NHCO(C_{1-4}$ alkyl), —$CH_2NHCO(C_{1-4}$ alkyl), $CONH_2$, $CONH(C_{1-4}$ alkyl), $CON(C_{1-4}$ alkyl)$_2$, $SO_2(C_{1-4}$ alkyl), $SO_2NH_2$, —$SO_2NH$ ($C_{1-4}$ alkyl), —$SO_2NH(C_{3-6}$ cycloalkyl), —$NHSO_2$ ($C_{1-4}$ alkyl), —$CH_2NHSO_2(C_{1-4}$ alkyl), and $Si(C_{1-4}$ alkyl)$_3$;

$R^e$ is, independently at each occurrence, selected from the group consisting of: H, $C_{1-4}$ alkyl, $CO(C_{1-4}$ alkyl), $CO_2$ ($C_{1-4}$ alkyl), $CO_2$(benzyl), and —$(CH_2)_n$-(phenyl optionally substituted with 0-2 halogens);

$R^f$ is, independently at each occurrence, selected from the group consisting of: $C_{1-4}$ alkyl, $C_{2-4}$ alkenyl, $CO_2(C_{1-4}$ alkyl), $CONH_2$, $C_{3-6}$ cycloalkyl, phenyl, and benzyl;

$R^g$ is, independently at each occurrence, selected from the group consisting of: halogen, OH, $C_{1-4}$ alkyl, $C_{2-4}$ alkenyl, $C_{1-4}$ haloalkyl, $C_{1-4}$ alkyoxy, $CO_2(C_{1-4}$ alkyl), $C_{3-6}$ cycloalkyl, and phenyl;

m is, independently at each occurrence, selected from 0, 1, and 2;

n is, independently at each occurrence, selected from 0, 1, 2, 3, and 4; and p is, independently at each occurrence, selected from 0, 1, and 2;

provided that:
(i) when $R^1$ is methyl, $R^2$ and $R^3$ are H, $R^5$ is OH, and L is —$(CH_2)_3$—, then $R^4$ is other than unsubstituted phenyl;
(ii) when L is $CH_2$, then $R^4$ is other than halogen mono-substituted phenyl or methoxy bi-substituted phenyl; or
(iii) when $R^1$ is methyl, $R^2$ and $R^3$ are H, $R^5$ is OH, and L is —$(CH_2)_2$—, then $R^4$ is other than methoxy mono-substituted indolyl.

2. A compound according to claim 1, wherein:

$R^1$ is independently selected from the group consisting of: $C_{1-6}$ alkyl substituted with 0-2 $R^a$, $C_{2-6}$ alkenyl substituted with 0-2 $R^a$, and —$(CH_2)_n$—W—$R^{1a}$;

W is independently selected from the group consisting of: a bond, NH, N($C_{1-4}$ alkyl), CO, CONH, CON($C_{1-4}$ alkyl), $SO_2$, $NHCO_2$, and $CHR^f$;

$R^{1a}$ is independently selected from the group consisting of: $C_{3-6}$ cycloalkyl substituted with 0-3 $R^c$, phenyl substituted with 0-3 $R^b$, naphthyl substituted with 0-2 $R^b$, tetrahydronaphthyl substituted with 0-2 $R^b$, dihydroindenyl substituted with 0-2 $R^c$, and a 5- to 10-membered heterocycle comprising: carbon atoms and 1-4 heteroatoms selected from N, $NR^e$, O, and $S(O)_p$; and wherein said heterocycle is substituted with 0-3 $R^c$;

$R^2$ is independently selected from the group consisting of: H, halogen, $CF_3$, $OCF_3$, $C_{1-6}$ alkyl substituted with 0-2 $R^a$, $C_{2-6}$ alkenyl substituted with 0-2 $R^a$, —$CO_2(C_{1-4}$ alkyl), —$SO_2$(phenyl), —$(CH_2)_n$—($C_{3-6}$ cycloalkyl substituted with 0-3 $R^c$), —$(CH_2)_n$-(phenyl substituted with 0-3 $R^b$), —$(CH_2)_n$-(naphthyl substituted with 0-3 $R^b$), and —$(CH_2)_n$-(5- to 10 membered heterocycle comprising: carbon atoms and 1-4 heteroatoms selected from N, $NR^e$, O, and $S(O)_p$), wherein said heterocycle is substituted with 0-3 $R^c$;

$R^3$ is independently selected from the group consisting of: H, halogen, $CF_3$, $OCF_3$, $C_{1-6}$ alkyl substituted with 0-2 $R^a$, and phenyl substituted with 0-2 $R^b$;

$R^4$ is independently selected from the group consisting of: $C_{5-6}$ cycloalkyl, phenyl, naphthyl, tetrahydronaphthyl, dihydroindenyl, and a 5- to 10-membered heterocycle comprising: carbon atoms and 1-4 heteroatoms selected from N, $NR^e$, O, and $S(O)_p$; and wherein each moiety is substituted with 0-3 $R^d$;

$R^5$ is independently selected from the group consisting of: OH, $O(C_{1-4}$ alkyl substituted with 0-1 $CO_2H$), CN, and $NR^7R^8$; and L is independently a hydrocarbon or hydrocarbon-heteroatom linker optionally substituted with 0-1 $R^g$; wherein said hydrocarbon linker has one to six carbon atoms and may be straight or branched, saturated or unsaturated; and said hydrocarbon-heteroatom linker has one to five carbon atoms and one group selected from O, —CO—, S, —SO—, —$SO_2$—, NH, and N($C_{1-4}$ alkyl);

provided that:
(i) when $R^1$ is methyl, $R^2$ and $R^3$ are H, $R^5$ is OH, and L is —$(CH_2)_3$—, then $R^4$ is other than unsubstituted phenyl;
(ii) when L is $CH_2$, then $R^4$ is other than halogen mono-substituted phenyl or methoxy bi-substituted phenyl; or
(iii) when $R^1$ is methyl, $R^2$ and $R^3$ are H, $R^5$ is OH, and L is —$(CH_2)_2$—, then $R^4$ is other than methoxy mono-substituted indolyl.

3. A compound according to claim 2, wherein:

$R^1$ is independently selected from the group consisting of: $C_{1-6}$ alkyl substituted with 0-2 $R^a$, $C_{2-6}$ alkenyl substituted with 0-2 $R^a$, and —$(CH_2)_n$—W—$R^{1a}$;

W is independently selected from the group consisting of: a bond, CO, CONH, CON($C_{1-4}$ alkyl), $SO_2$, and $CHR^f$;

$R^{1a}$ is independently selected from the group consisting of: $C_{3-6}$ cycloalkyl substituted with 0-3 $R^c$, phenyl substituted with 0-3 $R^b$, and a 5- to 6-membered heterocycle comprising: carbon atoms and 1-4 heteroatoms selected from N, $NR^e$, O, and $S(O)_p$; and wherein said heterocycle is substituted with 0-3 $R^c$;

$R^5$ is independently selected from the group consisting of: OH and $C_{1-6}$ alkoxy; and provided that:
(i) when $R^1$ is methyl, $R^2$ and $R^3$ are H, $R^5$ is OH, and L is —$(CH_2)_3$—, then $R^4$ is other than unsubstituted phenyl;
(ii) when L is $CH_2$, then $R^4$ is other than halogen mono-substituted phenyl or methoxy bi-substituted phenyl; or
(iii) when $R^1$ is methyl, $R^2$ and $R^3$ are H, $R^5$ is OH, and L is —$(CH_2)_2$—, then $R^4$ is other than methoxy mono-substituted indolyl.

4. A compound according to claim 3, wherein:

$R^1$ is independently selected from the group consisting of: H, $C_{1-4}$ alkyl substituted with 0-1 $R^a$, —$CH_2CO_2(C_{1-4}$ alkyl), cyclopropyl, cyclopropylmethyl, phenyl, 4-$CF_3$-phenyl, 3-halo-4-$CO_2(C_{1-4}$ alkyl)-phenyl, 2-($C_{1-4}$ alkoxy)-5-halo-phenyl, benzyl, 2-halo-benzyl, 3-$CF_3$-benzyl, 4-$CO_2$H-benzyl, 4-$CO_2(C_{1-4}$ alkyl)-benzyl, 4-$SO_2(C_{1-4}$ alkyl)-benzyl, 2-halo-phenethyl, 4-halo-phenethyl, 2-OH-phenethyl, —$SO_2$(phenyl), and pyrid-4-yl;

$R^2$ is independently selected from the group consisting of: H, halogen, $CF_3$, $OCF_3$, $C_{1-4}$ alkyl, $C_{2-4}$ alkenyl, —$SO_2$(phenyl), phenyl substituted with 0-2 $R^b$, naphthyl substituted with 0-2 $R^b$, and a heterocycle selected from: thienyl, oxadiazolyl, pyridyl, indolyl, quinolinyl, and isoquinolinyl; wherein said heterocycle is substituted with 0-2 $R^c$;

$R^3$ is independently selected from the group consisting of: H, $C_{1-4}$ alkyl and phenyl substituted with 0-2 $R^b$;

$R^4$ is independently selected from the group consisting of: phenyl substituted with 0-3$R^d$, naphthyl, tetrahydronaphthyl, pyrrolidinyl, morpholinyl,

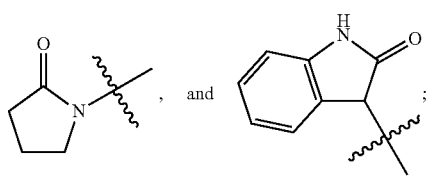 [SMILES: *N1CCCC1=O ; *C1C(=O)Nc2ccccc21]

L is independently selected from the group consisting of: $C_{1-6}$ alkylene, $C_{2-6}$ alkenylene, —O—$C_{2-5}$ alkylene-, —S—$C_{2-4}$ alkylene-, —$SO_2$—$C_{2-4}$ alkylene-, —$(CH_2)_{0-2}$ CH($C_{3-6}$ cycloalkyl)$(CH_2)_{0-2}$—, and —$(CH_2)_{0-2}$CH(Ph)$(CH_2)_{0-2}$—; wherein said alkylene and alkenylene may be straight or branched;

$R^a$ is, independently at each occurrence, selected from the group consisting of: halogen, OH, $C_{1-4}$ alkyl, $C_{1-4}$ alkoxy, $C_{1-4}$ haloalkyl, $CF_3$, $OCF_3$, $CO_2H$, and $CO_2(C_{1-4}$ alkyl);

$R^d$ is, independently at each occurrence, selected from the group consisting of: halogen, $C_{1-6}$ alkyl, $C_{1-4}$ alkoxy, $C_{1-4}$ haloalkyl, $CF_3$, $OCF_3$, $CO_2(C_{1-4}$ alkyl), and $NO_2$; and provided that:
(i) when $R^1$ is methyl, $R^2$ and $R^3$ are H, and L is —$(CH_2)_3$—, then $R^4$ is other than phenyl; or
(ii) when L is $CH_2$, then $R^4$ is other than phenyl halogen mono-substituted phenyl or methoxy bi-substituted phenyl.

5. A compound according to claim 4, wherein the compound is of Formula (II):

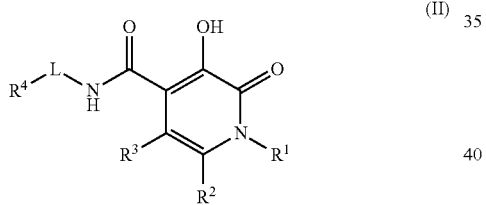

or a stereoisomer, a tautomer, or a pharmaceutically acceptable salt thereof, wherein:

$R^1$ is independently selected from the group consisting of: H, $C_{1-4}$ alkyl substituted with 0-1 $CF_3$, —$CH_2CO_2(C_{1-4}$ alkyl), cyclopropyl, cyclopropylmethyl, phenyl, 4-$CF_3$-phenyl, 3-halo-4-$CO_2(C_{1-4}$ alkyl)-phenyl, benzyl, 2-halo-benzyl, 3-$CF_3$-benzyl, 4-$CO_2H$-benzyl, 4-$CO_2(C_{1-4}$ alkyl)-benzyl, 4-$SO_2(C_{1-4}$ alkyl)-benzyl, 2-halo-phenethyl, 4-halo-phenethyl, 2-OH-phenethyl, and pyrid-4-yl;

$R^2$ is independently selected from the group consisting of: H, halogen, $C_{1-4}$ alkyl, $C_{2-4}$ alkenyl, $CF_3$, phenyl, 3-halo-phenyl, 4-halo-phenyl, 3-$C_{1-4}$ alkyl-phenyl, 3-$CF_3$-phenyl, 4-$CF_3$-phenyl, 3-$OCF_3$-phenyl, 4-$OCF_3$-phenyl, 4-OH-phenyl, 4-CN-phenyl, 3-$NH_2$-phenyl, 3-N($C_{1-4}$ alkyl)-2-phenyl, 3-$CO_2H$-phenyl, 3-$CONH_2$-phenyl, 4-$CONH_2$-phenyl, 3-CON($C_{1-4}$ alkyl)-2-phenyl, 4-CON($C_{1-4}$ alkyl)-2-phenyl, 3-$NHSO_2(C_{1-4}$ alkyl)-phenyl, 4-$NHSO_2(C_{1-4}$ alkyl)-phenyl, 3-$SO_2(C_{1-4}$ alkyl)-phenyl, 4-$SO_2(C_{1-4}$ alkyl)-phenyl, 3-$SO_2NH_2$-phenyl, 3-biphenyl, 4-biphenyl, 3-halo-4-halo-phenyl, 3-halo-5-halo-phenyl, 3-$C_{1-4}$ alkyl-4-halo-phenyl, 3-$CF_3$-5-halo-phenyl, 3-$CF_3$-4-halo-phenyl, 3-halo-4-$CF_3$-phenyl, 3-$CF_3$-4-OH-phenyl, 3,5-di$CF_3$-phenyl, 3-$OCF_2CHF_2$-5-halo-phenyl, 1-naphthyl, 2-naphthyl, thien-2-yl, thien-3-yl, 5-($C_{1-4}$ alkyl)-1,2,4-oxadiazol-3-yl, pyrid-4-yl, 1-$C_{1-4}$ alkyl-indol-5-yl, 3-quinolinyl, 5-quinolinyl, 6-quinolinyl, and 5-isoquinolinyl;

$R^3$ is independently selected from the group consisting of: H, $C_{1-4}$ alkyl, 3-halo-5-halo-phenyl, and 3-$CF_3$-5-halo-phenyl;

$R^4$ is independently selected from the group consisting of: phenyl, 2-($C_{1-4}$ alkyl)-phenyl, 3-($C_{1-4}$ alkyl)-phenyl, 4-($C_{1-4}$ alkyl)-phenyl, 2-($C_{1-4}$ alkoxy)-phenyl, 3-($C_{1-4}$ alkoxy)-phenyl, 4-($C_{1-4}$ alkoxy)-phenyl, 2-halo-phenyl, 3-halo-phenyl, 4-halo-phenyl, 2-$CF_3$-phenyl, 3-$CF_3$-phenyl, 4-$CF_3$-phenyl, 3-$OCF_3$-phenyl, 4-$OCF_3$-phenyl, 3-$CO_2(C_{1-4}$ alkyl)-phenyl, 4-$CO_2(C_{1-4}$ alkyl)-phenyl, 2-$NO_2$-phenyl, 3-$NO_2$-phenyl, 4-$NO_2$-phenyl, 2-halo-4-halo-phenyl, 3-halo-4-halo-phenyl, 3-halo-5-halo-phenyl, 2-halo-6-halo-phenyl, 1-naphthyl, 2-naphthyl, and

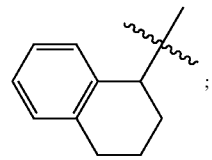 [SMILES: *C1CCCc2ccccc21]

and

L is independently selected from the group consisting of: $C_{1-6}$ alkylene, $C_{2-6}$ alkenylene, —O—$C_{2-5}$ alkylene-, —S—$C_{2-4}$ alkylene-, and —$(CH_2)_2CH(Ph)$—; wherein said alkylene and alkenylene may be straight or branched;

provided that when $R^1$ is methyl, $R^2$ is H, and L is —$(CH_2)_3$—, then $R^4$ is other than phenyl.

6. A compound according to claim 5, wherein:

$R^1$ is independently selected from the group consisting of: H, methyl, ethyl, isopropyl, isobutyl, $CH_2CF_3$, $CH_2CH_2CF_3$, —$CH_2CO_2Et$, cyclopropyl, cyclopropylmethyl, phenyl, 4-$CF_3$-phenyl, 3-F-4-$CO_2Me$-phenyl, benzyl, 2-F-benzyl, 3-$CF_3$-benzyl, 4-$CO_2H$-benzyl, 4-$CO_2Me$-benzyl, 4-$SO_2Me$-benzyl, 2-F-phenethyl, 4-F-phenethyl, 2-OH-phenethyl, and pyrid-4-yl;

$R^2$ is independently selected from the group consisting of: H, Br, ethyl, isopropyl, ethenyl, $CF_3$, phenyl, 3-F-phenyl, 4-F-phenyl, 3-Cl-phenyl, 4-Cl-phenyl, 3-Et-phenyl, 3-(i-Pr)-phenyl, 3-$CF_3$-phenyl, 4-$CF_3$-phenyl, 3-$OCF_3$-phenyl, 4-$OCF_3$-phenyl, 4-OH-phenyl, 4-CN-phenyl, 3-$NH_2$-phenyl, 3-N(Me)-2-phenyl, 3-$CO_2H$-phenyl, 3-$CONH_2$-phenyl, 4-$CONH_2$-phenyl, 3-CON(Me)-2-phenyl, 4-CON(Me)-2-phenyl, 3-$NHSO_2Me$-phenyl, 4-$NHSO_2Me$-phenyl, 3-$SO_2Me$-phenyl, 4-$SO_2Me$-phenyl, 3-$SO_2NH_2$-phenyl, 3-biphenyl, 4-biphenyl, 3,4-diF-phenyl, 3,5-diF-phenyl, 3-$CH_3$-4-F-phenyl, 3-$CF_3$-5-F-phenyl, 3-$CF_3$-4-Cl-phenyl, 3-$C_{1-4}$—$CF_3$-phenyl, 3-$CF_3$-4-OH-phenyl, 3,5-di$CF_3$-phenyl, 3-$OCF_2CHF_2$-5-F-phenyl, 1-naphthyl, 2-naphthyl, thien-2-yl, thien-3-yl, 5-Me-1,2,4-oxadiazol-3-yl, pyrid-4-yl, 1-Me-indol-5-yl, 3-quinolinyl, 5-quinolinyl, 6-quinolinyl, and 5-isoquinolinyl;

$R^3$ is independently selected from the group consisting of: H, methyl, 3-F-5-F-phenyl, and 3-CF$_3$-5-F-phenyl;

$R^4$ is independently selected from the group consisting of: phenyl, 2-Me-phenyl, 3-Me-phenyl, 4-Me-phenyl, 2-OMe-phenyl, 3-OMe-phenyl, 4-OMe-phenyl, 2-F-phenyl, 3-F-phenyl, 4-F-phenyl, 2-Cl-phenyl, 3-Cl-phenyl, 4-Cl-phenyl, 2-CF$_3$-phenyl, 3-CF$_3$-phenyl, 4-CF$_3$-phenyl, 3-OCF$_3$-phenyl, 4-OCF$_3$-phenyl, 3-CO$_2$Me-phenyl, 4-CO$_2$Me-phenyl, 2-NO$_2$-phenyl, 3-NO$_2$-phenyl, 4-NO$_2$-phenyl, 3,5-diF-phenyl, 2,4-diCl-phenyl, 3,4-diCl-phenyl, 2,6-diCl-phenyl, 1-naphthyl, 2-naphthyl, and

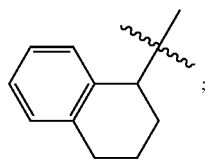

and

L is independently selected from the group consisting of: CH$_2$, —CH(CH$_3$)—, —(CH$_2$)$_2$—, —(CH$_2$)$_3$—, —(CH$_2$)$_4$—, —(CH$_2$)$_2$CH(CH$_3$)—, —(CH$_2$)$_3$CH(CH$_3$)—, —(CH$_2$)$_2$CH(Et)-, —(CH$_2$)$_2$—CH(CH=CH$_2$)—, —(CH$_2$)$_2$CH(Ph)-, —O(CH$_2$)$_2$—, —O(CH$_2$)$_3$—, —O(CH$_2$)$_4$—, —O(CH$_2$)$_2$CH(CH$_3$)—, and —S(CH$_2$)$_3$—;

provided that when $R^1$ is methyl, $R^2$ is H, and L is —(CH$_2$)$_3$—, then $R^4$ is other than phenyl.

7. A compound according to claim 6, wherein:

$R^1$ is independently selected from the group consisting of: H, methyl, ethyl, isopropyl, isobutyl, CH$_2$CF$_3$, —CH$_2$CO$_2$Et, cyclopropyl, cyclopropylmethyl, phenyl, 4-CF$_3$-phenyl, 3-F-4-CO$_2$Me-phenyl, benzyl, 2-F-benzyl, 4-CO$_2$H-benzyl, 4-CO$_2$Me-benzyl, 4-SO$_2$Me-benzyl, 4-F-phenethyl, 2-OH-phenethyl, and pyrid-4-yl;

$R^2$ is independently selected from the group consisting of: H, Br, ethyl, isopropyl, ethenyl, CF$_3$, phenyl, 3-F-phenyl, 4-F-phenyl, 4-Cl-phenyl, 3-Et-phenyl, 3-(i-Pr)-phenyl, 3-CF$_3$-phenyl, 4-CF$_3$-phenyl, 3-OCF$_3$-phenyl, 4-OCF$_3$-phenyl, 4-OH-phenyl, 4-CN-phenyl, 3-NH$_2$-phenyl, 3-N(Me)-2-phenyl, 4-CONH$_2$-phenyl, 3-CON(Me)-2-phenyl, 4-CON(Me)-2-phenyl, 3-NHSO$_2$Me-phenyl, 4-SO$_2$Me-phenyl, 3-SO$_2$NH$_2$-phenyl, 3-biphenyl, 4-biphenyl, 3,4-diF-phenyl, 3,5-diF-phenyl, 3-CH$_3$-4-F-phenyl, 3-CF$_3$-5-F-phenyl, 3-CF$_3$-4-Cl-phenyl, 3-Cl-4—CF$_3$-phenyl, 3-CF$_3$-4-OH-phenyl, 3,5-diCF$_3$-phenyl, 3-OCF$_2$CHF$_2$-5-F-phenyl, 1-naphthyl, thien-2-yl, thien-3-yl, pyrid-4-yl, 1-Me-indol-5-yl, 3-quinolinyl, 5-quinolinyl, 6-quinolinyl, and 5-isoquinolinyl;

$R^3$ is independently selected from the group consisting of: H, methyl, 3-F-5-F-phenyl, and 3-CF$_3$-5-F-phenyl;

$R^4$ is independently selected from the group consisting of: phenyl, 2-Me-phenyl, 3-Me-phenyl, 4-Me-phenyl, 3-OMe-phenyl, 2-F-phenyl, 3-F-phenyl, 4-F-phenyl, 2-Cl-phenyl, 3-Cl-phenyl, 4-Cl-phenyl, 2-CF$_3$-phenyl, 3-CF$_3$-phenyl, 4-CF$_3$-phenyl, 3-OCF$_3$-phenyl, 3-CO$_2$Me-phenyl, 4-CO$_2$Me-phenyl, 2-NO$_2$-phenyl, 3-NO$_2$-phenyl, 3,5-diF-phenyl, 2,4-diCl-phenyl, 3,4-diCl-phenyl, 2,6-diCl-phenyl, 1-naphthyl, 2-naphthyl, and

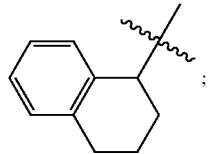 [SMILES: *C1CCCc2ccccc21]

and

L is independently selected from the group consisting of: CH$_2$, —CH(CH$_3$)—, —(CH$_2$)$_2$—, —(CH$_2$)$_3$—, —(CH$_2$)$_4$—, —(CH$_2$)$_2$CH(CH$_3$)—, —(CH$_2$)$_2$—CH(CH=CH$_2$)—, —O(CH$_2$)$_3$—, —O(CH$_2$)$_4$—, —O(CH$_2$)$_2$CH(CH$_3$)—, and —S(CH$_2$)$_3$—;

provided that when $R^1$ is methyl, $R^2$ is H, and L is —(CH$_2$)$_3$—, then $R^4$ is other than phenyl.

8. A compound according to claim 7, wherein:

$R^1$ is independently selected from the group consisting of: methyl, ethyl, isopropyl, isobutyl, CH$_2$CF$_3$, cyclopropyl, cyclopropylmethyl, phenyl, 4-CF$_3$-phenyl, 3-F-4-CO$_2$Me-phenyl, benzyl, 2-F-benzyl, 4-CO$_2$Me-benzyl, 4-SO$_2$Me-benzyl, 4-F-phenethyl, and pyrid-4-yl;

$R^2$ is independently selected from the group consisting of: H, Br, ethyl, isopropyl, ethenyl, CF$_3$, phenyl, 3-F-phenyl, 4-F-phenyl, 3-Et-phenyl, 3-(i-Pr)-phenyl, 3-CF$_3$-phenyl, 4-CF$_3$-phenyl, 3-OCF$_3$-phenyl, 4-OCF$_3$-phenyl, 4-OH-phenyl, 4-CN-phenyl, 3-CON(Me)-2-phenyl, 3-biphenyl, 4-biphenyl, 3,4-diF-phenyl, 3,5-diF-phenyl, 3-CF$_3$-5-F-phenyl, 3-CF$_3$-4-Cl-phenyl, 3-C$_{1-4}$—CF$_3$-phenyl, 3-CF$_3$-4-OH-phenyl, 3,5-diCF$_3$-phenyl, 3-OCF$_2$CHF$_2$-5-F-phenyl, 1-naphthyl, thien-2-yl, thien-3-yl, 3-quinolinyl, and 6-quinolinyl;

$R^3$ is independently selected from the group consisting of: H, methyl, 3-F-5-F-phenyl, and 3-CF$_3$-5-F-phenyl;

$R^4$ is independently selected from the group consisting of: phenyl, 2-Me-phenyl, 3-Me-phenyl, 4-Me-phenyl, 3-OMe-phenyl, 2-F-phenyl, 3-F-phenyl, 4-F-phenyl, 2-Cl-phenyl, 3-Cl-phenyl, 4-Cl-phenyl, 2-CF$_3$-phenyl, 3-CF$_3$-phenyl, 4-CF$_3$-phenyl, 3-CO$_2$Me-phenyl, 4-CO$_2$Me-phenyl, 2-NO$_2$-phenyl, 3-NO$_2$-phenyl, 3,4-diCl-phenyl, 2,6-diCl-phenyl, 1-naphthyl, and 2-naphthyl; and L is independently selected from the group consisting of: —(CH$_2$)$_2$—, —(CH$_2$)$_3$—, —(CH$_2$)$_4$—, —(CH$_2$)$_2$CH(CH$_3$)—, —O(CH$_2$)$_3$—, —O(CH$_2$)$_4$—, —O(CH$_2$)$_2$CH(CH$_3$)—, and —S(CH$_2$)$_3$—;

provided that when $R^1$ is methyl, $R^2$ is H, and L is —(CH$_2$)$_3$—, then $R^4$ is other than phenyl.

9. A compound according to claim 8, wherein the compound is of Formula (III):

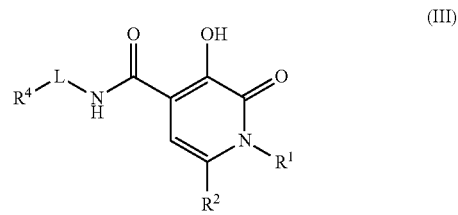

or a stereoisomer, a tautomer, or a pharmaceutically acceptable salt thereof.

10. A compound selected from:
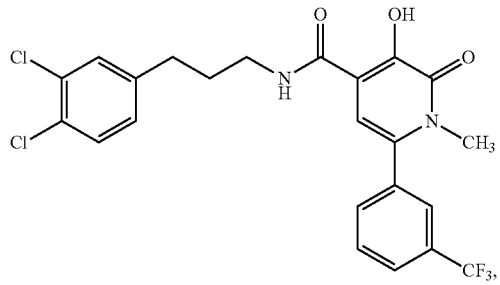
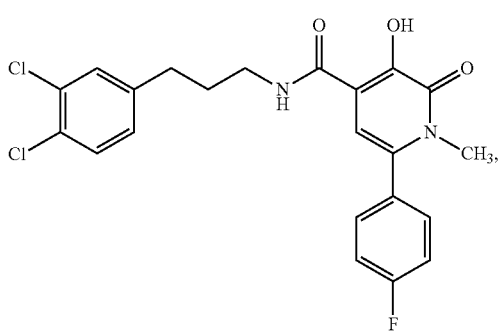
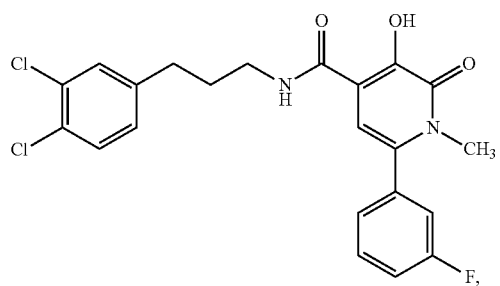
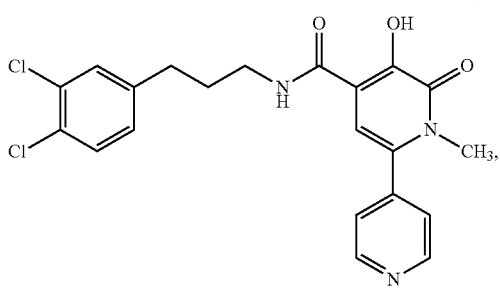
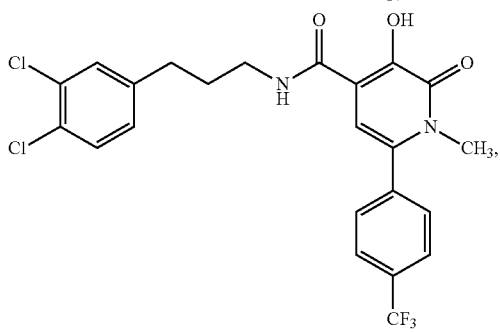
-continued
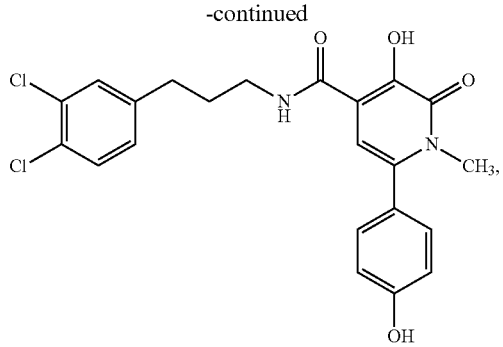
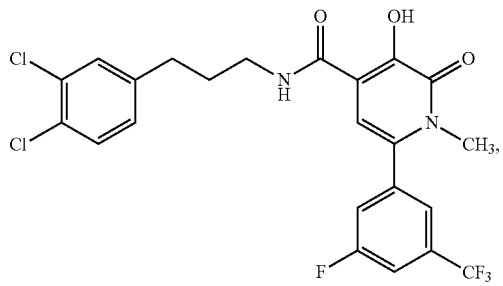
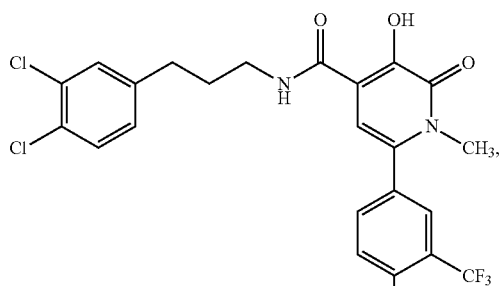
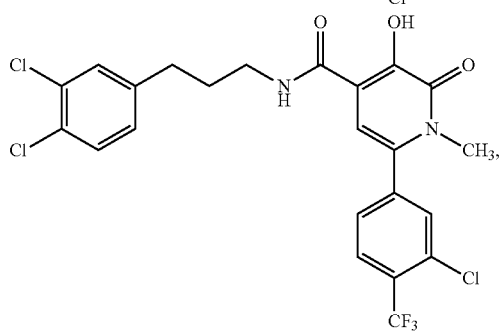
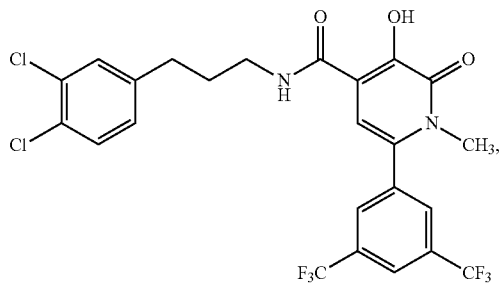

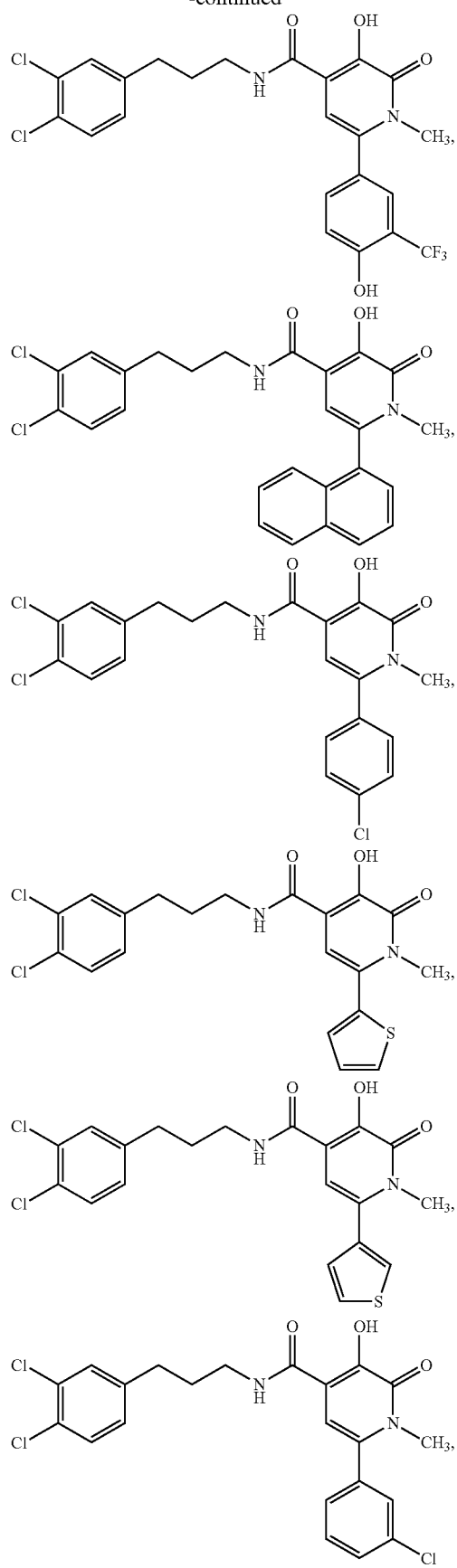
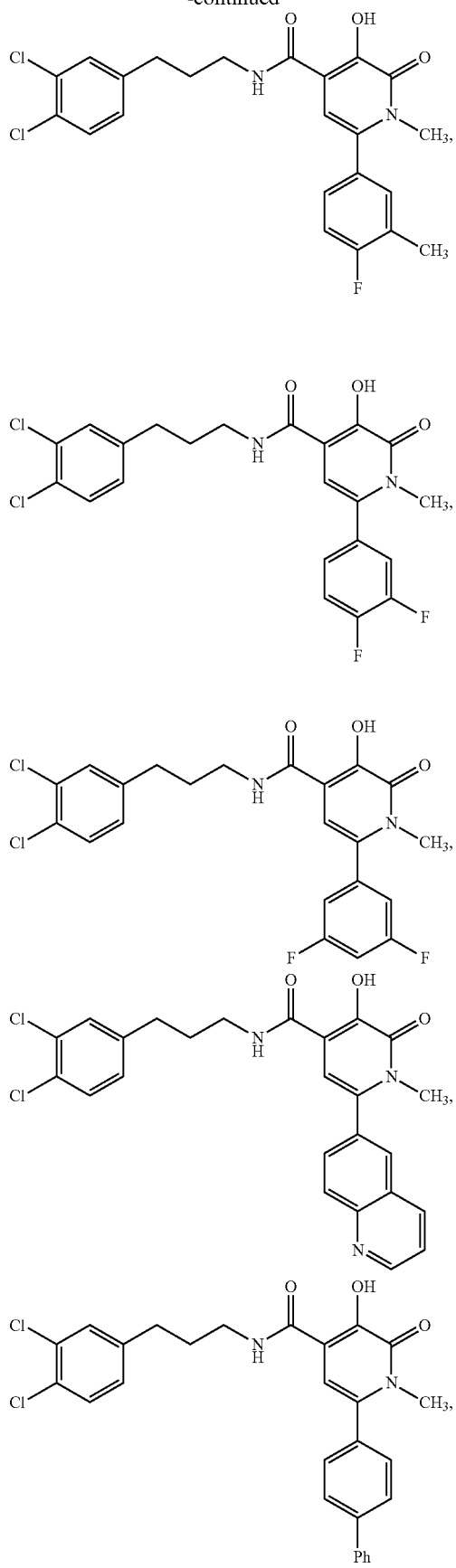

167
-continued
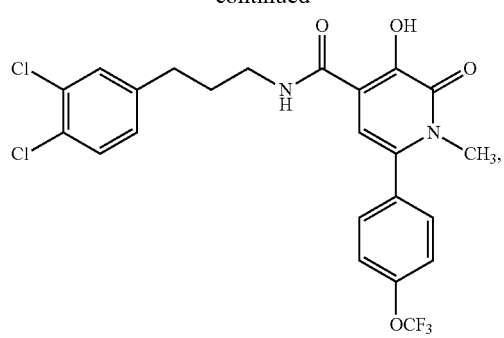
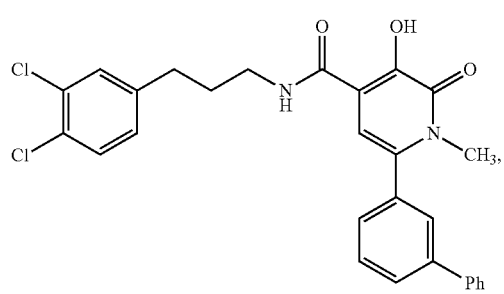
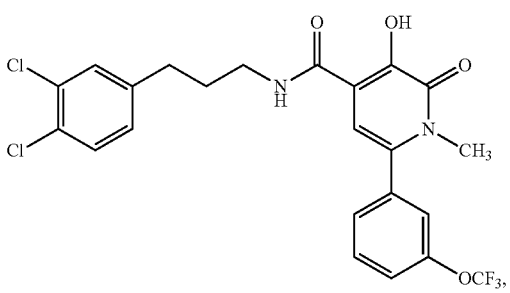
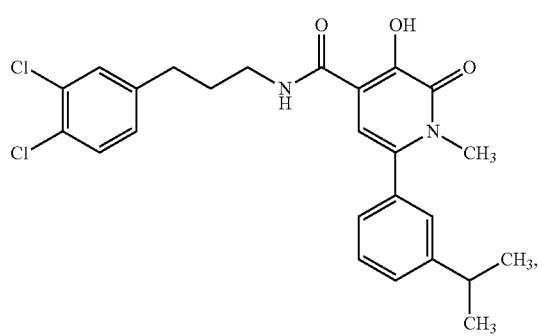
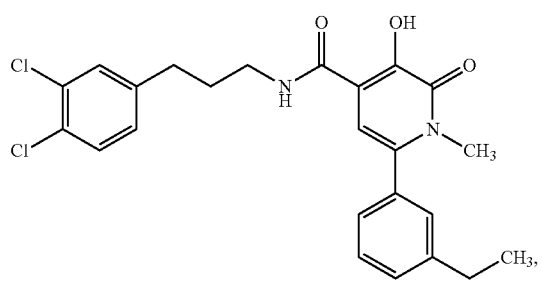
168
-continued
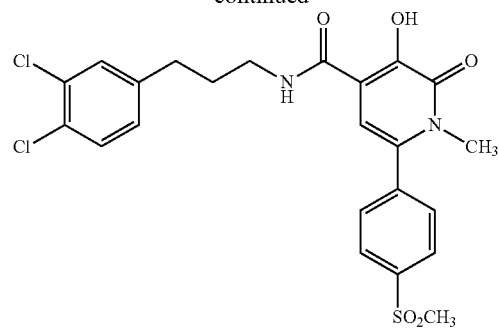
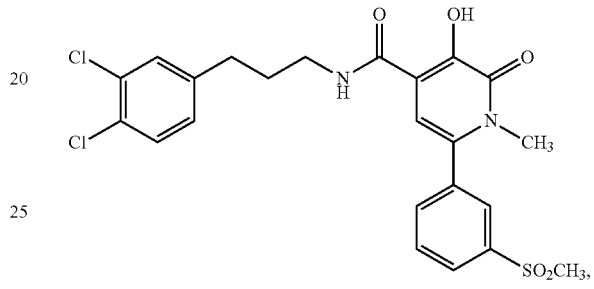
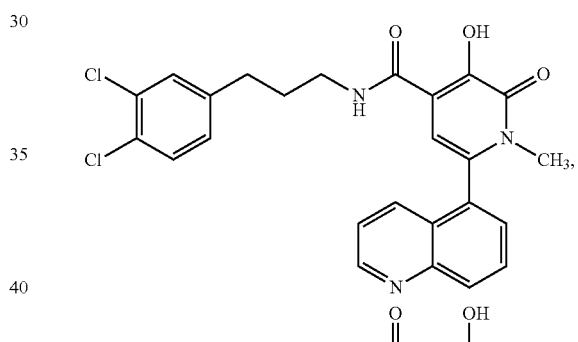
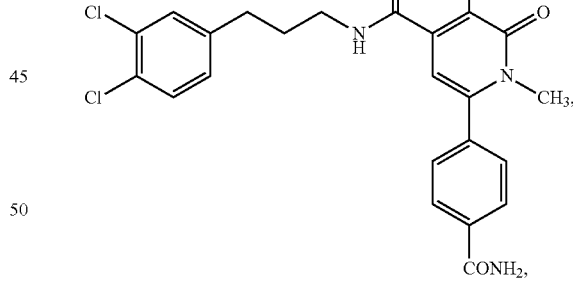
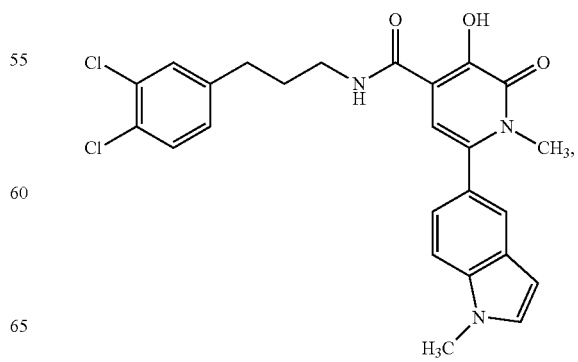

169
-continued
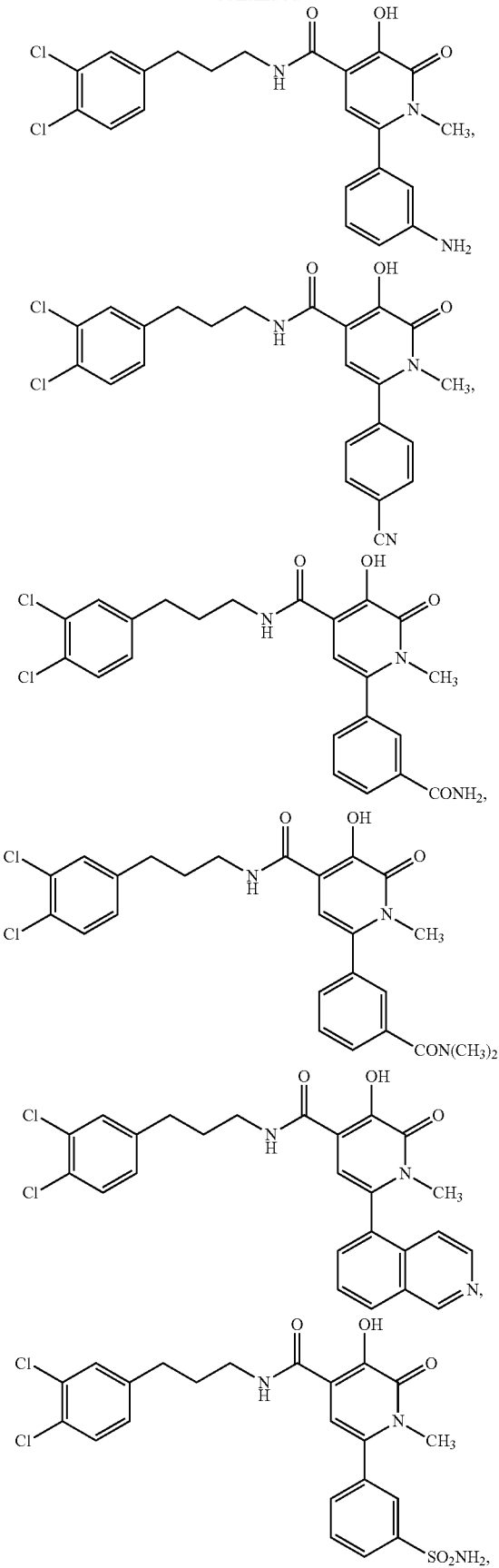
170
-continued
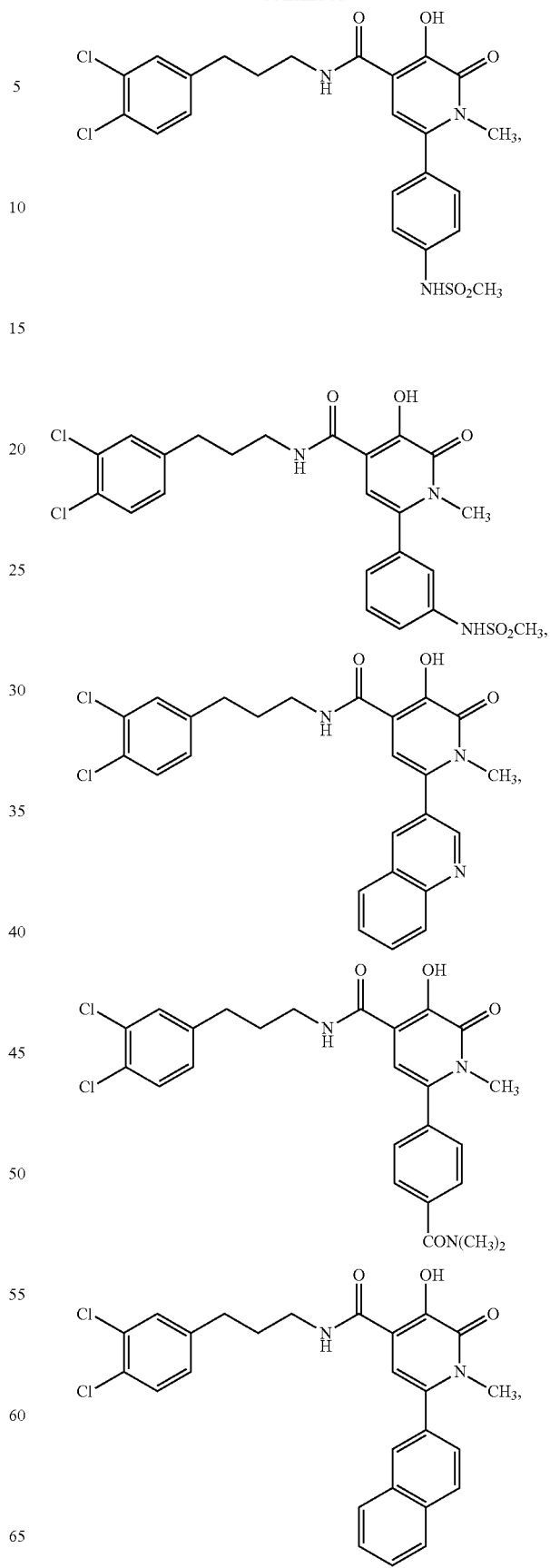

171
-continued
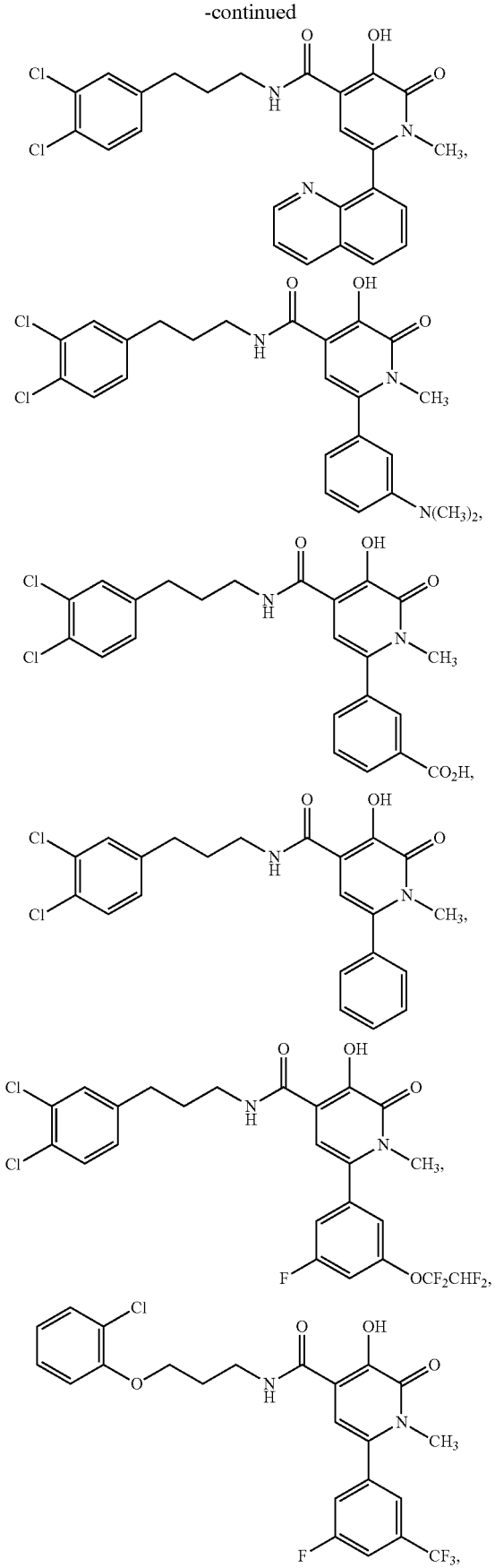
172
-continued
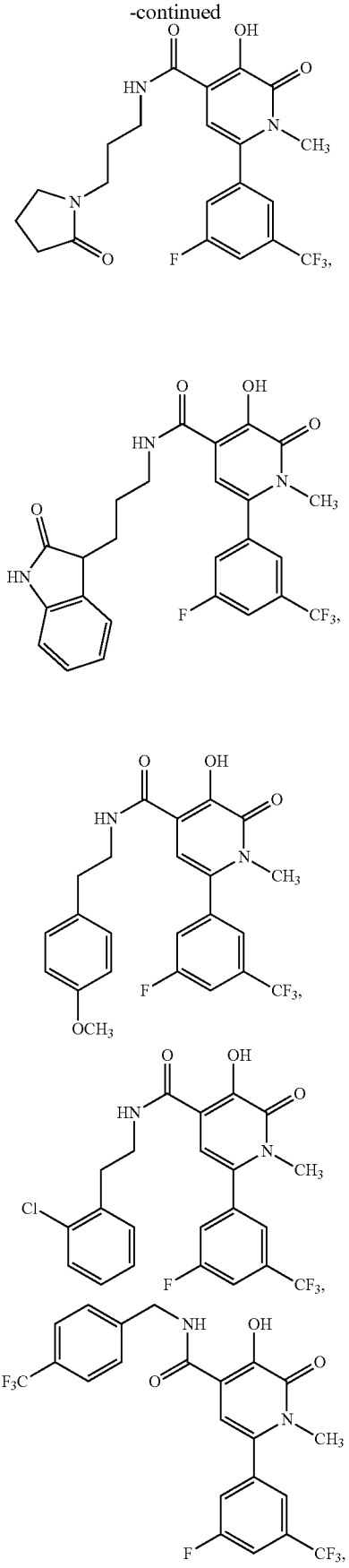

173
-continued
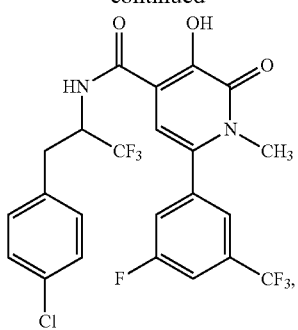
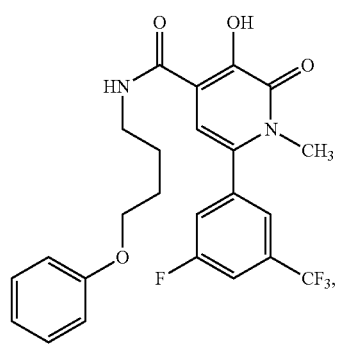
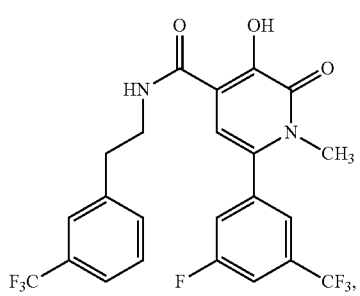
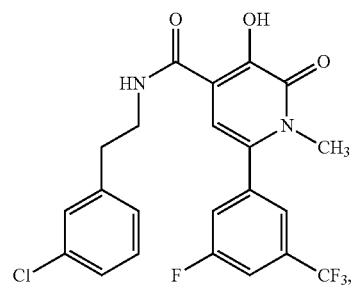
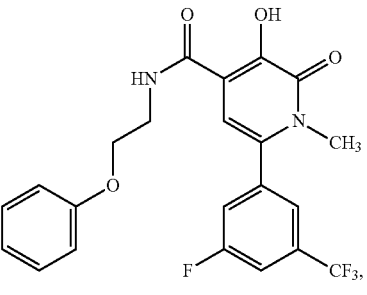
174
-continued
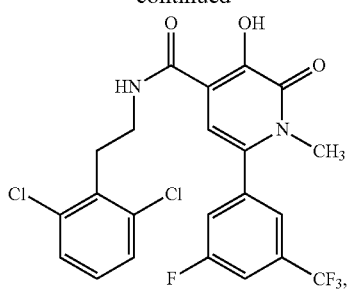
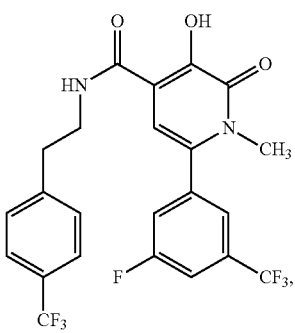
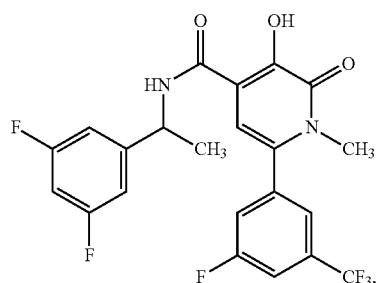
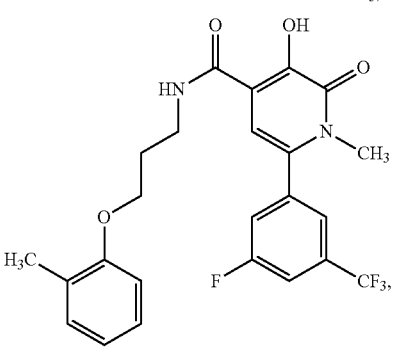
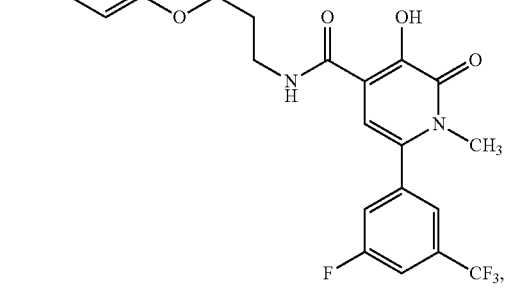

175
-continued
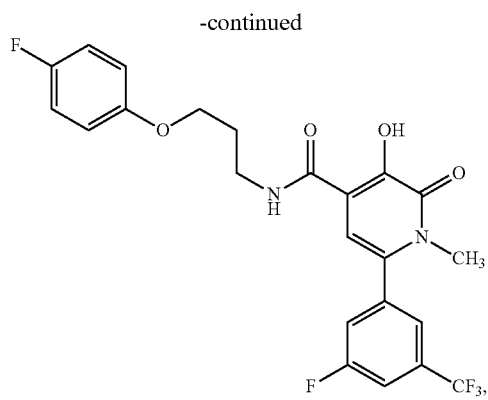
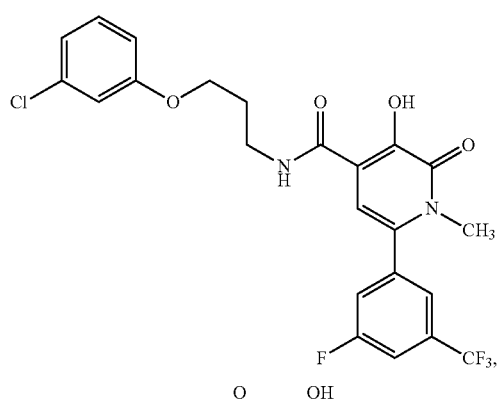
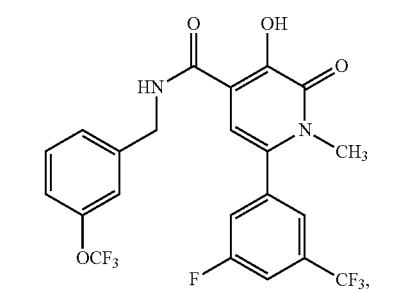
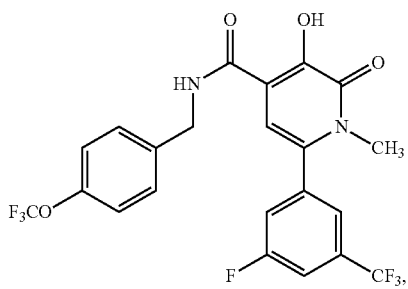
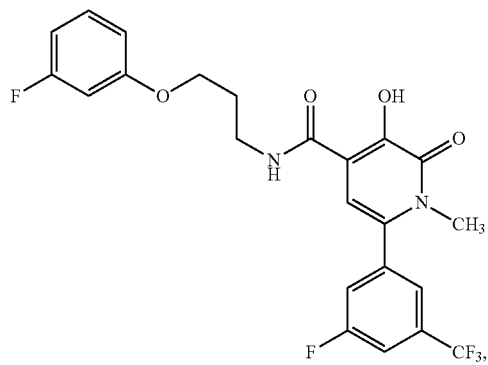
176
-continued
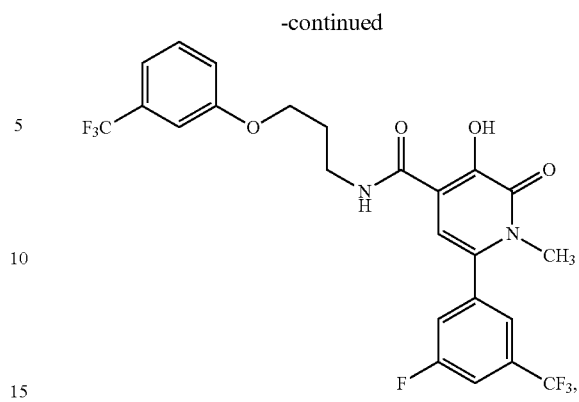
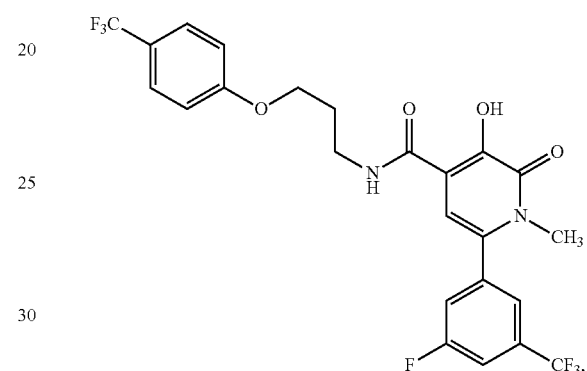
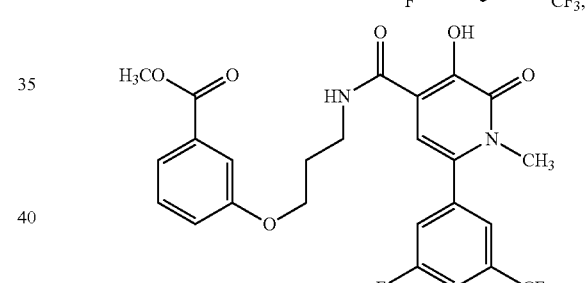
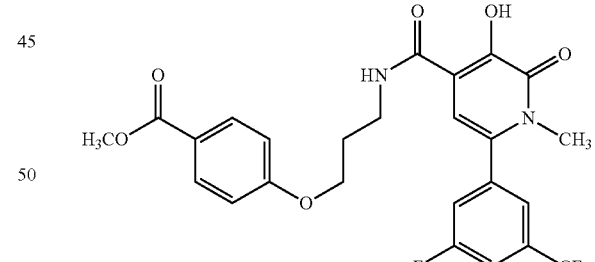
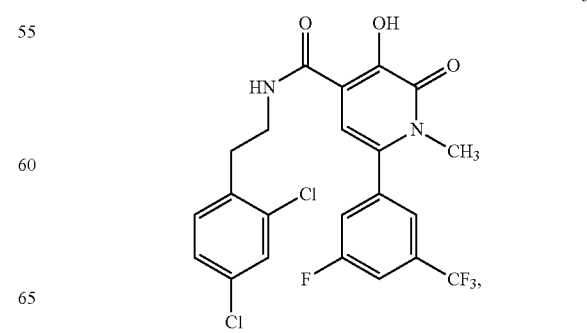

177
-continued
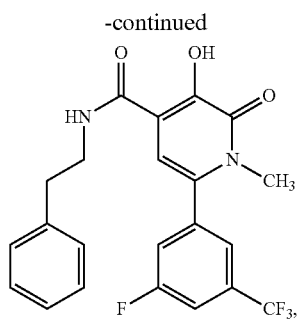
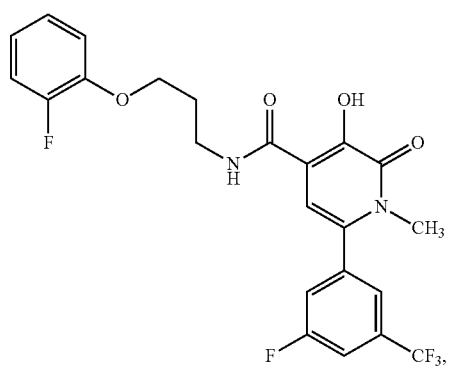
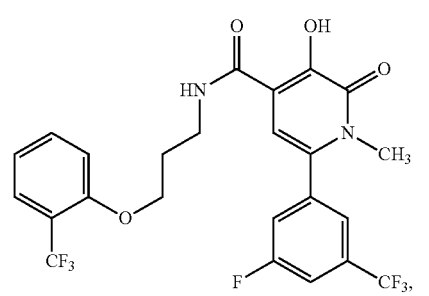
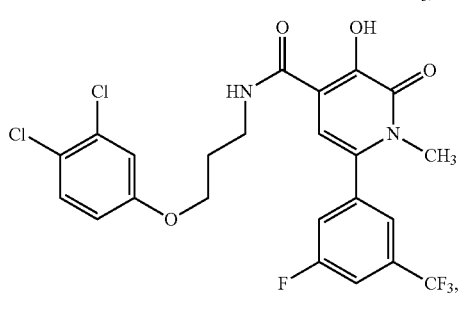
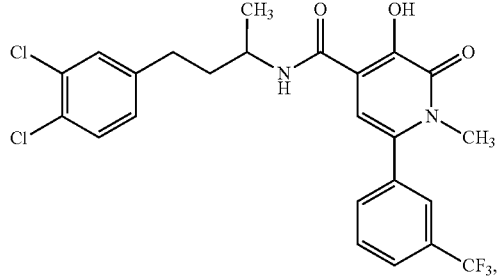
178
-continued
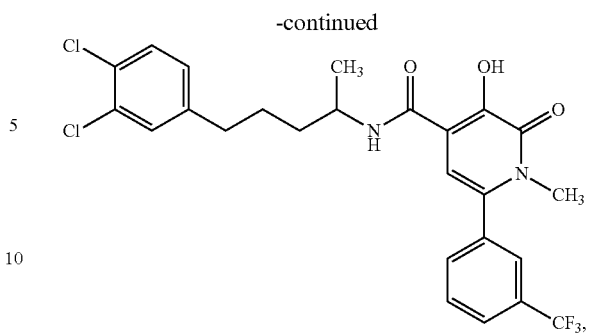
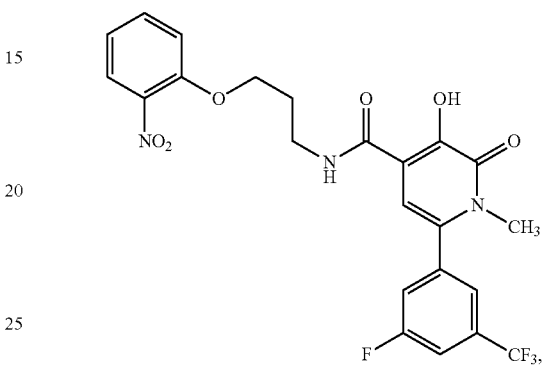
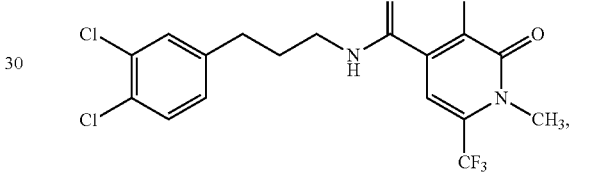
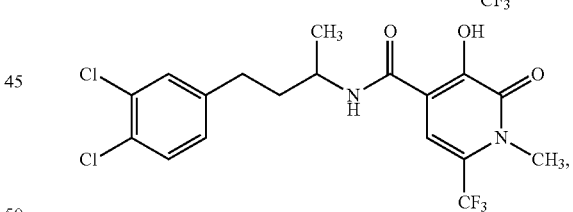
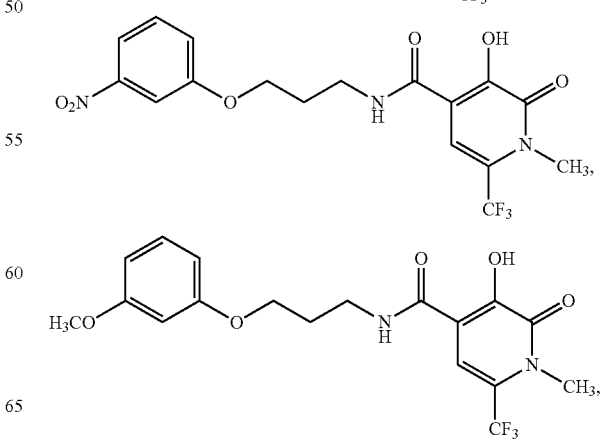

-continued

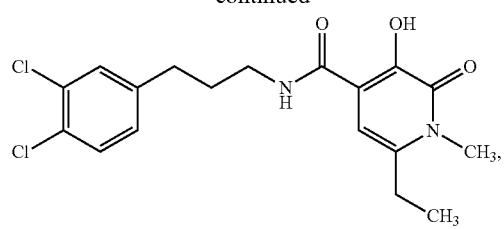
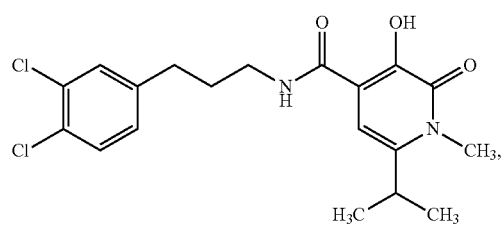
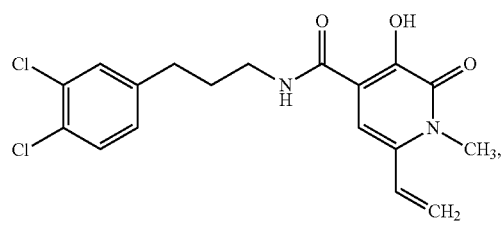
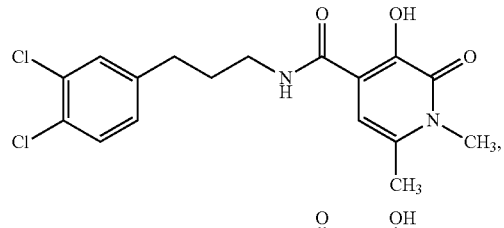
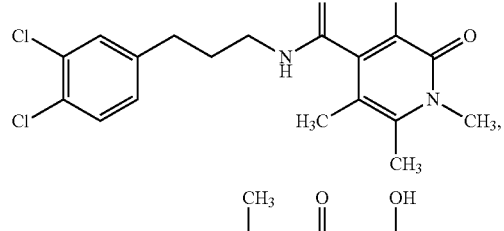
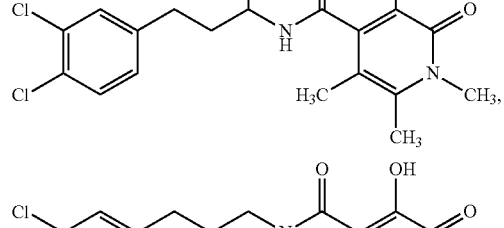
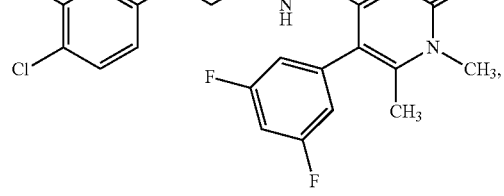
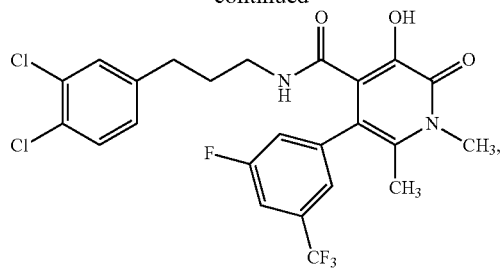
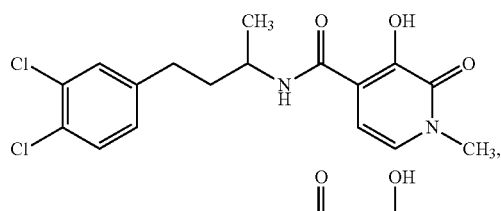
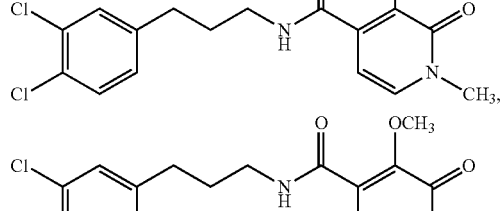
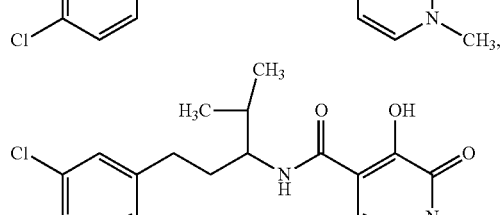
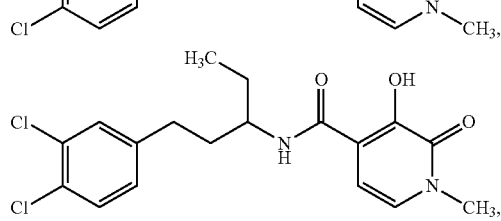
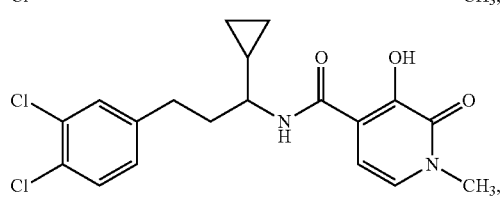
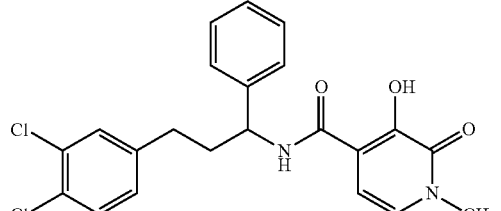
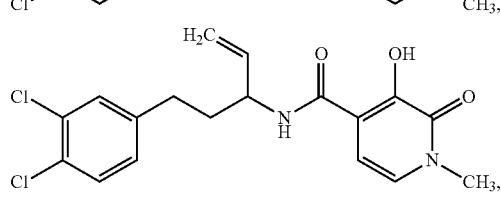

183
-continued
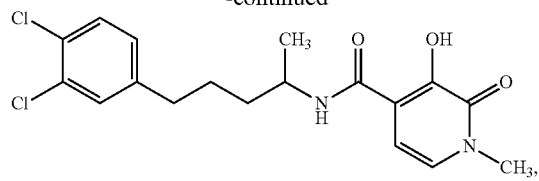
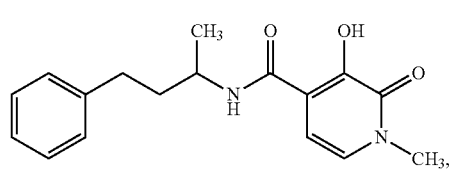
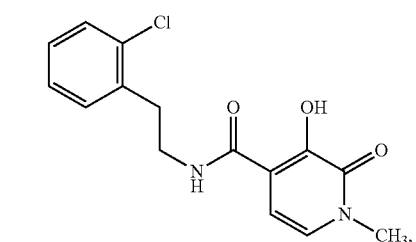
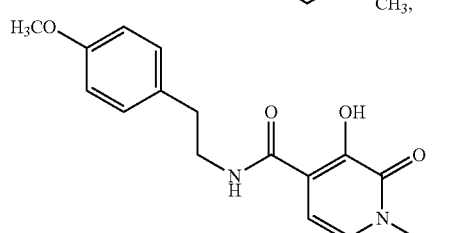
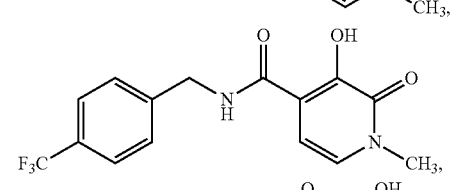
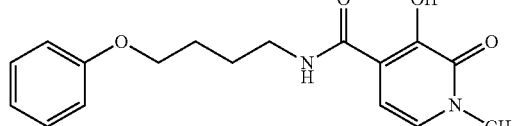
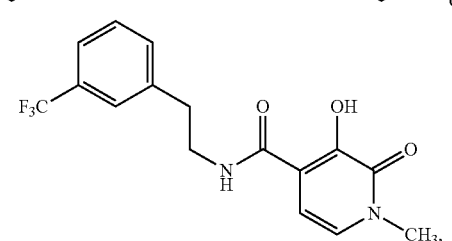
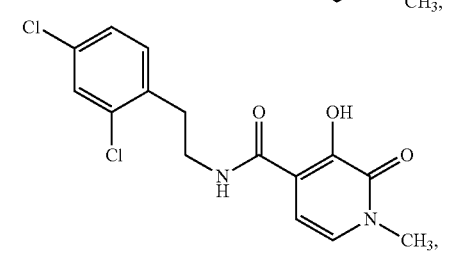
184
-continued
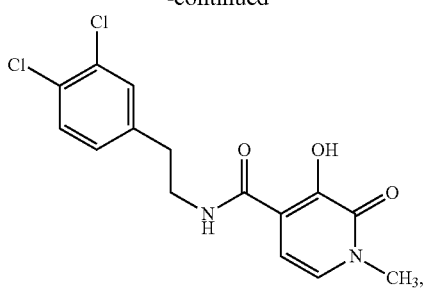
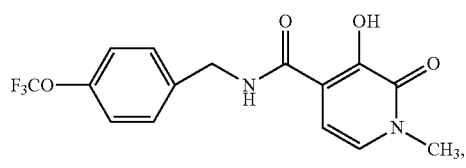
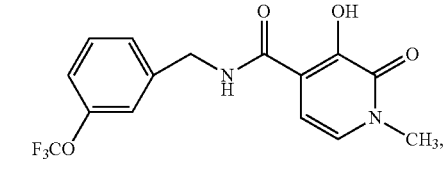
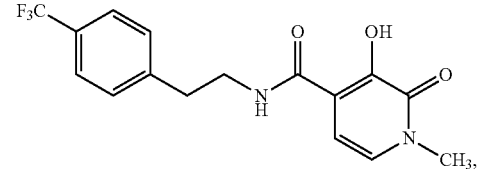
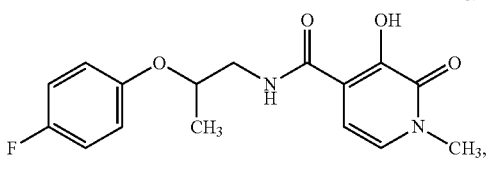
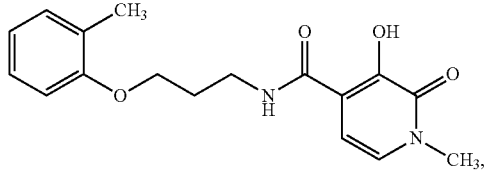
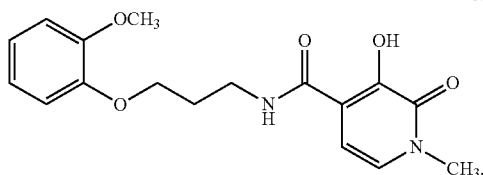
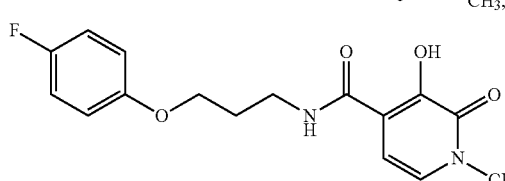
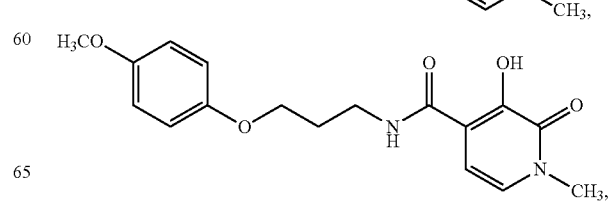

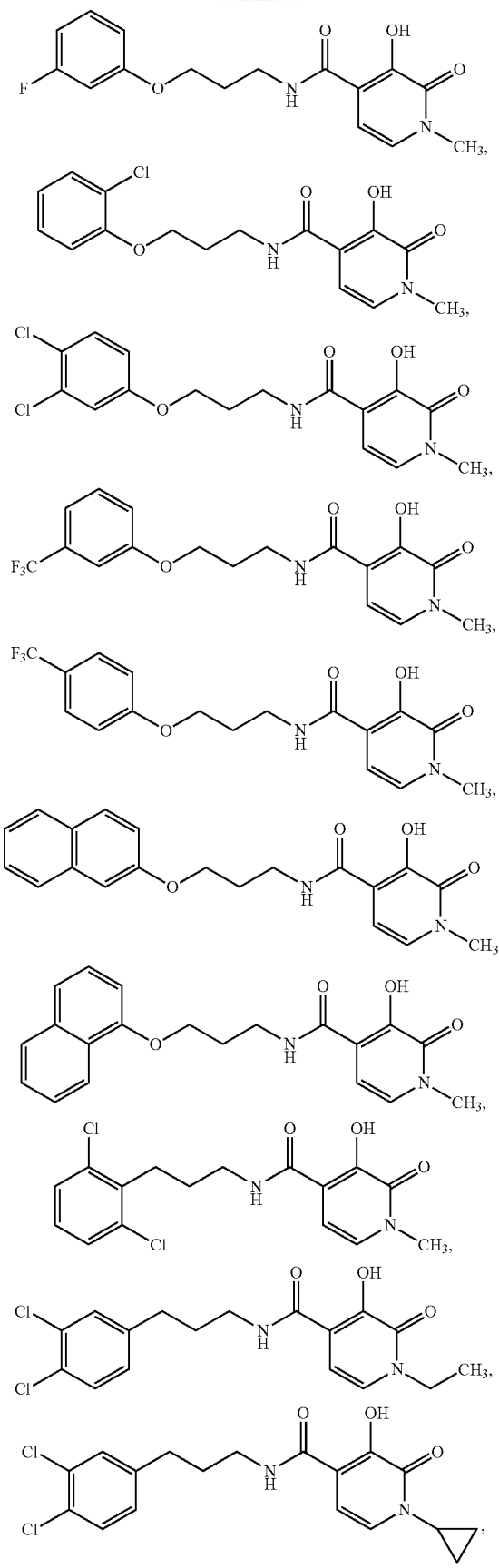
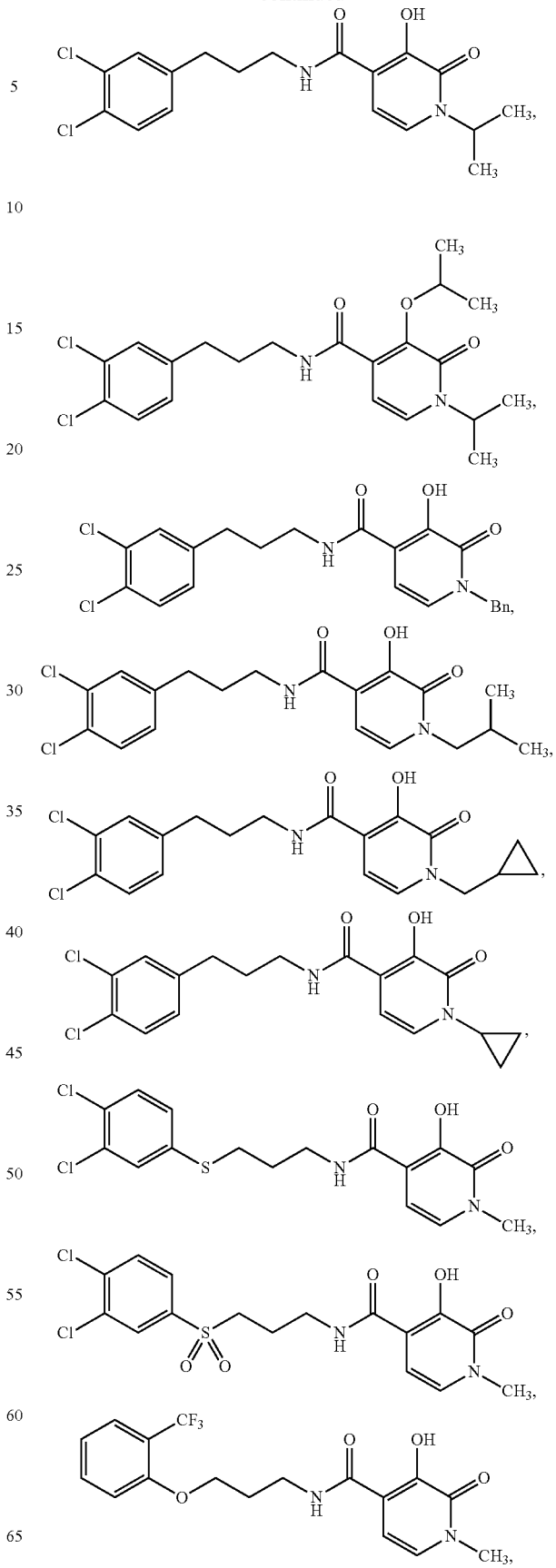

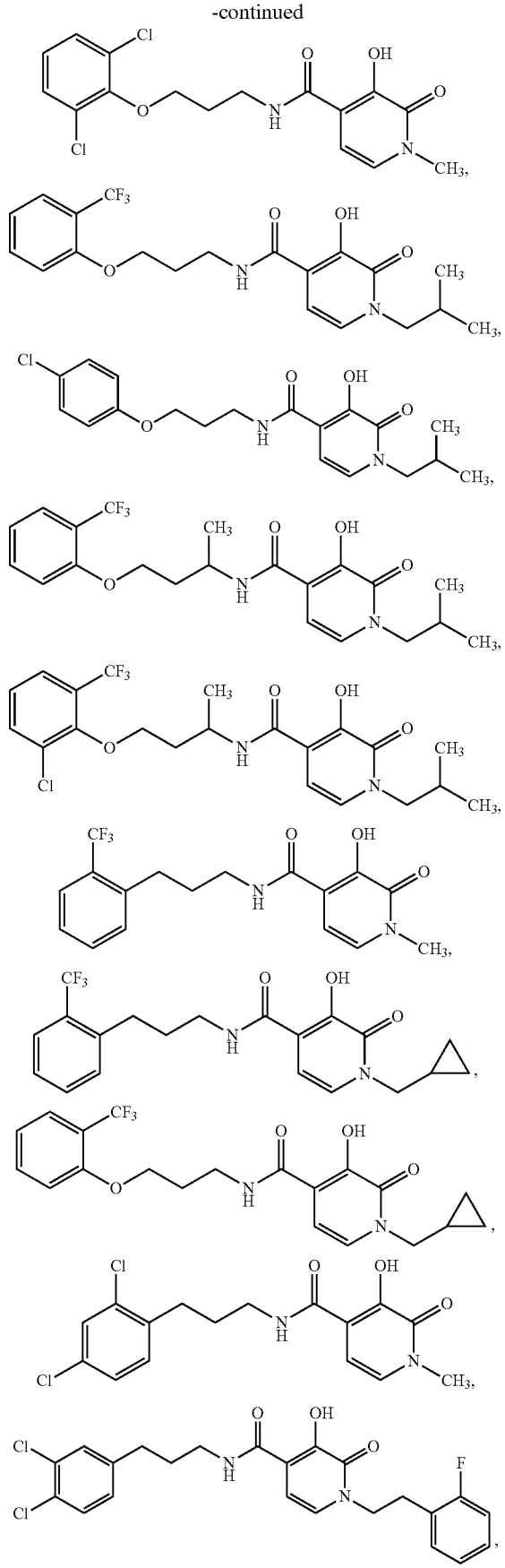
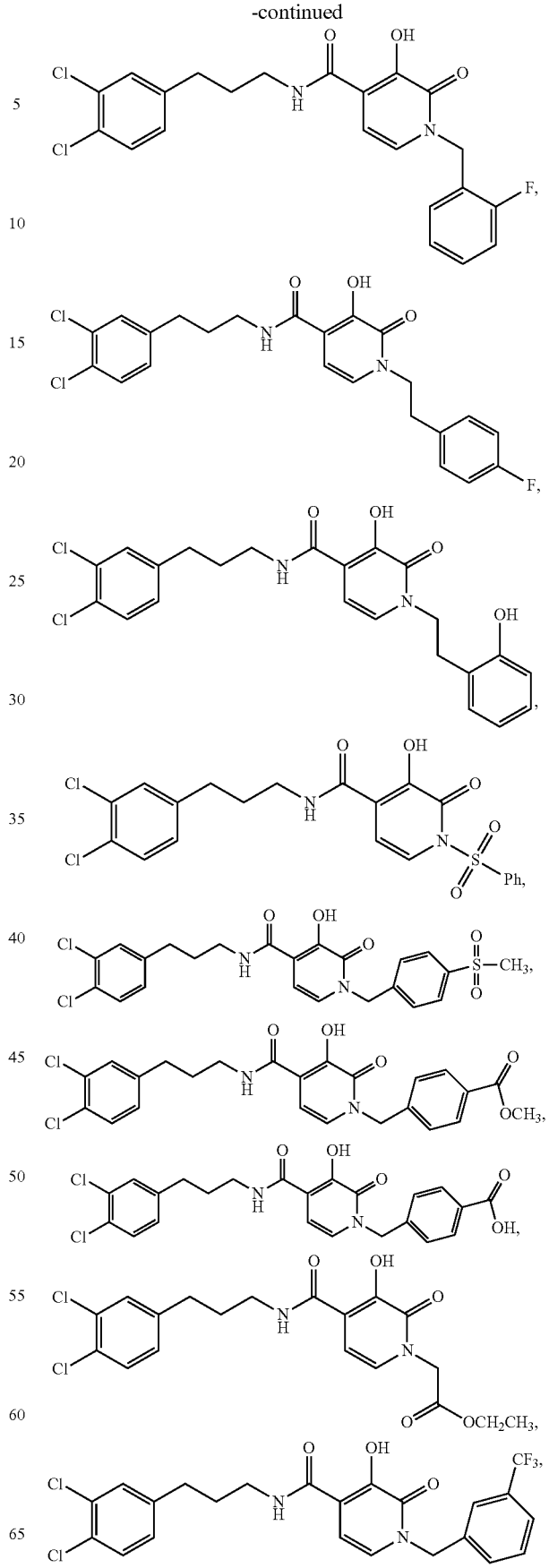

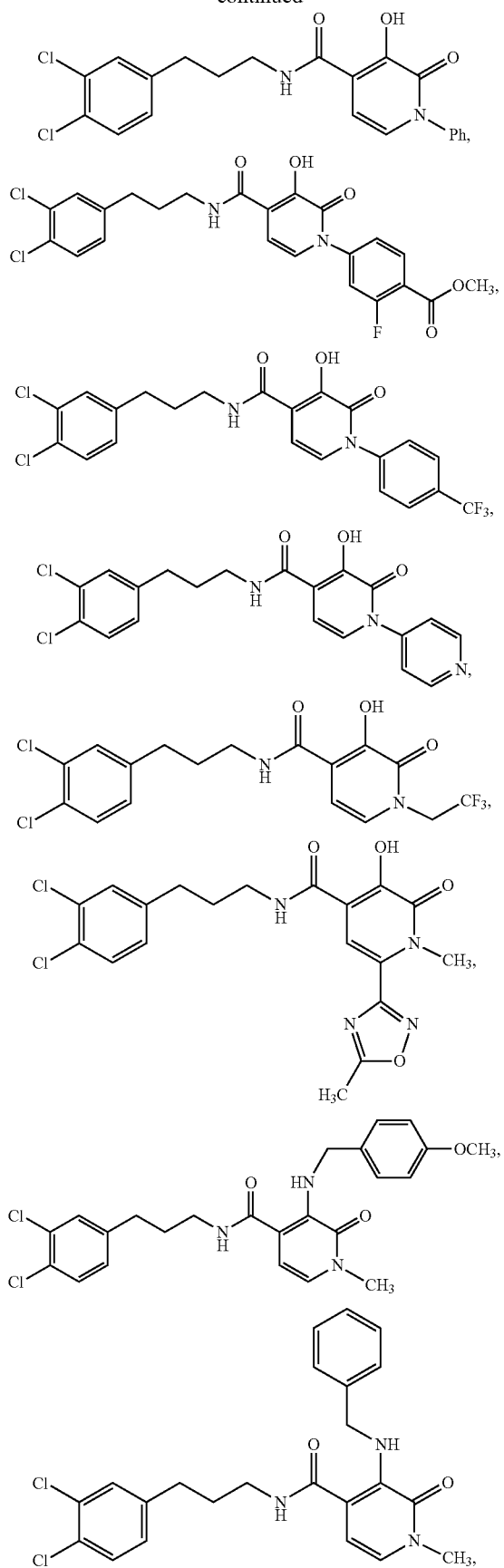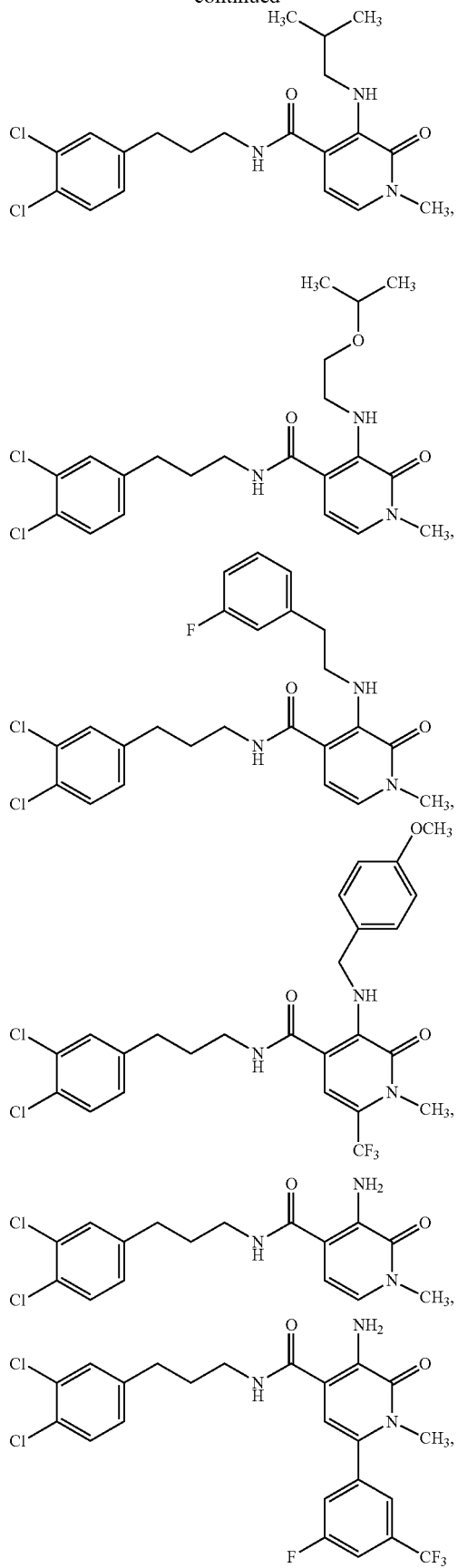

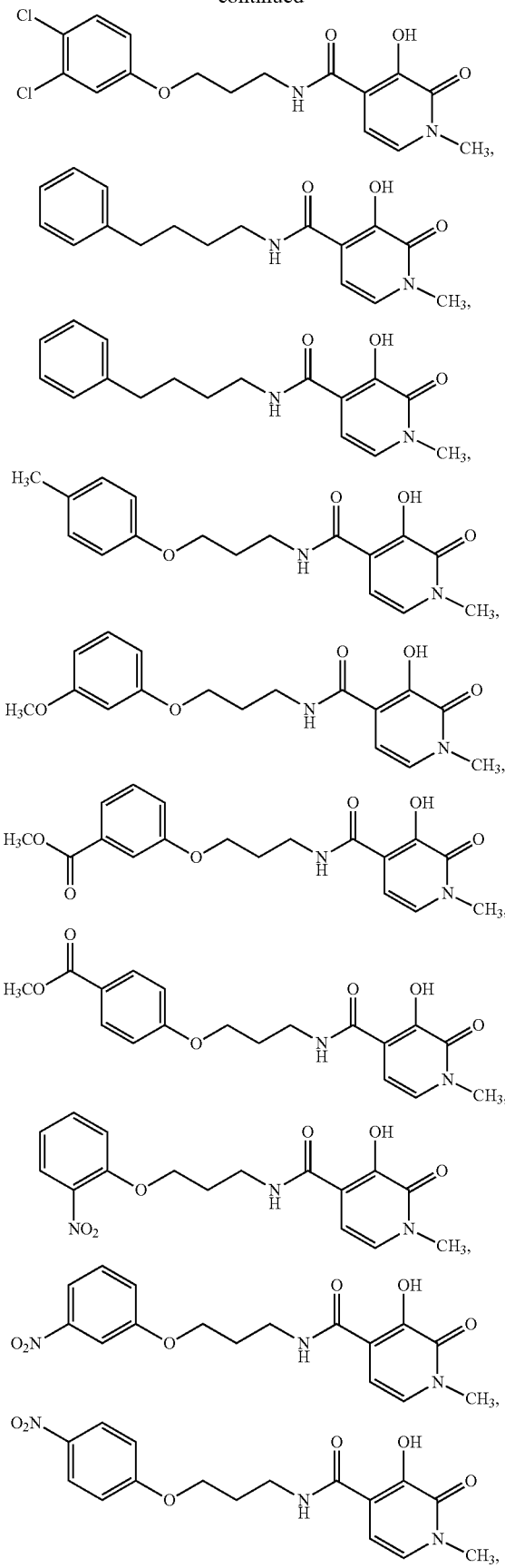
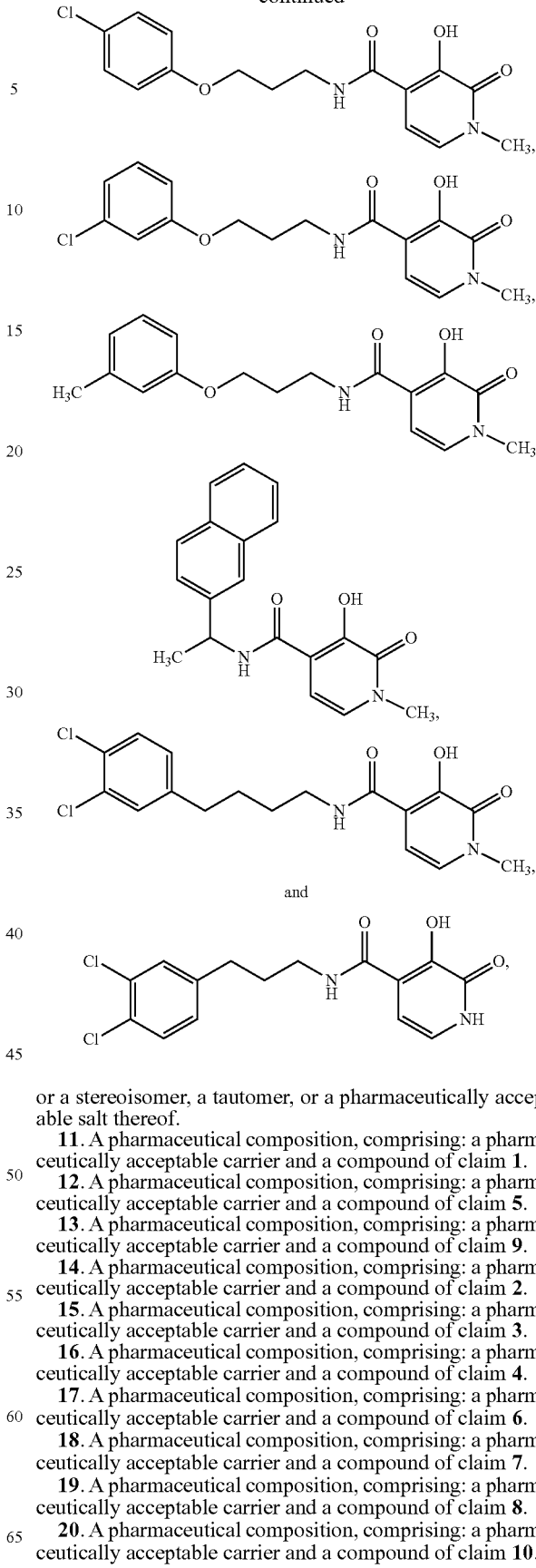

or a stereoisomer, a tautomer, or a pharmaceutically acceptable salt thereof.

11. A pharmaceutical composition, comprising: a pharmaceutically acceptable carrier and a compound of claim 1.
12. A pharmaceutical composition, comprising: a pharmaceutically acceptable carrier and a compound of claim 5.
13. A pharmaceutical composition, comprising: a pharmaceutically acceptable carrier and a compound of claim 9.
14. A pharmaceutical composition, comprising: a pharmaceutically acceptable carrier and a compound of claim 2.
15. A pharmaceutical composition, comprising: a pharmaceutically acceptable carrier and a compound of claim 3.
16. A pharmaceutical composition, comprising: a pharmaceutically acceptable carrier and a compound of claim 4.
17. A pharmaceutical composition, comprising: a pharmaceutically acceptable carrier and a compound of claim 6.
18. A pharmaceutical composition, comprising: a pharmaceutically acceptable carrier and a compound of claim 7.
19. A pharmaceutical composition, comprising: a pharmaceutically acceptable carrier and a compound of claim 8.
20. A pharmaceutical composition, comprising: a pharmaceutically acceptable carrier and a compound of claim 10.

* * * * *